United States Patent [19]

Sit et al.

[11] Patent Number: 4,897,490

[45] Date of Patent: Jan. 30, 1990

[54] ANTIHYPERCHOLESTEROLEMIC TETRAZOLE COMPOUNDS

[75] Inventors: Sing-Yuen Sit, Meriden; John J. Wright, Middletown, both of Conn.

[73] Assignee: Bristol-Meyers Company, New York, N.Y.

[21] Appl. No.: 151,513

[22] Filed: Feb. 18, 1988

Related U.S. Application Data

[63] Continuation-in-part of Ser. No. 18,542, Feb. 25, 1987.

[51] Int. Cl.$^4$ .................. C07D 405/06; C07D 257/02
[52] U.S. Cl. ........................................................ 548/253
[58] Field of Search ........................................ 548/253

[56]     References Cited
         U.S. PATENT DOCUMENTS

| | | | |
|---|---|---|---|
| 4,198,425 | 4/1980 | Mistui et al. | 424/279 |
| 4,375,475 | 3/1983 | Willard et al. | 549/29 X |
| 4,613,610 | 9/1986 | Wareing | 514/406 |
| 4,678,806 | 7/1987 | Baldwin et al. | 514/539 |
| 4,681,893 | 7/1987 | Roth | 574/422 |
| 4,739,073 | 4/1988 | Kathwala | 548/406 |

FOREIGN PATENT DOCUMENTS

| | | |
|---|---|---|
| 24348 | 3/1981 | European Pat. Off. . |
| 68038 | 1/1983 | European Pat. Off. . |
| 142146 | 5/1985 | European Pat. Off. . |
| 002131 | 6/1983 | Int'l Pat. Institute . |
| 002903 | 8/1984 | Int'l Pat. Institute . |
| 007054 | 12/1986 | Int'l Pat. Institute . |

OTHER PUBLICATIONS

Buchanan et al., J. Med. Chem., v. 12, (11-1969), pp. 1001 and 1002.
A. Endo, et al., Journal of Antibiotics, 29, 1346-1348, (1979).
A. W. Alberts, et al., J. Proc. Natl. Acad. Sci., U.S.A., 77, 3957, (1980).
G. E. Stokker, et al., J. Med. Chem., 28, 347-358, (1985).
W. F. Hoffman et al., J. Med. Chem., 29, 159-169, (1986).
G. E. Stokker, et al., J. Med. Chem., 29, 170-181, (1986).

Primary Examiner—David B. Springer
Attorney, Agent, or Firm—Aldo A. Algieri

[57] ABSTRACT

Compounds of the formula

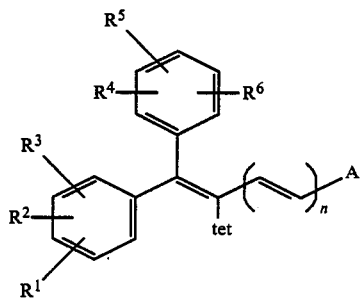

wherein
$R^1$ and $R^4$ each are independently hydrogen, halogen, $C_{1-4}$ alkyl, $C_{1-4}$ alkoxy, or trifluoromethyl;
$R^2$, $R^3$, $R^5$ and $R^6$ each are independently hydrogen, halogen $C_{1-4}$ alkyl or $C_{1-4}$ alkoxy;
tet is

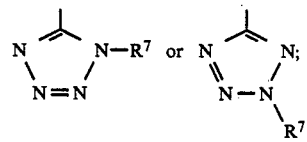

n is an integer of from 0 to 2, inclusive;
A is

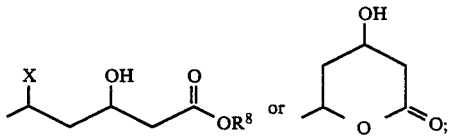

$R^7$ is hydrogen, $C_{1-4}$ alkyl, $C_{1-4}$ alkoxy(lower) alkyl or (2-methoxyethoxy)methyl;
X is —OH or =O; and
$R^8$ is hydrogen, a hydrolyzable ester group or a cation to form a non-toxic pharmaceutically acceptable salt, are novel antihypercholesterolemic agents which inhibit cholesterol biosynthesis. Intermediates and processes for their preparation are disclosed.

40 Claims, No Drawings

ANTIHYPERCHOLESTEROLEMIC TETRAZOLE COMPOUNDS

CROSS-REFERENCE TO RELATED APPLICATION

This application is a continuation-in-part of our prior, co-pending application Ser. No. 018,542, filed Feb 25, 1987.

BACKGROUND OF THE INVENTION

1. Field of the Invention The present invention provides novel tetrazole compounds which are potent inhibitors of the enzmye 3-hydroxy-3-methylglutaryl coenzyme A (HMG-CoA) reductase and, therefore, are useful in the treatment or prevention of hypercholesterolemia, hyperlipoproteinemia and atherosclerosis. The present invention also provides novel processes for the preparation of the tetrazole compounds and to certain intermediates in their preparation.

2. Disclosure Statement The natural Fermentation products Compactin (R=H) disclosed by A. Endo, et al. in /Journal of Antibiotics, 29, 1346-1348 (1976) and Mevinolin (R=CH$_3$) disclosed by A. W. Alberts, et al. in J. Proc. Natl. Acad. Sci. U.S.A., 77, 3957 (1980) are very active antihypercholesterolemic agents which limit cholesterol biosynthesis by inhibiting the enzyme HMG-CoA reductase, the rate-limiting enzyme and natural point of cholesterogenesis regulation in mammals, including man. Compactin (R=H) and Mevinolin (R=CH$_3$; also known as lovastatin) have the structures shown below:

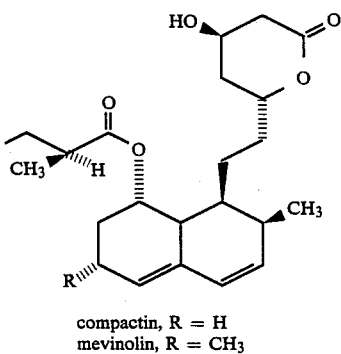

compactin, R = H
mevinolin, R = CH$_3$

A number of structurally related synthetic compounds useful in the treatment of hypercholesterolemia have also been disclosed in patents and other publications. The synthetic art most closely related is as follows:

U.S. Pat. No. 4,198,425, issued Apr. 15, 1980 to S. Mistui, et al. describes novel mevalonolactone derivatives useful for the treatment of hyperlipidemia and having the general formula

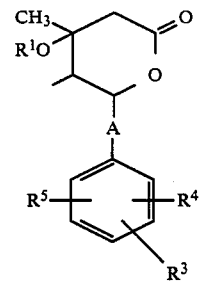

wherein A represents a direct linkage, methylene, ethylene, trimethylene or vinylene group and R$^3$, R$^4$ and R$^5$ represent various substituents.

European patent application EP-24,348 published Mar. 4, 1981 discloses new hypocholesterolemic and hypolipemic compounds having the structure

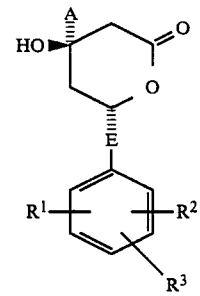

wherein A is H or methyl; E is a direct bond, —CH$_2$—, —(CH$_2$)$_2$—, —(CH$_2$)$_3$— or —CH=CH—; R$^1$, R$^2$ and R$^3$ each represent various substituents and the corresponding dihydroxy acids resulting from the hydrolytic opening of the lactone ring.

U.S. Pat. No. 4,375,475, issued Mar. 1, 1983 to A. K. Willard, et al. discloses essentially the same structures and is concordant to the above-mentioned EP-24,348 patent application.

European patent application EP-68,038 published Jan. 5, 1983 discloses and claims the resolved trans-enantiomer, process for its preparation and pharmaceutical composition thereof having the structure

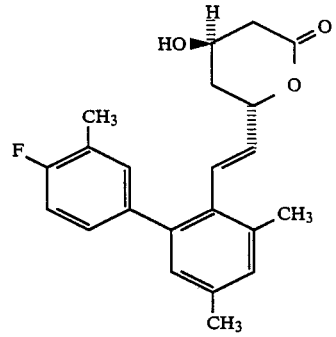

and the corresponding dihydroxy acid, or a pharmaceutically acceptable salt thereof.

International patent application WO 84/02131 published June 7, 1984 describes analogs of mevalonolactone having the structure

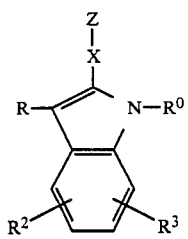

wherein: one of R and R⁰ is

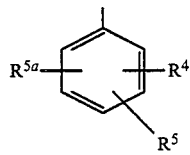

and the other is primary or secondary $C_{1-6}$ alkyl, $C_{3-6}$ cycloalkyl or phenyl-$(CH_2)_n$—;
X is —$(CH_2)_n$— or —CH=CH—;
n is 0, 1, 2 or 3;
z is

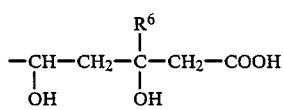

and
$R^4$, $R^5$, $R^{5a}$ and $R^6$ represent various substituents.

International patent application WO 84/02903 published Aug. 2, 1984 describes mevalonolactone analogs having the structures

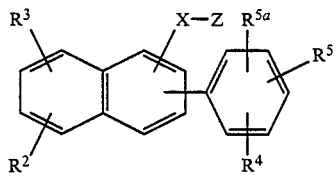  IA

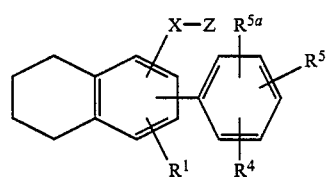  IB wherein
X is —$(CH_2)_n$—,

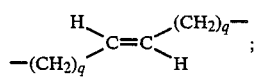

n=0, 1, 2, or 3 and both q's are 0 or one is 0 and the other is 1 and

—CH $$Z = -CH-CH_2-\underset{OH}{\overset{R^6}{C}}-CH_2-COOH$$

European patent application EP-142,146 published May 22, 1985 describes oxo- analogs of mevinolin-like antihypercholesterolemic agents having the structure

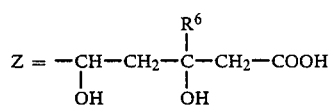

wherein E is —$CH_2$—$CH_2$—, —CH=CH— or
$)_3$—; and

Z is

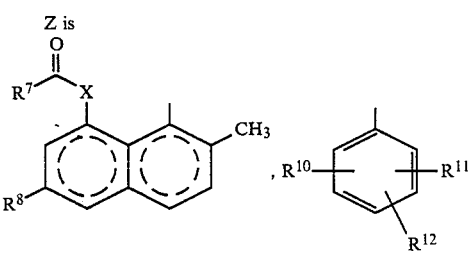

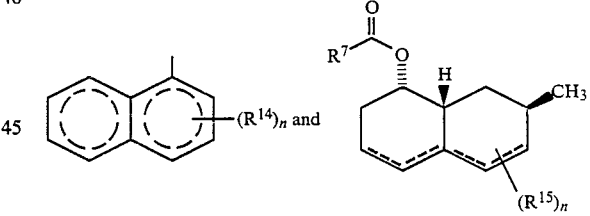

wherein the dotted lines represent possible double bonds there being 0, 1, or 2 double bonds.

In *J. Med. Chem.*, 28, 347–358 (1985), G. E. Stokker, et al. report the preparation and testing of a series of 5-substituted 3,5-dihydroxypentanoic acids and their derivatives.

In *J. Med. Chem.*, 29, 159–169 (1986), W. F. Hoffman, et al. describe the preparation and testing of a series of 7-(substituted aryl)-3,5-dihydroxy-6-heptenoic (heptanoic) acids and their lactone derivatives. One of the preferred compounds in the reported series has the structure

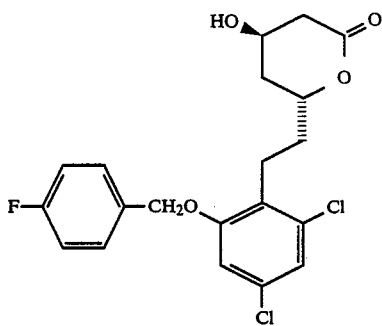

In *J. Med. Chem.*, 29, 170–181 (1986), G. E. Stokker, et al. report the synthesis of a series of 7-[3,5-disubstituted (1,1'-biphenyl)-2-yl]-3,5-dihydroxy-6-heptenoic acids and their lactones. Two of the preferred compounds reported in this article have the structures

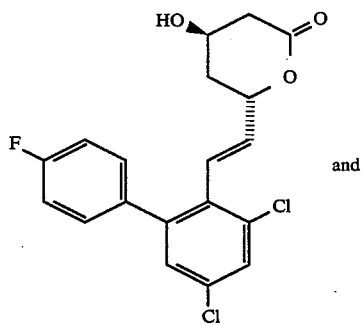

and

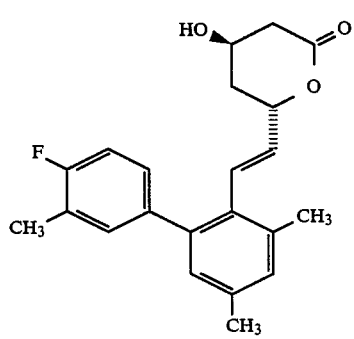

U.S. Pat. No. 4,613,610, issued Sept. 23, 1986 to J. R. Wareing describes pyrazole analogs of mevalonolactone and its derivatives useful for the treatment of hyperlipoproteinemia and atherosclerosis and having the general formula

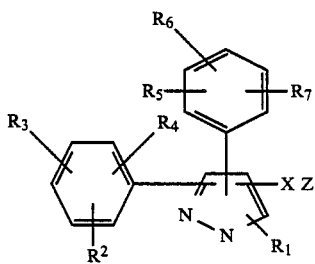

wherein X is $-(CH_2)_n-$, $-CH=CH-$, $-CH=CH-CH_2-$ or $-CH_2-CH=CH-$; n is 0, 1, 2 or 3, and $R^1$, $R^2$, $R^3$, $R^4$, $R^5$, $R^6$, $R^7$ and Z represent various substituents.

None of the cited patents and articles disclose or suggest the possibility of preparing the compounds of the present invention. The unique structural feature which incorporates a tetrazole moiety in the present compounds differs substantially from the cited art while exhibiting potent HMG-CoA activity.

SUMMARY OF THE INVENTION

This invention provides novel compounds having the formula

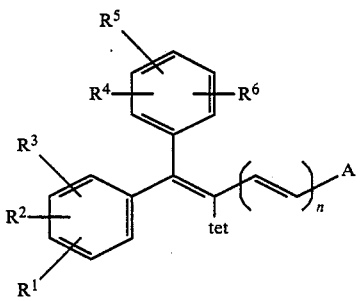

I wherein $R^1$, $R^2$, $R^3$, $R^4$, $R^5$ and $R^6$, tet, n and A are as defined below, which are potent inhibitors of the enzyme 3-hydroxy-3-methylglutaryl coenzyme A (HMG-CoA) reductase and are useful in the treatment of hypercholesterolemia, hyperlipoproteinemia and atherosclerosis. The present invention also provides useful intermediates, processes for their preparation and processes for the preparation of compounds of the Formula I.

DESCRIPTION OF THE INVENTION

The present invention provides novel tetrazole compounds which are inhibitors of the enzyme HMG-CoA reductase, which are useful in the treatment of hypercholesterolemia, hyperlipoproteinemia and atherosclerosis, and which have the formula

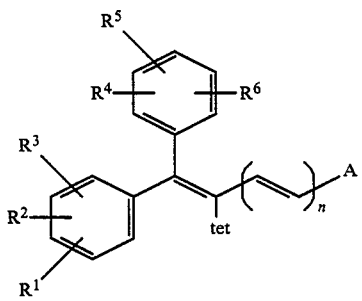

I wherein
$R^1$ and $R^4$ each are independently hydrogen, halogen, $C_{1-4}$ alkyl, $C_{1-4}$ alkoxy or trifluoromethyl;
$R^2$, $R^3$, $R^5$ and $R^6$ each are independently hydrogen, halogen, $C_{1-4}$ alkyl or $C_{1-4}$ alkoxy;
tet is

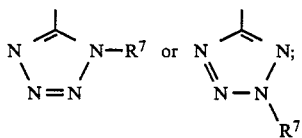

n is an integer of from 0 to 2, inclusive;
A is

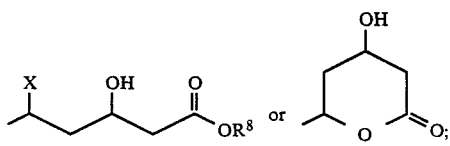

$R^7$ is hydrogen, $C_{1-4}$ alkyl, $C_{1-4}$ alkoxy(lower)alkyl or (2-methoxyethoxy)methyl;

X is —OH or =O, and $R^8$ is hydrogen, a hydrolyzable ester group or a cation to form a non-toxic pharmaceutically acceptable salt.

This invention also provides processes for the preparation of the compounds of Formula I and to intermediates in the preparation of compounds of Formula I.

The terms "$C_{1-4}$ alkyl", "$C_{1-6}$ alkyl" and "$C_{1-4}$ alkoxy" as used herein and in the claims (unless the context indicates otherwise) mean unbranched or branched chain alkyl or alkoxy groups such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. The term "(lower)alkyl" in the substituent "$C_{1-4}$ alkoxy(lower)alkyl" as used herein and in the claims means unbranched or branched chain alkyl groups containing from 1 to 4 carbon atoms, and preferably contain 2 carbon atoms. Unless otherwise specified in the particular instance, the term "halogen" as used herein and in the claims is intended to include chlorine, fluorine, bromine and iodine while the term "halide" as used herein and in the claims is intended to include chloride, bromide and iodide anion. The term "a cation to form a non-toxic pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as $C_{1-6}$ alkyl, phenylmethyl and pivaloyloxymethyl.

In the compounds of Formula I, it is intended that all of the double bonds are in the trans configuration, i.e., (E), as indicated in the structural formulae used herein and in the claims.

As the compounds of the present invention may possess one or two asymmetric carbon atoms, the invention includes all of the possible enantiomeric and diastereomeric forms of the compounds of Formula I as described herein and in the claims. The compounds of Formula I which contain two centers of asymmetry may produce four possible stereoisomers designated as the RR, RS, SR and SS enantiomers; all four stereoisomers are considered within the scope of this invention. Specifically, the compounds of Formula I having two asymmetric carbon atoms bearing the hydroxy groups in the 3 and 5 position may produce four possible stereoisomers which are designated as the (3R,5S), (3S,5R), (3R,5R) and (3S,5S) stereoisomers. As used herein and in the claims, the term "(±)-erythro" is intended to include a mixture of (3R,5S) and (3S,5R) enantiomers, and the term "(±)-threo" is intended to include a mixture of (3R,5R) and (3S,5S) enantiomers. The use of a single designation such as (3R,5S) is intended to include mostly one stereoisomer. The lactone forms of the compounds of Formula I also have two asymmetric carbon atoms at the 4 and 6 position, and the resulting four stereoisomers may be designated as the (4R,6S), (4S,6R) (4R, 6R) and (4S,6S) stereoisomers. As used herein and in the claims, the term "trans" lactone is intended to include a mixture of (4R,6S) and (4S,6R) enantiomers while the term "cis" lactone is intended to include a mixture of (4R,6R) and (4S,6S) enantiomers. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns.

If it is desired to prepare the (+) isomer of the compounds of Formula I, then the synthetic (±) isomer of the present invention may be resolved by resolution methods well-known to those skilled in the art. For example of a resolution procedure in this general class of compounds, U.S. Pat. No. 4,375,475 issued Mar. 1, 1983 to A. K. Willard, et al. describe the resolution of a racemic (±) trans lactone with excess d-(+)-α-methylbenzylamine (or the corresponding 1-(−)-α-methylbenzylamine), separating the resulting two diastereoisomeric amines and hydrolyizng to the corresponding, for example, sodium salt. The resulting salt may then be converted by conventional means to the corresponding acid, ester and lactone. Preferably, the optically active enantiomers of the compounds of Formula I may be prepared by stereoselective synthetic procedures, some of which are described herein. The use of optically active reagents in combination with the appropriate intermediate described herein would produce the desired enantiomer of the compound of Formula I.

Since the compounds of Formula I appear to contain varying amounts of solvent as ascertained mainly by elemental analysis, the present invention is intended to include solvates of the compounds of Formula I. In some cases, it appears that the products may be true solvates, while in other cases, the products may merely retain adventitious solvent or be a mixture of solvate plus some adventitious solvent. Preferably, the solvate is water and, most preferably, one to three moles of water. The examples below give the amount of solvent where appropriate in the analysis and melting points are those of the solvated product unless otherwise indicated.

In the compounds of Formula I, $R^1$, $R^2$, $R^3$, $R^4$, $R^5$, and $R^6$, independently, are preferably hydrogen, halogen, $C_{1-4}$ alkyl or $C_{1-4}$ alkoxy. More preferably, $R^1$ and $R^4$ are hydrogen and $R^2$, $R^3$, $R^5$ and $R^6$, independently, are hydrogen, fluoro, chloro, methyl or methoxy, and most preferably, $R^1$ and $R^4$ are hydrogen and $R^2$, $R^3$, $R^5$ and $R^6$, independently, are hydrogen, fluoro, methyl or methoxy. It is preferred that n is zero, 1, or 2 and more preferably n is 1. Preferably, tet is 1H-tetrazol-5-yl or 1-substituted-1H-tetrazol-5-yl. More preferably, tet is 1-methyl-1H-tetrazol-5-yl, 1-ethyl1H-tetrazol-5-yl, 1-methylethyl-1H-tetrazol-5-yl or 1-(2-methoxyethoxy)-methyl-1H-tetrazol-5-yl and most preferably, tet is 1-methyl-1H-tetrazol-5-yl. It is preferred that X is —OH or $=$O and most preferably X is —OH. Preferably, $R^8$ is hydrogen, $C_{1-6}$ alkyl or a pharmaceutically acceptable cation. Most preferably, $R^8$ is a pharmaceutically acceptable cation especially sodium or potassium.

In the compounds of Formula I wherein A contains two asymmetric carbon atoms bearing the hydroxy group, the erythro isomer is preferred and the (3R,5S) isomer being most preferred. In the compounds of Formula I wherein A contains two asymmetric carbon atoms in the lactone form, the trans isomer is preferred and the (4R,6S) isomer being most preferred.

The compounds of Formula I may be prepared by various procedures, preferably starting from a compound of the Formula IIa or IIb

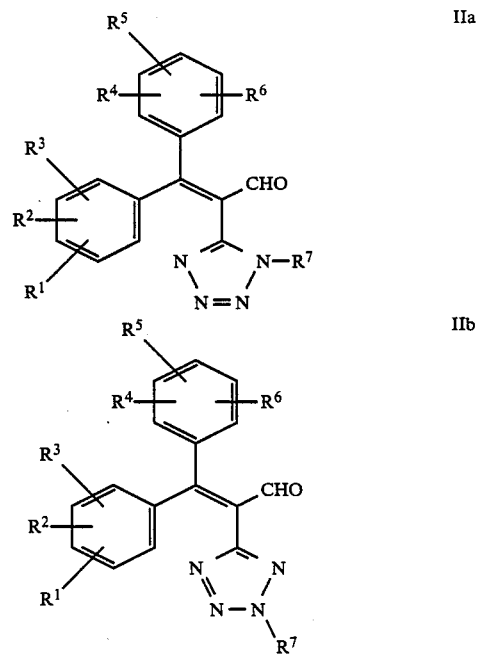

wherein $R^1$ and $R^4$ each are independently hydrogen, halogen, $C_{1-4}$ alkyl, $C_{1-4}$ alkoxy or trifluoromethyl; $R^2$, $R^3$, $R^5$ and $R^6$ each are independently hydrogen, halogen, $C_{1-4}$ alkyl or $C_{1-4}$ alkoxy; and $R^7$ is $C_{1-4}$ alkyl, $C_{1-4}$alkoxy(lower)alkyl, (2-methoxyethoxy)methyl or $R^{7a}$ in which $R^{7a}$ is triphenylmethyl.

The compounds of Formulae IIa and IIb may be prepared from the optionally substituted benzophenones III by aldol condensation to the tetra substituted olefin IV and conversion to the tetrazole ester V followed by alkylation of the tetrazole moiety and reduction of the ester group in compounds VI and VII with subsequent oxidation of the resulting alcohols VIII and IX, as shown in Reaction Scheme 1.

Reaction Scheme 1

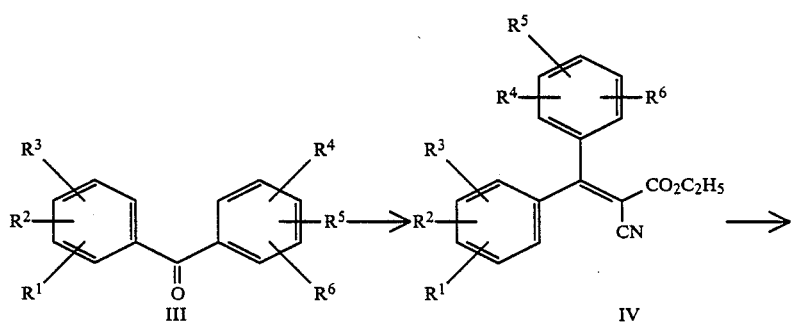

Reaction Scheme 1

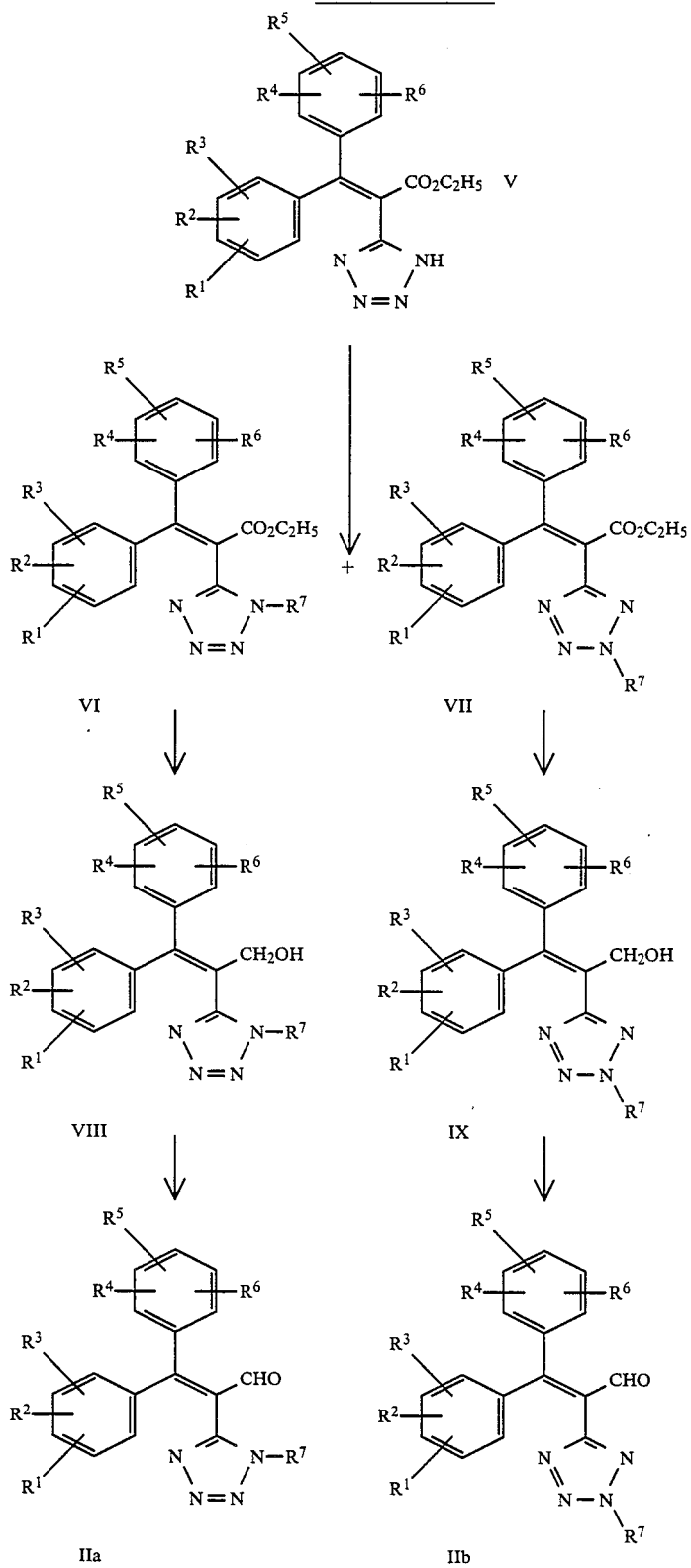

In Reaction Scheme 1, $R^1$, $R^2$, $R^3$, $R^4$, $R^5$, $R^6$, and $R^7$ are as previously defined. The optionally substituted benzophenones of the Formula III may be prepared by the general and well-known Friedel Crafts reaction of a substituted phenyl catalyzed by Lewis acids, e.g., with aluminum chloride in carbon tetrachloride at about 0° C. A large number of substituted benzophenones are known and their prepartion are described in the art while many others are commercially available. For example, many of the starting materials of Formula III are described by G. Olah in /Friedel-Crafts and Related Reactions, Vol. 3, Part 1 and 2, Interscience Publishers, New York, 1964 and references therein. The Friedel Crafts reaction may produce a mixture of benzophenones and, if so produced, the mixture may be separated by conventional techniques known in the art.

The appropriate benzophenone of the Formula III may be treated with ethyl cyanoacetate in a solvent mixture containing glacial acetic acid and an organic solvent such as benzene or toluene in the presence of a catalyst preferably β-alanine. The reaction is allowed to proceed at the reflux temperature of the solvent and the water which is produced is azeotropically removed with a Dean-Stark trap or similar apparatus until the production of the tetra substituted olefin IV is essentially complete. The nitrile group in compound IV is then converted to the heterocyclic tetrazole moiety of compound V by conducting the reaction with azidotributylstannane neat or in an inert organic solvent such as benzene, toluene or xylene at the reflux temperature of the solvent.

The 1H-tetrazole compound of Formula V may then be alkylated with various alkylating agents by methods well-known to those skilled in the art. Thus, the 1H-tetrazole of Formula V may be treated with a strong base such as sodium hydride in a non-reactive solvent, e.g., benzene, toluene, diethyl ether and N,N-dimethyl-formamide or mixture thereof at a temperature from −30° C. to about 50° C. and then with an alkylating agent, e.g., methyl iodide, ethyl iodide, bromotriphenylmethane, and the like or with isobutylene in the presence of strong acid such as sulfuric acid. The temperature is not critical and will usually depend on the alkylating agent employed. This non-specific alkylation produces an isomeric mixture of alkylated products which may be separated by conventional procedures such as crystallization or chromatography to give the desired 1-substituted tetrazole compounds VI and 2-substituted tetrazole compounds VII.

It should be appreciated by those skilled in the art that the combination of reaction conditions with the specific alkylating agent employed may produce predominately one isomer. For example, when the compound of Formula V wherein $R^1$ and $R^4$ are para-fluoro and $R^2$, $R^3$, $R^5$ $R^6$ are hydrogen, the alkylation of compound V with isobutylene produces predominately the 2-isomer tetrazole as is demonstrated in Example 32. Alternatively, the conditions of the alkylation reaction may be varied to produce the desired tetrazoles VI and VII in ratios varying from about 1:1 to about 5:1. When it is desired to prepare compounds of Formula I wherein $R^7$ is hydrogen, the alkylation of Compound V with a protecting group such as triphenylmethyl is preferred. In this instance, the 2-isomer of compound VII is predominately produced as is demonstrated in Example 106. Subsequent removal of the protecting group will then produce a compound of Formula I wherein $R^7$ is hydrogen. Thus, it should be evident to one skilled in the art that the relative amounts of alkylated products VI and VII may be influenced by the reaction conditions and reagents employed.

The tetrazole esters of the Formulae VI and VII may then be converted together as a mixture or, preferably, individually after separation by standard techniques to the alcohols VIII and IX, respectively, by a series of known reactions. According to one reaction route, the compound of Formula VI is first hydrolyzed by conventional methods, such as base hydrolysis, i.e., lithium hydroxide, potassium hydroxide and sodium hydroxide. The resulting acid (i.e. Example 5) is then converted to an acyl chloride (Example 6A) by reacting with a reagent such as oxalyl chloride in methylene chloride at reflux temperature and the resulting acyl chloride is reduced with a reducing agent, preferably, lithium aluminum hydride in tetrahydrofuran at −78° C. to produce the alcohols of the Formula VIII. The alcohols of Formula IX may be prepared from the ester of Formula VII by a similar series of reactions utilized to convert the esters VI to the alcohols VIII. Alternatively, and more preferably, the alcohols VIII and IX may be prepared in one step from the corresponding esters VI and VII by reduction with reducing agents such as diisobutylaluminum hydride in a non-reducible inert solvent such as methylene chloride, at low temperatures, preferably at about −78° C.

The mixture of allylic alcohols of Formulae VIII and IX may be readily oxidized by conventional oxidizing agents such as pyridinium chlorochromate in a non-reactive solvent, preferably, methylene chloride at ambient temperature. More preferably, the separated allylic alcohols of Formula VIII and IX may individually be oxidized in the same manner to produce the corresponding allylic aldehydes of Formula IIa and IIb.

The compounds of Formula I may be prepared from a compound of Formula IIa or IIb by various alternative reaction schemes via several classes of novel intermediates. It should be understood by those skilled in the art that the prepartion of compounds of Formula I wherein n is 0, 1 or 2 will necessarily involve three novel aldehyde intermediates. Thus, if it is desired to prepare compounds of Formula I wherein n=0, then the compound of Formula IIa or IIb is subjected to the appropriate anion alkylation as described herein. However, if it is desired to prepare compounds of Formula I wherein n=1 or 2 then the appropriate Wittig reactions are carried out in order to prepare the necessary novel homologous aldehydes X and XI for the 1-isomer and aldehydes XII and XIII for the 2-isomer, as shown in Reaction Schemes 2 and 3, respectively.

Reaction Scheme 2
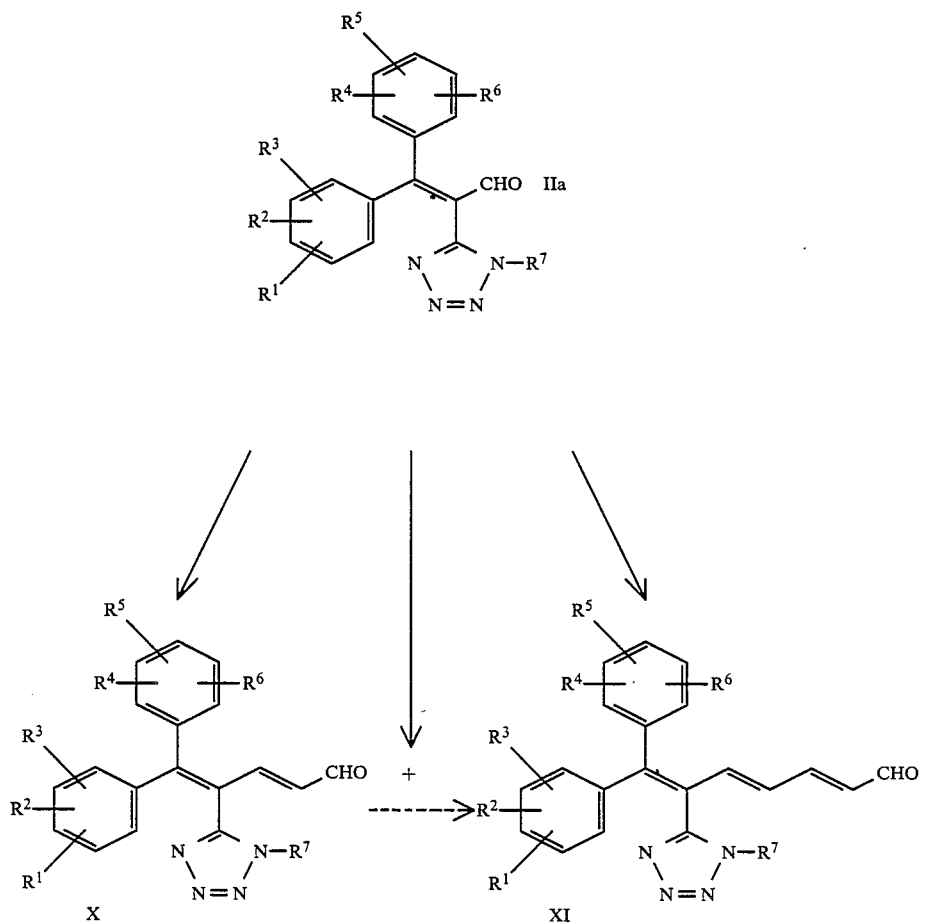
Reaction Scheme 3
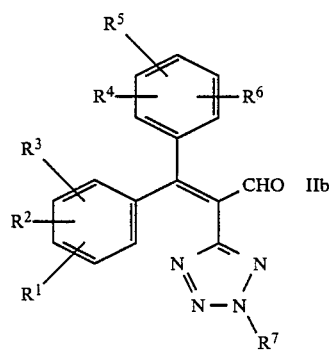

-continued
Reaction Scheme 3

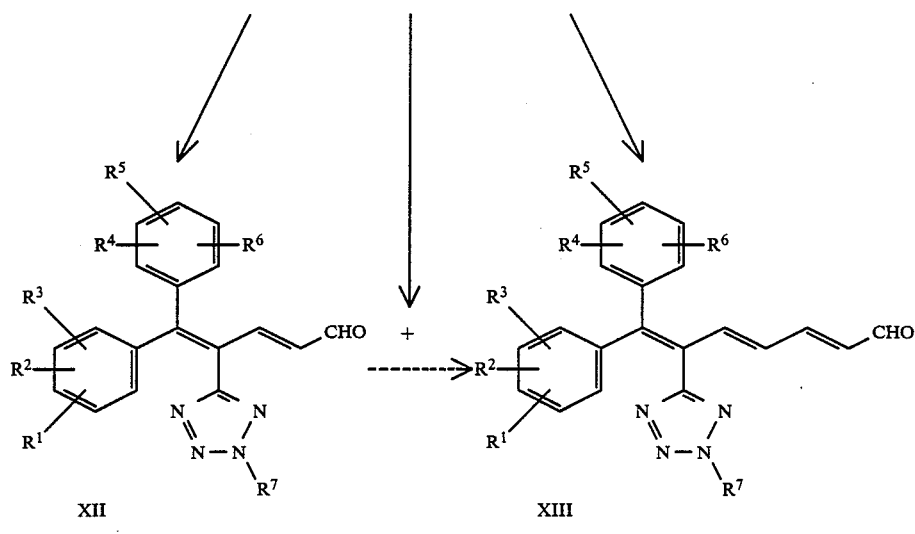

XII                XIII

In Reaction Schemes 2 and 3, $R^1$, $R^2$, $R^3$, $R^4$, $R^5$, $R^6$, $R^7$ are as previously defined and $R^7$ may also be $R^{7a}$ in which $R^{7a}$ is triphenylmethyl. For example, in Reaction Scheme 2, an allylic aldehyde of Formula IIa may be treated with triphenylphosphoranylidene acetaldehyde in a non-reactive solvent such as benzene, toluene, tetrahydrofuran, 1,2-dimethoxyethane and the like. The temperature of the reaction is not critical and can be conducted at from ambient temperature to the reflux temperature of the solvent. For convenience we prefer to conduct the reaction at reflux temperature. It should be understood and appreciated by those skilled in the art that the reaction conditions and the number of equivalents of triphenylphosphoranylidene acetaldehyde utilized per equivalent of a compound of Formula IIa is critical. If only one or slightly more than one equivalent of Wittig reagent is employed but the reaction conditions are not carefully controlled. e.g., time, temperature, mode of addition, etc., then there may be produced a mixture of diene aldehyde X and triene aldehyde XI. The ratio of aldehydes X and XI will naturally depend on the reaction conditions employed. In a specific example described herein, Example 8, there is produced about a 9:1 ratio of an aldehyde of general Formulae X and XI from the corresponding aldehyde of general Formula IIa. The wittig reaction may also be used to assist in the selective reaction and separation of compounds by utilizing less than one equivalent of the Wittig reagent to produce mostly the diene aldehyde X. For example, the use of half an equivalent of Wittig reagent as described in Example 69 provided the desired diene aldehyde X and unreacted aldehyde IIa which could now be more readily separated. Preferably, the reaction is conducted with about one equivalent of Wittig reagent under controlled reaction conditions, for example, as described in Example 77 to produce the desired diene aldehyde X without any detectable amount (by NMR) of the homologous triene aldehyde. However, if it is desired to prepare the triene aldehydes of Formula XI then the reaction of the aldehyde of Formula IIa is carried out with at least two equivalents of the Wittig reagent or, alternatively, the diene aldehyde X is reacted with an additional equivalent of the Wittig reagent to produce the triene aldehyde of Formula XI. Thus, it can be readily appreciated by those skilled in the art that the preparation of the desired homologated aldehydes X and XI wherein n is 1 or 2, respectively can be controlled as desired by employing the appropriate amount of Wittig reagent and reaction conditions.

Conversion of an aldehyde of Formula IIb to the corresponding homologated diene aldehyde of Formula XII and triene aldehyde of Formula XIII, as shown in Reaction Scheme 3, may be prepared by procedures similar to those described above for the preparation of the aldehydes of Formulae X and XI. It should be appreciated that some of the vinylogous aldehydes of Reaction Schemes 2 and 3 are readily and conveniently isolated while others being more difficult. In specific cases where the aldehydes were difficult to separate by the chromatography systems utilized herein, the mixture of aldehydes, for example, aldehydes X and XI are employed in the next step where the separation and isolation of diene and triene compounds may be more readily carried out by chromatography or other conventional techniques.

The compounds of Formula I wherein X is —OH may be prepared from a compound of the Formula IIa, IIb, X, XI, XII or XIII by the general reaction route shown in Reaction Scheme 4. For the purposes of discussion all the aldehydes of Reaction Schemes 2 and 3 are combined in one Formula and are designated as the compounds of Formula XIV wherein n is 0, 1 or 2 and $R^1$, $R^2$, $R^3$, $R^4$, $R^5$, and $R^6$ are as previously defined.

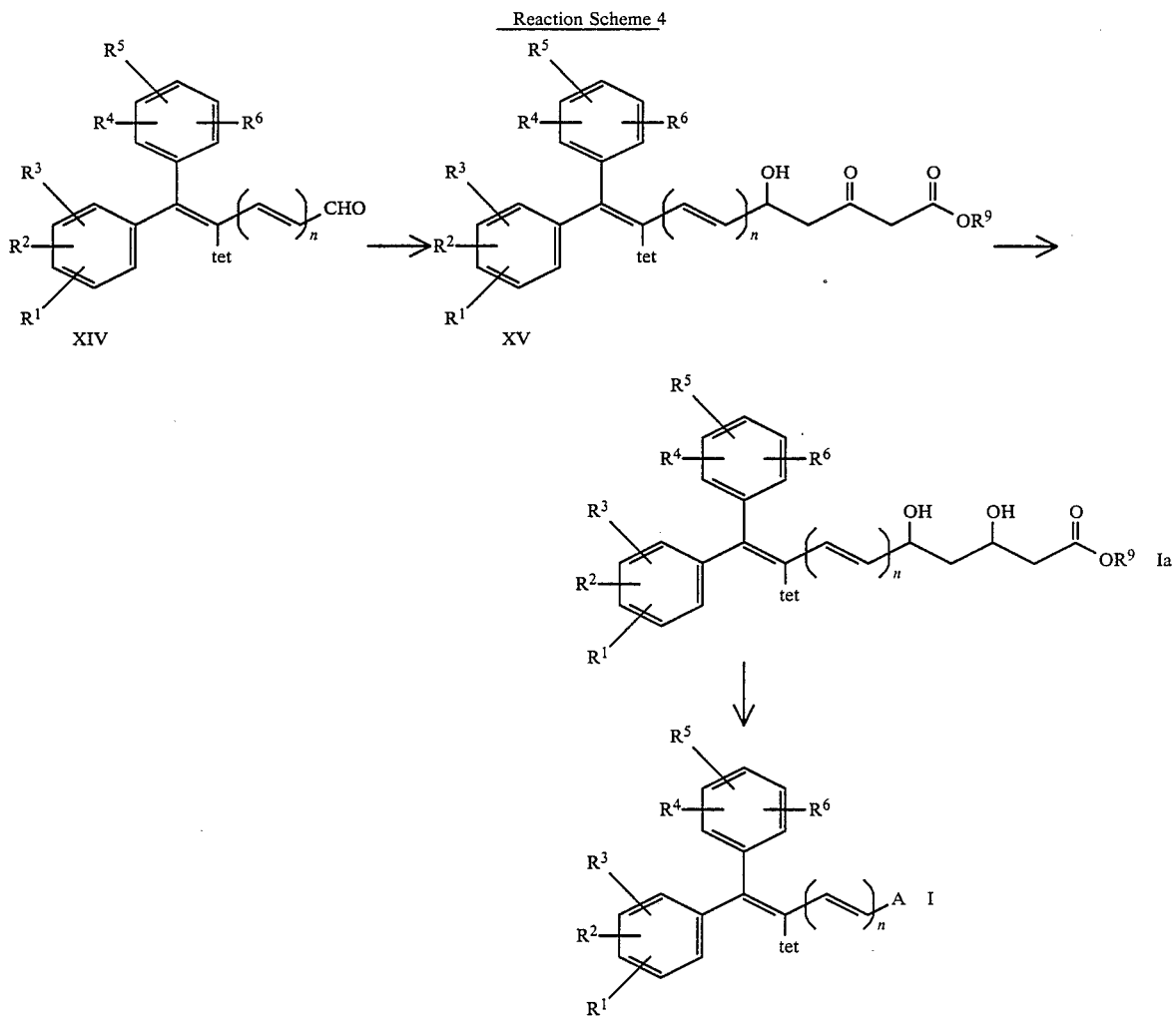

Reaction Scheme 4

In Reaction Scheme 4, the penultimate intermediate of Formula XV wherein $R^9$ is a hydrolyzable ester group such as methyl, ethyl and t-butyl ester may be prepared from the corresponding aldehyde of Formula XIV by reaction with the dianion of acetoacetate ester generated in situ, for example, as described in Examples 10 and 90. The reaction may be conducted in an inert organic solvent such as tetrahydrofuran at low temperatures from −78° C. to about 0° C. and preferably from about −78° C. to −40° C. until the reaction is essentially complete. If a compound of the Formula XV were prepared from a mixture of aldehydes of Formula XIV, then separation of the compounds of Formula XV especially wherein n is 1 and 2 may be advantageously separated and isolated at this stage by conventional techniques.

The ketone ester of Formula XV may be reduced to the dihydroxy ester of Formula Ia by reduction of the ketone radical with reducing agents well-known in the art, e.g., sodium borohydride, sodium cyanoborohydride, zinc borohydride, disiamylborane, diborane, ammonia borane, t-butylamine borane, pyridine borane, lithium tri-s-butylborohydride or other similar reducing agents which will not reduce nor reduce nor hydrolyze the carboxylic ester radical. Preferably, the reduction is carried out in a stereospecific manner by a two-step stereospecific reduction in order to maximize the production of the preferred erythro isomer of the compound of Formula I. The stereospecific reduction of a compound of Formula XV is carried out with trisubstitutedalkylboranes, preferably triethylborane, or alkoxydialkylboranes, preferably methoxydiethylborane or ethoxydiethylborane [*Tetrahedron Letters*, 28, 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethyl ether and 1,2-dimethoxyethane, preferably, tetrahydrofuran. The reduction is then completed by the addition of methanol. The resulting compound of Formula Ia produced from the stereospecific reduction contains two asymmetric carbon atoms bearing the hydroxy group in an erythro configuration. Thus, reduction of the ketone radical under the conditions employed herein produces mostly the erythro isomers of the compounds of Formula Ia and only a small amount of the less preferred threo isomers. The ratio of erythro-threo isomers produced will vary according to the specific compound utilized and the reaction conditions employed. Normally, this ratio will be approximately 9:1 to 9.8:0.2. However, the use of a non-specific reduction will normally produce a 1:1 mixture of isomers. Nevertheless, the mixture of isomers may be separated and purified by conventional techniques and then converted to the compounds of general Formula I in a conventional manner well-known to those skilled in the art.

The compounds of Formula I in which A is defined by X is —OH and $R^8$ is hydrogen (Ic), a hydrolyzable ester group (Ia) or a cation to form a non-toxic pharmaceutically acceptable salt (Ib) and in which A is in the form of a lactone (Id) may be prepared and, if desired, interconverted as shown in Reaction Scheme 5.

exchanged for another cation by treatment with ion-exchange resins.

The compound of Formula Ic may be cyclized to the corresponding lactone of Formula Id by conventional lactonization methods, for example, by heating the acid in an inert organic solvent such as benzene, toluene and xylene and azetropically removing the water which is produced or by treating the compound of Formula Ic in an inert organic solvent, e.g., toluene, benzene, diethyl ether or methylene chloride with an acid such as p-tol-

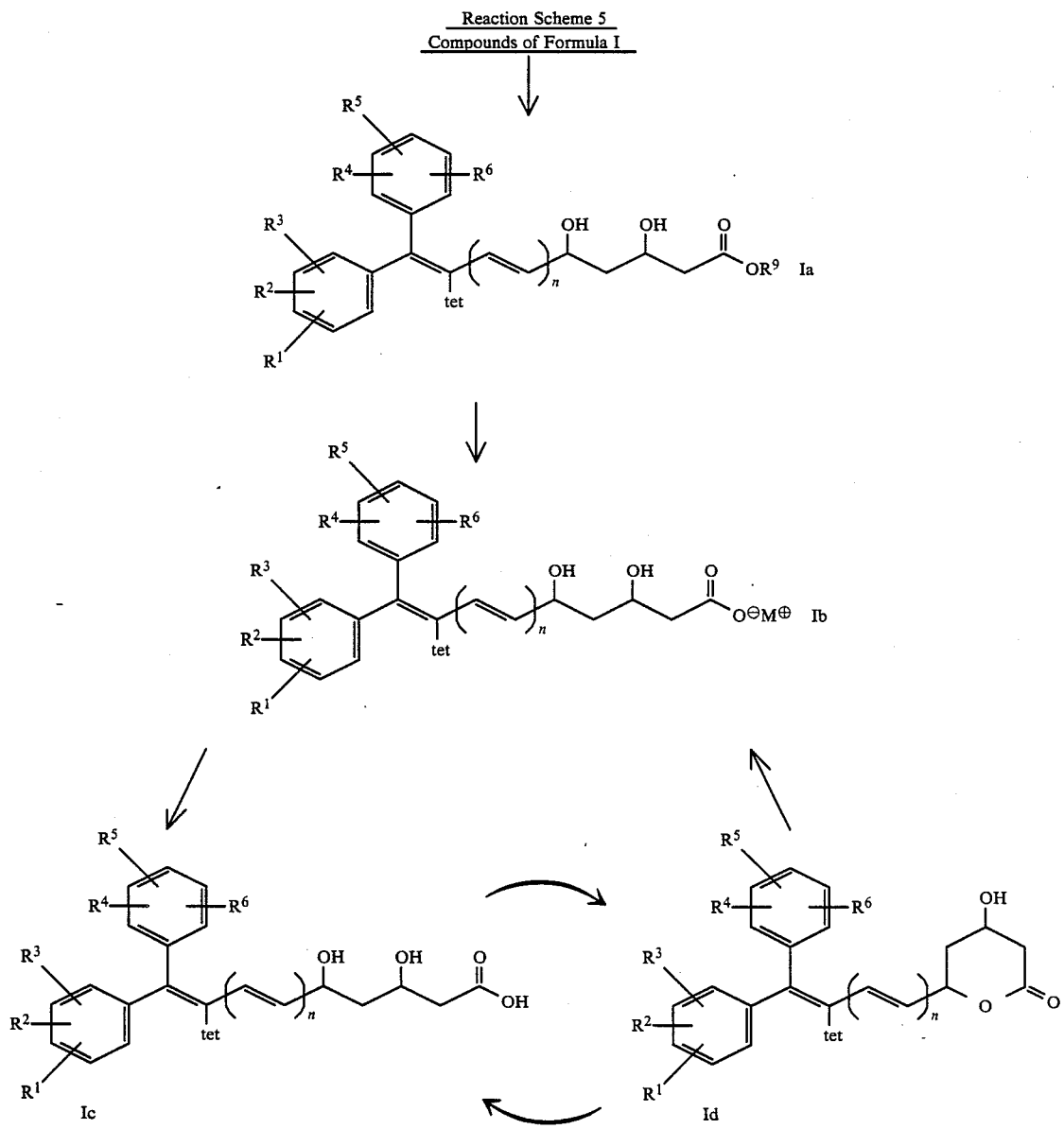

In Reaction Scheme 5, $R^1$, $R^2$, $R^3$, $R^4$, $R^5$, $R^6$, tet and n are as previously defined, $R^9$ is a hydrolyzable ester group and $M^\oplus$ is a cation. The preparation of a compound of Formula Ib from a compound of Formula Ia is preferably carried out by base hydrolysis with bases such as sodium hydroxide, potassium hydroxide and lithium hydroxide in an organic solvent such as tetrahydrofuran, ethanol and methanol at a temperature from 0° C. to about 50° C. The form of the cation is normally determined by the corresponding cation of the hydroxide employed. However, if desired, the cation may be uenesulfonic acid, in the presence of a drying agent, e.g., $NaSO_4$, $MgSO_4$ or molecular sieves. Preferably, the lactonization is carried out by activation of the carboxyl radical with a carbodiimide such as described in the Examples in an inert organic solvent such as tetrahydrofuran, and preferably, in methylene chloride or ethyl acetate at about ambient temperature to produce the lactone of Formula Id. If the relative stereochemical configuration of the two carbon atoms bearing the hydroxy groups are established as erythro in Formula Ic, then the lactonization will produce the preferred trans lactone of Formula Id, otherwise the lactonization will produce a mixture of trans and cis lactones.

The resulting lactone of Formula Id may, if desired, be hydrolyzed with base or acid to produce the compounds of Formula Ib or Formula Ic, respectively, or the lactone may be hydrolyzed in the presence of an alcohol to produce the compounds of Formula Ia.

The compounds of Formula I wherein X is =O in the definition of the substituent A may be produced by reaction of an appropriate aldehyde of Formula XIV with the phosphonate compound of Formula XVI as shown in Reaction Scheme 6.

Reaction Scheme 6

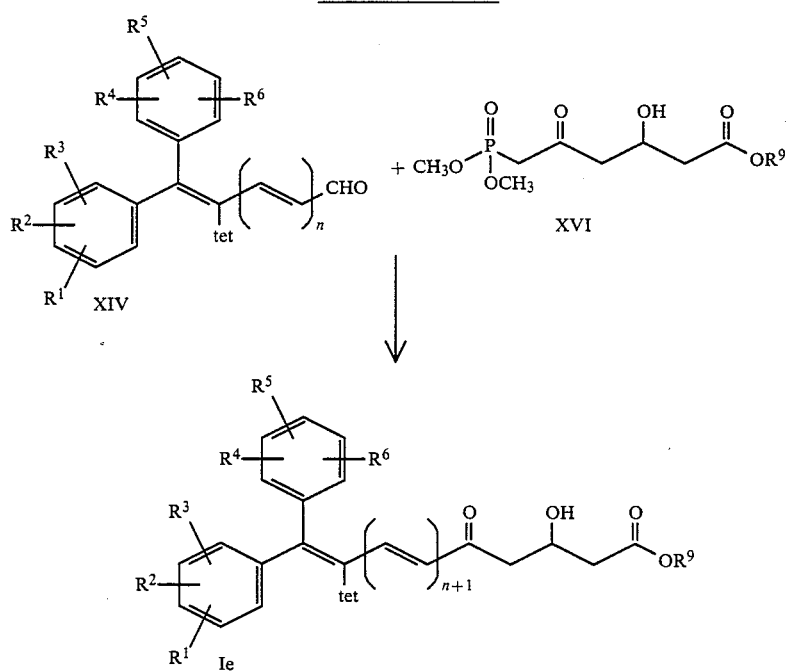

In Reaction Scheme 6, $R^1$, $R^2$, $R^3$, $R^4$, $R^5$, $R^6$, tet and n are as previously defined, and $R^9$ is a hydrolyzable ester group. The preparation of a compound of Formula Ie may be carried out as illustrated in Reaction Scheme 6 in an inert organic solvent such as acetonitrile, methylene chloride, chloroform, tetrahydrofuran and the like at a temperature of from 0° C. to the reflux temperature of the solvent and preferably at ambient temperature in the presence of a suitable organic base. Suitable organic bases include tertiary amines such as triethylamine, N-methylmorpholine, N-methylpiperidine, 1,4-diazabicyclo[2.2.2]octane ("DABCO"), 1,8-diazabicyclo[5.4.0]undec-7-ene("DBU"), 1,5-diazabicyclo[4.3.0]non-5-en("DBN") and the like. The resulting compound of Formula Ie wherein $R^9$ is a hydrolyzable ester group may, if desired, be hydrolyzed by conventional methods to produce compounds of the Formula I wherein $R^9$ is converted to the $R^8$ substituent as described herein and illustrated in Reaction Scheme 5.

In an alternate reaction route, a preferred embodiment of the compounds of Formula I wherein n is 1, X is —OH and tet is 1-methyl-1H-tetrazole-5-yl, may be prepared by the procedure described in Reaction Scheme 7.

Reaction Scheme 7

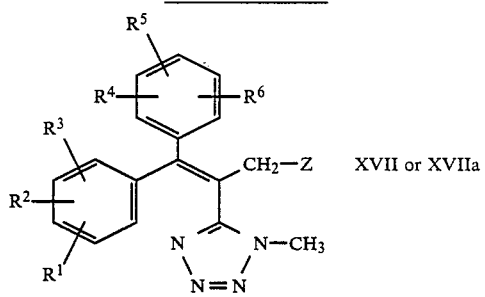

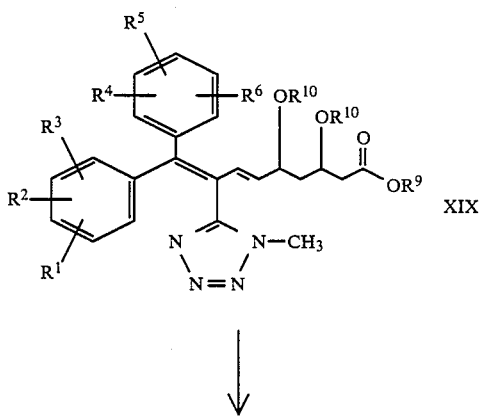

-continued
Reaction Scheme 7

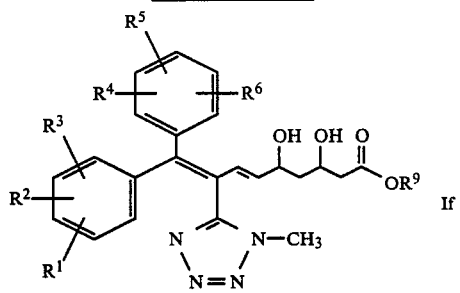

In Reaction Scheme 7, $R^1$, $R^2$, $R^3$, $R^4$, $R^5$, and $R^6$ are as previously defined, $R^9$ is a hydrolyzable ester group, $R^{10}$ is t-butyldiphenylsilyl and Z is

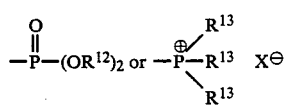

in which $R^{12}$ is $C_{1-4}$ alkyl, $R^{13}$ is phenyl which is unsubstituted or substituted by one or two $C_{1-4}$ alkyl or chloro substituents and X is bromo, chloro or iodo. The phosphonium salt of Formula XVII or phosphonate of Formula XVIIa which is described herein, in U.S. patent application Ser. No. 018,558, filed Feb. 25, 1987, and in the continuation-in-part U.S. patent application Ser. No. 151512 filed Feb. 18, 1988 (concurrently) by us and our colleagues Neelakantan Balasubramanian and Peter J. Brown may be reacted with the silyl protected aldehyde of Formula XVIII which is itself prepared by the procedures described in *Tetrahedron Letters*, 25, 2435 (1984) and also in U.S. Pat. No. 4,571,428 to produce the silyl protected compound of Formula XIX. The reaction may be carried out in an inert organic solvent such as tetrahydrofuran and N,N-dimethylformamide in the presence of a strong base, for example, lithium diisopropylamide, n-butyllithium or potassium t-butoxide at a temperature of about −78° C. to about 0° C. The compound of Formula XIX may then be readily desilylated by well-known procedures such as 48% hydrofluoric acid and preferably, with tetrabutylammonium fluoride in an inert organic solvent such as tetrahydrofuran and acetonitrile to produce the erythro compounds of Formula If, a more preferred embodiment of the compounds of Formula Ia. The $R^9$ substituent may then be converted to the $R^8$ substituent as described herein and illustrated in Reaction Scheme 5.

When it is desired to prepare mostly one stereoisomer of a compound of Formula I, it is preferred to employ optically pure starting materials. The various procedures which may be used to prepare one isomer of a compound of Formula I wherein X is —OH are illustrated in Reaction Schemes 8, 9 and 10. The most preferred isomer of a compound of Formula I wherein A is defined as

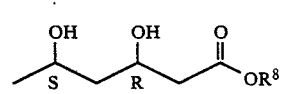

is the (3R, 5S) isomer, and the most preferred isomer of a compound of Formula I where A is defined as

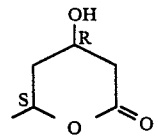

is the (4R,6S) isomer. It should be appreciated that it is necessary to have only one of the above definitions of A for compounds of Formula I since they may be interconverted as shown in Reaction Scheme 5. To illustrate the use of optically pure starting materials, the preparation of a preferred embodiment of compounds of Formula I such as the (3R,5S) isomer of compounds of Formula If by three synthetic routes are shown in Reaction Schemes 8, 9 and 10.

Reaction Scheme 8

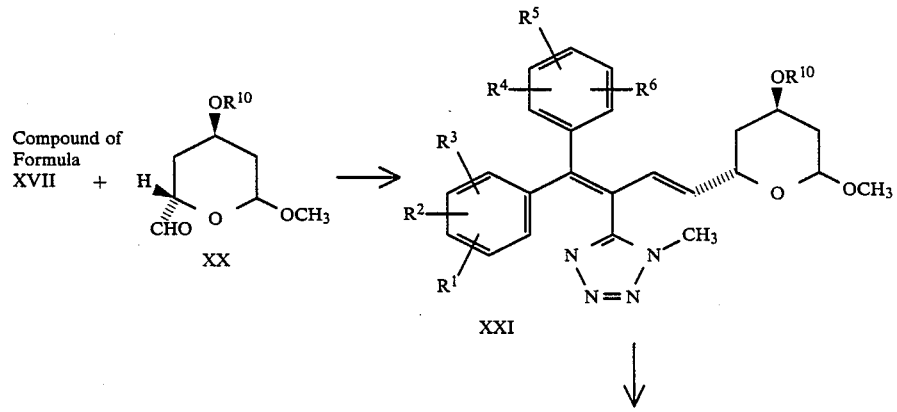

Reaction Scheme 8

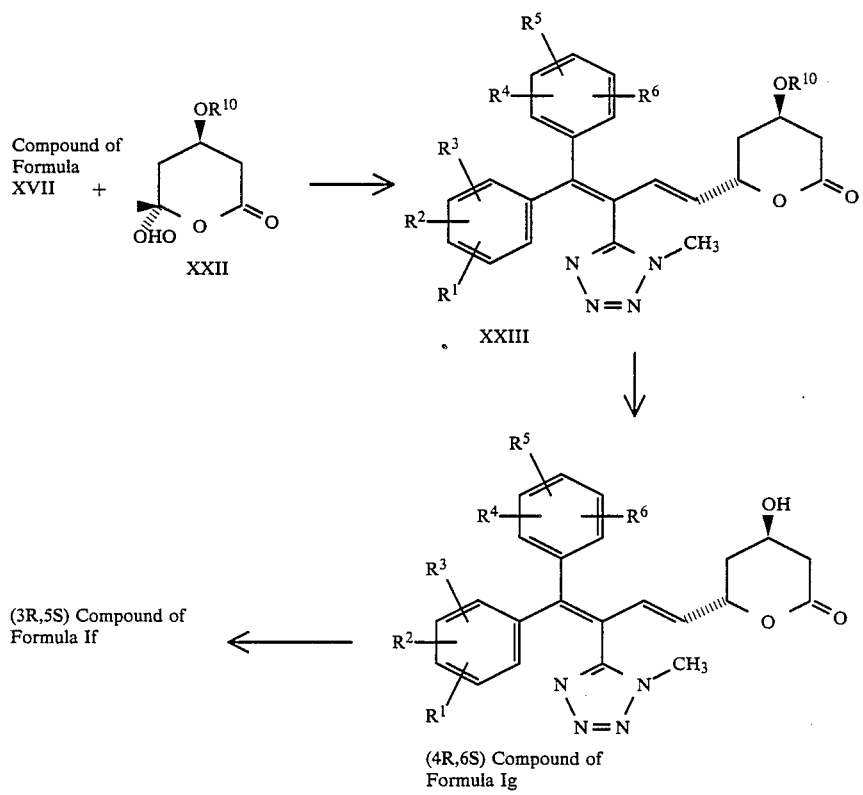

Compound of Formula XVII + XXII → XXIII → (4R,6S) Compound of Formula Ig → (3R,5S) Compound of Formula If In Reaction Scheme 8, $R^1$, $R^2$, $R^3$, $R^4$, $R^5$, $R^6$ are as previously defined and $R^{10}$ is t-butyldiphenyl-silyl. The starting materials XX and XXII are known and their preparation are described in *Tetrahedron Letters*, 23, 4305 (1982) and U.S. Pat. No. 4,613,610, respectively. The compound of Formula XVII or Formula XVIIa may be reacted with the compound of Formula XX in an inert organic solvent to produce the compounds of Formula XXI which then may be hydrolyzed with acid in a solvent mixture containing acetic acid, tetrahydrofuran and water followed by mild oxidation with pyridinium chlorochromate in methylene chloride to produce the desired trans-lactone of Formula XXIII. Alternatively, the trans-lactone of Formula XXIII may be produced directly by the condensation of a compound of Formula XVII and a compound of Formula XXII. Desilylation with 48% hydrofluoric acid in acetonitrile and preferably with tetrabutylammonium fluoride will produce the (4R,6S) enantiomer of a compound of Formula Ig which can then, if desired, be converted to the (3R,5S) enantiomer of a compound of Formula If.

Reaction Scheme 9

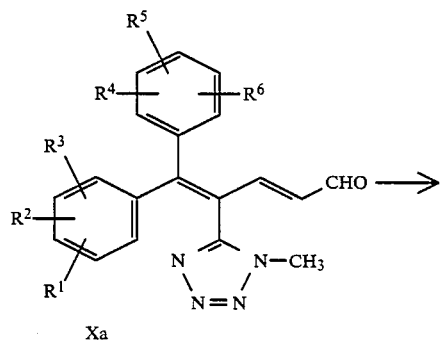

Xa

-continued
Reaction Scheme 9

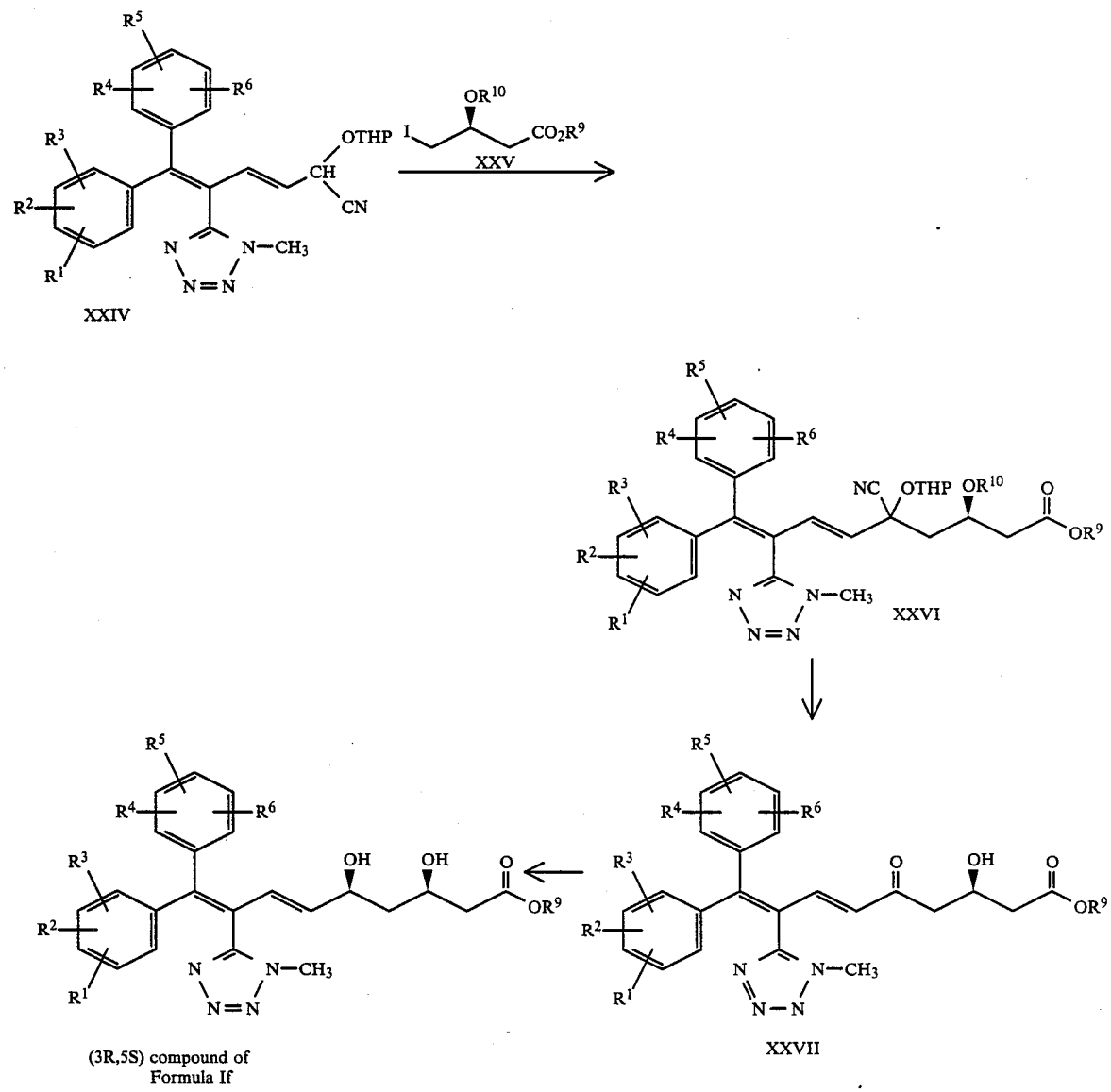

(3R,5S) compound of
Formula If

The second stereospecific route is shown in Reaction Scheme 9 wherein $R^1$, $R^2$, $R^3$, $R^4$, $R^5$, and $R^6$ are as previously defined, $R^9$ is a hydrolyzable ester group and $R^{10}$ is t-butyldimethylsilyl. The diene aldehyde of Formula Xa may be treated with sodium cyanide and the cyanohydrin thereby produced is converted to the tetrahydropyranyl (THP) derivative of Formula XXIV. The compound of Formula XXVI may be prepared by reacting the compound of Formula XXIV which is first treated with a strong base such as n-butyllithium with the iodo ester of Formula XXV. Preparation of the optically pure protected iodohydrin XXV wherein $R^{10}$ is t-butyldimethylsilyl and $R^9$ is methyl is described in Tetrahedron Letters, 25, 2951 (1985). Removal of the protecting groups may be carried out by acid hydrolysis to produce the keto-alcohol of Formula XXVII. The stereospecific reduction of a compound of Formula XXVII employing sodium borohydridetriethylborane or sodium borohydride-alkoxydialklborane as described herein may be used to reduce the 5-keto group to the desired (5S) stereochemistry to produce the (3R,5S) enantiomer of the compound of Formula If. Thus, Reaction Scheme 9 provides a method for the preparation of the (3R,5S) isomer of a compound of Formula I by utilizing the optically pure starting material XXV which provides the appropriately substituted carbon atom in the 3-position to direct the stereospecific reduction of the 5-keto function.

Reaction Scheme 10
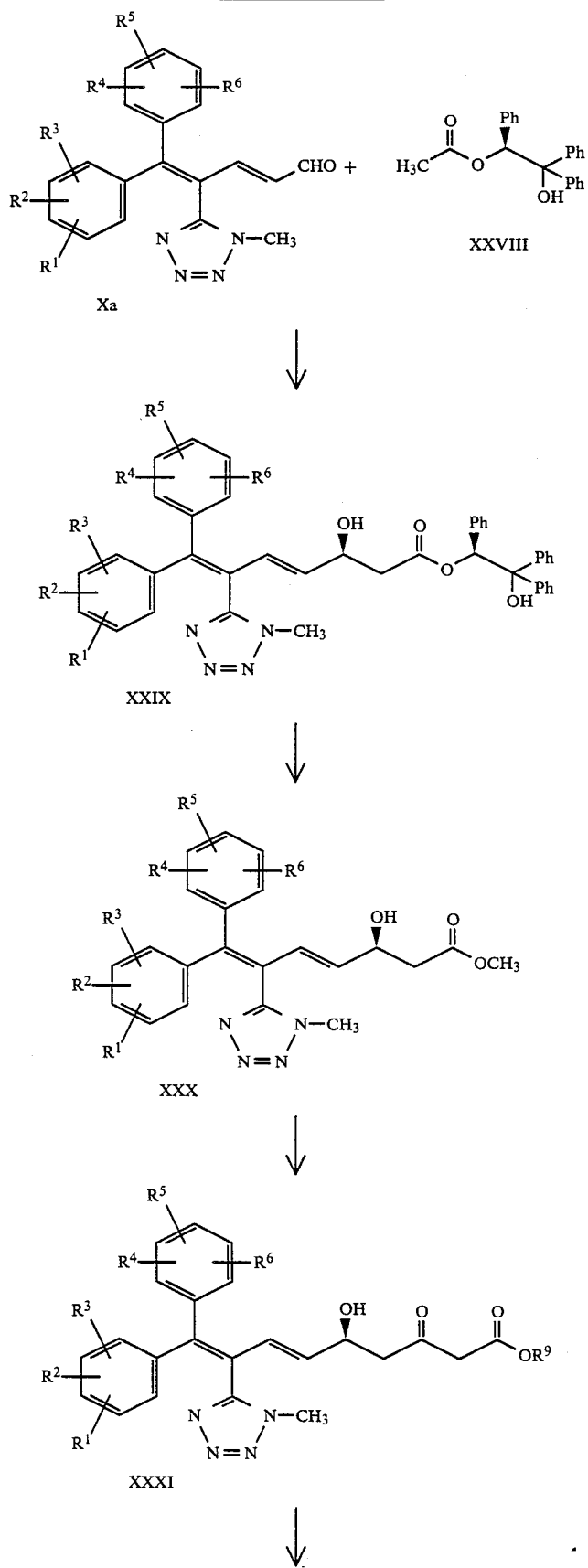

-continued

Reaction Scheme 10

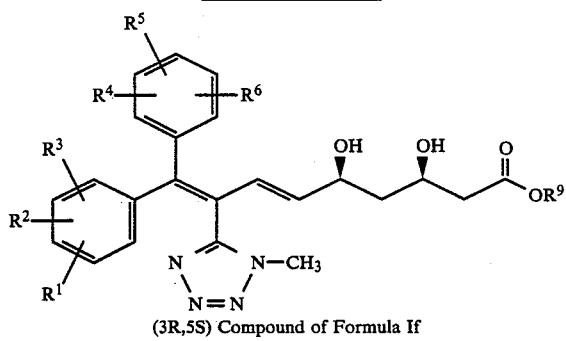

(3R,5S) Compound of Formula If

The third stereospecific route is shown in Reaction Scheme 10 wherein $R^1$, $R^2$, $R^3$, $R^5$, $R^6$ and $R^9$ are as previously defined. The starting material of Formula XXVIII is known and its preparation is described in *Tetrahedron Letters*, 25, 5031 (1984). The compound of the Formula XXVIII is first treated with a non-nucleophilic base, preferably lithium diisopropylamide in an inert solvent such as tetrahydrofuran and the enolate which is produced is then reacted with an allylic aldehyde of the Formula Xa to produce the triphenyl ester of Formula XXIX. When the compound of Formula XXIX is treated with sodium methoxide in methanol the methyl ester of Formula XXX may be isolated. When the methyl ester of Formula XXX is reacted with the anion of tert-butyl acetate which is generated in situ with a non-nucleophilic base such as lithium diisopropylamide there is thereby produced the keto ester of Formula XXXI. Alternatively, the preparation of a compound of Formula XXXI may be carried out by directly treating the triphenyl ester of Formula XXIX with the anion of t-butyl ester. Selective stereospecific reduction of the resulting keto functionality of Formula XXXI with sodium borohydride-triethylborane or sodium borohydridealkoxydialkylborane as described herein may be used to produce the (3R,5S) enantiomer of a compound of Formula If. Accordingly, Reaction Scheme 10 provides a method for the preparation of the (3R,5S) isomers of a compound of Formula I by employing the optically pure starting material XXVIII which provides the appropriately substituted carbon atom in the 5-position to direct the stereospecific reduction of the 3-keto function. In a specific example described herein wherein $R^1$ and $R^4$ are fluoro and $R^2$, $R^3$, $R^5$ and $R^6$ are hydrogen there is provided a method for the preparation of a compound of Formula If which is mostly the (3R,5S) enantiomer.

In a preferred embodiment of the invention the compounds of Formula I have the structure

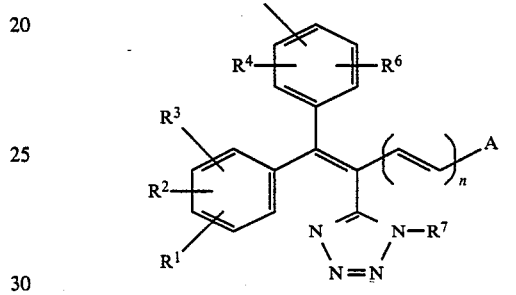

wherein
$R^1$ and $R^4$ each are independently hydrogen, halogen, $C_{1-4}$ alkyl, $C_{1-4}$ alkoxy or trifluoromethyl;
$R^2$, $R^3$, $R^5$ and $R^6$ each are independently hydrogen, halogen, $C_{1-4}$ alkyl or $C_{1-4}$ alkoxy;
n is an integer of from 0 to 2 inclusive;
A is

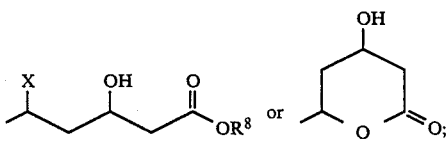

$R^7$ is hydrogen, $C_{1-4}$ alkyl, $C_{1-4}$ alkoxy(lower)alkyl or (2-methoxyethoxy)methyl;
X is —OH or =O; and
$R^8$ is hydrogen, a hydrolyzable ester group or a cation to form a non-toxic pharmaceutically acceptable salt.

In a more preferred embodiment of the invention the compounds of Formula I have the structure

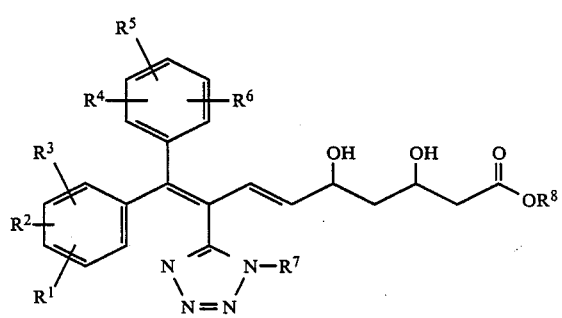

wherein $R^1$, $R^2$, $R^3$, $R^4$, $R^5$ and $R^6$ each are independently hydrogen, fluoro, chloro, methyl or methoxy; $R^7$ is $C_{1-4}$ alkyl; and $R^8$ is hydrogen, $C_{1-6}$ alkyl or a cation to form a non-toxic pharmaceutically acceptable salt. In a particularly preferred embodiment, $R^7$ is methyl.

In another more preferred embodiment of the invention the compounds of Formula I have the structure

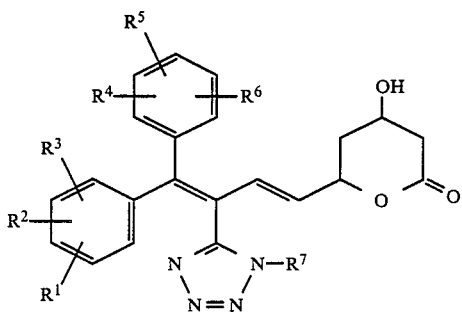

wherein $R^1$, $R^2$, $R^3$, $R^4$, $R^5$ and $R^6$ each are independently hydrogen, fluoro, chloro, methyl or methoxy; and $R^7$ is $C_{1-4}$ alkyl. In a particularly preferred embodiment, $R^7$ is methyl.

As presently envisaged, the particularly preferred compounds of the invention are (a) ethyl 9,9-bis(4-fluorophenyl)-3,5-dihydroxy-8-(1-methyl-1H-tetrazol-5-yl)-6,8-nonadienoate, (b) 9,9-bis(4-fluorophenyl)-3,5-dihydroxy-8-(1-methyl-1H-tetrazol-5-yl)-6,8-nonadienoic acid or a non-toxic pharmaceutically acceptable salt, (c) sodium 9,9-bis(4-fluorophenyl)-3,5-dihydroxy-8-(1-methyl-1H-tetrazol-5-yl)-6,8-nonadienoate, (d) (3R,5S) enantiomer of 9,9-bis(4-fluorophenyl)-3,5-dihydroxy-8-(1-methyl-1H-tetrazol-5-yl)-6,8-nonadienoic acid or a non-toxic pharmaceutically acceptable salt, (e) (3R,5S) enantiomer of sodium 9,9-bis(4-fluorophenyl)-3,5-dihydroxy-8-(1-methyl-1H-tetrazol-5-yl)-6,8-nonadienoate, (f) trans-6-[4,4-bis(4-fluorophenyl)-3-(1-methyl-1H-tetrazol-5-yl)-1,3-butadienyl]-tetrahydro-4-hydroxy-2H-pyran-2-one, (g) (4R,6S) enantiomer of trans-6-[4,4-bis(4-fluorophenyl)-3-(1-methyl-1H-tetrazol-5-yl)-1,3-butadienyl]-tetrahydro-4-hydroxy-2H-pyran-2-one, (h) 11,11-bis(4-fluorophenyl)-3,5-dihydroxy-10-(1-methyl-1H-tetrazol-5-yl)-6,8,10-undecatrienoic acid or a non-toxic pharmaceutically acceptable salt, (i) sodium 11,11-bis(4-fluorophenyl)-3,5-dihydroxy-10-(1-methyl-1H-tetrazol-5-yl)-6,8,10-undecatrienoate, (j) trans-6-[4,4-bis(4-fluorophenyl)-3-(2-methyl-2H-tetrazol-5-yl)-1,3-butadienyl]-tetrahydro-4-hydroxy-2H-pyran-2-one, (k) 9,9-bis(4-fluorophenyl)-3,5-dihydroxy-8-(2-methyl-2H-tetrazol-5-yl)-6,8-nonadienoic acid or a non-toxic pharmaceutically acceptable salt, (l) sodium 9,9-bis(4-fluorophenyl)-3,5-dihydroxy-8-(2-methyl-2H-tetrazol-5-yl)-6,8-nonadienoate, (m) 9,9-bis(4-fluorophenyl)-3-hydroxy-8-(1-methyl-1H-tetrazol-5-yl)-5-oxo-6,8-nonadienoic acid or a non-toxic pharmaceutically acceptable salt, (n) sodium 9,9-bis(4-fluorophenyl)-3-hydroxy-8-(1-methyl-1H-tetrazol-5-yl)-5-oxo-6,8-nonadienoate, (o) 9,9-bis(4-fluorophenyl)-3,5-dihydroxy-8-[1-(1-methylethyl)-1H-tetrazol-5-yl]-6,8-nonadienoic acid or a non-toxic pharmaceutically acceptable salt, (p) sodium 9,9-bis(4-fluorophenyl)-3,5-dihydroxy-8-[1-(1-methylethyl)-1H-tetrazol-5-yl]-6,8-nonadienoate, (q) ethyl 9,9-bis(4-fluorophenyl)-3,5-dihydroxy-8-[1-(1-methylethyl)-1H-tetrazol-5-yl]-6,8-nonadienoate, (r) 9,9-bis(4-fluoro-3-methylphenyl)-3,5-dihydroxy-8-(1-methyl-1H-tetrazol-5-yl)-6,8-nonadienoic acid or a non-toxic pharmaceutically acceptable salt, (s) sodium 9,9-bis(4-fluoro-3-methylphenyl)-3,5-dihydroxy-8-(1-methyl-1H-tetrazol-5-yl)-6,8-nonadienoate, (t) 9,9-bis(4-fluorophenyl)-3,5-dihydroxy-8-(1-ethyl-1H-tetrazol-5-yl)-6,8-nonadienoic acid or a non-toxic pharmaceutically acceptable salt, (u) sodium 9,9-bis(4-fluorophenyl)-3,5-dihydroxy-8-(1-ethyl-1H-tetrazol-5-yl)-6,8-nonadienoate.

(v) 9,9-bis(2,4-dimethylphenyl)-3,5-dihydroxy-8-(1-methyl-1H-tetrazol-5-yl)-6,8-nonadienoic acid or a non-toxic pharmaceutically acceptable salt, (w) sodium 9,9-bis(2,4-dimethylphenyl)-3,5-dihydroxy-8-(1-methyl-1H-tetrazol-5-yl)-6,8-nonadienoate, (x) 9,9-bis-(4-fluorophenyl)-3,5-dihydroxy-8-[1-(2-methoxyethoxy)-methyl-1H-tetrazol-5-yl]-6,8-nonadienoic acid or a non-toxic pharmaceutically acceptable salt, (y) sodium 9,9-bis(4-fluorophenyl)-3,5-dihydroxy-8-[1-(2-methoxyethoxy)methyl-1H-tetrazol-5-yl]-6,8-nonadienoate, (z) 9,9-bis(4-fluoro-2-methylphenyl)-3,5-dihydroxy-8-(1-methyl-1H-tetrazol-5-yl)-6,8-nonadienoic acid or a non-toxic pharmaceutically acceptable salt, (aa) sodium 9,9-bis(4-fluoro-2-methylphenyl)-3,5-dihydroxy-8-(1-methyl-1H-tetrazol-5-yl)-6,8-nonadienoate, (bb) 9,9-bis(2-fluoro-4-methylphenyl)-3,5-dihydroxy-8-(1-methyl-1H-tetrazol-5-yl)-6,8-nonadienoic acid or a non-toxic pharmaceutically acceptable salt, (cc) sodium 9,9-bis(2-fluoro-4-methylphenyl)-3,5-dihydroxy-8-(1-methyl-1H-tetrazol-5-yl)-6,8-nonadienoate.

In another aspect, this invention provides novel intermediates of the formula

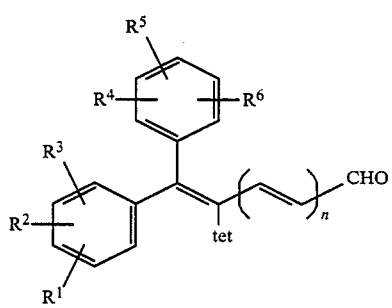

wherein $R^1$ and $R^4$ each are independently hydrogen, halogen, $C_{1-4}$ alkyl, $C_{1-4}$ alkoxy, or trifluoromethyl; $R^2$, $R^3$, $R^5$ and $R^6$ each are independently hydrogen, halogen, $C_{1-4}$ alkyl or $C_{1-4}$ alkoxy; tet is

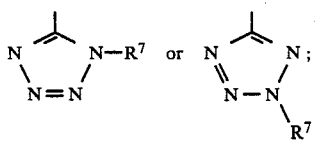

n is an integer of from 0 to 2, inclusive; and $R^7$ is $C_{1-4}$ alkyl, $C_{1-4}$ alkoxy(lower)alkyl, (2-methoxyethoxy)-methyl or $R^{7a}$ in which $R^{7a}$ is triphenylmethyl.

In a preferred embodiment, the compounds of Formula XIV have the structure

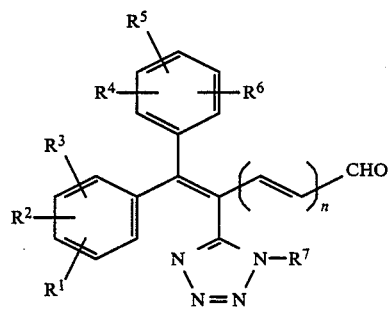

wherein $R^1$ and $R^4$ each are independently hydrogen, halogen, $C_{1-4}$ alkyl, $C_{1-4}$ alkoxy or trifluoromethyl; $R^2$, $R^3$, $R^5$ and $R^6$ each are independently hydrogen, halogen, $C_{1-4}$ alkyl or $C_{1-4}$ alkoxy; n is an integer of from 0 to 2, inclusive; and $R^7$ is $C_{1-4}$ alkyl, $C_{1-4}$ alkoxy(lower)alkyl or (2-methoxyethoxy)methyl.

In a more preferred embodiment, the compounds of Formula XIV have the structure

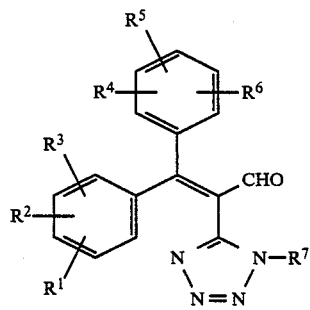

wherein $R^1$, $R^2$, $R^3$, $R^4$, $R^5$ and $R^6$ each are independently hydrogen, fluoro, chloro, methyl or methoxy; and $R^7$ is $C_{1-4}$ alkyl. In a particularly preferred embodiment, $R^7$ is methyl.

In another more preferred embodiment, the compounds of Formula XIV have the structure

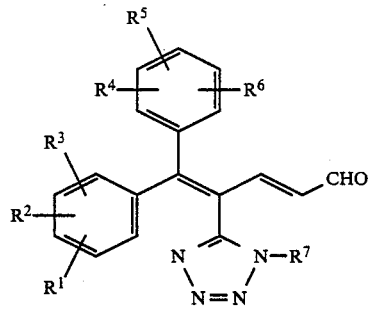

$R^1$, $R^2$, $R^3$, $R^4$, $R^5$ and $R^6$ each are independently hydrogen, fluoro, chloro, methyl or methoxy; and $R^7$ is $C_{1-4}$ alkyl. In a particularly preferred embodiment, $R^7$ is methyl.

In still another aspect, this invention provides novel intermediates of the formula

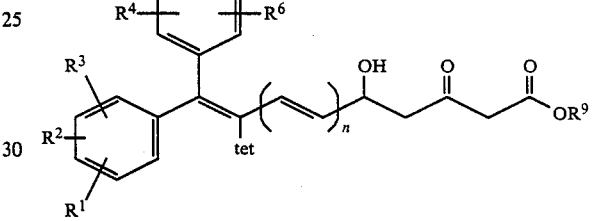

wherein $R^1$ and $R^4$ each are independently hydrogen, halogen, $C_{1-4}$ alkyl, $C_{1-4}$ alkoxy, or trifluoromethyl; $R^2$, $R^3$, $R^5$ and $R^6$ each are independently hydrogen, halogen, $C_{1-4}$ alkyl or $C_{1-4}$ alkoxy; n is an integer of from 0 to 2, inclusive; tet is

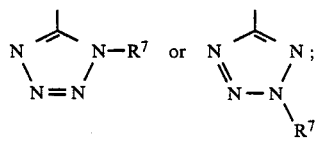

$R^7$ is $C_{1-4}$ alkyl, $C_{1-4}$ alkoxy(lower)alkyl, (2-methoxyethoxy)methyl or $R^{7a}$ in which $R^{7a}$ is triphenylmethyl; and $R^9$ is a hydrolyzable ester group.

In a preferred embodiment, the compounds of Formula XV have the structure

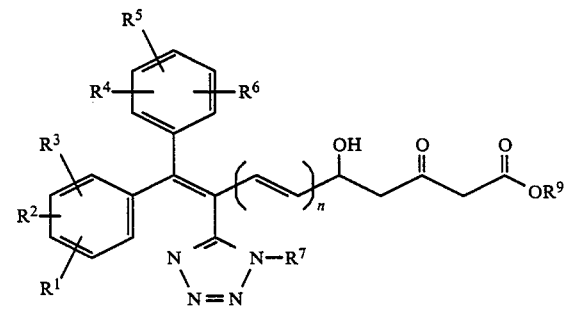

wherein $R^1$ and $R^4$ each are independently hydrogen, halogen, $C_{1-4}$ alkyl, $C_{1-4}$ alkoxy or trifluoromethyl; $R^2$, $R^3$, $R^5$ and $R^6$ each are independently hydrogen, halogen, $C_{1-4}$ alkyl or $C_{1-4}$ alkoxy; n is an integer of from 0 to 2, inclusive; $R^7$ is $C_{1-4}$ alkyl, $C_{1-4}$ alkoxy(lower)alkyl or (2-methoxyethoxy)methyl; and $R^9$ is a hydrolyzable ester group.

In a more preferred embodiment, the compounds of Formula XV have the structure

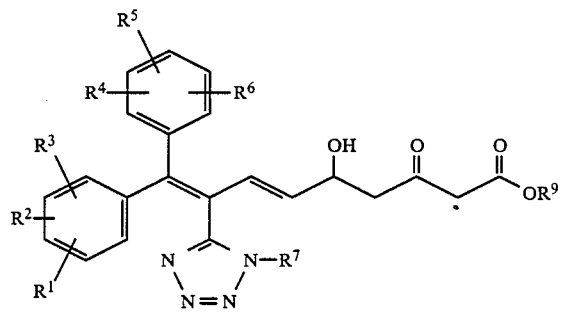

where $R^1$, $R^2$, $R^3$, $R^4$, $R^5$ and $R^6$ each are independently hydrogen, fluoro, chloro, methyl or methoxy; and $R^7$ is $C_{1-4}$ alkyl. In a particularly preferred embodiment, $R^7$ is methyl.

The compounds of Formula I are competitive inhibitors of the enzyme 3-hydroxy-3-methylglutaryl coenzyme A (HMG-CoA) reductase, the rate limiting enzyme in cholesterol biosynthesis, and therefore, are selective suppressors of cholesterol biosynthesis in animals, including man. Consequently, they are useful in the treatment of hypercholesterolemia, hyperlipoproteinemia and atherosclerosis. The biological activity of the compounds of Formula I may be demonstrated in the following three different biological tests.

Test A: In Vitro Inhibition of Microsomal HMG-CoA Reductase:

The intact, fully activated microsomal form of rat liver HMG-CoA reductase (subunit MW ca 100,000 daltons) was prepared as described by Parker, et al., *Biochem. Biophys. Res. Commun.*, 125, 629–635 (1984), and used as the source of enzyme for assays. HMG-CoA reductase activity was determined essentially by the method of Shapiro, et al., *Biochem. Biophys. Acta.*, 370, 369–377 (1974), with modifications as described by Ingebritsen and Gibson, *Meth. Enzymol.* 71, 486–497 (1981) with the exception that the internal standard $^3$H-mevalonolactone is added after termination of the assay. In this procedure, the enzyme is assayed by measuring the formation of product, $^{14}$C-mevalonate, from the substrate, [3-$^{14}$C]-HMG-CoA, in the presence of NADPH. The $^{14}$C-mevalonate is converted to its lactone and isolated by silica thin-layer chromatography (Whatman LK5D, developed in 50:50 benzene:acetone) in the presence of $^3$H-mevalonolactone as an internal standard. Assays were conducted under conditions in which product formation was linear with respect to time and enzyme concentration.

To measure reductase inhibition, test compounds dissolved in water or dimethylsulfoxide and diluted in buffer A (50 mM imidazole-HCl, 250 mM NaCl, 1 mM EDTA, 1 mM EGTA, 5 mM DTT, 20 μM leupeptin, pH=7.2) were incubated with aliquots of microsomes (80–160 μg protein in buffer A) followed by addition of d,1-[3-$^{14}$C]-HMG-CoA (0.33 mM, 2.0 dpm/picomole) and NADPH (3.0 mM). The 50 percent inhibitory concentration ($IC_{50}$) for each compound in Table 1 was calculated from the linear regression line of the percent decrease (from control) in enzyme activity vs. log concentration of inhibitor, determined using at least 4 dilutions of each test compound assayed in duplicate.

TABLE 1

| Inhibition of Microsomal HMG-CoA Reductase | |
|---|---|
| Compound of Example No. | $IC_{50}$ μmolar |
| 11 | >330 |
| 12 | 0.037 ± 0.01 |
| 13 | 1.09 ± 0.29 |
| 15 | 5.7 |
| 44 | 0.16 |
| 65 | 1.6 |
| 92 | 0.029 |
| 99 | 0.58 |
| 120 | 0.044 |
| 126 | 0.19 |
| 132 | 1.4 |

Test B: Isolated Hepatocyte Cholesterol Biosynthesis Assay:

Intact parenchymal hepatocytes were isolated from male Wistar rats (180–280 g) fed cholestyramine-containing or normal diet, using the collagenase perfusion method essentially as described by Seglen, in *Methods in Cell Biology* (D. Prescott, ed.) Vol. 13, pp. 29–83, Academic Press, New York (1976). Cell preparations were used only when viability (trypan blue exclusion) exceeded 90%. Cholesterol biosynthesis was determined as the incorporation by hepatocytes of $^3$H from [$^3$H]-water into total (cellular plus medium) 3β-hydroxy sterols as per Ingebritsen, et al., *J. Biol. Chem.*, 254, 9986–9989 (1979). Hepatocyte sterols and lipids were isolated by a modification of the methods described by Kates, in *Techniques in Lipidology*, (M. Kates, ed.), pp. 349, 360–363, North Holland Publ. Co., Amsterdam, 1972. To isolate sterols, cells are extracted with methanol:chloroform:water (2:1:0.8), the chloroform phase is separated and extracted with benzene to remove traces of water, then dried under nitrogen. The residue is saponified at 75° C. with 0.30 N NaOH in methanol:water (9:1). The alkaline mixture is then extracted three times with petroleum ether to yield the non-saponifiable lipids which include the free as well as initially esterified cholesterol. The extract is dried under nitrogen in the presence of carrier cholesterol (0.1 mg) and 10% benzene, and the residue is dissolved in acetone:ethanol (1:1). Finally, the 3β-hydroxysterols are precipitated with an excess of digitonin, the precipitate is washed in acetone, dried under nitrogen, and dissolved in toluene:methanol (1:1). The $^3$H-labelled sterols are quantified by liquid scintillation and corrected for counting efficiency. In some tests $^{14}$C-cholesterol was added to initial extractions as an index of recovery, which averaged 80±3%.

To measure inhibition of cholesterol synthesis, duplicate or triplicate aliquots of freshly isolated cells were suspended (100 mg cell net weight in 2.0 mL) in Eagle's Minimal Essential Medium containing bicarbonate and HEPES buffer, pH 7.35, plus 2% bovine serum albumin under a 95% $O_2$+5% $CO_2$ atmosphere. Cells were preincubated for 10 minutes with or without aliquots of test compounds added as water solutions of sodium salts or as dimethylsulfoxide solutions of lactones. Controls received vehicle alone. [$^3$H]-water (1.0 mCi per mL incubation volume) or 2-$^{14}$C-acetate (0.5 μCi per mL incubation volume) was then added to each and the cells were incubated with constant shaking for 60 minutes at 37°. These conditions produced time-linear incorporation of tritium or $^{14}C$ into sterols. The $IC_{50}$ for inhibition of sterol synthesis by test compounds which is shown in Table 2 was calculated from the linear regression curve of % inhibition (compared to controls) vs. log concentration using at least 4 concentrations of inhibitor. Test B therefore measures the ability of test substances to inhibit the intracellular synthesis of cholesterol.

TABLE 2

Inhibition of Isolated Hepatocyte Cholesterol Biosynthesis

| Compound of Example No. | $IC_{50}$ nmolar |
|---|---|
| 12 | 23.0 ± 11 |
| 13 | 24.0 |
| 138 | 7.4 |
| Mevinolin (Lovastatin) | 46.0 ± 26 |

Test C: In Vivo Acute Cholesterol Biosynthesis Inhibition in Rats:

Male Wistar rats (160–200 g, housed 2 per cage) were maintained on normal diet (Purina Rat Chow and water, ad libitum) for at least 7 days on a reversed lighting schedule (7:00 a.m. to 5:00 p.m. dark). Food was removed 15 hours prior to dosing. Compounds were administered at 8:00 a.m. by intragastric intubation using 0.5–1.0 mL of water or propylene glycol solutions of sodium salts, lactones, or esters of the test compounds. Controls received equal volumes of the vehicle.

Thirty minutes after receiving the test substances, rats were injected intraperitoneally with 0.9 mL of 0.9% NaCl containing approximately 120 $\mu$Ci per kg body weight of sodium $[1-^{14}C]$ acetate (1–3 mCi/mmol). After a 60 minute incorporation period, rats were sacrificed and liver and blood samples were obtained. Aliquots of plasma (1.0 mL) obtained by centrifugation of heparin+EDTA-treated blood, and aliquots of liver homogenates (equivalent to 0.50 g liver wet weight) were taken for determination of radiolabeled $3\beta$-hydroxy sterols. Sterol isolation for the liver samples followed the method of Kates as described above for the hepatocyte procedure (Test B) while the plasma samples were directly saponified followed by isolation of the digitonin-precipitable sterols. $^{14}C$-labelled sterols were quantified by liquid scintillation counting (efficiency corrected). Mean percent inhibition of $^{14}C$ incorporated into liver and into plasma cholesterol were calculated for groups of treated animals and compared to mean values for controls conducted simultaneously.

Therefore, Test C provides information on the ability of test substances to suppress the de novo biosynthesis of cholesterol in vivo in rats with oral dosing. For example, using Test C, the compound of Example 12 yielded a 50% Inhibitory Dose ($ED_{50}$) of 0.08 mg/kg for both plasma and liver cholesterol, and for the reference agent mevinolin, an $ED_{50}$ value of 0.04 mg/kg was obtained which was comparable to values obtained for mevinolin using a similar procedure [Alberts, et al., Proc. Natl. Acad. Sci., 77, 3957–3961 (1980)].

The results of the above in vitro and in vivo Tests A, B and C demonstrate that the compounds of Formula I inhibit cholesterol biosynthesis and, therefore, are useful in the treatment of hypercholesterolemia.

In another embodiment, this invention includes pharmaceutical compositions comprising at least one compound of Formula I in combination with a pharmaceutical carrier or diluent.

In another embodiment, this invention relates to a method of inhibiting cholesterol biosynthesis in an animal in need thereof, which comprises administering to said animal an effective cholesterol inhibitory dose of at least one compound of Formula I.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound of Formula I according to the invention.

The dosage of the compounds of Formula I will depend not only on such factors as the weight of the patient and mode of administration, but also on the degree of cholesterol biosynthesis inhibition desired and the potency of the particular compound being utilized. The decision as to the particular dosage to be employed (and the number of times to be administered per day) is within the discretion of the physician, and may be varied by titration of the dosage to the particular circumstances of this invention for the satisfactory inhibition or reduction of cholesterol biosynthesis, each oral dosage unit will contain the active ingredient in an amount of from about 0.01 mg/kg to about 10 mg/kg body weight, and most preferably from about 0.05 mg/kg to about 2 mg/kg body weight. The active ingredient will preferably be administered in equal doses from one to four times a day. However, usually a small dosage is administered, and the dosage is gradually increased until the optimal dosage for the host under treatment is determined.

A particularly preferred method for the preparation of the more preferred embodiment of the present invention having the formula

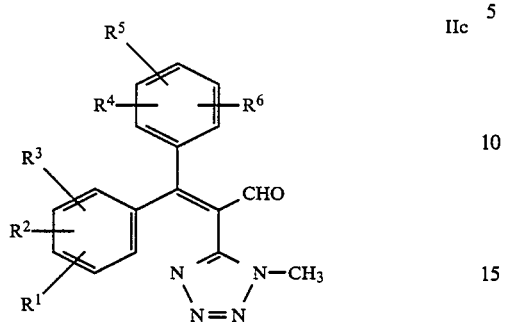
IIc wherein $R^1$, $R^2$, $R^3$, $R^4$, $R^5$ and $R^6$ are as previously defined; is described in U.S. patent application Ser. No. 018,558, filed February 25, 1987 and in the corresponding continuation-in-part U.S. patent application Ser. No. 151,512, filed Feb. 18, 1988 (concurrently) by us and our collegues Neelakantan Balasubramanian and Peter J. Brown.

The compounds of Formula IIc may be prepared by various procedures, and preferably from a compound of the formula

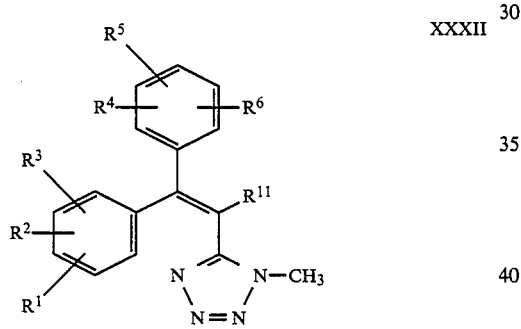
XXXII wherein $R^1$, $R^2$, $R^3$, $R^4$, $R^5$ and $R^6$ are as previously defined; and $R^{11}$ is hydrogen, $C_{1-6}$ alkoxycarbonyl or methyl.

The use of the compounds of Formula XXXII provides an efficient and selective process which avoids the alkylation mixtures described in Reaction Scheme 1.

The compounds of Formula XXXII may be prepared from the optionally substituted benzophenones of Formula III by alkylation with the appropriately 5-substituted 1-methyltetrzaole of Formula XXXIII followed by dehydration of the resulting tertiary alcohol of Formula XXXIV, as shown in Reaction Scheme 11.

Reaction Scheme 11

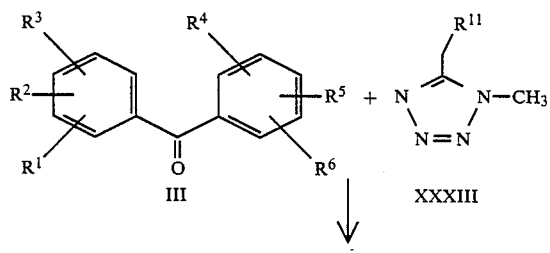

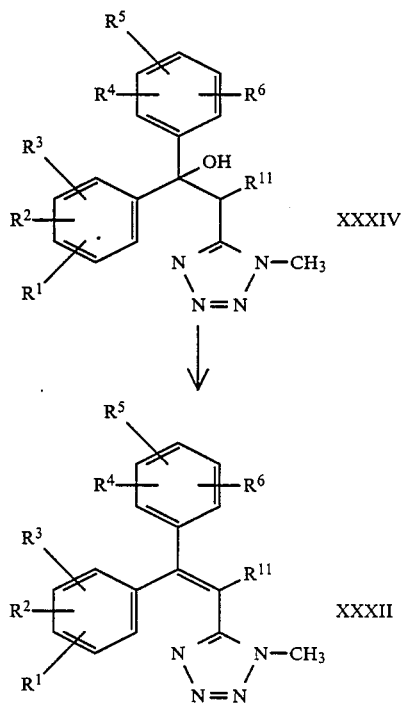

Reaction Scheme 11 (continued)

In Reaction Scheme 11, $R^1$, $R^2$, $R^3$, $R^4$, $R^5$, $R^6$ and $R^{11}$ are as previously defined. The optionally substituted benzophenones of the Formula III may be prepared by the general and well-known Friedel Crafts reaction. The starting material of Formula XXXIII wherein $R^{11}$ is hydrogen is commercially available while the starting materials wherein $R^{11}$ is $C_{1-6}$ alkoxycarbonyl or methyl may be prepared by reacting 1,5-dimethyltetrazole with a strong base such as butyllithium at a temperature of about $-70°$ C. to about $0°$ C. and the resulting anion thereof is added to or treated with, preferably, ethyl chloroformate or methyl iodide, respectively, as described herein.

The appropriate 5-substituted 1-methyltetrazole of Formula XXXIII may be treated with a strong base such as n-butyllithium at low temperatures of from about $-20°$ C. to about $-78°$ C., and preferably, from about $-40°$ C. to $-78°$ C. in an inert organic solvent, e.g., tetrahydrofuran, diethyl ether, 1,2-dimethoxyethane and the like. The resulting anion of Formula XXXIII may then be treated with the desired benzophenone of Formula III to produce the corresponding tertiary alcohols of Formula XXXIV.

The compounds of Formula XXXII may be prepared from the compounds of Formula XXXIV by conventional dehydration procedures. The dehydration may be carried out by heating the alcohol of Formula XXXIV in a suitable inert organic solvent, e.g., toluene, benzene or xylene with a small amount of organic or mineral acid such as p-toluenesulfonic acid or sulfuric acid in the presence of a drying agent, e.g., $Na_2SO_4$, $MgSO_4$, molecular sieves, etc., or preferably, the water which is produced is azeotropically removed with a Dean-Stark trap or similar apparatus. Alternatively, the alcohol of Formula XXXIV may simply be heated with potassium hydrogen sulfate at temperatures of about $190°$ C.

In the specific example wherein $R^{11}$ is ethoxycarbonyl, the reaction of ethyl 1-methyl-5-tetrazolylacetate with a benzophenone of Formula III may be conducted in the presence of titanium tetrachloride and carbon tetrachloride to directly produce, in one step, the corresponding olefin of Formula XXXII.

The preferred aldehydes of Formula IIc may be prepared by various procedures from the compounds of Formula XXXII depending on which $R^{11}$ substituent is employed in the procedure. Thus, it should be appreciated by those skilled in the art, that the compounds of Formula XXXII wherein $R^{11}$ is ethoxycarbonyl (XXXIIa), hydrogen (XXXIIc) or methyl (XXXIId) may be converted to the aldehydes of Formula IIc, as shown in Reaction Scheme 12.

preferably at about $-78°$ C. The resulting allylic alcohols of Formula XXXIIb may then be readily oxidized by conventional oxidizing agents such as pyridinium chlorochromate in a non-reactive solvent, preferably, methylene chloride at ambient temperature to produce the desired aldehyde of Formula IIc. The compounds of Formula XXXIIc may be converted directly to the aldehydes of Formula IIc by treating the anion of Formula XXXIIc, which is produced in situ in an inert organic solvent, e.g., tetrahydrofuran or 1,2-dimethoxyethane with a strong base such as n-butyllithium with ethyl formate.

The compounds of Formula IIc may also be prepared from the compounds of Formula XXXIId by first treating the compounds of Formula XXXIId with N-

Reaction Scheme 12

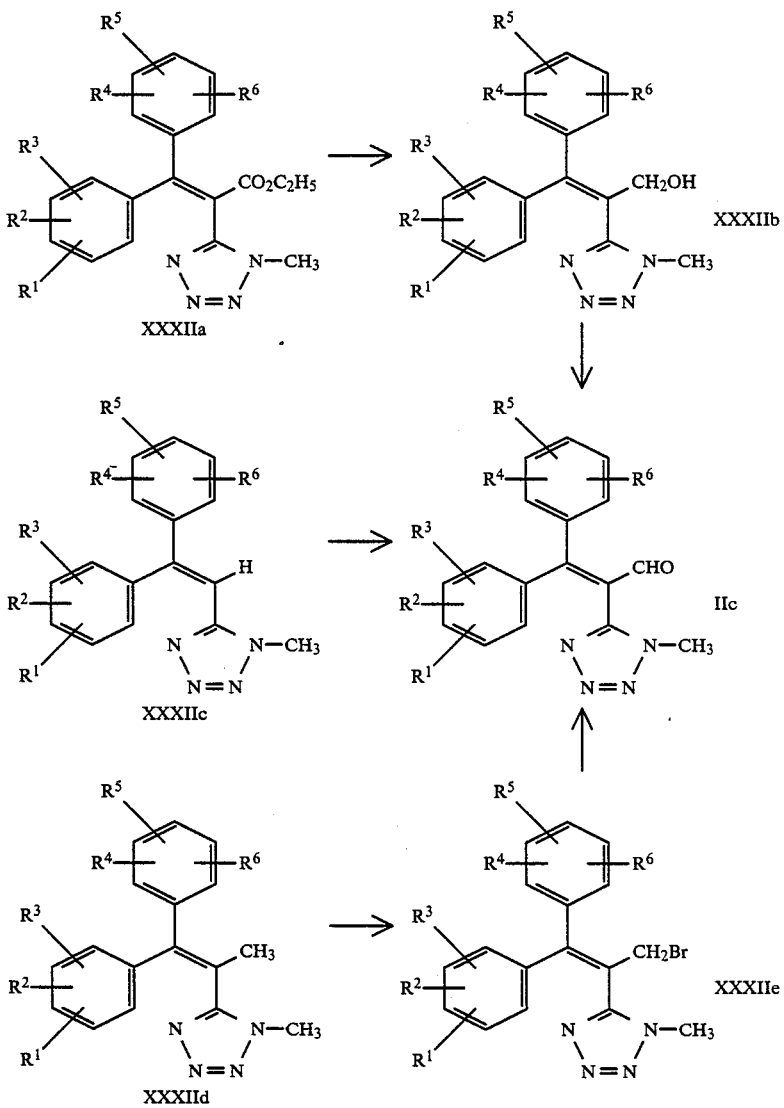

In Reaction Scheme 12, $R^1$, $R^2$, $R^3$, $R^4$, $R^5$ and $R^6$ are as previously defined. The alcohols of Formula XXXIIb may preferably be prepared in one step by reduction of the tetrazole ester of Formula XXXIIa with reducing agents such as diisobutylaluminum hydride in a non-reducible inert solvent such as methylene chloride and tetrahydrofuran, at low temperatures, and bromosuccinimide in the presence of a catalyst such as azobis isobutyronitrile or benzoyl peroxide in carbon tetrachloride, and then reacting the resulting allylic bromide of Formula XXXIIe with 2-nitropropane by the general procedure described herein and in *Org. Syn.*

*Coll. Vol.* IV, 932. Alternatively, the allylic bromide of Formula XXXIIe may be prepared from the alcohol of Formula XXXIIb by treatment with carbon tetrabromide and triphenylphosphine.

In an alternate and preferred procedure for the preparation of compounds of the Formula If there is provided intermediates of the Formulae XVII and XVIIa, as shown in Reaction Scheme 13.

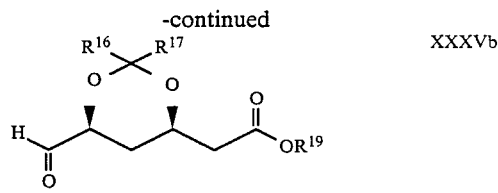

Reaction Scheme 13

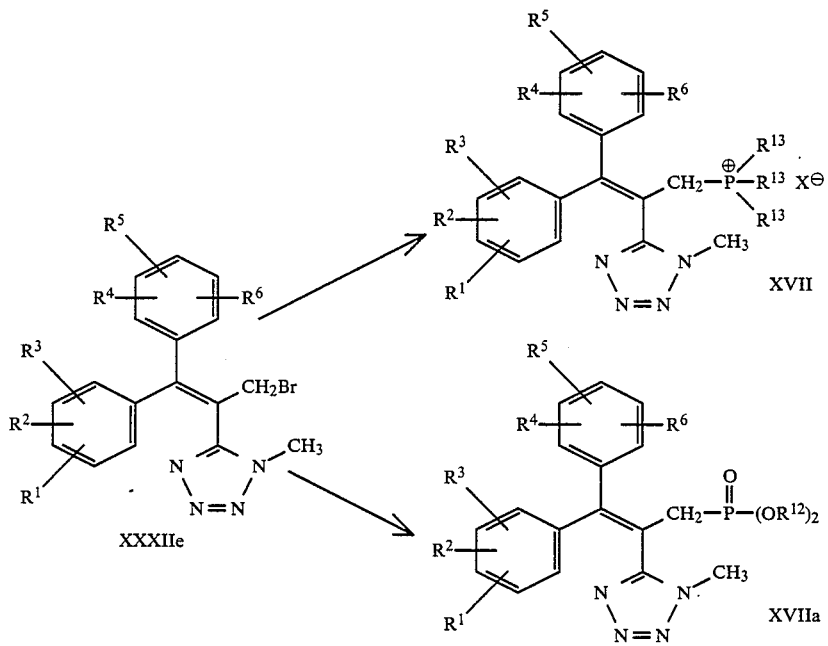

In Reaction Scheme 13, $R^1$, $R^2$, $R^3$, $R^4$, $R^6$, $R^{12}$, $R^{13}$ and X are as previously defined. The allylic bromide of Formula XXXIIe may be reacted in a conventional manner with phosphines such as triphenylphosphine in an inert organic solvent such as cyclohexane to produce the phosphonium salt of Formula XVII. Alternatively, the allylic bromide of Formula XXXIIe may be reacted in a conventional manner with phosphites such as trimethyl phosphite and triethyl phosphite either neat or in an inert organic solvent, and preferably, neat to produce the phosphonates of Formula XVIIa.

The intermediates of Formulae XVII or XVIIa may then be converted to the compounds of Formula If by a series of reactions shown in Reaction Scheme 7.

Another particularly preferred method for the preparation of compounds of the Formula If and Ig of the present invention is the use of intermediates having the formulae

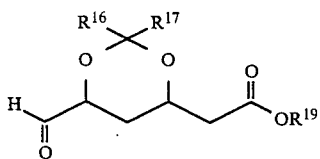

in substantially the cis form wherein $R^{16}$ and $R^{17}$ each are $C_{1-4}$alkyl or $R^{16}$ and $R^{17}$, taken together with the carbon atom to which they are attached, is cyclopentyl, cyclohexyl or cycloheptyl and $R^{19}$ is hydrogen, $C_{1-4}$alkyl or a metal cation. The preparation and use of the compounds of Formulae XXXVa and XXXVb is described in U.S. patent application Ser. No. 156,865, filed Feb. 18, 1989 (concurrently) by William T. Han and John J. Wright.

The substituted 1,3-dioxane compounds of Formula XXXVa, XXXVb and other similar compounds described herein also contain two asymmetric carbon atoms at the 4 and 6 position as shown below,

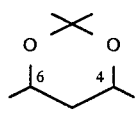

and the resulting four stereoisomers may be designated as the (4R,6S), (4S,6R), (4R,6R) and (4S,6S) stereoisomers. As used herein, the term "trans"-1,3dioxane is intended to include a mixture of (4R,6R) and (4S,6S) enantiomers while the term "cis"-1,3-dioxane is intended to include a mixture of (4R,6S) and (4S,6R) enantiomers. Since the most preferred enantiomer of the lactone compounds of Formula Ig has fortuitously the same (4R,6S) stereoisomeric designation as the most preferred enantiomer of the 1,3-dioxane intermediates, the additional designation of "trans" or "cis" is included to avoid any possible confusion.

The compounds of Formulae XXXVa and XXXVb may be prepared by the reaction of an aldehyde of Formula XXXVI with an ester of acetoacetic acid and then reacting a ketone or ketal with a compound of Formula XXXVIII followed by hydrolysis of the resulting 1,3-dioxane of Formula XXXIX and optionally resolving the acid of Formula XXXX, as shown in Reaction Scheme 14.

cial availability or the reaction conditions employed in the preparation. In a specific example described herein, a mixture containing mostly trans (E) isomer was employed. Even though a small percent of the other isomer may be present throughout the series of reactions shown in Reaction Scheme 14, it should be evident to those skilled in the art that the relative amount of isomers is not critical since the double bond is oxidized and thereby removed in the ozonolysis reaction.

The ketoester of Formula XXXVII may be reduced

Reaction Scheme 14

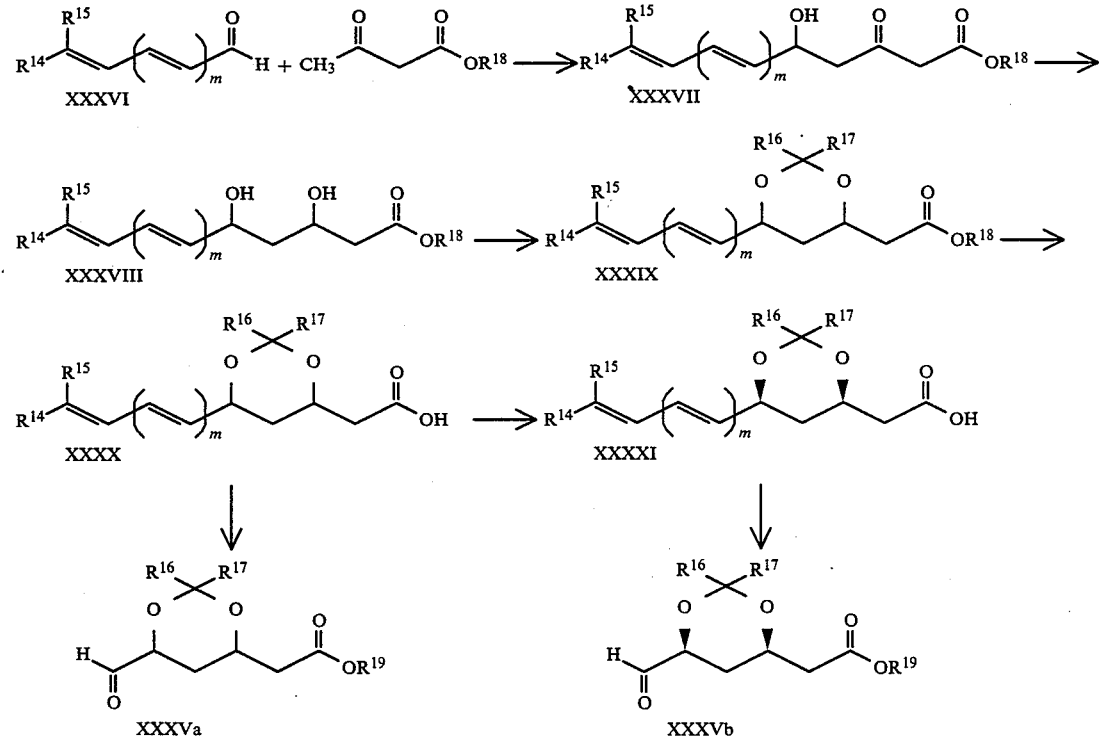

In Reaction Scheme 14, $R^{14}$ and $R^{15}$ each are independently hydrogen, $C_{1-6}$alkyl or phenyl which is optionally substituted by one or two $C_{1-4}$alkyl, halogen, $C_{1-4}$alkoxy or trifluoromethyl; $R^{18}$ is a hydrolyzable ester group, m is zero or 1 and $R^{16}$ and $R^{17}$ are as previously defined. The ketoester of Formula XXXVII may be prepared by the reaction of an ester of acetoacetic acid with an aldehyde of Formula XXXVI by procedures well-known to those skilled in the art in an inert organic solvent such as tetrahydrofuran at temperatures of about 0° C. to about −78° C. in the presence of a base such as sodium hydride, lithium diisopropylamide and n-butyllithium.

The starting materials of Formula XXXVI wherein m=0 and m=1 are known or may readily be prepared by known methods. The starting materials of Formula XXXVI wherein m=1 may also be prepared by the reaction of compounds of Formula XXXVI wherein m=0 with Wittig reagents such as triphenylphosphoranylidene acetaldehyde and other methods well-known in the art. It should be appreciated by those skilled in the art that the relative configuration of the double bond (m=0) or double bonds (m=1) in the starting materials of Formula XXXVI may be trans, cis or mixtures thereof. The relative amounts of each geometric isomer (E) or (Z) will be determined by commerto the dihydroxyester of Formula XXXVIII by reduction of the ketone group with reducing agents well-known in the art. Preferably, the reduction is carried out in a stereospecific manner by a two-step stereospecific reduction in order to maximize the production of the preferred erythro isomer of the dihydroxyester of Formula XXXVIII. The stereospecific reduction is carried out with trisubstitutedalkylboranes, preferably triethylborane or tri-n-butylborane, or alkoxydialkylboranes, preferably methoxydiethylborane or ethoxydiethylborane [*Tetrahedron Letters*, 28, 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethylether and 1,2-dimethoxyethane, preferably tetrahydrofuran. The reduction is then completed by the addition of methanol with or without the addition of aqueous hydrogen peroxide and buffer. Some of the compounds of Formula XXXVIII are known and described in U.S. Pat. No. 4,248,889 (issued Feb. 3, 1981) and U.S. Pat. No. 4,650,890 (issued Mar. 17, 1987).

The compounds of Formula XXXIX may be prepared from the compounds of Formula XXXVIII by reacting a ketone such as 2-propanone, 3-pentanone, cyclopentanone and cyclohexanone in a suitable inert organic solvent, e.g. toluene, benzene or xylene at temperatures of about 20° C. to the reflux temperature of the solvent employed in the presence of a small amount of organic, mineral or resin acid, e.g., p-toluenesulfonic acid and sulfuric acid and optionally removing the water which is formed with a drying agent, e.g., $Na_2SO_4$, $MgSO_4$ and molecular sieves or by azeotropical removal with a Dean-Stark trap or similar apparatus. The reaction of a compound of Formula XXXVIII with a ketone may also be carried out without solvent. Alternatively, the above reaction of compounds of Formula XXXIX may be carried out with a ketal such as 2,2-dimethoxypropane, 1,1-dimethoxycyclohexane and the like.

The compounds of Formula XXXVa wherein $R^{19}$ is a hydrolyzable ester group, and preferably, $C_{1-4}$alkyl may be prepared from the corresponding compounds of Formula XXXIX by oxidation of the olefinic group to an aldehyde group using conventional means. Alternatively, a compound of Formula XXXIX is first hydrolyzed by basic hydrolysis to a compound of Formula XXXX which is then oxidized to give a compound of Formula XXXVa wherein $R^{19}$ is hydrogen. A particularly convenient oxidation method is the reaction of a compound of Formula XXXIX or XXXX in an inert organic solvent such as methanol, ethyl acetate and methylene chloride with ozone at temperatures of about −50° C. to about −78° C. When the reaction with ozone is complete as evidence by the color of the reaction mixture, the intermediate ozonide is decomposed by the addition of a mild reducing agent, e.g., dimethyl sulfide and triphenylphosphine to give the desired aldehyde of Formula XXXVa.

The preferred cis-(4R,6S) aldehydes of Formula XXXVb may be prepared from the corresponding racemic acid of Formula XXXX by conventional resolution methods such as fractional crystallization after the introduction of a suitable salt-forming group. The resulting mixture of diastereoisomeric salts which is formed with an optically active salt-forming agent such as (1S,2R)-ephedrine and α-methylbenzylamine is separated and the separated resolved salt is converted to a compound of Formula XXXVb. Preferably, the salt-forming agent is (1S,2R)-ephedrine and the method of separation is by fractional crystallization. The resolution may be carried out in an inert organic solvent, and preferably, in a mixture of hydrocarbon-alcohol solvents, e.g., hexane-methanol mixture, in which the resolved salt may crystallize from the solution. If it is desired, the acid of Formula XXXVb may be converted to a salt wherein $R^{19}$ is a metal cation or to a hydrolyzable ester group wherein $R^{19}$ is $C_{1-4}$alkyl.

The most preferred antihypercholesterolemic compounds of Formulae XXXXIVa, XXXXIVb and Ig may be prepared from a compound of Formula XXXVa or XXXVb by the general procedures described herein, and in U.S. patent application Ser. No. 156,865, filed Feb. 18, 1988 (concurrently) by William T. Han and John J. Wright. The use of the aldehydes of Formula XXXVa is shown in Reaction Scheme 15 and the use of the chiral aldehydes of Formula XXXVb is shown in Reaction Scheme 16.

Reaction Scheme 15

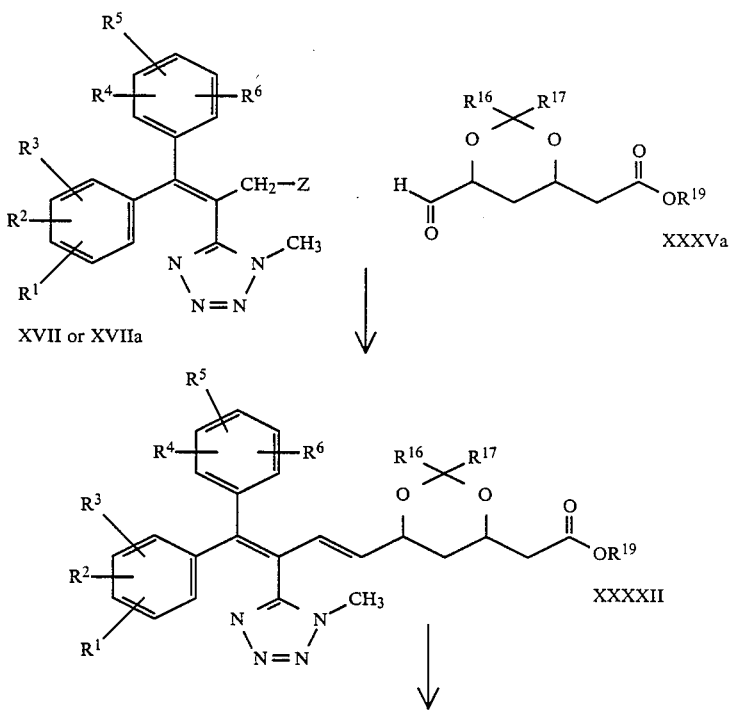

-continued
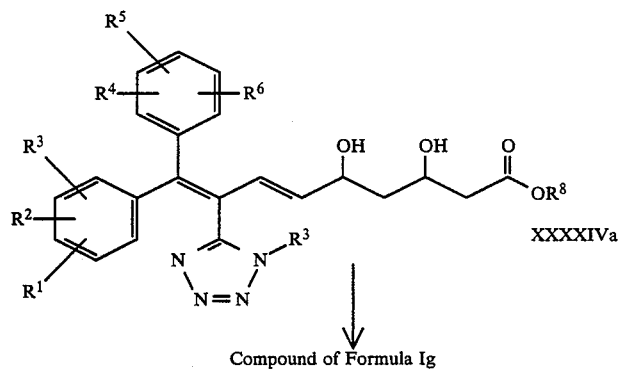
XXXXIVa
Compound of Formula Ig
Reaction Scheme 16
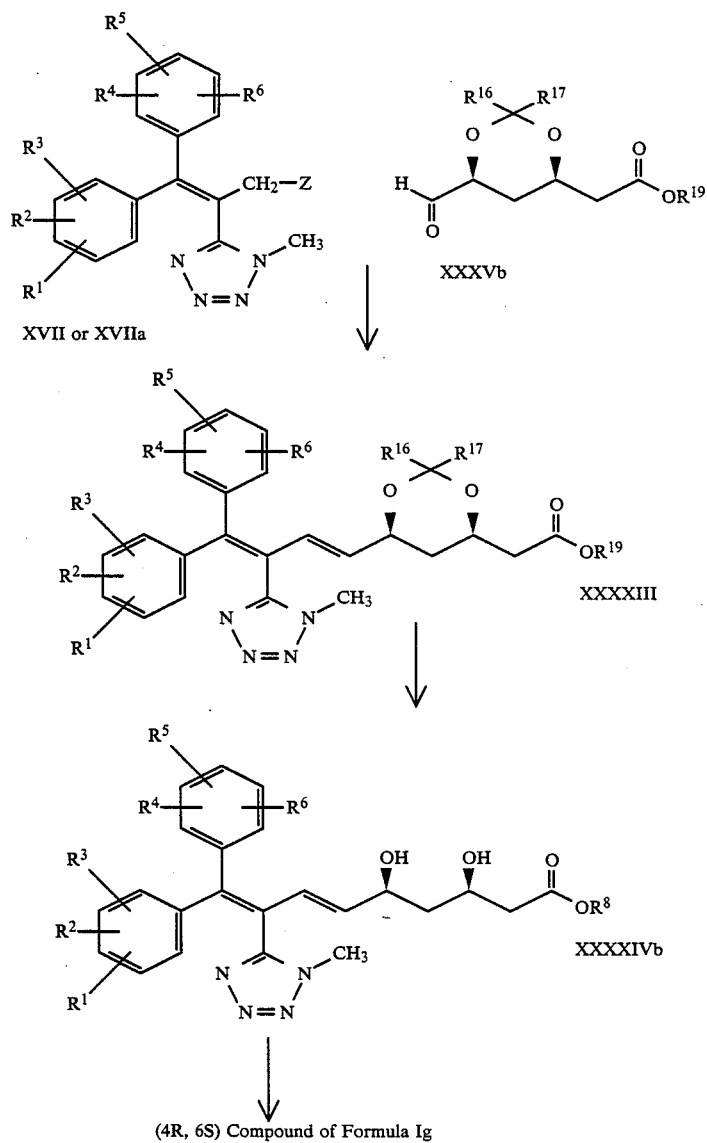
(4R, 6S) Compound of Formula Ig
In Reaction Schemes 15 and 16, $R^1$, $R^2$, $R^3$, $R^4$, $R^5$, $R^6$, $R^{16}$, $R^{17}$ and $R^{19}$ are previously defined and Z is

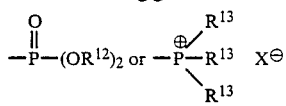

In still another aspect, the present invention provides prodrug forms of the preferred embodiment of the compounds of Formula I having the structure

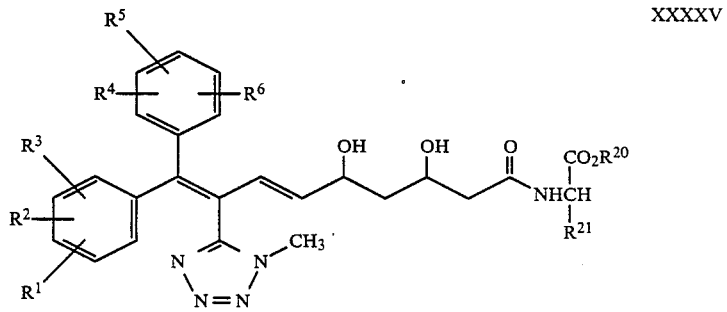

XXXXV wherein $R^1$, $R^2$, $R^3$, $R^4$, $R^5$ and $R^6$ are as previously defined, $R^{20}$ is hydrogen, $C_{1-6}$ alkyl or a metal cation and $R^{21}$ is $C_{1-6}$alkyl, hydroxy $C_{1-6}$alkyl, phenyl $C_{1-6}$alkyl, hydroxyphenyl $C_{1-6}$alkyl, amido $C_{1-6}$alkyl, $C_{1-6}$alkoxycarbonyl $C_{1-6}$alkyl, imidazol-4-yl-$C_{1-6}$alkyl, $C_{1-6}$alkylthio $C_{1-6}$alkyl, or indol-3-yl $C_{1-6}$alkyl in which the amido ester moiety is in the L-configuration.

In the compounds of Formula XXXXV, $R^1$, $R^2$, $R^3$, $R^4$, $R^5$ and $R^6$, independently, are preferably hydrogen, halogen, $C_{1-4}$alkyl or $C_{1-4}$alkoxy. More preferably, $R^1$ and $R^4$ are hydrogen and $R^2$, $R^3$, $R^5$, and $R^6$, independently, are hydrogen, fluoro, chloro, methyl or methoxy, and most preferably, $R^1$ and $R^4$ are hydrogen and $R^2$, $R^3$, $R^5$ and $R^6$, independently, are hydrogen, fluoro, methyl or methoxy. It is preferred that $R^{20}$ is hydrogen, $C_{1-2}$alkyl or a metal cation. Preferably, $R^{21}$ is $C_{1-4}$alkyl, hydroxy $C_{1-2}$alkyl, phenyl $C_{1-2}$alkyl, hydroxyphenyl $C_{1-2}$alkyl, amido $C_{1-2}$alkyl, $C_{1-2}$alkoxycarbonyl $C_{1-2}$alkyl, imidazol-4-yl $C_{1-2}$alkyl, $C_{1-2}$alkylthio $C_{1-2}$alkyl or indol-3-yl $C_{1-2}$alkyl in which the amido ester moiety is in the L-configuration. The stereoisomer of Formula XXXXV having two asymmetric carbon atoms bearing the hydroxy groups in the 3 and 5 position is preferably erythro and the most preferred stereoisomer is the (3R,5S) of Formula XXXXV.

The compounds of Formula XXXXV are prodrugs of the compounds of the present invention which are bioconverted following systemic administration to be useful antihypercholesterolemic agents. The most preferred amido acid and amido ester derivatives of Formula XXXXV may be prepared from the (4R,6S) compounds of Formula If by the general procedure described in U.S. Pat. No. 4,678,806 (July 7, 1987) to Baldwin et al. and illustrated for the most preferred isomer in Reaction Scheme 17.

in which $R^{12}$ is $C_{1-4}$alkyl, $R^{13}$ is phenyl which is unsubstituted or substituted by one or two $C_{1-4}$alkyl or chloro substituents and X is bromo, chloro or iodo. The preparation of the phosphonium salt of Formula XVII and the phosphonate of Formula XVIIa is described herein, and in Scheme 13. The reaction of a compound of Formula XVII or XVIIa with a compound of Formula XXXVa or Formula XXXVb to produce a compound of Formula XXXXII or XXXXIII, respectively, wherein $R^{19}$ is $C_{1-4}$alkyl may be carried out in an inert organic solvent such as tetrahydrofuran and N,N-dimethylformamide in the presence of a strong base such as n-butyllithium at a temperature of about $-50°$ C. to about $-78°$ C. When the reaction of a compound of Formula XVII or XVIIa is carried out with a compound of Formula XXXVa or XXXVb wherein $R^{19}$ is hydrogen, it is preferred to use two equivalents of a strong base such as n-butyllithium. Alternatively, the salt of a compound of Formula XXXVa or XXXVb may be prepared which is then treated with a compound of Formula XVII or XVIIa and a strong base. The methods of addition, salt formation and ylide preparation are well-known to those skilled in the art. The tetrazole compounds of Formula XXXXII or XXXXIII may be readily deprotected by well-known procedures such as mild acid, e.g., 0.2N HCl and 0.5N HCl in an inert organic solvent such as tetrahydrofuran to produce the erythro compounds of Formula XXXXIVa or the (3R,5S) compounds of Formula XXXXIVb which may then be converted to the trans compounds of Formula Ig or (4R,6S) compounds of Formula Ig in a conventional manner well-known to those skilled in the art.

Reaction Scheme 17

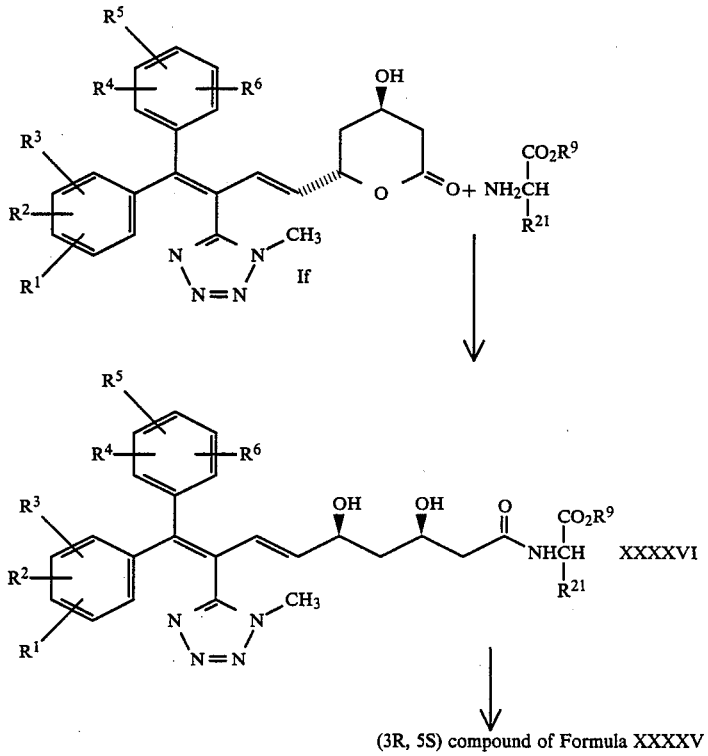

(3R, 5S) compound of Formula XXXXV

In Reaction Scheme 17, $R^1$, $R^2$, $R^3$, $R^4$, $R^5$, $R^6$ and $R^{21}$ are as previously defined and $R^9$ is a hydrolyzable ester group. The compounds of Formula If which are described herein may be reacted with an ester of the appropriate L-amino acid in an inert organic solvent such as tetrahydrofuran and preferably at the reflux temperature of the solvent to produce a compound of the Formula XXXXVI. If it is desired to prepare compounds of the Formula XXXXV wherein $R^{20}$ is hydrogen or a metal cation, then the compound of Formula XXXXV may be hydrolyzed under controlled conditions with dilute alkali hydroxide such as sodium hydroxide and potassium hydroxide in a conventional manner to produce a compound of Formula XXXXV.

The prodrug compounds of the present invention may be administered parenterally or, preferably, orally in the form of a capsule, a tablet, an injectable preparation or in a form described herein for the compounds of present invention. The oral dosage unit will contain the active ingredient in an amount of from about 0.01 mg/kg to about 10 mg/kg body weight to be administered in equal doses from one to four times a day.

The compounds of Formula XXXXV may also be co-administered with pharmaceutically acceptable non-toxic cationic polymers capable of binding bile acids in a non-reabsorbable form in the gastrointestinal tract, e.g., cholestyramine, colestipol and poly [methyl-(3-trimethylaminopropyl)iminotrimethylene dihalide]. The relative amounts of polymer to compounds of this invention is between about 10:1 to about 10,000:1.

DESCRIPTION OF SPECIFIC EMBODIMENTS

In the following examples, all temperatures are given in degrees Centigrade. Melting points were recorded on a Thomas-Hoover capillary melting point apparatus and boiling points were measured at specific pressures (mm Hg) and both temperatures are uncorrected. Proton magnetic resonance ($^1$H NMR) spectra were recorded on a Bruker AM 300, Bruker WM 360 or Varian T-60 CW spectrometer. All spectra were determined in CDCl$_3$, DMSO-d$_6$ or D$_2$O unless otherwise indicated and chemical shifts are reported in δ units downfield from the internal standard tetramethylsilane (TMS) and interproton coupling constants are reported in Hertz (Hz). Splitting patterns are designated as follows: s, singlet; d, doublet, t, triplet; q, quartet; m, multiplet; br, broad peak; and dd, doublet of doublet. Carbon-13 nuclear magnetic resonance ($^{13}$C NMR) spectra were recorded on a Bruker AM 300 or Bruker WM 360 spectrometer and were broad band proton decoupled. All spectra were determined in CDCl$_3$, DMSO-d$_6$ or D$_2$O unless otherwise indicated with internal deuterium lock and chemical shifts are reported in δ units downfield from tetramethylsilane. Infrared (IR) spectra were determined on a Nicolet MX-1 FT spectrometer from 4000 cm$^{-1}$ to 400 cm$^{-1}$, calibrated to 1601 cm$^{-1}$ absorption of a polystyrene film and are reported in reciprocal centimeters (cm$^{-1}$). Relative intensities are indicated as follows: s (strong), m (medium) and w (weak). Optical rotations [α]$_D^{25}$ were determined on a Perkin-Elmer 241 polarimeter in CHCl$_3$ at the concentrations indicated.

Gas chromatography-mass spectra (GC-MS) were determined on a Finnigan 4500 Gas chromatography-quadruple mass spectrometer at ionization potential of 70 eV. Mass spectra were also recorded on a Kratos MS-50 instrument utilizing the fast atom bombardment (FAB) technique. The mass data are expressed in the format: parent ion (M$^+$) or protonated ion (M+H)$^+$.

Analytical thin-layer chromatography (TLC) was carried out on precoated silica gel plates (60F-254) and visualized using UV light, iodine vapors and/or staining with one of the following reagents: (a) methanolic phosphomolybdic acid (2%) and heating; (b) reagent (a) followed by 2% cobalt sulphate in 5M $H_2SO_4$ and heating. Column chromatography, also referred to as flash column chromatography, was performed in a glass column using finely divided silica gel (32-63 m on silica gel-H) and pressures somewhat above atmospheric pressure with the indicated solvents. Ozonolysis reactions were done using a Welsbach ozonator style T-23. All evaporations of solvents were performed under reduced pressure. As used herein, the term hexanes is a mixture of isomeric $C_6$ hydrocarbons as specified by the American Chemical Society, and the term "inert" atmosphere is an argon or nitrogen atmosphere unless otherwise indicated. 048974901

EXAMPLE 1

Ethyl 2-cyano-3,3-bis(4-fluorophenyl)-2-propenoate

A mixture of 20.0 g (92 mmoles) of 4,4'-difluorobenzophenone, 11.0 g (97 mmoles) of ethyl cyanoacetate in a mixed solvent of 100 mL of dry benzene and 20 mL of glacial acetic acid containing a catalytic amount of β-alanine (0.9 g) was refluxed with separation of water using a Dean-Stark water trap. Separation of water was rapid during the first 2 hours (0.4 mL aqueous layer collected) but slower afterward. Azeotropic distillation was continued for a period of 14 days. Analytical TLC eluted with 10% EtOAc in hexanes (v/v) (Merck plate, 0.25 mm Silica gel-F) showed two spots at $R_f=0.2$ (desired product) and at $R_f=0.45$ (4,4'-difluorobenzophenone starting material). Crude reaction mixture was washed with water (40 mL×2), and the combined aqueous washes were extracted with EtOAc (150 mL×2). The organic layers were combined, dried over $MgSO_4$ and concentrated under reduced pressure to crystallize the product as pale cubic crystals. The crude product was collected, washed with 1:1 EtOAc in hexanes (v/v) then recrystallized from 8:1 (hexanes:ethyl acetate v/v) to give 16.2 g (56.3%) of analytical pure title compound; m.p.=114°-116° C.

IR (KBr) $\nu_{max}$: 3000 (s), 2225 (s), 1931 (vs), 1605 (s), 1513 (s), 1250 (s), 844 (s) cm$^{-1}$;

$^1$H NMR (CDCl$_3$) ⊕ : 1.19 (3H, t, J=7.1 Hz), 4.18 (2H, q, J=7.1 Hz), 7.08-7.15 (6H, m), 7.40-7.42 (2H, m);

$^{13}$C NMR (CDCl$_3$) δ : 13.75, 62.27, 104.05, 116,69, 115.53 (d, $^2J_{C-F}=22.7$ Hz), 115.88 (d, $^2J_{C-F}=22.7$ Hz), 131.64 (d, $^3J_{C-F}=9.1$ Hz), 132.66 (d, $^3J_{C-F}=9.1$ Hz), 134.25, 134,31, 134.36, 164.01 (d, $^1J_{C-F}=252.9$ Hz), 164.52 (d, $^1J_{C-F}=254.0$ Hz), 166.65 ppm.

Anal. Calcd. for $C_{18}H_{13}NO_2F_2$: C, 69.01; H, 4.15; N, 4.47. Found: C, 68,91; H, 4.15; N, 4.62.

EXAMPLE 2

Ethyl 3,3-bis(4-fluorophenyl)-2-(1H-tetrazol-5-yl)-2-propenoate

A dry 50 mL round bottom flask was charged with 5.0 g (16.0 mmoles) of ethyl 2-cyano-3,3-bis(4-fluorophenyl)-2-propenoate followed by 8.0 g (24.1 mmoles) of azidotributylstannane [prepared by the procedure described in Rev. Trav. Chim., 81, 202-5 (1962)] and 2.0 mL of reagent grade toluene. The heterogenous mixture was stirred and heated to reflux (110° C.) in an oil bath behind a safety shield. The solid starting material dissolved gradually forming a pale yellowish thick syrup and the homogenous mixture was stirred and refluxed for 20 hours. Analytical TLC eluted with 20% MeOH in CHCl$_3$ (v/v) showed the product at $R_f=0.26$ (streak). The crude reaction mixture was diluted with an equal volume of diethyl ether and was poured into a vigorously stirring saturated aqueous solution of KF (200 mL containing 2 mL of 48% HBF$_4$). A voluminous precipitate (Bu$_3$SnF) was observed soon after mixing and the hydrolysis was allowed to proceed for 16 hours. The suspension was filtered and the filtrate was extracted with EtOAc (100 mL×2). The organic layers were combined, dried over MgSO$_4$ and concentrated under reduced pressure. The title compound crystallized from the concentrate yielding 4.54 g (77%) of white analytical pure material; m.p.=159-161° C.

IR (KBr) $\nu_{max}$: 3438 (br), 1713 (vs), 1600 (s), 1510 (s), 1238 (s), 841 (s) cm$^{-1}$.

$^1$H NMR (CDCl$_3$) δ : 0.92 (3H, t, J=7.6 Hz), 3.98 (2H, q, J=7.6 Hz), 7.3-6.7 (8H, m), 10 (1H, v.br.);

$^{13}$C NMR (CDCl$_3$) δ : 166.52, 163.54 (d, $^1J_{C-F}=250.7$ Hz), 163.46, (d, $^1J_{C-F}=262.7$ Hz), 157.14, 136.40, 134.74, 131.71 (d, $^2J_{C-F}=67.2$ Hz), 131.59 (d, $^2J_{C-F}=66.4$ Hz), 115.75 (d, $^3J_{C-F}=18.9$ Hz), 115.45 (d, $^3J_{C-F}=18.1$ Hz) 62.11, 13.47 ppm.

Anal. Calcd. for $C_{18}H_{14}F_2N_4O_2$: C, 60.27; H, 4.06; N, 15.50. Found: C, 60.67; H, 3.96; N, 15.72.

EXAMPLE 3

Ethyl 3,3-bis(4-fluorophenyl)-2-(1-methyl-1H-tetrazol-5-yl)-2-propenoate and ethyl 3,3-bis(4-fluorophenyl)-2-(2-methyl-2H-tetrazol-5-yl)-2-propenoate

A. Ethyl 3,3-bis(4-fluorophenyl)-2-(1-methyl-1H-tetrazol-5-yl)-2-propenoate

To a solution of 0.5 g (1.40 mmoles) of ethyl 3,3-bis(4-fluorophenyl)-2-(1H-tetrazol-5-yl)-2-propenoate in 100 ml of dry benzene at 45° C. under argon was added sodium hydride 100 mg (60% in mineral oil 2.5 mmoles) in one single portion. The greyish suspension was stirred at 45° for 30 minutes then 1 mL (16.1 mmoles) of methyl iodide was added, and the flask was sealed with a rubber stopper. Alkylation was allowed to proceed at 40-45° C. for a total of four days. Analytical TLC eluted twice with 20% EtOAc in hexanes showed inly two isomeric products at $R_f=0.16$ (major isomer 4) and $R_f=0.22$ (minor isomer 5). The crude reaction mixture was washed with an equal volume of water and the aqueous phase was back extracted once with 50 mL of diethyl ether. The organic layers were combined, dried over MgSO$_4$ and concentrated under reduced pressure to give crude product. The product ratio for the 1-isomer:2-isomer was determined to be about 5.6:1 by gas chromatography and by $^1$H NMR spectroscopy.

The crude product mixture which was prepared as described above (5.0 g) was taken into 20 mL of hot ethyl acetate to which was added 40 mL of hot hexanes. The clear solution was allowed to cool slowly to room temperature to give 2.16 g (52%) of the title compound as colorless large needles; m.p.=144-145° C.

IR (KBr) $\nu_{max}$: 1713 (vs), 1600 (s), 1513 (s), 1325 (s), 1163 (s), 838 (s) cm$^{-1}$;

$^1$H NMR (CDCl$_3$) δ : 7.4-6.8 (8H, m), 4.06 (2H, q, J=7.1 Hz) 3.68 (3H, s), 1.00 (3H, t, J=7.1 Hz);

$^{13}$C NMR (CDCl$_3$) δ : 165.44, 163.6 (d, $^1J_{C-F}=250.7$ Hz), 163.4 (d, $^1J_{C-F}=252.9$ Hz) 156.85, 152.37, 135.88, 131.32 (d, $^3J_{C-F}=8.3$ Hz), 115.94 (d, $^8J_{C-F}=21.9$ Hz), 115.64 (d, $^2J_{C-F}=22.7$ Hz), 61.84, 33.76, 13.59 ppm;

Anal. Calcd. for $C_{19}H_{16}F_2N_4O_2$: C, 61.62; H, 4.35; N, 15.13, Found: C, 61.63; H, 4.45; N, 15.21.

B. Ethyl 3,3-bis(4-fluorophenyl)-2-(2-methyl-2H-tetrazol-5-yl)-2-propenoate

The residue (2.0 g) obtained from the filtrate of the recrystallization in Step A (containing about equal portions of the 1- and 2-methyl isomers) was purified by silica gel (35 g) chromatography. The appropriate fractions were collected, and evaporated to give crystalline product. Recrystallization from hexanesethyl acetate mixture (9:1; v/v) yielded the title compund; m.p.=117°-118° C.

IR (KBr) $\nu_{max}$: 1713 (vs), 1600 (s), 1506 (s), 1250 (sh), 1225 (vs), 850 (m) cm$^{-1}$;

$^1$H NMR(CDCl$_3$) δ : 7.4–6.8 (8H, m), 4.20 (3H, s), 406 (2H, q, J=7.1 Hz), 0.99 (3H, t, J=7.1 Hz);

$^{13}$C NMR (CDCl$_3$) δ : 167.12, 163.02 (d, $^1J_{C-F}$=272.6 Hz), 163.03 (d, $^1J_{C-F}$=225.7 Hz), 162.80, 152.59, 137.03 (d, $^4J_{C-F}$=4 Hz), 135.96 (d, $^4J_{C-F}$=3 Hz), 131.94 (d, $^3J_{C-F}$=8.3 Hz), 131.08 (d, $^3J_{C-F}$=8.3 Hz), 120.48, 115.37 (d, $^2J_{C-F}$=21.9 Hz), 115.26 (d, $^2J_{C-F}$=22.7 Hz) 61.41, 39.40, 13.61 ppm;

Anal. Calcd. for $C_{19}H_{16}F_2N_4O_2$: C, 61.62; H, 4.35; N, 15.13. Found: C, 61.77; H, 4.44; N, 15.38.

EXAMPLE 4

3,3-Bis(4-fluorophenyl)-2-(1-methyl-1H-tetrazol-5-yl)-2-propenoic acid

To a solution of ethyl 3,3-bis(4-fluorophenyl-2-(1-methyl-1H-tetrazol-5-yl)-2-propenoate 4.0 g (10.8 mmoles) in a mixture containing 20 mL of methanol and 20 mL tetrahydrofuran at 0° C. (ice-water bath) was added a solution of 3 Molar lithium hydroxide in H$_2$O (9 mL). Saponification reaction was allowed to proceed overnight (ca. 16 hours) forming a clear homogeneous solution. Analytical TLC eluted twice with 30% ethyl acetate in hexanes (v/v) showed the desired product at the origin. Crude reaction mixture was made acidic by adding 10 mL of 3 Molar HCl solution and the organic material was extracted twice into ethyl acetate (20 mL×2). Organic layers were combined, dried over MgSO$_4$ and concentrated under reduced pressure to give the product as a pale yellow solid. Recrystallization from EtOAc-hexanes mixture (1:9; v/v) yielded 3.8 g (100%) of the title compound; m.p.=205-206° C.

IR (KBr) $\nu_{max}$: 3438 (br), 2900 (br), 1725 (s), 1713 (s), 1600 (s), 1501 (s), 1231 (vs), 1156 (s), 850 (s) cm$^{-1}$;

$^1$H NMR (CDCl$_3$) δ : 7.9–6.4 (8H, m), 3.68 (3H, s);

$^{13}$C NMR (CDCl$_3$) δ : 166.57, 163.3 d, $^1J_{C-F}$=249.9 Hz), 163.03 (d, $^1J_{C-F}$=250 Hz), 155.68, 152.61, 135.58, 134.74, 131.75 (d, $^3J_{C-F}$=8.3 Hz), 131.28 (d, $^3J_{C-F}$=9.1 Hz) 117, 115.7 (d, $^2J_{C-F}$=22.6 Hz), 115.4 (d, $^2J_{C-F}$=22.6 Hz), 33.6 ppm;

Anal. Calcd. for $C_{17}H_{12}F_2N_4O_2$: C, 59.05; H, 3.53; N, 16.37. Found: C, 59.54; H, 3.58; N, 16.27.

EXAMPLE 5

3,3-Bis(4-fluorophenyl)-2-(2-methyl-2H-tetrazol-5-yl)-2-propenoic Acid

The general procedure of Example 4 was repeated, except that the ethyl 3,3-bis(4-fluorophenyl)- 2-(1-methyl-1H-tetrazol-5-yl)-2-propenoate utilized therein was replaced by ethyl 3,3-bis(4-fluorophenyl)-2-(2-methyl-2H-tetrazol-5-yl)-2-propenoate to yield after recrystallization from ethyl acetate-hexanes the title compound in essentially quantitative yield; mp=154°-155° C.

IR (KBr) $\nu_{max}$: 3438 (br), 3000 (br), 1675 (s), 1600 (s), 1503 (s), 1231 (s), 1225 (s), 1150 (s), 838 (s) cm$^{-1}$;

$^1$H NMR (CDCl$_3$-DMSO-d$_6$) δ : 7.33–7.28 (2H, m), 7.05–6.96 (4H, m), 6.87 (2H, t, J=8.64 Hz), 4.23 (3H, s);

$^{13}$C NMR (CDCl$_3$-DMSO-d$_6$) δ : 168.70, 163.05 (d, $^1J_{C-F}$=248.4 Hz), 163.07, 162.66 (d, $^1J_{C-F}$=249.9 Hz), 151.81, 136.81, 136.22, 131.83 (d, $^3J_{C-F}$=8.3 Hz), 131.20 (d, $^3J_{C-F}$=8.3 Hz), 121.04, 115.24 (d, $^2J_{C-F}$=21.9 Hz), 115.14 (d, $^2J_{C-F}$=21.1 Hz) ppm;

Anal. Calcd. for $C_{17}H_{12}F_2N_4O_2$: C, 59.65; H, 3.53; N, 16.37. Found: C, 59.56; H, 3.59; N, 16.36.

EXAMPLE 6

3,3-Bis(4-fluorophenyl)-2-(1-methyl-1H-tetrazol-5-yl)-2-propenal

A. 3,3-Bis(4-fluorophenyl)-2-(1-methyl-1H-tetrazol-5-yl)-2-propenyl chloride To a solution of dry (0.1 mmHg at 80° C.) 3,3-bis(4-fluorophenyl)-2-(1-methyl-1H-tetrazol-5-yl)2-propenoic acid 3.8 g (11.0 mmoles) in 20 mL of dry methylene chloride was added 4 mL (46.0 mmoles) of purified oxalyl chloride (redistilled over CaH$_2$) in one single portion. The reaction mixture was warmed gradually to reflux temperature for two hours. the mixture was evaporated under reduced pressure to remove volatile solvent, then excess oxalyl chloride was removed under vacuum (20 mmHg) at ambient temperature for 2 hours and under high vacuum (0.1 mmHg) at 50° C. for 16 hours to give the title compound.

B. 3,3-Bis(4-fluorophenyl)-2-(1-methyl-1H-tetrazol-5-yl)-2-propenol

The acyl chloride prepared in Step A was dissolved into 150 mL of tetrahydrofuran and was chilled to −78° C. under argon. To this pale brownish solution at −78° C. was added 8.0 mL lithium aluminum hydride in THF solutions (1.0 Molar). Analytical TLC after 15 minutes showed only one mobile spot at R$_f$=0.23 (50% EtOAc in hexanes v/v). The crude reaction mixture was diluted with 2M H$_2$SO$_4$ (20 ml). The aqueous layer was extracted with ethyl acetate (40 mL×2). Organic layers were combined, dried over MgSO$_4$ and concentated under reduced pressure to give 3.64 g (100%) of the title compound. The crude allylic alcohol was used immediaely in the next step without further purification. MS (CI): m/e=328 for (M+H)$^+$;

IR (KBr) $\nu_{max}$; 3388 (v.br), 1600 (s), 1501 (s), 1225 (s), 1156 (s), 838 (s), 750 (s), cm$^{-1}$;

$^1$H NMR (CDCl$_3$) δ : 7.5–6.9 (8H, m), 4.52 (2H, br), 3.42 (3H, s), 3.75 (1H, br, D$_2$O exchangeable);

$^1$H NMR (DMSO-d$_6$) δ : 7.5–6.9 (8H, m), 5.23 (1H, t, J=5.5 Hz), 4.27, (2H, d J=5.5 Hz), 354 (3H, s) ppm;

C. 3,3-Bis(4-fluorophenyl)-2-(1-methyl-1H-tetrazol-5-yl)-2-propenal

To a vigorously stirred solution of the crude allylic alcohol 3.64 g [prepared in Step B] in 40 mL of methylene chloride at room temperature was added 2.6 g (12.0 mmoles) of pyridinium chlorochromate in one single porion. Analytical TLC immediately afterward showed about 50% of product at R$_f$=0.34 along with the starting material at R$_f$=0.14 (eluted with 50% EtOAc:Hexanes v/v). The oxidation was allowed to proceed at room temperature for a total of 16 hours, during which all the starting material was consumed and TLC showed only product. The crude reaction suspension was filtered through a bed of silica gel, washed with one liter of 10% (v/v) ethyl acetate in hexanes and one liter of 20% (v/v) ethyl acetate in hexanes. The desired product crystallized upon concentration under reduced pressure to give 2.7 g (74%) of the title compound; m.p.=141°-142° C. MS (CI): m/e=326 for (M+H)+;

IR (KBr) $\nu_{max}$: 3075 (m), 2875 (m), 1675 (s), 1600 (s), 1501 (s), 1238 (s), 1156 (s), 850 (s), 750 (s), cm$^{-1}$;

$^1$H NMR (CDCl$_3$) δ : 9.63 (1H, s), 9.5–6.9 (8H, m), 3.74 (3H, s), $^{13}$C NMR (CDCl$_3$) δ : 188.92, 165.44, 164.68 (d, $^1J_{C-F}$=254.4 Hz), 164.10 (d, $^1J_{C-F}$=255.9 Hz); 151.34, 134.31, 133.77 (d, $^3J_{C-F}$=8.3 Hz), 132.69, 132.23 (d, $^3J_{C-F}$=7.5 Hz) 123.70, 116.26 (d, $^2J_{C-F}$=21.9 Hz), 116.18 (d, $^2J_{C-F}$=22.7 Hz), 34.10 ppm;

Anal. Calcd. for C$_{17}$H$_{12}$F$_2$N$_4$O: C, 62.58; H, 3.71; N, 17.17. Found: C, 62.41; H, 3.85; N, 16.98.

EXAMPLE 7

3,3-Bis(4-fluorophenyl)-2-(2-methyl-2H-tetrazol-5-yl)-2-propenal

The general procedure of Steps A, B, and C of Example 6 was repeated, except that the 3,3-bis(4-fluorophenyl)-2-(1-methyl-1H-tetrazol-5-yl)-2-propenoic acid utilized in Step A was replaced by 3,3-bis(4-fluorophenyl)-2-(2-methyl-2H-tetrazol-5-yl)-2-propenoic acid [prepared in Example 5] to yield the title compound as a gummy solid in 76% overall yield. MS (CI): m/e=326 for (M+H)+.

IR (KBr) $\nu_{max}$: 2863 (m), 2750 (w), 1681 (s), 1600 (s), 1503 (s), 1225 (s), 1156 (s), 838 (s), 752 (s), cm$^{-1}$;

$^1$H NMR (CDCl$_3$) δ : 9.65, 7.34–7.30 (2H, m), 7.15 (2H, t, J=8.5 Hz), 7.01–6.96 (2H, m), 6.88 (2H, t, J=8.4 Hz), 4.29 (3H, s);

$^{13}$C NMR (CDCl$_3$) δ : 190.08, 164.30 (d, $^1J_{C-F}$=254.4 Hz), 163.5 (d, $^1J_{C-F}$=252.17 Hz), 163.20, 161.37, 135.55, 133.49, 133.66 (d, $^3J_{C-F}$=7.6 Hz), 132.38 (d, $^3J_{C-F}$=9.1 Hz), 131.40, 127.54, 115.86 (d, $^2J_{C-F}$=26.4 Hz), 115.57 (d, $^2J_{C-F}$=28.7 Hz), 39.55 ppm;

Anal. Calcd. for C$_{17}$H$_{12}$F$_2$N$_4$O: C, 62.58; H, 3.71; N, 17.17. Found: C, 62.27; H, 4.22; N, 15.83.

EXAMPLE 8

5,5-Bis(4-fluorophenyl)-4-(1-methyl-1H-tetrazol-5-yl)-2,4-pentadienal

To a dry mixture of 3,3-bis(4-fluorophenyl)-2-(1-methyl-1H-tetrazol-5-yl)-2-propenal 0.70 g (2.1 mmoles) and triphenylphosphoranylidene acetaldehyde 0.72 g (2.5 mmoles) under argon at ambient temperature was added 20 mL of dry benzene. The suspension was warmed to reflux temperature under an argon atmosphere and the reaction was allowed to proceed at reflux temperature for 30 minutes. Analytical TLC eluted four times with 20% ethyl acetate in hexanes (v/v) showed only one spot for product at R$_f$=0.15. The crude reaction mixture was poured on a silica gel column saturated with hexanes. The desired product was eluted with 1.5 liters of 20% EtOAc in hexanes (v/v) to give 0.67 g (89%) of the title compund which appears homogeneous by TLC.

$^1$H NMR (CDCl$_3$) δ : 9.53 (1H, d, J=7.5 Hz), 7.47 (1H, d, J=15.7 Hz), 7.4–8.8, m), 5.80 (1H, dd, J$_1$=7.4 Hz, J$_2$=15.7 Hz), 4.11 (2H, q, J=7.1 Hz), 3.58 (3H, s), 1.26 (3H, t, J=7.1 Hz) ppm.

The proton NMR (300 MHz) of the above product showed that it contains about 10% of 7,7-bis(4-fluorophenyl)-6-(1-methyl-1H-tetrazol-5-yl)-2,4,6-heptatrienal as a side product which was not easily removed. This material was used in the next preparation without further purification.

EXAMPLE 9

5,5-Bis(4-fluorophenyl)-4-(2-methyl-2H-tetrazol-5-yl)-2,4-pentadienal

The general procedure of Example 8 was repeated, except that the 3,3-bis(4-fluorophenyl)-2-(1-methyl-1H-tetrazol-5-yl)-2-proenal utilized therein was replaced by 0.67 g (21.0 mmoles) of 3,3-bis(4-fluorophenyl)-2-(2-methyl-2H-tetrazol-5-yl)-2-propenal [prepared in Example 7]. The reaction was carried out with 0.64 g (21.0 mmoles) of triphenylphosphoranylidene acetaldehyde to yield 0.66 g (90.5%) of the title compound.

$^1$H NMR (CDCl$_3$) δ : 9.57 (1H, d, J=6.8 Hz), 7.50 (1H, d, J=16.5 Hz), 7.3–6.8 (8H, m), 5.94 (1H, dd, J=6.8, 16.5 Hz), 4.30 (3H, s) ppm.

EXAMPLE 10

Ethyl 9,9-bis(4-fluorophenyl)-5-hydroxy-8-(1-methyl-1H-tetrazol-5-yl)-3-oxo-6,8-nonadienoate and ethyl 11,11-bis(4-fluorophenyl)-5-hydroxy-10-(1-methyl-1H-tetrazol-5-yl)-3-oxo-6,8,10-undecatrienoate

A. Ethyl 9,9-bis(4-fluorophenyl)-5-hydroxy-8-(1-methyl-1H-tetrazol-5-yl)-3-oxo-6,8-nonadienoate To a chilled suspension (0° C., ice-water bath) of NaH (0.64 g, 16.0 mmoles) (60% in mineral oil) in 20 mL of dry tetrahydrofuran under argon was added ethyl acetoacetate 2.04 mL (16.0 mmoles) in 4 equal portions. The homogeneous clear solution was stirred at 0° C. for 30 minutes followed by the dropwise addition of 6.4 mL of 2.5 Molar n-BuLi (16.0 mmoles) over a period of 15 minutes. The orange dianion solution was stirred at 0° C. for an additional hour. The ice-water bath was replaced by an acetone-dry ice bath at −78° C. and the dianion was transferred via a cannula into a tetrahydrofuran (20 mL) solution containing 5,5-bis(4-fluorophenyl)-4-(1-methyl-1H-tetrazol-5-yl)-2,4-pentadienal (2.82 g, 8.01 mmoles). Analytical TLC showed the major desired product at R$_f$=0.15 (50% EtAOc in hexanes) and a minor product at R$_f$=0.2. The crude reaction mixture was diluted with 40 mL of 1N HCl and the aqueous layer was extracted with ethyl acetate (50 mL×2). The organic layers were combined, dried over MgSO$_4$ and concentrated under reduced pressure. The desired product was purified by flash silica gel column chromatography eluted with 20% EtOAc in hexanes (v/v) to give 2.26 g (58.5%) of the title compound. MS (CI): m/e=483 for (M+H)+.

IR (KBr) $\nu_{max}$; 3450 (v.br), 1738 (s), 1725 (s), 1606 (s), 1513 (vs), 1225 (s), 1163 (s), 844 (s) cm$^{-1}$;

$^1$H NMR (CDCl$_3$) δ : 7.4–6.8 (8H, m), 6.72 (1H, d, J=15.6 Hz), 4.63 (1H, m), 4.17 (2H, q, J=7.1 Hz), 4.13 (1H, m), 3.60 (3H, s), 3.52 (1H, d, J=3.9 Hz, D$_2$O exchangeable), 3.47 (2H, s), 2.74 (2H, d, J=6.0 Hz), 1.26 (3H, t, J=7.1 Hz) ppm;

$^{13}$C NMR (CDCl$_3$) δ : 164.21, 135.98, 132.34 (d, $^3J_{C-F}$=8.3 Hz), 131.45 (d, $^3J_{C-F}$=9.1 Hz), 115.74 (d, $^2J_{C-F}$=21.9 Hz), 115.74 (d, $^2J_{C-F}$=21.1 Hz), 100.86, 67.61, 61.58, 49.85, 49.07, 33.56, 14.10 ppm.

B. Ethyl 11,11-bis(4-fluorophenyl)-5-hydroxy-10-(1-methyl-1H-tetrazol-5-yl)-3-oxo-6,8,10-undecatrienoate The silica gel column from the above Step A was eluted further to give the minor product ($R_f$=0.2). Repeated flash silica gel chromatography with 20% EtOAc in hexanes as the eluting solvent yielded the title compound.

$^1$H NMR (CDCl$_3$) δ : 7.4–7.1 (4H, m), 6.9–6.8 (4H, m), 6.58 (1H, d, J=15.5 Hz), 6.31 (1H, dd, J=10.7, 15.0 Hz), 5.80, 1H, dd, J=10.7, 15.4 Hz), 5.66 (1H, dd, J=5.5, 15.1 Hz), 4.64 (1H, m), 4.18 (2H, q, J=6.9 Hz), 3.58 (3H, s) 3,46 (2H, s), 3.02 (1H, m), 2.75–2.72 (2H, m), 1.27 (3H, t, J=6.9 Hz) ppm.

EXAMPLE 11

Ethyl (±)-erythro-9,9-bis(4-fluorophenyl)-3,5-dihydroxy-8-(1-methyl-1H-tetrazol-5-yl)-6,8-nonadienoate To a solution of ethyl 9,9-bis(4-fluorophenyl)-5-hydroxy-8-(1-methyl-1H-tetrazol-5-yl)-3-oxo-6,8-nonadienoate (2.19 g, 4.53 mmoles) (dried under high vacuum at 30° C. for 48 hours) in 40 mL of anhydrous tetrahydrofuran at 0° C. (ice-water bath) under argon was added triethyl borane solution in tetrahydrofuran (4.8 mL, 4.8 mmoles) in one single portion. The mixture was stirred under argon for a total of one hour. The cooling ice-water bath was replaced with an acetone-dry ice bath and to the reaction mixture was added NaBH$_4$ (0.20 g, 5.3 mmoles) in one portion. The reaction suspension was stirred at −78° C. for two hours forming a clear homogeneous pale yellow solution. The crude reaction mixture was diluted with 40 mL of 1N HCl followed by extractions with EtOAc (40 mL×2). The organic layers were combined, dried over MgSO$_4$ and concentrated under reduced pressure to give the product as a thick syrup, it was further diluted with 300 mL of methanol and the solution was allowed to stand at room temperature for 16 hours before evaporation under reduced pressure. The crude product was purified by flash silica gel column chromatography using 2 liters of 30% EtOAc in hexanes as the eluting solvent. The appropriate fractions were collected and evaporated to give 1.48 g (68%) of the title compound. MS (CI): m/e=485 for (M+H)$^+$;

IR (KBr) $\nu_{max}$: 3438 (s), 1734 (s), 1600 (s), 1513 (s), 1225 (s), 1163 (s), 844 (s), cm$^{-1}$;

$^1$H NMR (DMSO-d$_6$) δ : 7.4–7.3 (4H, m) 7.04 (2H, t, J=8.9 Hz), 6.9–6.7 (2H, m), 6.52 (1H, dd, J=1, 15.2 Hz), 5.16 (1H, dd, J=5.6, 15.7 Hz), 4.89 (1H, d, J=4.8 Hz), 4.72 (1H, d, J=5.5 Hz) 4.13 (1H, m), 4.04 (2H, q, J=7.2 Hz), 3.85 (1H, m), 3.75 (3H, s), 2.42, (1H, dd, J=4.6, 15 Hz), 2.28 (1H, dd, J=8.3, 15 Hz), 5.5 (1H, m), 4.2 (1H, m), 1.17 (3H, t, J=7.2 Hz);

$^{13}$H NMR (DMSO-d$_6$) δ : 171.02, 163.51, 163.05, 153.03, 145.34, 139.46, 136.34, 132.2 (d, $^3J_{C-F}$=8.3 Hz), 131.0 (d, $^{13}J_{C-F}$=9.1 Hz), 125.14, 121.64, 115.41 (d, $^2J_{C-F}$=20.4 Hz), 115.13, (d, $^2J_{C-F}$=21.1 Hz), 67.79, 64.76, 59.50, 44.10, 42.34, 33.44, 14.01 ppm;

Anal. Calcd. for C$_{25}$H$_{26}$F$_2$N$_4$O$_4$: C, 61.98; H, 5.41; N, 11.56. Found: C, 61.51; H, 5.67; N, 11.12.

EXAMPLE 12

Sodium (±)-erythro-9,9-bis(4-fluorophenyl)-3,5-dihydroxy-8-(1-methyl-1H-tetrazol-5-yl)-6,8-nonadionate To a solution of ethyl 9,9-bis(4-fluorophenyl)-3,5-dihydroxy-8-(1-methyl-1H-tetrazol-5-yl)-6,8-nonadienoate (1.231 g, 2.54 mmoles) in 35 mL of tetrahydrofuran at 0° C. was added 1N NaOH solution 2.54 mL (1.0 equivalent) dropwise. The rate of addition should be slow enough to prevent the reaction mixture from changing color into deep amber or reddish. The reaction mixture was stirred for 30 minutes at 0° C. forming a clear homogeneous solution. The reaction mixture was allowed to warm to ambient temperature and saponification was allowed to proceed for an additional hour. Analytical TLC eluted with 20% MeOH in CHCl$_3$ (v/v) showed the desired product at $R_f$=0.2. Most of the organic solvent was evaporated at approximately 10° under reduced pressure (20 mmHg). The resulting thick syrup was diluted with 4 mL of water and then the solution was lyophilized at 0.01 mmHg to give 1.126 g (100%) of the title compound as a sodium salt which appears to contain about one mole of water; m.p.>100° C. decomposed.

IR (KBr) $\nu_{max}$: 3400 (v.br), 1600 (s), 1575 (s), 1513 (s), 1438 (s), 1404 (s), 1225 (s), 1156 (s), 838 (s) cm$^{-1}$;

$^1$H NMR (DMSO-d$_6$) δ : 7.3–7.4 (4H, m), 7.06 (1H, br, D$_2$O exchangeable), 7.00–7.06 (2H, m), 6.87–6.91 (2H, m), 6.49 (1H, d, J=15.7 Hz), 5.13 (1H, dd, J=5.4, 15.7 Hz), 5.05 (1H, br, D$_2$O exchangeable), 4.14 (1H, m), 3.74 (3H, s), 3.62 (1H, m), 1.99 (1H, dd, J=3.7, 13.5 Hz), 1.80 (1H, dd, J=8.5, 13.5 Hz), 1.43 (1H, m), 1.30 (1H, m);

$^{13}$C NMR (DMSO-d$_6$) δ : 175.87, 161.85 (d, $^1J_{C-F}$=246.1 Hz), 161.37 (d, $^1J_{C-F}$=246.9 Hz), 153.08, 144.97, 139.88, 136.40, 135.51, 132.22 (d, $^3J_{C-F}$=8.3 Hz), 130.97 (d, $^3J_{C-F}$=8.3 Hz). 124.66, 121.74, 115.42 (d, $^2J_{C-F}$=21.9 Hz), 115.12, (d, $^2J_{C-F}$=23.4 Hz), 68.23, 65.71, 44.50, 43.55, 33.45 ppm;

Anal. Calcd. for C$_{23}$H$_{21}$F$_2$N$_4$O$_4$Na H$_2$O: C, 55.64; H, 4.67; N, 11.28. Found: C, 55.24; H, 4.65; N, 10.85.

EXAMPLE 13

Trans-6-[4,4-bis(4-fluorophenyl)-3-(1-methyl-1H-tetrazol-5-yl)-1,3-butadienyl]-tetrahdro-4-hydroxy-2H-pyran-2one

A. (±)-Erythro-9,9-Bis(4-fluorophenyl)-3,5-dihydroxy-8-(1-methyl-1H-tetrazol-5-yl)-6,8-nonadienoic acid To a solution of ethyl (±)-erythro-9,9-bis(4-fluorophenyl)-3,5-dihydroxy-8-(1-methyl-1H-tetrazol-5-yl)-6,8-nonadienoate (0.64 g, 1.32 mmoles) in 25 mL of tetrahydrofuran at 0° C. was treated with 1.32 mL of 1.0 Molar NaOH solution. The pale yellow suspension was stirred at 0° C. for two hours forming a clear pale yellow solution. The crude reaction mixture was diluted with 5 mL of aqueous HCl (2N) solution and organic material was extracted into ethyl acetate (40 mL×2). The organic extracts were combined, dried over MgSO$_4$and concentrated under reduced pressure to give a pale yellow gum. The crude dihydroxy acid was rigorously dried under high vacuum (0.01 mm Hg at room temperature for 24 hours) before submitting for the next step.

B. Trans-6-[4,4-bis(4-fluorophenyl)-3-(1-methyl-1H-tetrazol-5-yl)-1,3-butadienyl]-tetrahydro-4-hydroxy-2H-pyran-2-one The dry acid from the above Step A was dissolved in 100 mL of dry methylene chloride under argon at room temperature followed by the addition of 1.7 g (4.0 mmoles) of 1-cyclohexyl-3-(2-morpholinoethyl)carbodiimide metho-p-toluenesulphonate. Lactonization was complete in less than 15 minutes as indicated by analytical TLC ($R_f$=0.12) eluted three times with 50% ethyl acetate in hexanes, Most of the solvent was evaporated under reduced pressure and the residue was washed with water (40 mL) followed by extractions with ethyl acetate (40 mL×2). The organic layers were combined, dried over MgSO$_4$ and concentrated under reduced pressure to give 0.54 g (89.7%) of the product. A pure sample of the product was obtained by passing through a short bed of silica gel eluted with 40% ethyl acetate in hexanes (v/v) to give the title compound which appears to contain about two moles of water. MS (CI): m/e=438 for (M+H)$^+$;

IR (KBr) $\nu_{max}$: 3425 (br), 1738 (v.s.), 1600 (s), 1513 (s), 1225 (vs), 1156 (s), 1038 (s), 838 (s) cm$^{-1}$;

$^1$H NMR (CDCl$_3$) δ : 7.26–7.21 (2H, m), 7.14 (2H, d, J=8.7 Hz), 6.86 (4H, d, J=6.8 Hz), 6.72 (1H, dd, J=0.8, 15.6 Hz), 5.34 (1H, dd, J=7.1, 15.6 Hz), 5.18 (1H, m), 4.37 (1H, m), 3.57 (3H, s), 2.68 (1H, dd, J=4.5, 18 Hz), 2.60 (1H, ddd, J=3.63, 2.5, 18 Hz), 2.44 (1H, d, J=2.6 H$_2$, D$_2$O exchangeable), 2.00 (1H, dt, J=18, 1.7 Hz), 1.79 (1H, td, J=2.7, 18 Hz) ppm;

$^{13}$C NMR (CDCl$_3$) δ : 169.20, 163, 162.5, 153.20, 148.81, 135.61, 134.95, 132.45 (d, $^3J_{C-F}$=8 Hz), 132.52, 131.51, (d, $^3J_{C-F}$=8 Hz), 130.04, 120.44, 115.95, (d, $^2J_{C-F}$=21.9 Hz), 115.83 (d, $^2J_{C-F}$=21.9 Hz), 75.67, 62.54, 38.58, 35.58, 33.64 ppm;

Anal. Calcd. for C$_{23}$H$_{20}$F$_2$N$_4$O$_3$ 2H$_2$O: C, 58.22; H, 5.10; N, 11.81. Found: C, 59.06; H, 4.45; N, 11.25.

A sample of the above lactone was crystallized from cyclohexane-benzene to give the title compound as a crystalline solid containing about one mole of benzene; m.p.=104°–106° C.

Anal. Calcd. for C$_{23}$H$_{20}$F$_2$N$_4$O$_3$ C$_6$H$_6$: C, 67.48; H, 5.07; N, 10.85. Found: C, 67.44; H, 5.23; N, 10.59

EXAMPLE 14

Ethyl (±)-erythro-9,9-(4-fluorophenyl)-3,5-dihydroxy-8-(2-methyl-2H-tetrazol-5-yl)-6,8-nonadienoate

A. Ethyl 9,9-bis(4-fluorophenyl)-5-hydroxy-8-(2-methyl-2H-tetrazol-5-yl)-3-oxo-6,8-nonadienoate The general procedure of Example 10, Step A was repeated, except that the 5,5-bis(4-fluorophenyl)-4-(1-methyl-1H-tetrazol-5-yl)-2,4-pentadienal utilized therein was replaced by 0.66 g (1.87 mmoles) of 5,5-bis(4-fluorophenyl)-4-(2-methyl-2H-tetrazol-5-yl)-2,4-pentadienal and there was thereby produced 0.53 g (59%) of the title compound after silica gel chromatography.

B. Ethyl (±)-erythro-9,9-bis(4-fluorophenyl)-3,5-dihydroxy-8-(2-methyl-2H-tetrazol-5-yl)-6,8-nonadienoate The product from the above Step A was treated with triethylborane and sodium borohydride following the general procedure described in Example 11 to give 0.36 g (69.5%) of the title compound after purification by silica gel chromatography.

$^1$H NMR (CDCl$_3$) δ : 7.30–7.22 (2H, m), 7.07 (2H, t, J=6.7 Hz), 6.89–6.86 (2H, m), 6.78 (2H, t, J=8.7 Hz), 6.66(1H, d, J=15.5 Hz), 5.39 (1H, dd, J=6.3, 15.5 Hz), 4.41 (1H, m), 4.2 (1H, m), 4.27 (3H, s), 4.18 (2H, q, J=7.1 Hz), 3.92 (1H, br, D$_2$O exchangeable), 3.69 (1H, br, D$_2$0 exchangeable), 2.47–2.42 (2H, m), 1.66–1.58 (2H, m), 1.26 (3H, t, J32 7.1 Hz);

$^{13}$C NMR (CDCl$_3$) δ : 172.29, 162.52 (d, $^1J_{C-F}$=249.9 Hz), 161.94 (d, $^1J_{C-F}$=248.4 Hz), 145.74, 137.59, 137.33, 136.87, 132.37 (d, $^3J_{C-F}$=8.3 Hz), 131.69 (d, $^3J_{C-F}$=8.3 Hz), 128.53, 124.90, 115.50 (d, $^2J_{C-F}$=21.1 Hz), 115.2 (d, $^2J_{C-F}$=20 Hz), 72.11, 68.07, 60.74, 42.52, 41.73, 39.42, 14.17 ppm.

EXAMPLE 15

Ethyl (±)-erythro-11,11-bis(4-fluorophenyl)-3,5-dihydroxy-10-(1-methyl-1H-tetrazol-5-yl)-6,8,10-undecatrienoate and Sodium (±)-erythro-11,11-bis(4-fluorophenyl)-3,5-dihydroxy-10-(1-methyl-1H-tetrazol-5-yl)-6,8,10-undecatrienoate

A. Ethyl (±)-erythro-11,11-bis(4-fluorophenyl)-3,5-dihydroxy-10-(1-methyl-1H-tetrazol-5-yl)-6,8,10-undecatrienoate The general procedure of Example 11 was repeated, except that the ethyl 9,9-bis(4-fluorophenyl) 5-hydroxy-8-(1-methyl-1H-tetrazol-5-yl)-3-oxo-6,8-nonadienoate utilized therein was replaced by 0.12 g of ethyl 11,11-bis(4-fluorophenyl)-5-hydroxy-10-(1-methyl-1H-tetrazol-5-yl)-3-oxo-6,8,10-undecatrienoate [prepared in Example 10, Step B] and there was thereby produced 50 mg (42%) of the title compound after silica gel chromatography.

$^1$H NMR (CDCl$_3$) δ : 7.4–6.8 (8H, m), 6.57 (1H, d, J=15.4 Hz), 6.29 (1H, dd, J=10.8, 15.1 Hz), 5.80 (1H, dd, J=10.7, 15.4 Hz), 5.07 (1H, dd, J=5.7, 15.1 Hz), 4.44 (1H, q, J=5.8 Hz), 4.24 (1H, m), 4.16 (2H, q, J=7.1 Hz), 3.83 (1H, br, D$_2$O exchangeable), 3.65 (1H, br. D$_2$O exchangeable), 3.58 (3H, s), 2.47 (2H, d, J=6.3 Hz), 1.62 (2H, m), 1.28 (3H, t, J=7.1 Hz);

$^{13}$C NMR (CDCl$_3$) δ : 172.43, 162.87 (d, $^1J_{C-F}$=257.46 Hz), 162.47 (d, $^1J_{C-F}$=249.91 Hz), 153.45, 146.20, 138.62, 135.98, 135.50, 133.98, 132.39 (d, $^3J_{C-F}$=8.3 Hz), 131.48 (d, $^3J_{C-F}$=8.3 Hz), 131.18, 129.80, 129.16, 121.95, 115.75 (d, $^2J_{C-F}$=22.0 Hz), 115.67 (d, $^2J_{C-F}$=22.0 Hz), 71.72, 68.34, 60.82, 42.45, 41.57, 33.54, 14.16 ppm.

B. Sodium (±)-erythro-11,11-bis(4-fluorophenyl)-3,5-dihydroxy-10-(1-methyl-1H-tetrazol-5-yl)-6,8,10-undecatrienoate The product from the above Step A was saponified by the general procedure described in Example 12 to produce the title compound in quantitative yield.

$^1$H NMR (DMSO-d$_6$) δ : 7.5–6.8 (8H, m), 6.44 (1H, d, J=15.5 Hz), 6.17 (1H, dd, J=11.4, 14.8 Hz), 5.7 (2H, m) 4.14 (1H, q, J=5.5 Hz), 3.7 (2H, br, D$_2$O exchangeable), 3.67 (3H, s), 3.90 (1H, m), 2.02 (1H, d, J=11.7 Hz), 1.84 (1H, dd, J=8.6, 14.4 Hz), 1.46 (1H, m), 1.29 (1H, m) ppm.

$^{13}$C NMR (DMSO-d$_6$) δ : 176.12, 152.81, 141.50, 136.25, 135.62, 134.02, 132.35, 132.24, 127.72, 128.04, 122.17, 115.48 (d, $^2J_{C-F}$=21.9 Hz), 115.19 (d, $^2J_{C-F}$=21.1 Hz), 68.31, 65.73, 44.59, 43.57, 33.40 ppm.

EXAMPLE 16

Trans-6-[4,4-bis(4-fluorophenyl)-3-(2-methyl-2H-tetrazol-5-yl)-1,3-butadienyl]-tetrahydro-4-hydroxy-2H-pyran-2-one The general procedure of Example 13, Step A and Step B were repeated, except that the ethyl (±)-erythro-9,9-bis(4-fluorophenyl)-3,5-dihydroxy-8-(1-methyl-1H-tetrazol-5-yl)-6,8-nonadienoate utilized therein was replaced by 370 mg of ethyl 9,9-bis(4-fluorophenyl)-3,5-dihydroxy 8-(2-methyl-2H-tetrazol-5-yl)-6,8-nonadienoate and there was thereby produced 146 mg (44%) of the title compound after silica gel chromatography. MS (CI): m/e=439 for (M+H)$^+$;

IR (KBr) $\nu_{max}$: 3438 (v.br), 1731 (s), 1600 (s), 1503 (vs), 1219 (vs), 1153 (s), 1056 (m), 1031 (m), 838 (s) cm$^{-1}$;

$^1$H NMR (CDCl$_3$) δ : 7.29–6.82 (8H, m), 6.69 (1H, d J=15.6 Hz), 5.44 (1H, dd, J=9.0, 15.6 Hz), 5.24 (1H, m), 4.27 (3H, s), 4.30 (1H, m), 4.21 (1H, s, D$_2$O exchangeable), 3.69 (1H, br.s D$_2$O exchangeable), 2.6–2.4 (2H, m), 2.1–1.7 (2H, m);

$^{13}$C NMR (CDCl$_3$) δ : 169.94, 162.70 (d, $^1J_{C-F}$=249.2 Hz), 162.12 (d, $^1J_{C-F}$=249.9 Hz), 147.68, 147.47, 137.27, 136.11, 132.36, (d, $^3J_{C-F}$=8.3 Hz), 131.71 (d, $^3J_{C-F}$=8.3 Hz), 131.17, 131.10, 130.88, 128.62, 124.28), 115.52 (d, $^2J_{C-F}$=20.4 Hz), 114.95 (d, $^2J_{C-F}$=21.9 Hz), 76.16, 62.33, 39.49, 38.66, 35.99 ppm;

Anal. Calcd. for C$_{23}$H$_{20}$F$_2$N$_4$O$_3$ 2H$_2$O: C, 58.22; H, 5.10; N, 11.81. Found: C, 58.92; H, 4.62; N, 11.21.

EXAMPLE 17

Sodium (±)-erythro-9,9-bis(4-fluorophenyl)-3,5-dihydroxy-8-(2-methyl-2H-tetrazol-5-yl)-6,8-nonadienoate The general procedure of Example 12 was repeated, except that the ethyl (±)-erythro-9,9-bis(4-fluorophenyl)-3,5-dihydroxy-8-(1-methyl-1H-tetrazol-5-yl)-6,8-nonadienoate utilized therein was replaced with ethyl 9,9-bis(4-fluorophenyl)-3,5-dihydroxy-8-(2-methyl-1H-tetrazol-5-yl)-6,8-nonadienoate and there was thereby produced after lyophilization a quantitative yield of the title compound as a sodium salt which appears to contain about one mole of water.

IR (KBr) $\nu_{max}$: 3413 (v.br), 1600 (s), 1575 (s), 1500 (s), 1400 (s), 1219 (s), 1088 (s) cm$^{-1}$;

$^1$H NMR (DMSO-d$_6$) δ : 7.36–6.82 (8H, m), 6.50 (1H, d, J=15.5 Hz), 5.28 (1H, dd, J=5.8, 15.5 Hz), 5.0 (1H, br, D$_2$O exchangeable), 4.9 (1H, br. D$_2$O exchangeable), 4.28 (3H, s), 4.13 (1H, d, J=5.94 Hz), 3.64 (1H, m), 2.03 (1H, dd, J=3.6, 14.9 Hz), 1.85, (1H, dd, J=8.7, 14.9 Hz), 1.5–1.2 (2H, m);

$^{13}$C NMR (DMSO-d$_6$) δ : 176.25, 103.18, 161.47, (d, $^1J_{C-F}$=240 Hz), 143.15, 137.60, 136.40, 125.48, 115.12, 114.46, 68.52, 65.84, 44.61, 43.55 ppm.

Anal. Calcd. for C$_{23}$H$_{21}$F$_2$N$_4$O$_4$Na H$_2$O: C, 55.64; H, 4.67; N, 11.29. Found: C, 55.22; H, 4.79; N, 11.21.

EXAMPLE 18

Phenylmethyl 9,9-bis(4-fluorophenyl)-3-hydroxy-8-(1-methyl-1H-tetrazol-5-yl)-5-oxo-6,8-nonadienoate 3,3-(4-fluorophenyl)-2-(1-methyl-1H-tetrazol-5-yl)prop-2-enal (2.50 g, 7.7 mmoles), phenylmethyl 6-(dimethylphosphono)-3-hydroxy-5-oxohexanoate (3.93 g, 11 mmoles), and anhydrous lithium bromide (1.40 g) were combined in acetonitrile, and treated with 1,8-diazobicyclo-[5.4.0]undec-7-ene (1.2 mL, 8.0 mmoles). The mixture was stirred under argon at 23° C. for 44 hours before concentrating in vacuo. The residue was partitioned between CH$_2$Cl$_2$ (50 mL) and ice cold H$_3$PO$_4$ (100 mL). The organic layer was washed with water (2×50 mL), dried over anhydrous Na$_2$SO$_4$, and evaporated to give 4.2 g of an orange foam. The crude product was preabsorbed onto silica and flash chromatographed three times on a silica gel (10–40) column with 40% ethyl acetate/hexane as the eluting solvent to give 0.36 g of the title compound. MS (CI): m/e=545 for (M+H)$^+$;

IR (KBr) $\nu_{max}$: 3440 (OH), 1735 cm$^{-1}$ (C(=O)OCH$_2$);

$^1$H NMR (CDCl$_3$) δ : 2.50 (d, 2H, C-2 or C-4 CH$_2$, J=6.2), 2.63 (d, 2H, C-2 or C-4 CH$_2$, J=5.9), 3.33 (s, 1H, OH), 3.50 (s, 3H, NCH$_3$), 4.42 (m, 1H, CHOH), 5.09 (s, 2H, —OCH$_2$), 5.80 (d, 1H, C-5 olefinic H, J=16), 6.85–7.34 (m, 13H, ArH), 7.52 (d, 1H, C-7 olefinic H, J=16).

EXAMPLE 19

Sodium (±)-9,9-bis(4-fluorophenyl)-3-hydroxy-8-(1-methyl-1H-tetrazol-5-yl)-5-oxo-6,8-nonadienoate Phenylmethyl 9,9-bis(4-fluorophenyl)-3-hydroxy-8-(1-methyl-1H-tetrazol-5-yl)-5-oxo-6,8-nonadienoate (0.34g, 0.62 mmole) was dissolved in tetrahydrofuran (4mL) and water (1mL). 1N Sodium hydroxide (0.62 mL, 0.62 mmole) was added, and the solution was stirred for 6 hours at 24° C. The mixture was diluted with water (10 mL) and washed with diethyl ether (3×50 mL). The aqueous portion was lyophilized to give 0.17 g (52%) of the title compound; m.p.=166°–180° C. (dec.).

IR (KBr) $\nu_{max}$: 1585 cm$^{-1}$ (COO$^-$);

$^1$H NMR (DMSO-d$_6$) δ : 1.76 (dd, 1H, C-4 CH, J=8.4,16), 1.97 (dd, 1H, C-4 CH, J=3.5,16), 2.42 (m, 1H, C-2 CH$_2$), 3.71 (s, 3H, NCH$_3$), 3.93 (m, 1H, CHOC), 5.80 (d, 1H, C-6 olefinic H, J=16), 6.89–6.94 (m, 2H, ArH), 7.06–7.12 (m, 2H, ArH), 7.30 (d, 1H, C-7 olefinic H, J=16), 7.38–7.41 (m, 4H, ArH).

Anal. Calcd. for C$_{23}$H$_{19}$F$_2$N$_4$O$_4$Na 3.5H$_2$O: C, 51.21; H, 4.86; N, 10.39. Found: C, 51.44; H, 3.97; N, 9.46.

EXAMPLE 20

Ethyl 3,3-bis(4-fluorophenyl)-2-[1-(1-methylethyl)-1H-tetrazol-5-yl)]-2-propenoate and ethyl 3,3-bis(4-fluorophenyl)-2-[2-(1-methylethyl)-2H-tetrazol-5-yl]-2-propenoate A. Ethyl 3,3-bis(4-fluorophenyl)-2-[2-(1-methylethyl) 2H-tetrazol-5-yl]-2-propenoate To a chilled (−78° C., dry ice-acetone) solution of ethyl 3,3-bis(4-fluorophenyl)-2-(1-H-tetrazol-5-yl)-2-propenoate (2.6 g, 7.3 mmoles) [prepared in Example 2] in 20 mL of dried N,N-dimethylformamide under argon was added NaH (0.44 g, 11.0 mmoles; 60% in mineral oil) followed by reagent grade 2-iodopropane (2.0 mL, 20.0 mmoles) in one single portion. The thick reaction mixture was stirred under argon at −78° C. for 30 minutes and the mixture was allowed to warm to room temperature slowly over a period of 16 hours. Analytical TLC eluted once with 50% ethyl acetate in hexanes showed only one spot at R$_f$=0.86. The white suspension was diluted with 40 mL of half saturated brine followed by 20 mL of ethyl acetate. The aqueous layer was washed with ethyl acetate (2×20 mL). The organic layers were combined, dried over MgSO$_4$ and concentrated under reduced pressure. Analytical TLC eluted four times with 8% (v/v) ethyl acetate in hexanes showed two spots at R$_f$=0.38(21) and R$_f$=0.49 (21a). The desired products were purified by silica gel column chromatography eluted with 8% EtOAc in hexanes. The fast moving product was collected to give 1.64 g (56.5%) of the title compound. MS (CI): m/e=399 for (M+H)$^+$;

$^1$H NMR(CDCl$_3$) δ : 7.29–6.85 (8H, m), 4.94 (1H, heptet, J=6.7 Hz), 4.09 (2H, q, J=6.9 Hz), 1.50 (6H, d, J=6.8 Hz), 1.01 (3H, t, J=6.9 Hz);

$^{13}$C NMR (CDCl$_3$) δ : 167.04, 163.20 (d, $^1$J$_{C-F}$=284.4 Hz), 162.82 (d, $^1$J$_{C-F}$=240 Hz), 152.65, 136.85, 136.19, 131.83 (d, $^3$J$_{C-F}$=8.3 Hz), 131.04 (d, $^3$J$_{C-F}$=8.3 Hz), 115.97, 115.85, 115.34 (d, $^2$J$_{C-F}$=21.9 Hz), 115.11 (d, $^2$J$_{C-F}$=21.9 Hz), 61.38, 56.48, 22.04, 13.68 ppm.

B. Ethyl 3,3-bis(4-fluorophenyl-2-[1-(1-methylethyl)-1H-tetrazol-5-yl]-2-propenoate The silica gel column from the above Step A was eluted further with 8% EtOAc in hexanes to give the slower moving product (R$_f$=0.38). The appropriate fractions were collected to give 0.95 g (32.7%) of the title compound. MS (CI): m/e=399 for (M+H)$^+$;

$^1$H NMR (CDCl$_3$) δ : 7.25–6.85 (8H, m), 4.30 (1H, heptet, J=6.8 Hz), 4.04 (2H, q, J=7.1 Hz), 1.26 (6H, d, J=6.8 Hz), 1.01 (3H, t, J=7.1 Hz);

$^{13}$C NMR (CDCl$_3$) δ : 165.6, 162.7 (d, $^1$J$_{C-F}$=200 Hz), 155.7, 135.8, 134.2, 132.1 (d, $^3$J$_{C-F}$=8.3 Hz), 131.0 (d, $^3$J$_{C-F}$=6.8 Hz), 115.8 (d, $^2$J$_{C-F}$=21.9 Hz), 115.7 (d, $^2$J$_{C-F}$=21.9 Hz), 61.81, 51.07, 22.18, 13.61 ppm.

EXAMPLE 21

3,3-Bis(4-fluorophenyl)-2-[1-(1-methylethyl)-1H-tetrazol-5-yl]-2-propenal

A. 3,3-Bis(4-fluorophenyl)-2-[1-(1-methylethyl)-1H-tetrazol-5-yl]-2-propenoic acid To a chilled (0° C.) solution of ethyl 3,3-bis(4-fluorophenyl)-2-[1-(1-methylethyl)-1H-tetrazol-5-yl]-2-propenoate (0.95 g, 2.39 mmoles) in 20 mL of 1:1 (v/v) mixture of tetrahydrofuran and methanol was added an aqueous solution of LiOH (4.0 mL, 3 Molar) in one single portion. The reaction mixture was stirred at 0° C. for 15 minutes followed by warming up to ambient temperature. Saponification was allowed to proceed at room temperature for four hours forming a very pale clear solution. The crude reaction mixture was diluted with 12 mL of 2M H$_2$SO$_4$ and the product was extracted into diethyl ether (40 mL×2). The organic layers were combined, dried over MgSO$_4$, concentrated under reduced pressure and then vigorously dried under high vacuum (0.01 mmHg) at room temperature for 24 hours to yield the title compound. The propenoic acid was then utilized in the next step without further purification.

B. 3,3-Bis(4-fluorophenyl)-2-[1-(1-methylethyl)-1H-tetrazol-5-yl]-2-propenol chloride A solution of the dried acid prepared in Step A in 20 mL of dry methylene chloride at room temperature was treated with 4 mL of oxalyl chloride (redistilled over CaH$_2$). The mixture was refluxed under an argon atmosphere for two hours forming a light brownish solution. Most of the volatile solvents were evaporated under reduced pressure and the last traces of oxalyl chloride were removed under high vacuum (0.01 mmHg) at room temperature for 12 hours to give the title compound.

C. 3,3-Bis(4-fluorophenyl)-2-[1-(1-methylethyl)-1H-tetrazol-5-yl]-2-propenol The acid chloride prepared in Step B was dissolved in 20 ml of dry tetrahydrofuran followed by the slow addition of 1.8 mL of lithium aluminum hydride (1.0 Molar in tetrahydrofran) under an argon atmosphere at −78° C. Analytical TLC eluted once with 30% EtOAc in hexanes (v/v) showed the alcohol product at R$_f$=0.46. The crude reaction mixture was poured into dilute H$_2$SO$_4$(2N in H$_2$O) and the desired product was extracted with three portions (40 mL×3)) of diethyl ether. The organic extracts were combined, dried over MgSO$_4$ and concentrated under reduced pressure to give 1.07 g of the title compound which was used without further purification in the next step.

D. 3,3-Bis(4-fluorophenyl)-2-[1-(1-methylethyl)-1H-tetrazol-5-yl]-2-propenal The allylic alcohol (0.96 g) prepared in Step C was dissolved in 45 mL of dry methylene chloride at room temperature and to this vigorousy stirred solution was added 0.64 g (2.96 mmoles) pyridinium chlorchromate in one single portion. After the reaction mixture was stirred for four hours an analytical TLC eluted once with 10% EtOAc in hexanes (v/v) and twice with 20% EtOAc in hexanes (v/v) showed one major product spot at R$_f$=0.22. The crude mixture was poured onto a bed of silica gel about ½ inches thick and eluted with 20% EtOAc in hexanes to give 0.51 g (53%) of the title compound. MS (CI): m/e=355 for (M+H)$^+$.

EXAMPLE 22

3,3-Bis(4-fluorophenyl)-2-[2-(1-methylethyl)-2H-tetrazol-5-yl]-2-propenal

The general procedure of Example 21, Steps A, B, C, and D were repeated, except that the ethyl 3,3-bis(4-flurophenyl)-2-[1-(1-methylethyl)-1H-tetrazol-5-yl]-2-propenoate utilized therein was replaced by ethyl 3,3-bis(4-fluorophenyl)-2-[2-(1-methylethyl)-2H-tetrazol-5-yl]-2-propenoate and there was thereby produced in 88% yield the title compound.

EXAMPLE 23

Ethyl 9,9bis(4-fluorophenyl)-5-hydroxy-8-[1-(1-methylethyl)-1H-tetrazol-5-yl]-3-oxo-6,8-nonadienoate and ethyl 11,11-bis(4-fluorophenyl)-5-hydroxy-10-[1-(1-methylethyl)-1H-tetrazol-5-yl]-3-oxo-6,8,10-undecatrienoate

A. 5,5-Bis(4-fluorophenyl)-4-[1-(1-methylethyl)-1H-tetrazol-5-yl]-2,4-pentadienal and 7,7-bis(4-fluorophenyl)-6-[1-(1-methylethyl)-1H-tetrazol-5-yl]-2,4,6-heptatrienal To a dry mixture of 3,3-bis(4-fluorophenyl)-2-[1-(1-methylethyl)-1H-tetazol-5-yl]-2-propenal (0.51 g, 1.4 mmoles) and triphenylphosphoranylidene acetaldehyde (0.48 g, 1.6 mmoles) under argon at room temperature was added 24 mL dry benzene. The pale brownish suspension was vigorously stirred and heated in an oil bath at about 120° C. The mixture was heated rapidly and reflux was continued overnight (ca. 16 hours). Analytical TLC of the brownish solution eluted five times with 20% EtOAc in hexanes (v/v) showed only one spot at $R_f=0.26$; no traces of the starting aldehyde were detected. The crude reaction mixture was chromatographed on a silica gel column and eluted with about 1 liter of 25% EtOAc in hexanes (v/v). The appropriate fractions yielded 0.54 g (99%) of a mixture of the title compounds which was homogeneous by TLC. This material was used in the next step without further purification.

B. Ethyl 9,9-bis(4-fluorophenyl)-5-hydroxy-8-[1-(1-methylethyl)-1H-tetrazol-5-yl]-3-oxo-6,8nonadienoate and ethyl 11,11-bis(4-fluorophenyl)-5-hydroxy-10-[1-(1-methylethyl)-1H-tetrazol-5-yl]-3-oxo-6,8,10-undecatrienoate Dianon of ethyl acetoacetate (0.36 mL, 2.8 mmoles) in tetrahydrofuran (2.5 mL) was generated as described in Example 10 using NaH (0.11 g, 2.8 mmoles) (60% in mineral oil) and 2.5M n-BuLi in hexane (1.2 mL, 3.0 mmoles) at 0° C. under argon. The dianion solution, after being chilled to −78° C., was transferred via a cannula into a tetrahydrofuran (5 mL) solution at −78° C. containing 0.52 g (1.4 mmoles) of dienal and trienal compounds prepared in Step A. The reaction mixture was stirred at −78° C. under argon for 15 minutes. Analytical TLC eluted twice with 50% EtOAc in hexanes showed mostly one spot at $R_f=0.41$ along with a minor component at $R_f=0.47$. The pale brownish reaction mixture was diluted with 5 mL of 2M $H_2SO_4$ and extacted with EtOAc (40 mL×2). The organic layers were combined, dried over $MgSO_4$ and concentrated under reduced pressure. The products were purified and isolated by silica gel column chromatography using 20% EtOAc in hexanes (v/v) as the eluting solvent. The appropriate fractions with $R_f=0.41$ were combined and evaporated to give 0.29 g (41%) of the title compound ethyl 9,9-bis(4-fluorophenyl)-5-hydroxy-8-[1-(1-methylethyl)-1H-tetrazol-5-yl]-3-oxo-6,8-nonadienoate. $^1$H NMR (CDCl$_3$) δ : 7.29–7.25 (2H, m), 7.12 (2H, t, J=8.64 Hz), 6.93–6.81 (4H, m), 6.75 (1H, d, J=15.5 Hz), 5.27 (1H, dd, J=5.64, 15.5 Hz), 4.62 (1H br.q, J=5.7 Hz), 4.29 (1H, heptet, J=6.6 Hz), 4.17 (2H, q, J=9.1 Hz), 3.46 (2H, br.s), 2.72 (2H, d, J=6.0 Hz), 1.26 (3H, t, J=9.1 Hz), 1.3–1.2 (6H, br. hump) ppm.

The appropriate fracions with $R_f=0.47$ were combined and evaporated to give 0.13 G (17.3%) of the title compound ethyl 11,11-bis(4-fluorophenyl)-5-hydroxy-10-[1-(1-methylethyl)-1H-tetrazol-5-yl]-3-oxo-6,8,10-undecatrienoate.

$^1$H NMR (CDCl$_3$) δ : 7.29–7.22 (2H, m), 7.20–7.10 (2H, m), 6.91–6.80 (4H, m), 6.59 (1H, d, J=15.4 Hz), 6.29 (1H, dd, J=10.7, 15.2 Hz), 5.70 (1H, dd, J=10.7, 15.4 Hz), 5.84 (1H, dd, J=9.9, 15.5 Hz), 4.62 (2H, br), 4.27 (1H, heptet, J=6.6 Hz), 4.17 (2H, q, J=7.0 Hz), 3.46 (2H, s), 3.1 (1H, br, D$_2$O exchangeable), 2.75–2.69 (2H, m), 1.26 (3H, t, J=7.0 Hz), 1.38–1.05 (6H, br. humps, hindered rotation on isopropyl group) ppm.

EXAMPLE 24

Ethyl 9,9-bis(4-fluorophenyl)-5-hydroxy-8-[2-(1-methylethyl)-2H-tetrazol-5-yl]-3-oxo-6,8-nonadienoate and Ethyl 7,7-bis(4-fluorophenyl)-5-hydroxy-6-[2-(1-methylethyl)-2H-tetrazol-5-yl]-3-oxo-6-heptenoate The general procedure of Example 23, Step A was repeated, except that the 3,3-bis(4-fluorophenyl)-2-[1-(1-methylethyl)-1H-tetrazol-5-yl]-2-propenal utilized therein was replaced by 3,3-bis(4-fluorophenyl)-2-[2-(1-methylethyl)-2H-tetrazol-5-yl]-2-propenal and there was thereby produced mostly 5,5-bis(4-fluorophenyl)-4-[2-(1-methylethy)-2H-tetrazol-5-yl]-2,4-pentadienal in 82% yield; MS (CI): m/e=381 for (M+H)$^+$. This product was then subjected to the general procedure of Example 23, Step B and there was thereby produced ethyl 9,9-bis(4-fluorophenyl)-5-hydroxy-8-[2-(1-methylethyl)-2H-tetrazol-5-yl]-3-oxo-6,8-nonadienoate containing some inseparable rthyl 7,7-bis(4-fluorophenyl)-5-hydroxy-6-[2-(1-methylethyl)-2H-tetrazol-5-yl]-3-oxo-6heptenoate in 69% yield.

$^1$H NMR (CDCl$_3$) δ : 7.31–7.11 (2H, m), 7.10–7.04 (2H, m), 6.91–6.78 (4H, m), 6.72 (1H, d, J=15.5 Hz), 5.46 (1H, dd, J=5.91, 15.7 Hz), 4.95 (1H, heptet J=6.8 Hz), 4.64 (1H, br.S), 4.17 (2H, q, J=7.2 Hz), 3.46 (2H, s), 2.75–2.72 (2H, m), 1.49 (6H, d, J=6.8 Hz), 1.28 (3H, t, J=7.2 Hz) ppm.

EXAMPLE 25

Ethyl (±)-erythro-9,9-bis(4-fluorophenyl)-3,5-dihydroxy-8-[1-(1-methylethyl)-1H-tetrazol-5-yl]-6,8-nonadienoate A solution of ethyl 9,9-bis(4-fluorophenyl)-5-hydroxy-8-[1-(1-methylethyl)-1H-tetrazol-5-yl]-3-oxo-6,8-nonadienoate 0.29 g (0.57 mmole) in 6 mL of dry tetrahydrofuran at 0° C. (ice-water bath) under argon, was treated with 0.65 mL of triethylborane in tetrahydrofuran (1.0 Molar solution). The reaction mixture was stirred at −5° C. to 0° C. for an hour before it was chilled to −78° C. (dry ice-acetone bath) under argon. To this pale yellow solution was added solid NaBH$_4$ (25 mg, 0.66 mmole) and the reduction was allowed to proceed at −78° C. for a period of two hours. The reduction was accelerated by adding 25 μL of absolute CH$_3$OH. After an additional hour, analytical TLC eluted once with 1:1 (v/v) EtOAc in hexanes showed complete disappearance of the starting material. The cold reaction mixture was diluted with 20 mL 1M H$_2$SO$_4$ and organic material was extracted into EtOAc (40 mL×2). The organic layers were combined, dried over MgSO$_4$ and concentrated under reduced pressure to give a pale yellow syrup. The syrup was redissolved in 200 mL of MeOH and the solution was allowed to stand at room temperature overnight. Analytical TLC eluted twice with 50% EtOAc in hexanes showed mostly one major spot at $R_f=0.32$. Purification by silica gel column chromatography using 30% (v/v) EtOAc in hexanes yielded 0.23 g (79%) of the title compound.

IR (KBr) $\nu_{max}$: 3438 (v.br), 1731 (s), 1600 (s), 1503 (s), 1225 (s), 1156 (s), 838 (s), 750 (s) cm$^{-1}$;

$^1$H NMR (CDCl$_3$) δ : 7.29–7.25 (2H, m), 7.12 (2H, t, J=8.6 Hz), 6.61–6.93 (4H, m), 6.73 (1H, d, J=15.8 Hz), 5.25 (1H, dd, J=15.8, 6.5 Hz), 4.42 (1H, q, J=5Hz), 4.30 (1H, heptet, J=6.7 Hz), 4.22 (1H, m), 4.22 (2H, v.br. D$_2$O exchangeable), 4.16 (2H, q, J=7.2 Hz), 2.47–2.45

(2H, m), 1.59–1.57 (2H, m), 1.26 (3H, t, J=7.2 Hz), 1.4–1.0 (6H, br, hindered rotation on the isopropyl group);

$^{13}$C NMR (CDCl$_3$) δ : 172.26, 162.8 (d, $^1J_{C-F}$=250.7 Hz), 162.41 (d, $^1J_{C-F}$=250.7 Hz), 152.10, 146.19, 138.44, 137.88, 135.98, 135.40, 132.32 (d, $^3J_{C-F}$=8.3 Hz), 131.72 (d $^3J_{C-F}$=8.3 Hz), 127.61, 121.81, 115.71, (d, $^2J_{C-F}$=21.1 Hz), 115.48 (d, $^2J_{C-F}$=21.1 Hz), 71.63, 68.20, 60.77, 50.78, 42.29, 41.68, 24-20 (v.br for isopropyl signal due to restricted rotation), 14.14 ppm;

Anal. Calcd. for C$_{27}$H$_{30}$F$_2$N$_4$O$_4$: C, 59.11; H, 6.25; N, 10.21. Found: C, 60.40; H, 5.66; N, 9.91.

EXAMPLE 26

Ethyl (±)-erythro-11,11-bis(4-fluorophenyl)-3,5-dihydroxy-10-[1-(1-methylethyl)-1H-tetrazol-5-yl]-6,8,10-undecatrienoate The general procedure of Example 25 was repeated, except that the ethyl 9,9-bis(4-fluorophenyl)-5-hydroxy-8-[1-(1-methylethyl)-1H-tetrazol-5-yl]-3-oxo-6,8-nonadienoate utilized therein was replaced by ethyl 11,11-bis(4-fluorophenyl)-5-hydroxy-10-[1-(1-methylethyl)-1H-tetrazol-5-yl]-3-oxo-6,8,10-undecatrienoate (0.13 g, 0.24 mmole) and there was thereby produced 140 mg of the title compound.

$^1$H NMR (CDCl$_3$) δ : 7.29–7.22 (2H, m), 7.13 (2H, t, J=8.6 Hz, 6.92–6.80 (4H, m), 6.58 (1H, d, J=15.4 Hz), 6.27 (1H, dd, J=10.7, 15.1 Hz), 5.70 (1H, dd, J=10.6, 15.5 Hz), 5.66 (1H, dd, J=5.8, 15.4 Hz), 4.43 (1H, q, J=6.0 Hz), 4.27 (1H, heptet, J=6.5 Hz), 4.24 (1H, m), 4.15 (2H, q, J=7.2 Hz), 3.91 (1H, br, D$_2$O exchangeable) 3.78 (1H, br, D$_2$O exchangeable), 2.48–2.43 (2H, m), 1.65–1.58 (2H, m), 1.42–1.32 and 0.97–0.67 (v.br. humps for isopropyl signals), 1.26 (3H, , J=7.2 Hz) ppm.

EXAMPLE 27

Ethyl (±)-erythro-9,9-bis(4-fluorophenyl)-3,5-dihydroxy-8-[2-(1-methylethyl)-2H-tetrazol-5-yl]-6,8-nonadienoate and ethyl (±)-erythro-7,7-bis(4-fluorophenyl)-3,5-dihydroxy-6-[2-(1-mehylethyl)-2H-tetrazol-5-yl]-6-heptenoate The general procedure of Example 25 was repeated, except that the ethyl 9,9-bis(4-fluorophenyl)-5-hydroxy-8-[1-(1-methylethyl)-1H-tetrazol-5-yl]-3-oxo-6,8-nonadienoate utilized therein was replaced by ethyl 9,9-bis(4-fluorophenyl)-5-hydroxy-8-[2-(1-methylethyl)-2H-tetrazol-5-yl]-3-oxo-6,8-nonadienoate containing some ethyl 7,7-bis(4-fluorophenyl)-5-hydroxy-6-[2-(1-methylethyl)-2H-tetrazol-5-yl]-3-oxo-6-heptenoate [prepared in Example 24] and there was thereby produced after silica gel column chromatography the title compounds in 53% and 38% yield, respectively.

$^1$H NMR (CDCl$_3$) δ: 7.28–7.23 (2H, m), 7.07 (2H, t, J=8.6 Hz), 6.86–6.71 (4H, m), 6.66 (1H, d, J=15.7 Hz), 5.45 (1H, dd, J=6.4, 15.8 Hz), 4.95 (1H, heptet, J=6.7 Hz), 4.43 (1H, br), 4.22 (1H, br), 4.16 (2H, q, J=7.2 Hz), 3.90 (1H, br, D$_2$O exchangeable), 3.64 (1H, br. D$_2$O exchangeable), 2.47–2.43 (2H, m), 1.67–1.60 (2H, m), 1.48 (6H, d, J=6.7 Hz), 1.25 (3H, t, J=7.2 Hz);

$^{13}$C NMR (CDCl$_3$) δ : 172.32, 163.77, 162.53 (d, $^1J_{C-F}$=248.4 Hz), 161.86 (d, $^1J_{C-F}$=247.6 Hz), 145.61, 137.88, 137.05, 136.28, 132.38 (d, $^1J_{C-F}$=8.3 Hz), 131.64 (d, $^3J_{C-F}$=8.3 Hz), 131.19, 131.08, 128.36, 125.42, 115.58 (d, $^2J_{C-F}$=21.9 Hz), 114.67 (d, $^2J_{C-F}$=21.9 Hz), 72.15, 68.08, 60.74, 56.41, 42.54, 41.73, 22.04, 14.17 ppm and $^1$H NMR (CDCl$_3$) δ : 7.30–7.26 (2H, m), 7.07 (2H, t, J=8.6 Hz), 6.94–6.70 (2H, m), 6.83–6.77 (2H, m), 4.92 (1H, heptet, J=6.7 Hz), 4.24 (1H, m), 4.92 (1H, m, methine proton adjacent to one of the hydroxy groups), 4.14 (2H, q, J=7.1 Hz), 4.00 (1H, d, J=6.5 Hz, D$_2$O exchangeable), 3.54 (1H, d, J=2.5 Hz), 2.45–2.42 (2H, m), 1.85 (2H, t, J=6.1 Hz), 1.48 (3H, d, J=6.8 Hz), 1.47 (3H, d, J=6.8 Hz), 1.25 (3H, t, J=7.1 Hz), $^{13}$C NMR (CDCl$_3$) δ : 172.18, 162.91, 162.51, (d, $^1J_{C-F}$=248.4 Hz), 162.00 (d, $^1J_{C-F}$=246.9 Hz), 146.44, 137.33, 135.98, 131.26 (d, $^3J_{C-F}$=8.3 Hz), 131.19 (d, $^1J_{C-F}$=8.3 Hz), 128.33, 115.52 (d, $^2J_{C-F}$=21.1 Hz), 114.73 (d, $^2J_{C-F}$=21.9 Hz), 71.31, 67.77, 60.65, 56.50, 41.85, 41.45, 21.98, 14.18 ppm, respectively.

EXAMPLE 28

Sodium (±)-erythro-9,9-bis(4-fluorophenyl)-3,5-dihydroxy-8-[1-(1-methylethyl)-1H-tetrazol-5-yl]-6,8-nonadienoate To a solution of ethyl (±)-erythro-9,9-bis(4-fluorophenyl)-3,5-dihydroxy-8-[1-(1-methylethyl)-1H-tetrazol-5-yl]-6,8-nonadienoate (230 mg, 0.45 mmole) in 10 mL of tetrahydrofuran at 0° C. (ice-water bath) was added 450 L (1.0 equivalent) of 1N NaOH solution. The emulsion was stirred at 0° C. for one hour forming a clear homogeneous solution. Analytical TLC eluted twice with 50% EtOAc in hexanes showed only one immobile spot at the origin. Most of the volatile solvents were removed under reduced pressure at 10°–15° C. and the aqueous solution was lyophilized under high vacuum at 0° C. to give the title compound in quantitative yield; m.p.>120° C. decomposed.

IR (KBr) ν$_{max}$: 3438 (v.br), 1600 (s), 1581 (s), 1513 (s), 1400 (s), 1225 (s), 1160 (s), 838 (s) cm$^{-1}$;

$^1$H NMR (DMSO-d$_6$) δ : 7.41–7.29 (4H, m), 7.07–6.91 (4H, m), 6.53 (1H, d, J=15.6 Hz), 5.06 (1H, dd, J=5.4, 15.7 Hz), 4.48 (1H, heptet, J=6.6 Hz), 4.14 (1H, q, J=5.9 Hz), 3.64 (1H, m), 3.8–3.2 (2H br. humps), 2.02 (1H, dd, J=3.6, 15.0 Hz), 1.84 (1H, dd, J=8.4, 14.9 Hz), 1.5–1.3 (1H, m), 1.3–1.1 (1H, m), 1.15 (6H, br.s, isopropyl signals showed restricted rotation);

$^{13}$C NMR (DMSO-d$_6$) δ : 176.30, 161.82 (d, $^1J_{C-F}$=246.1 Hz), 161.41 (d, $^1J_{C-F}$=246.9 Hz), 151.53, 144.45, 139.87, 136.11, 135.45, 132.14 (d, $^3J_{C-F}$=8.3 Hz), 131.28 (d, $^3J_{C-F}$=8.3 Hz), 125.39, 122.23, 115.44 (d, $^2J_{C-F}$=21.9 Hz), 115.05 (d, $^2J_{C-F}$=21.9 Hz), 68.14, 65.68, 50.05, 44.48, 43.48, 22.06 ppm;

Anal. Calcd. for C$_{25}$H$_{25}$F$_2$N$_4$O$_4$Na 2H$_2$O: C, 55.35; H, 5.39; N, 10.32. Found: C, 54.63; H, 4.79; N, 9.35.

EXAMPLE 29

Sodium (±)-erythro-11,11-bis(4-fluorophenyl)-3,5-dihydroxy-10-[1-(1-methylethyl)-1H-tetrazol-5-yl]-6,8,10-undecatrienoate The product of Example 26 was subjected to the general procedure of Example 28 and there was thereby produced the title compound in quantitative yield; m.p.>100° C. decomposed.

IR (KBr) ν$_{max}$: 3425 (v.br), 1600 (s), 1575 (sh, s), 1513 (s), 1400 (s), 1225 (s), 1163 (s), 838 (s) cm$^{-1}$;

$^1$H NMR (DMSO-d$_6$) δ : 7.42–7.30 (4H, m), 7.14–7.03 (2H, m), 6.92–6.87 (2H, m), 6.46 (1H, d, J=15.4 Hz), 6.17 (1H, dd, J=14.8, 15.4 Hz), 5.72 (1H, dd, J=5.2, 14.9 Hz), 5.61 (1H, dd, J=10.9, 15.3 Hz), 5.0 (1H, br), 4.48 (1H, heptet, J=6.6 Hz), 4.12 (1H, m), 3.64 (1H, br), 2.01 (1H, d, J=12.6 Hz), 1.84 (1H, dd, J=8.0, 14.3 Hz), 1.6–0.8 (6H, v.br. hump, isopropyl signals showed restricted rotation);

$^{13}$C NMR (DMSO-d$_6$) δ : 175.93, 162 (d, $^1J_{C-F}$250 Hz), 161 (d, $^1J_{C-F}$250 Hz), 151.35, 144.71, 141.56, 136.09, 135.57, 133.82, 132.31 (d, $^3J_{C-F}$=8.3 Hz), 131.41 (d, $^3J_{C-F}$=8.3 Hz), 128.65, 127.61, 122.58, 115.46 (d, $^2J_{C-F}$=21.1 Hz), 115.14 (d, $^2J_{C-F}$=21.9 Hz), 68.41, 65.83, 50.11, 44.65, 43.51, 22.07 (v.br signals for isopropyl carbon) ppm.

EXAMPLE 30

Sodium (±)-erythro-9,9-bis(4-fluorophenyl)-3,5-dihydroxy-8-[2-(1-methylethyl)-2H-tetrazol-5-yl]-6,8-nonadienoate The ethyl 9,9-bis(4-fluorophenyl)-3,5-dihydroxy-8-[2-(1-methylethyl)-2H-tetrazol-5-yl]-6,8nonadienoate prepared in Example 27 was treated by the general procedure of Example 28 and there was thereby produced the title compound a in quantitative yield; m.p.>120° C. decomposed.

IR (KBr) $\nu_{max}$: 3438 (v.br), 1600 (s), 1513 (s), 1483 (m), 1400 (m), 1321 (s), 1225 (s), 1188 (m), 1156 (s), 838 (S) cm$^{-1}$;

$^1$H NMR (DMSO-d$_6$) δ : 7.29–7.22 (4H, m), 6.95 (2H, t, J=8.8 Hz), 6.84–6.78 (2H, m), 6.53 (1H, d, J=15.6 Hz), 5.34 (1H, dd, J=5.6, 15.6 Hz), 5.02 (1H, heptet, J=6.7 Hz), 4.15 (1H, q, J=5.9 Hz), 3.65 (1H, q, J=4.0 Hz), 3.37 (2H, br.S, D$_2$O exchangeable), 2.04 (1H, dd, J=15.0, 3.5 Hz), 1.85 (1H, dd, J=8.6, 15.1 Hz), 1.40 (6H, d, J=6.7 Hz), 1.47–1.23 (2H, br. humps);

$^{13}$C NMR (DMSO-d$_6$) δ : 176.28, 162.88, 161.59 (d, $^1J_{C-F}$=246.13 Hz), 160.94 (d, $^1J_{C-F}$=245.4 Hz), 143.20, 139.49, 137.81, 136.26, 132.06 (d, $^3J_{C-F}$=8.3 Hz), 131.30 (d, $^3J_{C-F}$=8.3 Hz), 130.93, 126.00, 125.85, 115.32 (d, $^2J_{C-F}$=21.9 Hz), 114.46 (d, $^2J_{C-F}$=21.9 Hz), 79.09, 68.53, 65.83, 55.72, 44.64, 43.53, 30.36, 21.69 ppm.

Anal. Calcd. for C$_{25}$H$_{25}$F$_2$N$_4$O$_4$Na 2H$_2$O: C, 55.35; H, 5.39; N, 10.32; Found: C, 55.96; H, 4.86; N, 10.27.

EXAMPLE 31

Sodium (±)-erythro-7,7-bis(4-fluorophenyl)-3,5-dihydroxy-6-[2-(1-methylethyl)-2H-tetrazol-5-yl]-6-heptenoate The ethyl 7,7-bis(4-fluorophenyl)-3,5-dihydroxy-6-[2-(1-methylethyl)-2H-tetrazol-5-yl]-6-heptenoate prepared in Example 27 was treated by the general procedure of Example 28 and there was thereby produced the title compound in quantitative yield; m.p.>120° C. decomposed.

IR (KBr) $\nu_{max}$: 3438 (s, v.br), 1600 (s), 1575 (s), 1512 (s), 1406 (s), 1225 (s), 1156 (s), 838 (s) cm$^{-1}$;

$^1$H NMR (DMSO-d$_6$) δ : 7.41–7.36 (2H, m), 7.23 (2H, t, J=8.7 Hz), 6.93 (2H, t, J=8.8 Hz), 6.86–6.82 (2H, m), 4.98 (1H, heptet, J=6.7 Hz), 4.67 (1H, t, J=6.7 Hz), 3.76 (1H, m), 3.35 (br.S, D$_2$O exchangeable), 1.99 (1H, dd, J=3, 15.0 Hz), 1.80–1.63 (3H, m), 1.41 (3H, d, J=6.4 Hz), 1.38 (3H, d, J=6.5 Hz);

$^{13}$C NMR (DMSO-d$_6$) δ : 176.42, 161.34 (d, $^1J_{C-F}$=244.6 Hz), 160.7 (d, $^1J_{C-F}$=237.1 Hz), 162.25, 143.93, 137.88, 136.44, 131.11 (d, $^3J_{C-F}$=8.0 Hz), 130.85 (d, $^3J_{C-F}$=8.0 Hz), 114.97 (d, $^2J_{C-F}$=21.1 Hz), 114.33 (d, $^2J_{C-F}$=21.1 Hz) 67.76, 65.80, 55.40, 43.12, 42.89, 30,33, 21.78, 21.58 ppm (nonequivalent isopropyl signals);

Anal. Calcd. for C$_{23}$H$_{23}$F$_2$N$_4$O$_4$Na H$_2$O: C, 55.42; H, 5.05; N, 11.24; Found: C, 56.01; H, 4.94; N, 10.79.

EXAMPLE 32

Ethyl 3,3-bis(4-fluorophenyl)-2-[2-(1,1-dimethyl-ethyl)-2H-tetrazol-5-yl]-2-propenoate To a stired suspension of 10 mg of 10 g of ethyl 3,3-bis-(4-fluorophenyl)-2-(1H-tetrazol-5-yl)-2-propenoate in 250 mL dry diethyl ether cooled at −50° C. was slowly added 60 mL of liquid isobutylene (previously condensed from gaseous material in a dry·ice-alcohol bath). With continued stirring and cooling, 50 mL of concentrated H$_2$SO$_4$ was added slowly and carefully. The mixture was then sealed in a stainless steel Parr container and stirred at −30° C. for 40 hours. After releasing the pressure, the mixture was added slowly and carefully to excess saturated NaHCO$_3$ solution. The aqueous mixture was extracted with diethyl ether, dried over Na$_2$SO$_4$ and concentrated in vacuo to give 7.8 g (67.8%) of the title compound, m.p. 143–144° C.

IR (KBr) $\nu_{max}$: 3438 (v.br.), 1738 (s), 1625 (s), 1600 (s), 1240 (s), 1225 (s), 842 (s) cm$^{-1}$;

$^1$H NMR (CDCl$_3$) δ : 7.29–7.24 (2H, m), 7.07–6.84 (6H, m), 4.10 (2H, q), 1.59 (9H, s), 1.03 (3H, t) ppm.

Anal. Calcd. for C$_{21}$H$_{22}$F$_2$N$_4$O$_2$: C, 64.07; H, 5.38; N, 13.58. Found: C, 64.15; H, 5.25, N, 13.58.

EXAMPLE 33

3,3-Bis (4-fluorophenyl)-2-[2-(1,1-dimethylethyl)-2H-tetrazol-5-yl]-2-propenal

A. 3,3-Bis(4-fluorophenyl)-2-[2-(1,1-dimethylethyl)-2H-tetrazol-5-yl]-2-propenol To a stired solution of ethyl 3,3-bis(4-fluorophenyl)-2-[2-(1,1-dimethylethyl)-2H-tetrazol-5-yl]-2-propenoate (2.0 g, 4.8 mmoles) in dry methylene chloride (10 mL) under argon at −78° C. was added 10 mL of diisobutylaluminum hydride solution (1.0 Molar solution in methylene chloride) over a period of three minues. The reduction was llowed to proceed at −78° C. under argon for two hours. Analytical TLC eluted twice with 20% (v/v) ethyl acetate in hexanes showed no starting material at R$_f$=0.42 and a major spot at R$_f$=0.14 for desired product. The crude reaction mixture (at −78° C.) was diluted with 10 mL of 2N HCl followed by extractions with ethyl acetate (40 mL×2). The organic layers were combined, dried over MgSO$_4$, evaporated under reduced pressure and dried under high vacuum at room temperature overnight to give the title compound which was used without further purification in the next step.

$^1$H NMR (60 MHz) (CDCl$_3$) δ : 7.4–6.9 (8H, m), 9.7 (≈1/4H, s, small amount of aldehyde), 4.6 (2H, d, J=6 Hz), 1.56 (9H, s) ppm.

B. 3,3-Bis(4-fluorophenyl)-2-[2-(1,1-dimethylethyl)-2H-tetrazol-5-yl]-2-propenal The crude allylic alcohol prepared in Step A was dissolved in 60 mL of dry methylene chloride and to this vigorously stirred solution at room temperature under argon was added pyridinium chlorochromate (1.2 g, 5.5 mmoles) in one single portion. The slightly exothermic oxidation was allowed to proceed at room temperature for two hours. Analytical TLC eluted twice with 20% (v/v) ethyl acetate in hexanes showed the aldehyde at $R_f=0.35$. The crude reaction mixture was chromatographed on a silica gel column and eluted with 1 liter of 5% (v/v) ethyl acetate in hexanes to give 1.59 g (89%) of a TLC homogenous product. Recrystallization from EtOAc-hexanes mixture yielded pure title compound; m.p. 131°-133° C.

IR (KBr) $\nu_{max}$: 3488 (m), 1669 (s), 1600 (s), 1508 (s), 1475 (m), 1231 (s), 1219 (s), 1156 (s), 850 (s) cm$^{-1}$;

$^1$H NMR (CDCl$_3$) δ : 9.72 (1H, s), 7.38–7.33 (2H, m), 7.17 (2H, t, J=8.6 Hz), 7.00–6.84 (4H, m), 1.63 (9H, s);

$^{13}$C NMR (CDCl$_3$) δ : 190.14, 164.27 (d, $^1J_{C-F}$=246.1 Hz), 163.35 (d, $^1J_{C-F}$=240 Hz), 162.5, 160.9, 135.82, 133.58, (d, $^3J_{C-F}$=8.3 Hz), 132.26 (d, $^3J_{C-F}$=8.3 Hz), 128.4, 115.85 (d, $^2J_{C-F}$=21.9 Hz), 115.22 (d, $^2J_{C-F}$=21.9 Hz), 63.95, 29.24 ppm;

Anal. Calcd. for C$_{20}$H$_{18}$F$_2$N$_4$O: C, 65.21; H, 4.92; N, 15.21. Found: C, 65.33; H, 4.93; N, 15.44.

EXAMPLE 34

5,5-Bis(4-fluorophenyl)-4-[2-(1,1-dimethylethyl)-2H-tetrazol-5-yl]-2,4-pentadienal To a warm, stirring solution of 3,3-bis(4-fluorophenyl)-2-[2-(1,1-dimethylethyl)-2H-tetrazol-5-yl]2-propenal (1.59 g, 4.3 mmoles) in 60 mL of dry benzene under argon was added triphenylphosphoranylidene acetaldehyde (1.45 g, 4.7 mmoles) in one single portion. The reagents dissolved rapidly into the warm (55° C.) solution and the homogeneous mixture was gradually heated to reflux for 16 hours. Analytical TLC eluted five times with 20% (v/v) ethyl acetate in hexanes showed the desired product at $R_f$=0.52. The crude reaction mixture was chromatographed on a silica gel column and eluted with 10% (v/v) ethyl acetate in hexanes to give 1.7 g of product. Recrystallization from EtOAc-hexanes mixture yielded pure title compound; m.p.=171°-174° C.

IR (KBr) $\nu_{max}$: 3000 (s), 1675 (s), 1669 (s), 1600 (s), 1508 (s), 1225 (s), 1159 (s), 1119 (s), 843 (s) cm$^{-1}$;

$^1$H NMR (CDCl$_3$) δ : 9.55 (1H, d, J=7.4 Hz), 7.50 (1H, d, J=15.6 Hz), 7.33–7.26 (2H, m), 7.18–7.13 (2H, m), 6.92–6.79 (4H, m), 5.96 (1H, dd, J=7.5, 15.6 Hz), 1.63 (9H, s);

$^{13}$C NMR (CDCl$_3$) δ : 193.38, 163.5 (d, $^1J_{C-F}$=240 Hz), 162.5 (d, $^1J_{C-F}$=240 Hz), 154.5, 151.5, 149.49, 137.0, 135.5, 132.81 (d, $^3J_{C-F}$=8.3 Hz), 132.05 (d, $^3J_{C-F}$=8 Hz), 115.80 (d, $^2J_{C-F}$=21.9 Hz), 114.98 (d, $^2J_{C-F}$=21.9 Hz), 64.3, 29.23 ppm;

Anal. Calcd. for C$_{22}$H$_{20}$F$_2$N$_4$O: C, 66.99; H, 5.10; N, 14.18. Found: C, 67.14; H, 5.17; N, 14.55.

EXAMPLE 35

Ethyl (±)-erythro-9,9-bis(4-fluorophenyl)-3,5-dihydroxy-8-[2-(1,1-dimethylethyl)-2H-terazol-5-yl)-6,8-nonadienoate.

A. Ethyl 9,9bis(4-fluorophenyl)-5-hydroxy-8-[2-(1,1-dimethylethyl)-2H-tetrazol-5-yl)-3-oxo-6,8-nonadienoate A solution of the dianion of ethyl acetoacetate (400 μL, 3.1 mmoles) in 8 mL of dry tetrahydrofuran was generated as described in Example 10 using 130 mg (3.2 mmoles) of NaH (60% in mineral oil) and 2.5M n-BuLi in hexanes (1.27 mL, 3.2 mmoles) at 0° C. under argon. The orange dianion solution, after being chilled to −78° C., was transferred via a cannula into a tetrahydrofuran (12 mL) solution at −78° C. containing 5,5-bis(4-fluorophenyl)-4-[2-(1,1-dimethylethyl)-2H-tetrazol-5-yl]-2,4-pentadienal (0.96 g, 2.4 mmoles). The reaction mixture was stirred at −78° C. for five minutes. Analytical TLC eluted once with 50% (v/v) EtOAc in hexanes showed the major product spot at $R_f$=0.35. The reaction mixture was diluted with 20 mL of 1N HCl and the organic material was extracted with EtOAc (20 mL×2). The organic layers were combined, dried over MgSO$_4$, evaporated under reduced pressure, and dried under high vacuum (0.001 mmHg) at ambient temperature overnight (16 hours) to give the title compound which was used in the next step without further purification.

B. Ethyl (±)-erythro-9,9-bis(4-fluorophenyl)-3,5-dihydroxy-8-[2-(1,1-dimethylethyl)-2H-tetazol-5-yl)-6,8-nonadienoate The crude ketone from Step A was dissolved in 10 mL of dry tetrahydrofuran under argon at 0° C. To this pale brownish solution was added 3.0 mL of 1.0 Molar triethylborane in tetrahydrofuran. The mixture was allowed to stir at 0° C. for 1.5 hours before it was chilled to −78° C. (dry ice-acetone bath). To this stirring solution was added 120 mg (3.2 mmoles) of NaBH$_4$ and the reduction was allowed to proceed at −78° C. for a period of three hours. The cold reaction mixture was diluted with 10 mL of 1N HCl and the product was extracted into ethyl acetate (40 mL×2). The organic layers were combined, dried over MgSO$_4$ and evaporated to dryness. The crude product was redissolved into 200 mL of absolute methanol and the solution was stirred for 16 hours. Analytical TLC eluted with 50% (v/v) ethyl acetate in hexanes showed only one major spot at $R_f$=0.31. Silica gel column chromatography using 10–20% EtOAc in hexanes as the eluting solvent yielded 1.07 g (83.5%) of the title compound.

IR (KBr) $\nu_{max}$: 3438 (s), 1731 (s), 1600 (s), 1503 (v.s.), 1225 (s), 1156 (s), 838 (s), 750 (s) cm$^{-1}$;

$^1$H NMR (CDCl$_3$) δ : 7.28–7.24 (2H, m), 7.07 (2H, t, J=8.6 Hz), 6.86–6.73 (4H, m), 6.69 (1H, d, J=15.7 Hz), 5.48 (1H, dd, J=6.3, 15.8 Hz), 4.44 (1H, m), 4.23 (1H, m), 4.16 (2H, q, J=7.0 Hz), 3.85 (1H, br, D$_2$O exchangeable), 3.50 (1H, br. D$_2$O exchangeable), 2.48–2.45 (2H, m), 1.69–1.54 (2H, m), 1.59 (9H, s), 1.26 (3H, t, J=7.0 Hz);

$^{13}$C NMR (CDCl$_3$) δ : 172.38, 162.5 (d, $^1J_{C-F}$=249.2 Hz), 161.82 (d, $^1J_{C-F}$=2.48.4 Hz), 145.53, 137.96, 136.96, 136.29, 132.35 (d, $^3J_{C-F}$=8.3 Hz), 131.61 (d, $^3J_{C-F}$=7.6 Hz), 128.39, 125.58, 115.31 (d, $^2J_{C-F}$=21.9 Hz), 114.59 (d, $^2J_{C-F}$=21.9 Hz), 72.24, 68.10, 63.75, 60.75, 42.52, 41.62, 29.16, 14.15 ppm.

Anal. Calcd. for C$_{28}$H$_{32}$F$_2$N$_4$O$_4$·H$_2$O: C, 61.75; H, 6.29; N, 10.28. Found: C, 61.22; H, 6.03; N, 10.02.

EXAMPLE 36

Sodium (±)-erythro-9,9-bis(4-fluorophenyl)-3,5-dihydroxy-8-[2-(1,1-dimethylethyl-2H-tetrazol-5-yl)-6,8-nonadienoic acid, sodium salt To a solution of ethyl (±)-erythro-9,9-bis(4-fluorophenyl)-3,5-dihydroxy-8-[2-(1,1-dimethylethyl)-2H-tetrazol-5-yl-6,8-nonadienoate (330 mg, 0.63 mmole) in 6 mL of tetrahydrofuran at 0° C. was added 630 μL of 1 Molar NaOH solution. The turbid suspension was stirred at 0° C. for 30 minutes and then at ambient temperature for an additional 2.5 hours forming a clear homogeneous solution. Analytical TLC eluted once with 50% (v/v) ethyl acetate in hexanes showed no starting material other than the immobil spot at the origin. Most of the volatile solvents were evaporated under reduced pressure at about 10°–15° C. The solution of the sodium salt of the product was lyophilized under high vacuum to give 320 mg (quantitative) of the title compound; m.p. >120° C. decomposed.

IR (KBr) $\nu_{max}$: 3413 (v.br), 1600 (s), 1575 (s), 1503 (s), 1338 (s), 1225 (s), 1156 (s), 838 (s) cm$^{-1}$;

$^1$H NMR (DMSO-d$_6$) δ: 7.29 (4H, d, J=7.2 Hz), 6.95 (2H, t, J=8.9 Hz), 6.83–6.78 (2H, m), 6.53 (1H, d, J=15.5 Hz), 5.37 (1H, dd, J=5.6, 15.6 Hz), 5.0 (1H, br. D$_2$O exchangeable), 4.16 (1H, q, J=6.1 Hz), 3.67 (1H, m), 3.37 (1H, br. D$_2$O exchangeable, 2.05 (1H, dd, J=15.1, 3.5 Hz), 1.86 (1H, dd, J=8.6, 15.1 Hz), 1.53–1.29 (2H, m), 1.54 (9H, s);

$^{13}$C NMR (DMSO-d$_6$) δ: 176.40, 162.50, 161.54 (d, $^1J_{C-F}$=246.1 Hz), 160.98 (d, $^1J_{C-F}$=259.7 Hz), 143.15, 139.54, 137.87, 136.23, 132.0 (d, $^3J_{C-F}$=8.3 Hz), 131.25 (d, $^3J_{C-F}$=7.6 Hz), 125.91, 115.31 (d, $^2J_{C-F}$=21.9 Hz), 114.43 (d, $^2J_{C-F}$=21.9 Hz), 68.45, 65.75, 63.35, 44.64, 43.52, 28.53 ppm.

Anal. Calcd. for C$_{26}$H$_{27}$F$_2$N$_4$O$_4$Na H$_2$O: C, 56.11; H, 5.61; N, 10.07. Found: C, 56.96; H, 5.06; N, 9.99.

EXAMPLE 37

4,4'-Difluoro-3,3'-dimethylbenzophenone

2-Fluorotoluene (8 ml, 73 mmoles) was added to a vigorously stirred mixture of aluminum chloride (61.43 g, 460 mmoles) and carbon tetrachloride (135 ml) at 0° C. After 10 minutes 2-fluorotoluene (92 ml, 837 mmoles) in carbon tetrachloride (75 mL) was added dropwise over 4 hours and the mixture stirred for 2 hours at 0° C. *WARNING: A spontaneous vigorous reaction occurred after the addition of 2-fluorotoluene.* The mixture was cooled to −20° C. and quenched with 2N HCl (250 mL). The organic layer was separated, washed with brine and dried (MgSO$_4$). The solvent was removed by evaporation and the residue dissolved in benzene (200 mL) and treated with water (200 mL) and acetic acid (50 ml). After stirring for 15 hours, the organic layer was separated, dried (MgSO$_4$) and evaporated. Crystallization from ethanol afforded 50 g (49%) of the title compound; m.p.=128°–130° C.

IR (KBr) $\nu_{max}$: 1650 cm$^{-1}$.

$^1$H NMR (CDCl$_3$) δ: 7.66 (d, J=7.3 Hz, 2H), 7.58 (m, 2H), 7.09 (t, J=8.8 Hz, 2H), 2.32 (s, 6H).

Anal. Calcd. for C$_{15}$H$_{12}$F$_2$O: C, 73.16; H, 4.91. Found: C, 72.96; H, 4.80.

EXAMPLE 38

1,1-Bis(4-fluoro-3-methylphenyl)-2-(1-methyl-1H-tetrazol-5-yl) ethanol

A solution of 1,5-dimethyltetrazole (2.55 g, 26 mmoles) in dry tetrahydrofuran (15 ml) at −78° C. was treated with n-butyllithium (12.5 ml of a 2.5M solution in hexane, 31.2 mmoles) and the mixture stirred for 15 minutes. 4,4'-Difluoro-3,3'-dimethylbenzophenone (5 g, 20.3 mmoles) in dry tetrahydrofuran (20 ml) was added, the mixture stirred for 1 hour, then quenched with 2N HCl (250 ml). The aqueous phase was extracted with ethyl acetate (3×50 ml) and the combined organic layer was dried (MgSO$_4$) and evaporated. The residue was purified by silica gel column chromatography using 20% (v/v) EtOAc-hexane as eluent to afford 3.7 g, (52%) of the product. Recrystallization from EtOAc-hexanes yielded the title compound; m.p. 41°–42° C.

IR (KBr) $\nu_{max}$: 3400 (br) cm$^{-1}$;

$^1$H NMR (CDCl$_3$) δ: 7.20 (d, J=7.1 Hz), 2M), 7.10 (m, 2H), 6.88 (t, J=8.6 Hz, 2H), 4.84 (s, 1H), 3.77 (s, 3H), 3.71 (s, 2H), 2.20 (s, 6H);

Anal. Calcd. for C$_{18}$H$_{18}$F$_2$N$_4$O: C, 62.79; H, 5.27; N, 16.27. Found: C, 62.73; H, 5.32; N, 16.16.

EXAMPLE 39

1,1-Bis(4-fluoro-3-methylphenyl)-2-(1-methyl-1H-tetrazol-5-yl)ethene

A mixture of 1,1-bis(4-fluoro-3-methylphenyl)-2-(1-methyl-1H-tetrazol-5-yl)ethanol (3.58 g, 10.9 mmoles) and potassium hydrogen sulfate (530 mg) was heated at 195° C. for 1.5 hours. The mixture was cooled to 70° C. and chloroform (50 ml) was added. The insoluble material was removed by filtration and the filtrate evaporated. The residue was crystallized from EtOAc-Hexane to afford 3.38 g (100%) of the title compound; m.p.=138°–139° C.

$^1$H NMR (CDCl$_3$) δ: 7.20–6.80 (m, 6H), 6.65 (s, 1H), 3.56 (s, 3H), 2.28 (s, 3H), 2.18 (s, 3H).

Anal. Calcd. for C$_{18}$H$_{16}$F$_2$N$_4$: C, 66.25; H, 4.95; N, 17.17. Found: C, 66.15; H, 5.05; N, 17.24.

EXAMPLE 40

3,3-Bis(4-fluoro-3-methylphenyl)-2-(1-methyl-1H-tetrazol-5-yl)-2-propenal

A solution of 1,1-bis(4-fluoro-3-methylphenyl)-2-(1-methyltetrazol-5-yl)ethene (3.58 g, 11.0 mmoles)) in dry tetrahydrofuran (20 mL) at −78° C. was treated with n-butyllithium (5.3 ml of 2.5M solution in hexane; 13.25 mmoles) and the mixture stirred at −78° C. for 0.5 hours. Ethyl formate (1.33 ml; 1.22 g, 16.5 mmoles) was added and the mixture was allowed to warm up to 23° C. over 1 hour, then quenched with 2N HCl (250 mL). The aqueous phase was extracted with ethyl acetate (3×50 mL) and the combined organic layers were dried (MgSO$_4$) and evaporated. The residue was purified by chromatography using 20% EtOAc-Hexane as eluent to afford 2.2 g (57%) of the title compound as a foam. MS (CI): m/e=355 for (M+H)$^+$;

IR (KBr) $\nu_{max}$: 1660 cm$^{-1}$;

$^1$H NMR (CHCl$_3$) δ: 9.62 (s, 1H), 7.25–7.05 (m, 3H), 6.85–6.65 (m, 3H), 3.73 (s, 3H), 2.34 (s, 3H), 2.13 (s, 3H).

Anal. Calcd. for C$_{19}$H$_{16}$F$_2$N$_4$O: C, 64.41; H, 4.56; N, 15.82. Found: C, 64.60; H, 4.70, N, 15.62.

EXAMPLE 41

5,5-Bis(4-fluoro-3-methylphenyl)-4-(1-methyl-1H-tetrazol-5-yl)-2,4-pentadienal

To a mixture of 3,3-bis(4-fluoro-3-methylphenyl)-2-(1-methyl-1H-tetrazol-5-yl)-2-propenal (2.12 g, 5.98 mmoles) and triphenylphosphoranylidene acetaldehyde (1.89 g, 6.22 mmoles) under an argon atmosphere was added dry benzene (26 mL). The suspension was quickly warmed to reflux under argon in an oil bath. The solids dissolved very rapidly at the reflux temperature and the color became dark brownish. The reaction was allowed to proceed at reflux temperature for a total of 60 minutes. Analytical TLC eluted ten times with 20% (v/v) ethyl acetate in hexanes showed the desired product at R$_f$=0.35. The crude reaction mixture was poured over a short bed of silica gel and eluted with 2 liters of 20% (v/v) ethyl acetate in hexanes to give 2.12 g (93.3%) of the title compound (TLC homogeneous). MS (CI): m/e=381 for (M+H)+;

IR (KBr) $\nu_{max}$: 1679 (s), 1606 (s), 1591 (s), 1500 (s), 1438 (m), 1250 (s), 1231 (s), 1138 (s), 1125 (s) cm$^{-1}$;

$^1$H NMR (CHCl$_3$) δ: 9.53 (1H, d, J=7.47 Hz), 7.44 (1H, d, J=16.0 Hz), 7.15–7.09 (3H, m), 6.9–6.7 (3H, m), 5.80 (1H, dd, J=15.6, 7.44 Hz), 3.55 (3H, s), 2.33 (3H, d, J=1.9 Hz), 2.11 (3H, d, J=1.8 Hz);

$^{13}$C NMR (CDCl$_3$) δ: 192.51, 162.4 (d, $^1J_{C-F}$=250.7 Hz) 162.0 (d, $^1J_{C-F}$=250 Hz), 156.23, 152.57, 147.82, 134.88, 134.83, 134.37, 133.77 (d, $^3J_{C-F}$=6.04 Hz), 133.19, (d, $^3J_{C-F}$=6.04 Hz), 131.94, 130.04 (d, $^3J_{C-F}$=8.31 Hz), 129.32 (d, $^3J_{C-F}$=8.31 Hz), 126.22, 126.00, 119.57, 115.66 (d, $^2J_{C-F}$=23.4 Hz), 115.59 (d, $^2J_{C-F}$=23.41 Hz), 33.64, 14.59, 14.36 ppm;

Anal. Calcd. for C$_{21}$H$_{18}$F$_2$N$_4$O: C, 66.31; H, 4.77; N, 14.73. Found: C, 66.36; H, 4.71; N, 14.15.

EXAMPLE 42

Ethyl 9,9-bis(4-fluoro-3-methylphenyl)-5-hydroxy-8-(1-methyl-1H-tetrazol-5-yl)-3-oxo-6,8-nonadienoate A solution of the dianion of ethyl acetoacetate (1.42 mL, 11.1 mmoles) in dry tetrahydrofuran (15 mL) was generated as described in Example 10 using 450 mg (11.3 mmoles) of NaH (60% in mineral oil) and 4.5 mL (11.1 mmoles) of 2.5M n-BuLi in hexane at 0° C. under argon. The orange dianion solution, after being chilled to −78° C., was transferred via a cannula into a tetrahydrofuran (15 mL) solution containing 5,5-bis(4-fluoro-3-methylphenyl)-4-(1-methyl-1H-tetrazol-5-yl)-2,4-pentadienal (2.12 g, 5.6 mmoles) at −78° C. The reaction mixture was stirred at −78° C. for 15 minutes. Analytical TLC eluted once with 50% (v/v) ethyl acetate in hexanes showed a major product at R$_f$=0.16. The reaction mixture was diluted with 20 mL of 1N HCl and the organic residues were extracted with ethyl acetate (30 mL×2). The organic layers were combined, dried over MgSO$_4$ and concentrated under reduced pressure to give a pale syrup. The crude product was chromatographed on a silica gel column eluted with 35% (v/v) ethyl acetate in hexanes to give 1.39 g (48.7%) of the title compound. MS (CI): m/e=511 for (M+H)+;

IR (KBr) $\nu_{max}$: 3219 (v.s, br), 3000 (s), 1744 (s), 1719 (s), 1500 (s), 1325 (m), 1250 (s), 1231 (s), 1119 (s), 1035 (s), 735 (s) cm$^{-1}$;

$^1$H NMR(CDCl$_3$) δ: 7.1–7.0 (3H, m), 6.8–6.6 (3H, m), 6.68 (1H, d, J=15.63 Hz), 5.30 (1H, dd, J=5.76, 15.63 (Hz), 4.63 (1H, br), 4.18 (2H, q, J=6.96 Hz), 3.54 (3H, s), 3.44 (2H, s), 2.93 (1H, br, D$_2$O exchangeable), 2.65–2.75 (2H, m), 2.29 (3H, d, J=1.65 Hz), 2.08 (3H, d, J=1.41 Hz), 1.27 (3H, t, J=6.96 Hz);

$^{13}$C NMR (CDCl$_3$) δ: 166.66, 161.52 (d, $^1J_{C-F}$=248.40 Hz), 161.13 (d, $^1J_{C-F}$=250.66 Hz), 153.53, 148.08, 135.64, 135.26, 135.03, 133.44 (d, $^3J_{C-F}$=4.53 Hz), 132.71 (d, $^3J_{C-F}$=4.53 Hz) 129.58 (d, $^3J_{C-F}$=8.31 Hz), 128.73 (d, $^3J_{C-F}$=7.55 Hz), 128.36, 125.33, 125.44, 120.47, 115.21 (d, $^2J_{C-F}$=21.90 Hz), 67.93, 61.59, 49.86, 49.07, 33.56, 14.46 (d, $^3J_{C-F}$=11.33 Hz), 14.33, 14.09 ppm;

Anal. Calcd. for C$_{27}$H$_{28}$F$_2$N$_4$O$_4$ H$_2$O: C, 61.36; H, 5.72, N, 10.60. Found: C, 62.47; H, 5.59; N, 8.23.

EXAMPLE 43

Ethyl (±)-erythro-9,9-bis(4-fluoro-3-methylphenyl)-3,5-dihydroxy-8-(1-methyl-1H-tetrazol-5-yl)-6,8-nonadienoate The ethyl 9,9-bis(4-fluoro-3-methylphenyl)-5-hydroxy-8-(1-methyl-1H-tetrazol-5-yl)-3-oxo-6,8-nonadienoate (1.39 g, 2.7 mmoles) prepared in Example 42 was dissolved in 30 mL of tetrahydrofuran under argon at 0° C. (ice-water bath). To this yellow solution was added 3 mL (3.0 mmoles) of triethylborane solution in tetrahydrofuran (1M in tetrahydrofuran) in one single portion. The solution was stirred at 0° C. for one hour before it was chilled to −78° C. (dry ice-acetone bath). To this stirring pale yellow solution was added dry NaBH$_4$ (0.12 g, 3.2 mmoles) and the reaction was allowed to proceed at −78° C. for an additional hour. The crude reaction mixture at −78° C. was diluted with 20 mL of 1N HCl and the cold suspension was allowed to warm to room temperature. The organic residues were extracted with ethyl acetate (30 mL×2) and the organic layers were combined, dried over MgSO$_4$ and concentrated under reduced pressure to give a thick syrup. The crude material was redissolved into 250 ml of methanol and the solution was allowed to stand at room temperature for 16 hours. Analytical TLC of the methanolic solution (eluted twice with 50% (v/v) ethyl acetate in hexanes) showed the product at R$_f$=0.10. The product was purified by silica gel column chromatography eluted with 20% (v/v) ethyl acetate in hexanes. The appropriate fractions were collected to give 0.95 g (68%) of the title compound. MS (CI): m/e=513 for (M+H)+;

IR (KBr) $\nu_{max}$: 3438 (s), 3000 (s), 1735 (s), 1500 (s), 1441 (s), 1250 (s), 1230 (s), 1119 (s) cm$^{-1}$;

$^1$H NMR (CDCl$_3$) δ: 7.08–7.02 (3H, m), 6.77 (1H, t, J=8.91 Hz), 6.69–6.63 (2H, m), 6.66 (1H, d, J=15.7 Hz), 5.31 (1H, dd, J=6.12, 15.7 Hz), 4.42 (1H, br) 4.22 (1H, br), 4.16 (2H, q, J=7.2 Hz), 3.80 (1H, br. D$_2$O exchangeable), 3.72 (1H, br. D$_2$O exchangeable), 3.56 (3H, s), 2.45 (2H, d, J=6.12 Hz), 2.28 (3H, d, J=1.65 Hz), 2.08 (3H, d, J=1.5 Hz), 1.8–1.57 (2H, m), 1.26 (3H, t, J=7.2 Hz);

$^{13}$C NMR (CDCl$_3$) δ: 172.47, 161.1 (d, $^1J_{C-F}$=248.4 Hz), 153.66, 147.5, 137.66, 137.31, 135.78, 133.36, 132.68 (d, $^3J_{C-F}$=6.04 Hz), 129.58 (d, $^3J_{C-F}$=8.31 Hz), 128.68 (d, $^3J_{C-F}$=8.31 Hz), 127.43, 125.50, 115.16 (d, $^2J_{C-F}$=22.65 Hz), 71.98, 68.40, 60.88, 42.37, 41.45, 33.56, 14.53, 14.33, 14.15 ppm;

Anal. Calcd. for C$_{27}$H$_{30}$F$_2$N$_4$O$_4$: C, 63.27; H, 5.90; N, 10.93. Found: C, 62.80; H, 6.17; N, 10.34.

EXAMPLE 44

Sodium (±)-erythro-9,9-bis(4-fluoro-3-methylphenyl)-3,5-dihydroxy-8-(1-methyl-1H-tetrazol-5-yl)-6,8-nonadienoate To a solution of ethyl (±)-erythro-9,9-bis(4-fluoro-3-methylphenyl)-3,5-dihydroxy-8-(1-methyl-1H-tetrazol-5-yl)-6,8-nonadienoate (0.80 g, 1.56 mmoles) in tetrahydrofuran (20 mL) at 0° C. under argon was added 1.0N NaOH solution (1.56 mL) in one single portion. The pale yellow emulsion was stirred at 0° C. (ice-water bath) for two hours forming a pale transparent solution. Analytical TLC eluted with 20% (v/v) methanol in CHCl$_3$ showed product at R$_f$=0.16. Most of the volatile organic solvents were evaporated under reduced pressure and the desired product was lyophilized under high vacuum to give 0.8 g (quantitative) of the title compound which appears to contain about one mole of water.

IR (KBr) $\nu_{max}$: 3425 (v.br), 1575 (s), 1500 (s), 1438 (s), 1400 (s), 1225 (s), 1116 (s) cm$^{-1}$;

$^1$H NMR (DMSO-d$_6$) δ: 7.26–7.19 (3H, m), 6.95 (1H, t, J=8.91 Hz), 6.78–6.70 (2H, m), 6.49 (1H, d, J=15.5 Hz), 5.13 (1H, dd, J=5.43, 15.5 Hz), 4.15 (1H, br. q, J=6.03 Hz), 3.68 (3H, s), 3.67 (1H, br), 3.45 (2H, v.br, D$_2$O exchangeable), 2.26 (3H, br.s), 2.05 (3H, br.s), 2.05 (1H, br), 1.85 (1H, dd, J=8.37, 14 Hz), 1.55–1.25 (2H, m);

$^{13}$C NMR (DMSO-d$_6$) δ: 175.09, 159.03 (d, $^1J_{C-F}$=242.36 Hz), 160.08 (d, $^1J_{C-F}$=242.36 Hz), 151.84, 144.17, 138.35, 135.01 (d, $^3J_{C-F}$=3.78 Hz) 134.12 (d, $^3J_{C-F}$=3.02 Hz), 131.83 (d, $^3J_{C-F}$=4.53 Hz), 130.83 (d, $^3J_{C-F}$=3.78 Hz), 128.34 (d, $^3J_{C-F}$=8.31 Hz), 127.11 (d, $^3J_{C-F}$=8.31 Hz), 123.84, 123.52, 123.30, 123.10, 112.87, 120.49, 113.99 (d, $^2J_{C-F}$=22.65 Hz), 113.69 (d, $^2J_{C-F}$=23.41 Hz), 67.66, 65.12, 44.12, 43.24, 33.18, 14.0, 14.15 ppm;

Anal. Calcd. for C$_{25}$H$_{25}$F$_2$N$_4$O$_4$Na 2H$_2$O: C, 55.35; H, 5.39; N, 10.33. Found: C, 55.01; H, 5.01; N, 9.82.

EXAMPLE 45

Ethyl 3,3-bis(4-fluorophenyl)-2-(1-ethyl-1H-tetrazol-5-yl)-2-propenoate and ethyl 3,3-bis(4-fluorophenyl)-2-(2-ethyl-2H-tetrazol-5-yl)-2-propenoate

A. Ethyl 3,3-bis(4-fluorophenyl)-2-(2-ethyl-2H-tetrazol-5-yl)-2-propenoate

To a solution of 10.0 g (0.028 mole) of ethyl 3,3-bis(4-fluorophenyl)-2-(1H-tetrazol-5-yl)-2-propenoate [prepared in Example 2] in 75 mL of N,N-dimethylformamide was added 1.2 g of 60% sodium hydride (0.03 mole) in mineral oil was added. After stirring for 0.5 hour, the sodium hydride had dissolved and 8.5 g (0.056 mole) of iodoethane was added. The solution was stirred at room temperature for 16 hours, diluted to 400 mL with water and extracted with CH$_2$Cl$_2$. The extracts were dried and concentrated in vacuo. The residue was triturated with hexane to remove mineral oil. The residue was absorbed onto silica gel by dissolving in CH$_2$Cl$_2$ and adding dry silica gel, then concentrating in vacuo to a dry powder. This material was transferred to the top of a silica gel column and eluted with 10% (v/v) ethyl acetate in hexane to give 4.9 g (45.5%) of the title compound; m.p.=113–114.5° C.

IR (KBr) $\nu_{max}$: 1710 (s), 1601 (s), 1505 (s), 1160 (s), 596 (s), 550 (s) cm$^{-1}$;

$^1$H NMR (CDCl$_3$) δ: 7.31–7.28 (m, 2H), 7.11–6.85 (m, 6H), 4.56 (q, 2H), 4.10 (q, 2H), 1.51 (t, 3H), 1.02 (t, 3H) ppm;

$^{13}$C NMR (CDCl$_3$) δ: 167.03, 165.62 (d), 165.28 (d), 162.64, 160.64 (d), 160.34 (d), 152.76, 136.86 (d), 136.00 (d), 131.92 (d), 131.75 (d), 131.10 (d), 130.92 (d), 115.53 (d), 115.35 (d), 115.13 (d), 114.96 (d), 61.41, 48.31, 14.51, 13.70 ppm;

Anal. Calcd. for C$_{20}$H$_{18}$F$_2$N$_4$O$_2$: C, 62.50; H, 4.73; N, 14.59. Found: C, 62.28; H, 4.72; N, 14.51.

B. Ethyl 3,3-bis(4-fluorophenyl)-2-(1-ethyl-1H-tetrazol-5-yl)-2-propenoate

The appropriate fractions obtained from continued elution of the silica gel column of Step A with 10% (v/v) ethyl acetate in hexane were evaporated to yield 5.1 g (47.4%) of the title compound; m.p. 97°–99° C.

IR (KBr) $\nu_{max}$: 1720 (s), 1605 (s), 1507 (s), 1160 (s), 845 (s), 540 (s) cm$^{-1}$;

$^1$H NMR (CDCl$_3$) δ: 7.40–6.90 (m, 8H), 4.00 (q, 2H), 3.88 (q, 2H), 1.16 (t, 3H), 1.00 (t, 3H) ppm;

Anal. Calcd. for C$_{20}$H$_{18}$F$_2$N$_4$O$_2$: C, 62.50; H, 4.73; N, 14.58. Found: C, 62.27; H, 4.73; N, 14.51.

EXAMPLE 46

3,3-Bis(4-fluorophenyl)-2-(1-ethyl-1H-tetrazol-5-yl)-2-propenol

To a solution of ethyl 3,3-bis(4-fluorophenyl)-2-(1-ethyl-1H-tetrazol-5-yl)-2-propenoate (1.0 g, 2.6 mmoles) at −78° in CH$_2$Cl$_2$ was rapidly added 7.8 mL (7.8 mmoles) of diisobutylaluminum hydride solution (1.0 Molar in methylene chloride). After stirring for 45 minutes, the mixture was quenched with 1N HCl solution. The organic layer was separated, dried (MgSO$_4$) and concentrated in vacuo. The residual oil was triturated with hexane to give 0.9 g (100%) of the title compound; m.p.=103°–111° C.

$^1$H NMR (CDCl$_3$) δ: 7.41–7.34 (m, 2H), 7.18–7.09 (m, 2H), 6.91–6.87 (m, 4H), 4.7 (s, 2H), 3.80 (q, 2H), 1.21 (t, 3H) ppm;

$^{13}$C NMR (CDCl$_3$) δ: 166.04, 165.91 (d), 165.47 (d), 161.08, 160.84, 156.02, 135.78 (d), 134.22 (d), 131.73 (d), 131.69 (d), 131.55 (d), 131.51 (d), 116.01 (d), 115.94 (d), 115.57 (d), 115.50 (d), 61.91, 42.85, 14.13 ppm;

Anal. Calcd. for C$_{18}$H$_{16}$F$_2$N$_4$O: C, 63.16; H, 4.72; N, 16.37. Found: C, 62.99; H, 4.73; N. 16.40.

EXAMPLE 47

3,3-Bis(4-fluorophenyl)-2-(2-ethyl-2H-tetrazol-5-yl)-2-propenol

The general procedure of Example 46 was repeated, except that the ethyl 3,3-bis(4-fluorophenyl)-2-(1-ethyl-1H-tetrazol-5-yl)-2-propenoate utilized therein was replaced with 1.0 g of ethyl 3,3-bis(4-fluorophenyl)-2-(2-ethyl-2H-tetrazol-5-yl)-2-propenoate and there was thereby produced 0.9 g of the title compound; m.p.=82°–84° C.

$^1$H NMR (CDCl$_3$) δ: 7.30–7.33 (m, 2H), 7.08–6.87 (m, 6H), 4.57 (d, 2H), 4.48 (d, 2H), 2.88 (t, 1H), 1.43 (t, 1H);

$^{13}$C NMR (CDCl$_3$) δ: 165.04, 164.82 (d), 164.67 (d), 160.12, 159.78, 147.08, 137.56 (d), 136.45 (d), 131.47 (d), 131.43 (d), 131.34 (d), 131.25 (d), 115.53 (t), 115.13 (t), 114.72 (d), 62.89, 48.24, 14.40 ppm;

Anal. Calcd. for C$_{18}$H$_{16}$F$_2$N$_4$O: C, 63.16; H, 4.72; N, 16.37. Found: C, 63.22; H, 4.74; N. 16.41.

EXAMPLE 48

3,3-Bis(4-fluorophenyl)-2-(1-ethyl-1H-tetrazol-5-yl)-2-propenal

Pyridinium chlorochromate (0.9 g) was added to a solution of 0.8 g (2.3 mmoles) of the 3,3-bis(4-fluorophenyl)-2-(1-ethyl-1H-tetrazol-5-yl)-2-propenol in methylene chloride. The solution became bright yellow and then darkened with the formation of a dark gummy precipitate. After stirring at room temperature for 16 hours, the mixture was poured directly onto a silica gel column and eluted with methylene chloride to give 0.65 g (83%) of the title compound; m.p.=144°–145° C.

IR (KBr) $\nu_{max}$: 1680 (s), 1600 (s), 1515 (s), 1135 (s), 855 (s), 840 (s);

¹H NMR (CDCl₃) δ: 9.65 (1H, s), 7.36-7.20 (4H, m), 7.05-6.88 (4H, m), 4.01 (2H, q), 1.38 (3H, t);

¹³C NMR (CDCl₃) δ: 189.02, 167.07 (d), 166.51 (d), 164.68, 162.04, 150.41, 133.65 (d), 133.49 (d), 132.34 (d), 132.18 (d), 124.11, 116.46 (d), 116.34 (d), 116.02 (d), 115.90 (d), 43.00, 14.34 ppm;

Anal. Calcd. for C₁₈H₁₄F₂N₄O: C, 63.53; H, 4.15; N, 16.47. Found: C, 62.90, H, 4.13; N, 16.37.

EXAMPLE 49

3,3-Bis(4-Fluorophenyl)-2-(2-ethyl-2H-tetrazol-5-yl)-2-propenal

The reaction of 4.0 g (12.0 mmoles) of 3,3-bis(4-fluorophenyl)-2-(2-ethyl-2H-tetrazol-5-yl)-2-propenol with pyridinium chlorochromate (4.5 g) was carried out by the procedure described in Example 48 and there was thereby produced 3.25 g (79.7%) of the title compound; m.p.=138°-139° C.

¹H NMR (CDCl₃) δ: 9.70 (1H, s), 7.39-7.32 (2H, m), 7.23-7.14 (2H, m), 7.04-6.86 (4H, m), 4.62 (2H, q), 1.56 (3H, t);

¹³C NMR (CDCl₃) δ: 190.04, 166.71 (d), 165.86 (d), 163.01, 161.68, 161.16 (d), 160.86 (d), 135.62 (d), 135.55 (d), 133.69 (d), 133.53 (d), 132.37 (d), 137.19 (d), 127.74, 116.06 (t), 115.59 (t), 115.17 (t), 48.45, 14.59 ppm;

Anal. Calcd. for C₁₈H₁₄F₂N₄O: C, 63.53; H, 4.15; N, 16.47. Found: C, 63.53, H, 4.11; N, 16.74.

EXAMPLE 50

5,5-Bis(4-fluorophenyl)-4-(1-ethyl-1H-tetrazol-5-yl)-2,4-pentadienal

A solution of 3,3-bis(4-fluorophenyl)-2-(1-ethyl-1H-tetrazol-5-yl)-2-propenal (0.65 g, 1.9 mmoles) and 0.64 g (2.1 mmoles) of triphenylphosphoranylidene acetaldehyde in benzene was heated at reflux temperature for 2 hours. The solution was concentrated in vacuo and the residue purified by silica gel column chromatography eluting with CH₂Cl₂ to give 0.55 g (79.7%) of the title compound, m.p.=163°-165° C.

¹H NMR (CDCl₃) δ: 9.54 (1H, d), 7.49 (1H, d), 7.42-6.96 (8H, m), 5.76 (1H, dd), 8.89 (2H, q), 1.27 (3H, t);

¹³C NMR (CDCl₃) δ: 192.41, 166.21 (d), 165.77 (d), 161.18, 160.71, 155.04, 151.58, 150.10, 148.34, 148.27, 147.91, 138.90, 134.97, 134.53, 132.77, 132.60, 132.20, 132.03, 120.35, 116.43, 116.26, 116.03, 115.78, 42.66, 14.30 ppm;

Anal. Calcd. for C₂₀H₁₆F₂N₄O: C, 65.57; H, 4.41; N, 15.30. Found: C, 65.32; H, 4.77; N, 14.76.

EXAMPLE 51

5,5-Bis(4-fluorophenyl)-4-(2-ethyl-2H-tetrazol-5-yl)-2,4-pentadienal

The procedure of Example 50 was repeated using 3.25 g (9.5 mmoles) of 3,3-bis(4-fluorophenyl)-2-(2-ethyl-2H-tetrazol-5-yl)-2-propenal and 3.05 g (10.0 mmoles) of triphenylphosphoranylidene acetaldehyde and there was thereby produced 3.3 g (95%) of the title compound; m.p.=117°-120° C.

¹H NMR (CDCl₃) δ: 9.54 (1H, d), 7.49 (1H, d), 7.34-7.11 (4H, m), 7.00-6.78 (4H, m), 5.94 (1H, dd), 4.60 (2H, q), 1.52 (3H,t);

¹³C NMR (CDCl₃) δ: 193.23, 165.83, 165.08, 162.91, 160.83, 160.10, 154.47, 151.28, 149.46, 140.21, 132.89, 132.72, 132.13, 132.00, 130.56, 116.00, 115.56, 115.28, 114.89, 48.46, 14.63 ppm;

Anal. Calcd. for C₂₀H₁₀F₂N₄O: C, 65.57; H, 4.41; N, 15.30. Found: C, 65.36; H, 4.40; N, 15.64.

EXAMPLE 52

Ethyl 9,9-bis(4-fluorophenyl)-5-hydroxy-8-(1-ethyl-1H-tetrazol-5-yl)-3-oxo-6,8-nonadienoate To a solution of 0.5 g (1.4 mmoles) of 5,5-bis(4-fluorophenyl)-4-(1-ethyl-1H-tetrazol-5-yl)2,4-pentadienal in tetrahydrofuran at −50° C., was added 1.75 mL of 0.8M (1.4 mmoles) of a freshly prepared solution of ethyl acetoacetate dianion [described in Example 10]. The solution was stirred for 30 minutes at −50° C. and then allowed to warm to −10° C. during the next 30 minutes. The solution was quenched with 1N HCl and extracted with methylene chloride. The organic extracts were dried and concentrated in vacuo. The residue was purified by silica gel column chromatography eluting with chloroform to give 0.4 g of the title compound as an oil. MS (CI): m/e=497 for (M+H)⁺;

¹H NMR (CDCl₃) δ: 7.29-7.11 (4H, m), 6.87-6.83 (4H, m), 6.72 (1H, d), 5.24 (1H, dd), 4.62 (1H, m), 4.16 (2H, q), 3.88 (2H, q), 3.44 (2H, s), 3.30 (1H, d), 2.71 (2H, d), 1.25 (3H, t) ppm;

¹³C NMR (CDCl₃) δ: 166.69, 165.31, 164.92, 160.32, 159.95, 152.64, 146.82, 136.7, 135.98, 135.34, 135.26, 135.18, 132.38, 132.20, 131.62, 131.45, 128.26, 121.25, 115.92, 115.78, 115.48, 115.34, 91.48, 67.75, 61.51, 49.87, 49.14, 42.55, 14.27, 14.09 ppm.

EXAMPLE 53

Ethyl 9,9-bis(4-fluorophenyl)-5-hydroxy-8-(2-ethyl-2H-tetrazol-5-yl)-3-oxo-6,8-nonadienoate To a solution of 5,5-bis(4-fluorophenyl)-4-(2-ethyl-2H-tetrazol-5-yl)-2,4-pentadienal (2.0 g) in 20 mL of tetrahydrofuran at −40° C. was added 6.9 mL of 0.8M (5.5 mmoles) freshly prepared solution of ethyl acetoacetate dianion [described in Example 10]. The solution was stirred at −40° C. for 30 minutes and then allowed to warm to −10° C. After a total of one hour, the reaction was quenched with 1N HCl. The mixture was extracted with chloroform, dried over MgSO₄ and concentrated in vacuo. The residue was purified by silica gel column chromatography to give 0.4 g of pure title compound. MS (EI): m/e=496 for M⁺;

¹H NMR (CDCl₃) δ: 7.29-7.22 (2H, m), 7.13-7.04 (2H, m), 6.90-6.78 (4H, m), 6.71 (1H, d), 4.68-4.48 (3H, m), 4.15 (2H, q), 3.45 (2H, s), 2.73 (3H, d with broad shoulder), 1.49 (3H, t), 1.27 (3H, t) ppm;

¹³C NMR (CDCl₃) δ: 164.95, 164.28, 163.91, 159.99, 159,39, 145.98, 137.64, 137.56, 136.20, 136.06, 135.21, 132.42, 132.25, 131.71, 131.53, 128.90, 115.54, 115.10, 114.93, 114.48, 91.31, 68.11, 61.44, 49.93, 49.36, 48.28, 14.62, 14.10 ppm;

An additional quantity of 1.55 g of crude title compound was also obtained which was used without further purification.

EXAMPLE 54

Ethyl (±)-erythro-9,9-bis(4-fluorophenyl)-3,5-dihydroxy-8-(1-ethyl-1H-tetrazol-5-yl)-6,8-nonadienoate To a solution of ethyl 9,9-bis(4-fluorophenyl)-5-hydroxy-8-(1-ethyl-1H-tetrazol-5-yl)-3-oxo-6,8-nonadienoate (0.5 g, 1.0 mmole) in tetrahydrofuran at 0°

C. was added 1.1 mL (1.1 mmoles) of triethylborane solution (1.0M solution in tetrahydrofuran). The solution was stirred for 2.5 hours and then cooled to −78° C. Sodium borohydride (0.08 g, 2.0 mmoles) was added followed by 0.5 mL of methanol. After stirring for 2.5 hours at −78° C., the mixture was diluted with an equal volume of hexane and quenched with 1N HCl followed by extractions with ethyl acetate. The organic extracts were dried (MgSO$_4$) and concentrated in vacuo and then dissolved in methanol and stirred at room temperature for 16 hours. The solution was concentrated in vacuo and the product was purified by silica gel column chromatography eluting with 2% methanol in chloroform to give 0.3 g of the title compound as an oil. MS (EI): m/e=498 for M+;

$^1$H NMR (CDCl$_3$) δ: 7.27–7.13 (4H, m), 6.88–6.84 (4H, m), 6.71 (1H, d), 5.28 (1H, dd), 4.18 (1H, m), 4.17 (3H, q over broad m), 3,88 (2H, q), 3.71 (2H, dd), 2.45 (2H, d), 1.59 (3H, t), 1.28 (3H, t), ppm.

$^{13}$C NMR (CDCl$_3$) δ: 172.37, 165.26, 164.87, 160.31, 159.90, 146.38, 137.77, 135.89, 135.82, 135.28, 132.29, 132.17, 131.61, 131.43, 127.39, 121.48, 115.89, 115.75, 115.49, 115.30, 71.80, 60.86, 42.48, 42.25, 41.47, 14.26, 14.28 ppm.

EXAMPLE 55

Ethyl (±)-erythro-9,9-bis(4-fluorophenyl)-3,5-dihydroxy-8-(2-ethyl-2H-tetrazol-5-yl)-6,8-nonadienoate and ethyl (±)-erythro-7,7-bis(4-fluorophenyl)-3,5-dihydroxy-6-(2-ethyl-2H-tetrazol-5-yl)-6-heptenoate A. Ethyl (±)-erythro-9,9-bis(4-fluorophenyl)-3,5-dihydroxy-8-(2-ethyl-2H-tetrazol-5-yl)-6,8-nonadienoate To a solution of 1.55 g (3.0 mmoles) of crude ethyl 9,9-bis(4-fluorophenyl)-5-hydroxy-8-(2-ethyl-2H-tetrazol-5-yl)-3-oxo-6,8-nonadienoate (prepared in Example 53) in tetrahydrofuran at 0° C. was added 3.3 mL (3.3 mmoles) of 1M triethylborane solution (1.0M solution in tetrahydrofuran). After stirring for 2.5 hours, the solution was cooled to −78° C. and 0.25 g (6.3 mmoles) of sodium borohydride followed by 1.2 mL of methanol were added. After stirring for an additional 2.5 hours, the reaction mixture was diluted with an equal volume of hexane and quenched with 1N HCl. The mixture was extracted with ethyl acetate and the combined organic phase was dried (MgSO$_4$) and concentrated in vacuo. The residue was dissolved in methanol and stirred at room temperature for 16 hours. The methanol solution was concentrated in vacuo and the residue purified by silica gel chromatography eluting with 1% CH$_3$OH in CHCl$_3$. The appropriate fractions were combined and evaporated under reduced pressure to give 0.64 g of the title compound as an oil. MS (EI): m/e=498 for M+;

$^1$H NMR (CDCl$_3$) δ: 7.30–7.02 (4H, m), 6.80–6.72 (4H, m), 6.68 (1H, d), 5.45 (4H, dd), 4.52 (2H, q), 4.48 (1H, m), 4.15 (3H, q over m), 3.72 (1H, m), 2.45 (2H, dd), 1.67 (2H, m), 1.45 (3H, t), 1.25 (3H, t) ppm;

$^{13}$C NMR (CDCl$_3$) δ: 164.92, 164.29, 164.11, 163.99, 159.98, 159.34, 145.65, 141.24, 137.69, 134.64, 136.83, 136.29, 136.21, 132.39, 132.23, 131.69, 131.51, 128.40, 125.09, 115.53, 115.10, 114.93, 114.51, 72.17, 68.09, 60.78, 48.26, 42.50, 41.66, 14.68, 14.19 ppm.

B. Ethyl (±)-erythro-7,7-bis(4-fluorophenyl)-3,5-dihydroxy-6-(2-ethyl-2H-tetrazol-5-yl)-6-heptenoate The appropriate fractions from the elution of the silica gel column in Step A were combined and evaporated to give 0.2 g of the title compound; m.p. 124°–128° C. MS (EI): m/e=473 for MH+;

$^1$H NMR (CDCl$_3$) δ: 7.32–6.78 (8H, m), 4.93 (1H, m), 4.55 (2H, q), 4.17 (3H, q over m), 3.88 (1H, d), 3.64 (1H, d), 2.45 (2H, dd), 1.83 (2H, m), 1.46 (3H, t), 1.27 (3H, t) ppm;

$^{13}$C NMR (CDCl$_3$) δ: 177.18, 164.94, 164.44, 163.16, 160.01, 159.51, 146.58, 137.11, 137.05, 135.92, 135.86, 131.31, 131.15, 130.98, 127.98, 115.73, 115.31, 115.01, 114.58, 71.44, 68.56, 67.86, 65.28, 60.72, 48.33, 42.44, 41.74, 41.44, 41.36, 14.53, 14.21 ppm;

Anal. Calcd. for C$_{24}$H$_{26}$F$_2$N$_4$O$_4$ 0.5 H$_2$O: C, 59.87; H, 5.66; N, 11.64. Found: C, 59.62; H, 5.62; N, 11.21.

EXAMPLE 56

Sodium (±)-erythro-9,9-bis(4-fluorophenyl)-3,5-dihydroxy-8-(1-ethyl-1H-tetrazol-5-yl)-6,8-nonadienoate A solution of 1.0 g (2.0 mmoles) of ethyl 9,9-bis(4-fluorophenyl)-3,5-dihydroxy-8-(1-ethyl-1H-tetrazol-5-yl)-6,8-nonadienoate and 2 mL (2.0 mmoles) 1N sodium hydroxide in 25 mL of ethanol was stirred for 45 minutes. The reaction mixture was concentrated in vacuo and the residue was dissolved in water. The aqueous solution was lyophilized in vacuo to yield the title compound which appears to contain about one mole of water; m.p.=193°–203° C. MS (FAM): m/e=493 for (M+H)+;

IR (KBr) ν$_{max}$: 3200 (v.br), 1650 (br), 1600 (s), 1580 (s), 1510 (s), 1410 (br), 1230 (s), 850 cm$^{-1}$;

$^1$H NMR (CDCl$_3$) δ: 7.37–7.29 (4H, m), 7.05–6.88 (4H, m), 6.50 (1H, d), 5.08 (1H, dd), 4.12 (1H, m), 4.04 (2H, q), 3.62 (1H, m), 3.35 (2H), 2.03–1.78 (2H, m), 1.46–1.23 (2H, m), 1.18 (3H, t) ppm;

Anal. Calcd. for C$_{24}$H$_{23}$F$_2$N$_4$O$_4$Na H$_2$O: C, 56.48; H, 4.94; N, 10.98. Found: C, 56.28; H, 4.96; N, 10.56.

EXAMPLE 57

Sodium (±)-erythro-9,9-bis(4-fluorophenyl)-3,5-dihydroxy-8-(2-ethyl-2H-tetrazol-5-yl)-6,8-nonadienoate A solution of 0.65 g (1.3 mmoles) of ethyl (±)-erythro-9,9-bis(4-fluorophenyl)-3,5-dihydroxy-8-(2-ethyl-2H-tetrazol-5-yl)-6,8-nonadienoate and 1.3 mL (1.3 mmoles) 1N sodium hydroxide solution in 25 mL ethanol was stirred for 1 hour. The reaction solution was concentrated in vacuo and the residue was dissolved in water. The aqueous solution was lyophilized in vacuo to yield the title compound; m.p.=170°–190° C. MS (FAB): m/e=493 for (M+H)+;

IR (KBr) ν$_{max}$: 3200 (v.br), 1650 (br), 1605 (s), 1580 (s), 1512 (s), 1410 (br), 1230 (s), 850 (s) cm$^{-1}$;

$^1$H NMR (DMSO-d$_6$) δ: 7.34–6.79 (8H, m), 6.50 (1H, d), 5.31 (1H, dd), 5.0 (1H, br.m), 4.58 (2H, q), 4.13 (1H, m), 3.63 (1H, m), 3.35 (1H, br.m), 2.03–1.78 (2H, m), 1.46–1.21 (2H, m), 1.34 (3H, t) ppm.

Anal. Calcd. for C$_{24}$H$_{23}$F$_2$N$_4$O$_4$Na 1.3 H$_2$O: C, 55.88; H, 5.00; N, 10.86. Found: C, 55.41; H, 4.67; N, 10.54.

EXAMPLE 58

Sodium (±)-erythro-7,7-bis(4-fluorophenyl)-3,5-dihydroxy-6-(2-ethyl-2H-tetrazol-5-yl)-6-heptenoate A solution of 0.2 g (0.45 mmoles) of ethyl (±)-erythro-7,7-bis(4-fluorophenyl)-3,5-dihydroxy-6-(2-ethyl-2H-tetrazol-5-yl)-6-heptenoate (prepared in Example 55, Step B) and 0.45 mL (0.45 mmoles) 1N sodium hydroxide solution in 10 mL ethanol was stirred for 1 hour. The reaction solution was concentrated under reduced pressure and the residue was dissolved in methanol. The aqueous solution was lyophilized in vacuo to yield the title compound.

$^1$H NMR (CDCl$_3$) δ: 7.3–6.7 (8H, m), 5.7 (2H, br.m), 4.8 (1H, m), 4.4 (2H, q), 3.9 (1H, m), 3.65 (1H, m), 2.7 (2H, m), 1.9 (2H, m), 1.2 (3H, t) ppm;

$^{13}$C NMR (CDCl$_3$) δ: 179.64, 164.64, 164.26, 163.27, 163.59, 159.71, 159.35, 145.67, 137.52, 137.46, 136.06, 135.98, 131.34, 131.20, 129.12, 115.65, 115.22, 114.86, 114.44, 70.30, 58.26, 48.18, 18.41, 14.48 ppm;

Anal. Calcd for C$_{22}$H$_{21}$F$_2$N$_4$O$_4$Na 2H$_2$O: C, 52.59; H, 5.02; N, 11.16. Found: C, 52.81; H, 5.32; N, 9.64.

EXAMPLE 59

1,1-Bis(2,4-dimethylphenyl)-2-(1-methyl-1H-tetrazol-5-yl)ethanol.

A solution of 1,5-dimethyltetrazol (8.9 g, 91.0 mmoles) in 100 mL of dry tetrahydrofuran at −60° C. was treated with n-butyl lithium (48 mL of 1.89M solution, 91.0 mmoles). After stirring for 20 minutes, 2,2′,4,4′-tetramethylbenzophenone (18 g, 76 mmoles) [prepared by the procedure described in J. Am. Chem. Soc., 81, 4858 (1959)] in 50 mL dry tetrahydrofuran was added and the solution was stirred for 1 hour during which time it was allowed to warm to −20° C. The reaction was quenched with 1N HCl, then extracted with chloroform. The combined organic extracts were dried (MgSO$_4$) and evaporated to give 22 g of the title compound; m.p.=175°–177° C.

IR (KBr) ν$_{max}$: 3390 (br), 1620 (s), 1460 (s), 1200 (s), 820 (s) cm$^{-1}$;

$^1$H NMR (CDCl$_3$) δ: 7.26 (2H, d), 6.95–6.83 (4H, m), 4.00 (1H, s), 3.82 (2H, s), 3.41 (3H, s), 2.23 (6H, s), 1.83 (6H, s) ppm;

$^{13}$C NMR (CDCl$_3$) δ: 152.34, 139.28, 137.32, 135.79, 133.24, 126.26, 125.92, 77.47, 35.04, 32.99, 21.28, 20.76 ppm;

Anal. Calcd. for C$_{20}$H$_{24}$N$_4$O: C, 71.41; H, 7.20; N, 16.67. Found: C, 70.82; H, 7.26; N, 16.45.

EXAMPLE 60

1,1-Bis(2,4-dimethylphenyl)-2-(1-methyl-1H-tetrazol-5-yl)ethene.

A mixture of 1,1-bis(2,4-dimethylphenyl)-2-(1-methyl-1H-tetrazol-5-yl)ethanol (1.8 g, 5.4 mmoles) and potassium hydrogen sulfate (100 mg) was placed in an oil bath preheated to 190° C. After 15 minutes, the melt was cooled and methylene chloride added to the residue. The insolubles were removed and the solution evaporated. The residue was crystallized from isopropyl ether to give 1.2 g of the title compound; m.p.=143°–143.5° C.

IR (KBr) ν$_{max}$: 2930 (s), 1635 (s), 1620 (s), 1510 (s), 1450 (s), 820 (s), 740 (s) cm$^{-1}$;

$^1$H NMR (CDCl$_3$) δ: 7.15–6.80 (6H, m), 6.60 (1H, s), 3.40 (3H, s), 2.36 (3H, s), 2.30 (3H, s), 2.18 (3H, s), 1.85 (3H, s) ppm;

$^{13}$C NMR (CDCl$_3$) δ: 154.18, 152.21, 138.54, 138.38, 138.06, 135.67, 135.40, 135.18, 131.78, 131.72, 129.90, 129.66, 126.77, 126.55, 111.99, 33.65, 21.02, 20.69, 19.95 ppm;

Anal. Calcd. for C$_{20}$H$_{22}$N$_4$: C, 75.45; H, 6.97; N, 17.60. Found: C, 75.04; H, 7.03; N, 17.63.

EXAMPLE 61

3,3-Bis(2,4-dimethylphenyl)-2-(1-methyl-1H-tetrazol-5-yl)-2-propenal

A solution of 1,1-bis(2,4-dimethylphenyl)-2-(1-methyl-1H-tetrazol-5-yl)ethene (1.0 g, 3.1 mmoles) in 10 mL dry tetrahydrofuran was treated with n-butyl lithium (1.64 mL of 1.89M solution, 3.1 mmoles) at −78° C. After stirring with cooling for 30 minutes, ethyl formate (0.3 g, 4.0 mmoles) was added and the mixture stirred with cooling for 2 hours. The reaction was quenched with 1N HCl and extracted with chloroform. The combined organic fractions were dried (MgSO$_4$) and evaporated. The residue was purified by column chromatography on silica gel eluting with 10% (v/v) ethyl acetate in hexane to give 0.9 g of product as an oil. Trituration of the oil with isopropyl ether gave the title compound as a solid; m.p.=117°–120° C. MS (CI): m/e=347 for (M+H)$^+$;

$^1$H NMR (CDCl$_3$) δ: 9.58 (1H, s), 7.25–6.78 (7H, m), 3.70 (3H, s), 2.40 (3H, s), 2.25 (3H, s), 2.20 (3H, s), 1.90 (3H, s) ppm;

$^{13}$C NMR (CDCl$_3$) δ: 189.49, 168.80, 151.05, 140.87, 140.26, 137.06, 135.86, 134.87, 133.28, 132.04, 129.60, 126.62, 125.28, 34.17, 21.21, 21.06, 20.37, 20.07 ppm;

Anal. Calcd. for C$_{21}$H$_{22}$N$_4$O: C, 72.81; H, 6.41; N, 16.18; Found: C, 72.99; H, 6.43; N, 16.09.

EXAMPLE 62

5,5-Bis(2,4-dimethylphenyl)-4-(1-methyl-1H-tetrazol-5-yl)-2,4-pentadienal

A solution of 3,3-bis(2,4-dimethylphenyl)-2-(1-methyl-1H-tetrazol-5-yl)-2-propenal (4.5 g, 13.0 mmoles) and triphenylphosphoranylidene acetaldehyde (4.1 g, 13.0 mmoles) in benzene was heated at reflux temperature for 6 hours. The reaction mixture was evaporated under reduced pressure and the residue was purified by column chromatography on silica gel eluting with 10% (v/v) ethyl acetate in hexane to give 5.9 g of the title compound as an oil. MS (CI): m/e=373 for (M+H)$^+$;

IR (KBr) ν$_{max}$: 1742 (s), 1680, 1615, 1450 (s), 1130 (s), 830 (s), 810 (s) cm$^{-1}$;

$^1$H NMR (CDCl$_3$) δ: 9.42 (1H, d), 7.3 (1H, d), 7.14–6.85 (6H, m), 5.80 (1H, dd), 3.52 (3H, s), 2.35 (3H, s), 2.20 (6H, s), 1.85 (3H, s) ppm;

$^{13}$C NMR (CDCl$_3$) δ: 192.53, 158.44, 152.18, 150.60, 148.18, 139.45, 139.25, 136.14, 135.98, 135.18, 134.63, 131.78, 131.70, 131.28, 130.10, 126.45, 126.25, 121.26, 33.61, 20.90, 20.71, 20.18, 20.11 ppm;

Anal. Calcd. for C$_{23}$H$_{24}$N$_4$O: C, 74.17; H, 6.50; N, 15.05. Found: C, 72.82; H, 6.85; N, 13.33.

EXAMPLE 63

Ethyl 9,9-bis(2,4-dimethylphenyl)-5-hydroxy-8-(1-methyl-1H-tetrazol-5-yl)-3-oxo-6,8-nonedienoate The general procedure of Example 42 was repeated, except that the 5,5-bis(4-fluoro-3-methylphenyl)-4-(1-methyl-1H-tetrazol-5-yl)-2,4-pentadienal utilized therein was replaced with 5.9 g (16.0 mmoles) of 5,5-bis(2,4-dimethylphenyl)-4-(1-methyl-1H-tetrazol-5yl)-2,4-pentadienal and the crude material that was thereby produced was purified by silica gel column chromatography eluting with 1% (v/v) methanol in methylene chloride to give 4 g of the title compound.

$^1$H NMR (CDCl$_3$) δ: 7.10–6.95 (3H, m), 6.83–6.75 (3H, m), 6.50 (1H, d), 5.30 (1H,dd), 4.60 (1H, m), 4.14 (2H, q), 3.60 (3H, s), 3.43 (2H, s), 3.0 (1H, bs), 2.70 (2H, d), 2.35 (3H, s), 2.20 (3H, s), 1.90 (3H, s), 1.28 (3H, t) ppm;

$^{13}$C NMR (CDCl$_3$) δ: 202.15, 166.59, 153.39, 149.71, 138.17, 136.15, 135.98, 135.81, 135.32, 134.96, 131.63, 131.42, 130.34, 130.04, 128.22, 126.36, 126.21, 122.03, 67.91, 61.34, 49.79, 49.24, 33.76, 21.06, 20.89, 20.49, 20.28, 14.02 ppm;

Anal. Calcd. for C$_{29}$H$_{34}$N$_4$O$_4$: C, 69.31; H, 6.82; N, 11.15. Found: C, 68.29; H, 6.91; N, 10.88.

EXAMPLE 64

Ethyl (±)-erythro-9,9-bis(2,4-dimethylphenyl)-3,5-dihydroxy-8-(1-methyl-1H-tetrazol-5-yl)-6,8-nonadienoate The general procedure of Example 43 was repeated, except that the ethyl 9,9-bis(4-fluoro-3-methylphenyl)-5-hydroxy-8-(1-methyl-1H-tetrazol-5-yl)-3-oxo-6,8-nonadienoate utilized therein was replaced with 4 g (8.0 mmoles) of ethyl 9,9-bis(2,4-dimethylphenyl)-5-hydroxy-8-(1-methyl-1H-tetrazol-5-yl)-6,8-nonadienoate and the crude material that was thereby produced was purified by silica gel column chromatography eluting with 1% (v/v) methanol in methylene chloride to give 2.5 g of the title compound. MS (CI): m/e=505 for (M+H)$^+$;

$^1$H NMR (CDCl$_3$) δ: 7.10–6.90 (3H, m), 6.85–6.68 (3H, m), 6.43 (1H, d), 5.30 (1H, dd), 4.40 (1H, m), 4.35–4.08 (3H, q over m), 3.90 (1H, s), 3.78 (1H, s), 3.58 (3H, s), 2.47 (2H, d), 2.30 (3H, s), 2.15 (6H, s), 1.88 (3H, s), 1.60 (2H, m), 1.25 (3H, t) ppm;

$^{13}$C NMR (CDCl$_3$) δ: 172.23, 153.67, 149.39, 149.31, 138.18, 136.87, 136.14, 135.95, 135.52, 131.75, 131.54, 130.17, 127.62, 126.47, 126.32, 122.37, 72.05, 68.26, 60.76, 42.48, 41.70, 33.86, 21.18, 21.00 20.64, 20.40, 14.21 ppm;

Anal. Calcd. for C$_{29}$H$_{36}$N$_4$O$_4$: C, 69.03; H, 7.20; N, 11.11. Found: C, 68.13; H, 7.25; N, 10.84.

EXAMPLE 65

Sodium (±)-erythro-9,9-Bis(2,4-dimethylphenyl)-3,5-dihydroxy-8-(1-methyl-1H-tetrazol-5-yl)-6,8-nonadienoate To a solution of ethyl (±)-erythro-9,9-bis-(2,4-dimethylphenyl)-3,5-dihydroxy-8-(1-methyl-1H-tetrazol-5-yl)-6,8-nonadienoate (2.5 g, 4.95 mmoles) in ethanol was added sodium hydroxide solution (4.95 mL of 1.0N solution, 4.95 mmoles). After stirring for 1.5 hours, analytical TLC eluted with 25% (v/v) ethyl acetate in hexane showed no starting material. The solution was concentrated in vacuo and the desired product was lyophilized under high vacuum to produce the title compound as a beige powder. MS (FAB): m/e=498 for M+;

IR (KBr) ν$_{max}$: 3200 (v.br), 1620 (shoulder), 1580 (br), 1450, 1410, 705 (s) cm$^{-1}$;

$^1$H NMR (D$_2$0) δ: 6.93–6.41 (6H, m), 6.31 (1H, d), 5.21 (1H, dd), 4.23–4.17 (1H, m), 3.93 (1H, m), 3.66 (3H, s), 3.59 (2H, q), 2.31–2.10 (2H, m), 2.01 (3H, s), 1.73 (3H, s), 1.67 (3H, s), 1.65–1.48 (1.5H, m), 1.12 (≈2H, t) ppm;

Anal. Calcd. for C$_{27}$H$_{31}$N$_4$O$_4$Na 0.7 mole EtOH: C, 64.27; H, 6.69; N, 10.56 Found: C, 64.48; H, 6.84; N, 10.56.

EXAMPLE 66

Ethyl 3,3-bis(4-fluorophenyl)-2-[1-(2-methoxyethoxy)methyl-1H-tetrazol-5-yl]-2-propenoate and ethyl 3,3-bis(4-fluorophenyl)-2-[2-(2-methoxyethoxy)methyl-2H-tetrazol-5-yl]-2-propenoate Sodium hydride (0.67 g of 60% in mineral oil, 14.0 mmoles) was added to a solution of ethyl 3,3-bis(4-fluorophenyl)-2-(1H-tetrazol-5-yl)-2-propenoate (5.0 g, 14.0 mmoles) [prepared in Example 2] in dimethylformamide (50 mL) and the mixture stirred to give a clear solution. MEM chloride (2-methoxyethoxymethyl chloride) (3.5 g, 28.0 mmoles) was then added and the mixture stirred for 64 hours. The mixture was diluted with water (200 mL) and extracted with methylene chloride. The organic extracts were dried (MgSO$_4$) and the solution concentrated in vacuo to give 6 g of the title compounds as an oil in approximately 1:1 ratio as ascertained by $^1$H NMR. MS (CI): m/e=445 for (M+H)$^+$;

$^1$H NMR (CDCl$_3$) δ: 7.29–6.84 (8H, m), 5.84 (2H, s), 5.43 (2H, s), 4.06 (2H, m), 3.53–3.40 (4H, m), 3.37 (3H, s), 0.99 (3H, m) ppm;

$^{13}$C NMR (CDCl$_3$) δ: 166.23, 165.90, 165.78, 165.59, 165.12, 163.15, 162.34, 160.93, 160.77, 160.62, 160.20, 157.36, 153.61, 152.20, 136.66, 136.61, 135.94, 135.88, 134.53, 134.45, 132.20, 132.03, 131.88, 131.73, 131.19, 131.03, 130.87, 120.04, 115.85, 115.66, 115.49, 115.42, 115.22, 115.05, 114.96, 95.54, 92.21, 80,97, 76.79, 71.69, 71.10, 70,95, 69.53, 69.09, 67.37, 66.73, 61.70, 61.38, 58.89, 36.35, 31.30, 27.80, 26.76, 17.65, 13.60, 13.52 ppm;

EXAMPLE 67

3,3-Bis(4-fluorophenyl)-2-[1-(2-methoxyethoxy)methyl-1H-tetrazol-5-yl]-2-propenol and 3,3-bis(4-fluorophenyl)-2-[2-(2-methoxyethoxy)methyl-2H-tetrazol-5-yl]-2-propenol A solution of diisobutylaluminum hydride (65 mL of 1M solution, 65.0 mmoles) in methylene chloride was added to a solution containing ethyl 3,3-bis(4-fluorophenyl)-2-[1-(2-methoxyethoxy)methyl-1H-tetrazol-5-yl]-2-propenoate and ethyl 3,3-bis(4-fluorophenyl)-2-[2-(2-methoxyethoxy)methyl-2H-tetrazol-5-yl]-2-propenoate (6.0 g, 13.0 mmoles) [prepared in Example 66] in methylene chloride (50 mL) at −78° C. After stirring for 3 hours at −78° C., the reaction was hydrolyzed by the addition of excess 1N HCl. The aqueous layer was separated and extracted with methylene chloride. The combined organic extracts were dried and concentrated in vacuo to give 5.2 g of the title compounds as an oil in approximately 1:1 ratio as ascertained by $^1$H NMR. MS (EI): m/e=402 for M+;

Anal. Calcd. for C$_{20}$H$_{20}$F$_2$N$_4$O$_3$: C, 59.70; H, 5.02; N, 13.93. Found: C, 59.89; H, 5.09; N, 13.99.

EXAMPLE 68

3,3-Bis(4-fluorophenyl)-2-[1-(2-methoxyethoxy)methyl-1H-tetrazol-5-yl]-2-propenal and 3,3-bis(4-fluorophenyl)-2-[2-(2-methoxyethoxy)methyl-2H-tetrazol-5-yl]-2-propenal Pyridinium chlorochromate (6.6 g) was added to a solution containing 3,3-bis(4-fluorophenyl)-2-[1-(2-methoxyethoxy)methyl-1H-tetrazol-5-yl]-2-propenol and 3,3-bis(4-fluorophenyl)-2-[2-(2-methoxyethoxy)methyl-2H-tetrazol-5-yl]-2-propenol (5.2 g, 13.0 mmoles) [prepared in Example 67] in methylene chloride. After stirring for 18 hours at room temperature, the reaction had darkened with formation of a gummy precipitate. The reaction mixture was decanted and the methylene chloride solution was concentrated in vacuo. The residue was purified by column chromatography on silica gel eluting with methylene chloride to give 3 g of the title compounds as an oil in approximately 1:1 ratio, as ascertained by $^1$H NMR. MS (EI): m/e=400 for M+;

$^1$H NMR (CDCl$_3$) δ: 9.73 (1H, s), 9.60 (1H, s), 7.44–6.91 (9H, m), 5.92 (2H, s), 5.57 (2H, s), 3.68–3.38 (7H, m) ppm;

$^{13}$C NMR (CDCl$_3$) δ: 189.62, 188.78, 166.87, 166.57, 166.34, 165.68, 165.60, 163.17, 161.85, 161.65, 161.55, 161.29, 160.66, 151.11, 134.39, 134.33, 133.43, 133.55, 133.37, 133.08, 132.42, 132.25, 132.06, 129.34, 129.19, 128.96, 127.22, 123.65, 116.12, 115.94, 115.69, 115.50, 115.26, 115.07, 80.92, 77.01, 70.87, 69.40, 69.26, 68.83, 62.06, 58.78, 50.23, 46.41 ppm;

Anal. Calcd. for C$_{20}$H$_{18}$F$_2$N$_4$O$_3$: C, 60.00; H, 4.54; N, 13.99. Found: C, 58.11, H, 4.65; N, 13.19.

EXAMPLE 69

3,3-Bis(4-fluorophenyl)-2-[2-(2-methoxyethoxy)methyl-2H-tetrazol-5-yl]-2-propenal and 5,5-bis(4-fluorophenyl)-4-[1-(2-methoxyethoxy)methyl-1H-tetrazol-5-yl]-2,4-pentadienal

A.
3,3-Bis(4-fluorophenyl)-2-[2-(2-methoxyethoxy)methyl-2H-tetrazol-5-yl]-2-propenal A solution containing 3,3-bis(4-fluorophenyl)-2-[1-(2-methoxyethoxy)methyl-1H-tetrazol-5-yl]-2-propenal and 3,3-bis(4-fluorophenyl)-2-[2-(2-methoxyethoxy)methyl-2H-tetrazol-5-yl]-2-propenal (3.5 g, 8.75 mmoles) [prepared in Example 68] and triphenylphosphoranylideneacetaldehyde (1.33 g, 4.4 mmoles) in benzene (50 mL) was heated at reflux temperature for 6 hours. The reaction mixture was concentrated in vacuo and the residue purified by column chromatography on silica gel eluting with 15% (v/v) ethyl acetate in hexane. Concentration of the appropriate fractions yielded an effective separation and isolation of unreacted title compound. MS (CI): m/e=401 for (M+H)+;

$^1$H NMR (CDCl$_3$) δ: 9.70 (1H, s), 7.40–6.80 (9H, m), 5.85 (2H, s), 3.60–3.40 (4H, m), 3.35 (3H, s) ppm;

$^{13}$C NMR (CDCl$_3$) δ: 189.66, 166.66, 165.76, 163.21, 161.72, 163.21, 161.72, 161.64, 160.75, 149.10, 135.46, 135.38, 133.61, 133.44, 133.27, 133.16, 132.79, 132.64, 132.31, 132.14, 131.94, 131.86, 127.32, 116.01, 115.91, 115.56, 115.14, 80.99, 70.91, 69.46, 58.89 ppm;

B.
5,5-Bis(4-fluorophenyl)-4-[1-(2-methoxyethoxy)methyl-1H-tetrazol-5-yl]-2,4-pentadienal Continued elution of the silica gel column from the above Step A yielded the desired product. The appropriate fractions were combined and evaporated under reduced pressure to yield 1.1 g of the title compound. MS (CI): m/e=427 for (M+H)+;

$^1$H NMR (CDCl$_3$) δ: 9.60 (1H, d), 7.45 (1H, d), 7.38–6.80 (8H, m), 5.70 (1H, dd), 5.30 (2H, s), 3.68–3.40 (4H, m) 3.30 (3H, s) ppm;

$^{13}$C NMR (CDCl$_3$) δ: 192.42, 166.17, 165.72, 161.16, 160.70, 155.23, 152.49, 147.96, 135.04, 134.96, 134.55, 134.48, 132.90, 132.73, 132.21, 132.04, 131.85, 119.94, 116.31, 116.08, 115.87, 115.64, 76.67, 71.01, 69.53, 58.96 ppm.

EXAMPLE 70

5,5-Bis(4-fluorophenyl)-4-[2-(2-methoxyethoxy)methyl-2H-tetrazol-5-yl]-2,4-pentadienal A solution of 3,3-bis(4-fluorophenyl)-2-[2-(2-methoxyethoxy)methyl-2H-tetrazol-5-yl]-2-propenal (1.4 g, 3.5 mmoles) and triphenylphosphoranylideneacetaldehyde (1.3 g, 4.3 mmoles) [isolated in Example 69, Step A] in 25 mL of benzene was heated at reflux temperature for 12 hours. The reaction mixture was evaporated under reduced pressure and the residue purified by column chromatography on silica gel eluting with 20% (v/v) ethyl acetate in hexane to give 0.9 g of the title compound as an oil. MS (CI): m/e=427 for (M+H)+;

$^1$H NMR (CDCl$_3$) δ: 9.52 (1H, d), 7.48 (1H, d), 7.32–7.10 (4H, m), 6.92–6.75 (4H, m), 5.85 (3H, s over dd), 3.6–3.5 (4H, m), 3.35 (3H, s) ppm;

$^{13}$C NMR (CDCl$_3$) δ: 193.07, 165.85, 165.04, 163.50, 160.85, 160.07, 154.72, 149.12, 136.61, 136.59, 135.29, 135.24, 133.64, 133.47, 132.84, 132.67, 132.35, 132.13, 131.96, 131.91, 123.79, 115.99, 115.55, 115.35, 114.93, 81.12, 70,96, 69.55, 58.98 ppm.

EXAMPLE 71

Ethyl 9,9-bis(4-fluorophenyl)-5-hydroxy-8-[1-(2-methoxyethoxy)methyl-1H-tetrazol-5-yl]-3-oxo-6,8-nonadienoate Ethyl acetoacetate dianion (2.6 mL of a freshly prepared 1M solution as described in Example 10) was added to a solution of 5,5-bis(4-fluorophenyl)-4-[1-(2-methoxyethoxy)methyl-1H-tetrazol-5-yl]-2,4-pentadienal (1.1 g, 2.6 mmoles) in 15 mL of tetrahydrofuran at −40° C. After stirring for 2 hours, analytical TLC eluted with 25% (v/v) ethyl acetate in hexane showed starting aldehyde and therefore, another 1.2 mL of dianion solution was added. The reaction mixture was allowed to warm to 0° C. and then quenched with 1N HCl. The mixture was extracted with methylene chloride, dried (MgSO$_4$) and concentrated in vacuo. The residue was purified by column chromatography on silica gel eluting with 1% (v/v) methanol in methylene chloride to give 0.9 g of the title compound as an oil. MS (CI): m/e=557 for (M+H)+;

$^1$H NMR (CDCl$_3$) δ: 7.5–6.6 (9H, m), 5.43 (2H, s), 5.00 (1H, dd), 4.6 (1H, m), 3.7–3.4 (6H, s over m), 3.30 (3H, s), 2.72 (2H, d), 1.22 (3H, t) ppm.

EXAMPLE 72

Ethyl 9,9-bis(4-fluorophenyl)-5-hydroxy-8-[2-(2-methoxyethoxy)methyl-2H-tetrazol-5-yl]-3-oxo-6,8-nonadienoate Ethyl acetoacetate dianion (2.1 mL of freshly prepared 1M solution as described in Example 10) was added to a solution of 5,5-bis(4-fluorophenyl)-4-[2-(2-methoxyethoxy)methyl-2H-tetrazol-5-yl]-2,4-pentadienal (0.9 g, 2.0 mmoles) in 15 mL of tetrahydrofuran at −50° C. After stirring for 1 hour, another 1 mL of dianion solution was added and the mixture stirred for an additional 30 minutes. The reaction mixture was quenched with 1N HCl and then extracted with methylene chloride. The organic extracts were dried (MgSO$_4$) and concentrated in vacuo. The residue was purified by column chromatography on silica gel eluting with 1% (v/v) methanol in methylene chloride to give 0.55 g of the title compound. MS (CI): m/e=557 for (M+H)$^+$;

$^1$H NMR (CDCl$_3$) δ: 7.30–7.05 (4H, m), 6.90–6.70 (5H, m), 5.85 (2H, s), 5.35 (1H, dd), 4.70–4.53 (1H, m), 4.17 (2H, q), 3.48 (4H, m), 3.38 (3H,s), 2.72 (2H, d), 1.26 (3H, t) ppm;

$^{13}$C NMR (CDCl$_3$) δ: 202.03, 190.30, 166.60, 164.88, 164.36, 164.15, 159.92, 146.22, 137.49, 137.41, 135.13, 132.29, 132.13, 131.63, 131.47, 131.18, 131.05, 131.02, 130.93, 128.67, 124.46, 115.45, 115.03, 114.92, 114.51, 91.16, 80.80, 70.84, 69.28, 67.96, 61.37, 58.90, 49.82, 49.18, 14.01 ppm.

EXAMPLE 73

Ethyl (±)-erythro-9,9-bis(4-fluorophenyl)-3,5-dihydroxy-8-[1-(2-methoxyethoxy)methyl-1H-tetrazol-5-yl]-6,8-nonadienoate To a solution of ethyl 9,9-bis(4-fluorophenyl)-5-hydroxy-8-[1-(2-methoxyethoxy)methyl-1H-tetrazol-5-yl]-3-oxo-6,8-nonadienoate (0.9 g, 1.6 mmoles) in tetrahydrofuran (20 mL) at −10° C. was added triethylborane (2.1 mL of 1M solution) and the mixture stirred for 45 minutes during which time the initially yellow solution became colorless. The solution was cooled to −78° C. and sodium borohydride (0.13 g, 3.2 mmoles) and methanol (0.75 mL) were added. After 2 hours at −78° C., the solution was diluted with 50 mL of hexane and hydrolyzed with 1N HCl. The aqueous layer was separated and extracted with ethyl acetate. The combined organic solutions were dried (MgSO$_4$) and concentrated in vacuo. The residue was dissolved in methanol (30 mL) and the solution stirred for 40 hours. The solution was concentrated in vacuo and the residue purified by column chromatography on silica gel elution with 1% (v/v) methanol in methylene chloride to give 0.4 g of the title compound. MS (CI): m/e=559 for (M+H)$^+$;

$^1$H NMR (CDCl$_3$) δ: 7.4–6.8 (8H, m), 6.65 (1H, d), 5.40 (2H, s), 4.95 (1H, dd), 4.4–3.5 (8H, m), 3.30 (3H, s), 2.40 (2H, d), 1.80–1.35 (2H, m), 2.20 (3H, t) ppm.

EXAMPLE 74

Ethyl (±)-erythro-9,9-bis(4-fluorophenyl)-3,5-dihydroxy-8-[2-(2-methoxyethoxy)methyl-2H-tetrazol-5-yl]-6,8-nonadienoate To a solution of ethyl 9,9-bis(4-fluorophenyl)-5-hydroxy-8-[2-(2-methoxyethoxy)methyl-2H-tetrazol-5-yl]-3-oxo-6,8-nonadienoate (0.9 g, 1.6 mmoles) in tetrahydrofuran (15 ml) at −0° C. was added triethylborane (2.1 mL of 1M solution, 2.1 mmoles) and the solution stirred for 1.5 hours during which time the yellow color disappeared. The mixture was cooled to −75° C. and sodium borohydride (0.13 g, 3.2 mmoles) and methanol (0.9 mL) were added. After stirring for 2 hours, the solution was diluted with 50 mL of hexane and hydrolyzed by addition of 1N HCl. The aqueous layer was separated and extracted with ethyl acetate. The combined organic fractions were dried (MgSO$_4$) and concentrated in vacuo. The residue was dissolved in methanol and the solution stirred for 16 hours. The methanolic solution was concentrated in vacuo and the residue purified by column chromatography on silica gel eluting with 1.5% (v/v) methanol in methylene chloride to give 0.6 g of the title compound. MS (CI): m/e=559 for (M+H)$^+$;

$^1$H NMR (CDCl$_3$) δ: 7.38–7.04 (4H,m), 6.92–6.65 (5H, m), 6.92 (2H, s), 6.40 (1H, dd), 4.45 (1H, m), 4.15 (3H, q over m), 3.43 (4H, s), 3.32 (3H, s), 2.45 (2H, d), 1.72–1.65 (2H, m), 1.25 (3H, t) ppm;

$^{13}$C NMR (CDCl$_3$) δ: 172.45, 165.05, 164.69, 164.32, 160.12, 159.40, 146.06, 137.75, 137.70, 136.96, 136.13, 132.44, 132.28, 131.82, 131.66, 131.40, 131.25, 131.05, 128.32, 124.91, 115.65, 115.40, 115.23, 114.92, 114.69, 80.97, 72.25, 71.05, 69.48, 68.22, 60.90, 59.15, 42.53, 41.06, 14.27 ppm.

EXAMPLE 75

Sodium (±)-erythro-9,9-Bis(4-fluorophenyl)-3,5-dihydroxy-8-[1-(2-methoxyethoxy)methyl-1H-tetrazol-5-yl]-6,8-nonadienoate A solution of ethyl (±)-erythro-9,9-bis(4-fluorophenyl)-3,5-dihydroxy-8-[1-(2-methoxyethoxy)methyl-1H-tetrazol-5-yl]-6,8-nonadienoate (0.3 g, 0.54 mmole) and sodium hydroxide (0.54 mL of a 1N solution, 0.54 mmole) in ethanol (15 mL) was stirred for 3 hours. The solution was concentrated in vacuo and the desired product was lyophilized under high vacuum to produce 250 mg of the title compound which appears to contain about two moles of water; m.p.=110°–135° C. MS (FAB): m/e=553 for (M+H)$^+$;

$^1$H NMR (D$_2$O) δ: 7.38–7.33 (2H, m), 7.22–7.18 (2H, t), 6.98–6.89 (4H, m), 6.67 (1H, d), 5.50 (2H, s), 5.23 (1H, dd), 4.27 (1H, m), 3.93 (1H, m), 3.61–3.46 (4H, m), 3.28 (3H, s), 2.30–2.28 (2H, m), 1.68–1.50 (2H, m) ppm;

$^{13}$C NMR (D$_2$O) δ: 181.37, 165.49, 165.02, 162.75, 162.27, 149.52, 138.74, 137.38, 136.57, 133.84, 133.75, 132.97, 132.88, 129.29, 121.34, 116.98, 116.73, 116.49, 78.19, 72.00, 71.02, 70.74, 68.31, 59.58, 46.05, 44.11 ppm;

Anal. Calcd. for C$_{26}$H$_{27}$F$_2$N$_4$O$_6$ Na 2H$_2$O: C, 53.06; H, 5.31; N, 9.53. Found: C, 53.36; N, 5.04; N, 9.02.

EXAMPLE 76

Sodium (±)-erythro-9,9-Bis(4-fluorophenyl)-3,5-dihydroxy-8-[2-(2-methoxyethoxy)methyl-2H-tetrazol-5-yl]-8,9-nonadienoate A solution of ethyl (±)-erythro-9,9-bis(4-fluorophenyl)-3,5-dihydroxy-8-[2-(2-methoxyethoxy)methyl-2H-tetrazol-5-yl]-6,8-nonadienoate (0.45 g, 0.81 mmoles) and sodium hydroxide (0.81 mL of a 1N solution, 0.81 mmoles) in ethanol (10 mL) was stirred for 30 minutes. The solution was concentrated in vacuo and the desired product was lyophilized under high vacuum to produce 350 mg of the title compound as an orange powder; m.p.=175°–190° C. MS (FAB): m/e=551 for (M-H)⁻;

IR (KBr) $\nu_{max}$: 3400 (v.br), 1603, 1585, 1515 (s), 1410 (br), 1230 842 (s) cm⁻¹;

¹H NMR (D₂O) δ: 7.17–7.11 (2H, m), 7.02–6.97 (2H, t), 6.81–6.58 (5H, m), 5.86 (2H, s), 5.35 (1H, dd), 4.26 (1H, m), 3.97–3.93 (1H, m), 3.41–3.24 (4H, m), 3.22 (3H, s), 2.33–2.21 (2H, m), 1.67–1.48 (2H, m) ppm;

Anal. Calcd. for $C_{26}H_{27}F_2N_4O_6$ Na 0.5H₂O: C, 55.62; H, 5.03; N, 9.98; H₂O, 1.60. Found: C, 55.46; H, 5.03; N, 9.79; H₂O, 1.89.

EXAMPLE 77

5,5-Bis(4-fluorophenyl)-4-(1-methyl-1H-tetrazol-5-yl)-2,4-pentadienal

To a mixture of 3,3-bis(4-fluorophenyl)-2-(1-methyl-1H-tetrazol-5-yl)-2-propenal (71.6 g, 0.22 mole) and triphenylphosphoranylidene acetaldehyde (66.8 g, 0.22 mole) was added 1.1 liters of dry benzene and the suspension was heated to reflux temperature over a period of 30 minutes. The reaction was allowed to proceed at reflux temperature for 2 hours. Analytical TLC eluted five times with 30% (v/v) ethyl acetate in hexanes showed only one major spot at $R_f$=0.37 for the desired product. The crude hot reaction mixture was diluted with an equal volume of hexane and the warm mixture was quickly filtered through a bed of activated charcoal. The filtrate was allowed to stand at room temperature from which 58.12 g (75.2%) of the desired product was collected. A second crystallization from the filtrate yielded mostly triphenylphosphine oxide. Concentration of the filtrate yielded an additional amount of the desired product to give a total of 71 g (91.8%) of the title compound. The combined material was recrystallized from ethyl acetate-hexane to give pure title compound; m.p.=164°–165° C. A ¹H NMR of the recrystallized material showed no detectable double homologated product.

Anal. Calcd. for $C_{19}H_{14}F_2N_4O$: C, 64.77; H, 4.01; N, 15.90. Found: C, 65.20; H, 4.09; N, 16.03.

EXAMPLE 78

3,3-Bis(4-fluorophenyl)-2-(1-methyl-1H-tetrazol-5-yl)propenal

A.

1,1-Bis(4-fluorophenyl)-2-(1-methyl-1H-tetrazol-5-yl)ethanol

To a solution of 1,5-dimethyltetrazole (0.98 g, 10.0 mmoles) in tetrahydrofuran (20 mL) at −30° C. was added n-butyl lithium (4.7 mL of 2.14M solution, 10.0 mmoles). After stirring for 0.25 hour, the solution was cooled to −50° C. and 4,4'-difluorobenzophenone (1.74 g, 8.0 mmoles) was added. After stirring for 1 hour at −50° C. and 1 hour at −10° C., the reaction was quenched with 1N hydrochloric acid. The mixture was extracted with methylene chloride, dried and evaporated in vacuo. The residue was purified by column chromatography on silica gel eluting with 40% (v/v) ethyl acetate in hexane to give 2.0 g of the title compound; m.p.=116°–118° C.

Anal. Calcd. for $C_{16}H_{14}F_2N_4O$: C, 60.76; H, 4.47; N, 17.72. Found: C, 60.62; H, 4.52; N, 17.63.

B.

1,1-Bis(4-fluorophenyl)-2-(1-methyl-1H-tetrazol-5-yl)ethene

A mixture of 1,1-bis(4-fluorophenyl)-2-(1-methyl-1H-tetrazol-5-yl)ethanol (4.2 g, 12.7 mmoles) [prepared in Step A] and potassium hydrogen sulfate was heated at 195° C. for 0.5 hour. After cooling, the mixture was dissolved in chloroform and washed with water. The organic layer was dried and evaporated in vacuo. The residue was triturated with diethyl ether to give 3.9 g of the title compound; m.p.=169°–171° C.

Anal. Calcd. for $C_{16}H_{12}F_2N_4$: C, 64.43; H, 4.06; N, 18.88. Found: C, 63.93; H, 4.00; N, 19.25.

C.

3,3-Bis(4-fluorophenyl)-2-(1-methyl-1H-tetrazol-5-yl)propenal

To a finely divided suspension of 1,1-bis(4-fluorophenyl)-2-(1-methyl-1H-tetrazol-5-yl)ethene (1.0 g, 3.3 mmoles) [prepared in Step B] in tetrahydrofuran (10 mL) at −80° C. was added n-butyl lithium (1.54 mL of 2.14M solution), 3.3 mmoles) with the formation of a dark violet color. After stirring for 40 minutes at −80° C., ethyl formate (0.32 g, 4.3 mmoles) was added and the mixture stirred for 2.5 hours at −80° C. The mixture was hydrolyzed with 1N hydrochloric acid and extracted with methylene chloride. The extracts were dried (MgSO₄) and evaporated in vacuo. The residue was triturated with diethyl ether to give 0.77 g of yellow solid, m.p. 128°–131° C. The solid was crystallized from isopropyl acetate-hexane to give 0.55 g of the title compound; m.p.=130°–132° C.

Anal. Calcd. for $C_{17}H_{12}F_2N_4O$: C, 62.58; H, 3.71; N, 17.18. Found: C, 62.15; H, 3.82; N, 16.75.

EXAMPLE 79

5,5-Bis(4-fluorophenyl)-4-(1-methyl-1H-tetrazol-5yl)-2,4-pentadienal

A solution of 3,3-bis(4-fluorophenyl)-2-(1-methyl-1H-tetrazol-5-yl)propenal (1.0 g, 3.07 mmoles) and triphenylphosphoranylidene acetaldehyde (0.93 g, 3.07 mmoles) in benzene was heated at reflux for 1 hour. The benzene was removed in vacuo and the residue was purified by column chromatography on silica gel eluting with 15% (v/v) ethyl acetate in hexane to give 0.7 g of the title compound; m.p.=156°–157.5° C.

Anal. Calcd. for $C_{19}H_{14}F_2N_4O$: C, 64.77; H, 4.01; N, 15.91. Found: C, 65.13; H, 4.05; N, 15.71.

EXAMPLE 80

3,3-Bis(4-fluorophenyl)-2-(1-methyl-1H-tetrazol-5-yl-2-propenal

A. 5-Ethyl-1-methyl-1H-tetrazole

To a slurry of 1,5-dimethyltetrazole (4.9 g, 0.05 mole) in dry tetrahydrofuran (50 mL) was added 2.5M n-butyllithium in hexanes (20 mL, 0.05 mole) over a period of 15 minutes at −78° C. under an inert atmosphere. This mixture was stirred for 30 minutes and a yellowish precipitate formed during this time. Methyl iodide (3.7 mL, 0.06 mole) was then added over a period of 15 minutes. After stirring for an additional 30 minutes, the clear reaction mixture was diluted with water and extracted with ethyl acetate (3×50 mL). The aqueous layer was washed with chloroform (2×25 mL), and the combined organic layer was dried over sodium sulfate and concentrated under reduced pressure to give an oil. The oil was purified by distillation to give 5.2 g (92%) of the title compound; b.p.=89°–90° C. at 0.05 mm Hg.

$^1$H NMR (CDCl$_3$) δ: 4.05 (s, 3H), 2.86 (q, 2H), 1.41 (t, 3H);

$^{13}$C NMR (CDCl$_3$) δ: 156.0, 33.24, 16.75, 11.20.

B.
1,1-Bis(4-fluorophenyl)-2-(1-methyl-1H-tetrazol-5-yl)propanol

To a solution of 5-ethyl-1-methyl-1H-tetrazole (5.6 g, 0.05 mole) [prepared in Step A] in 60 mL of dry tetrahydrofuran was added 2.5M n-butyllithium (20 mL, 0.05 mole) in hexane over 5 minutes at −78° C. (bath temperature) under an inert atmosphere. The mixture was stirred for 30 minutes and a solution of 4,4′-difluorobenzophenone (10.8 g, 0.5 mole) in 25 mL of dry tetrahydrofuran was added over 5 minutes. This mixture was stirred for an additional 2 hours while the bath temperature was slowly warmed to −20° C. The reaction was quenched with 1N HCl and extracted with ethyl acetate (3×50 mL) and chloroform (3×50 mL). The combined organic layer was dried over sodium sulfate and concentrated under reduced pressure to give a white solid. The solid was purified by crystallization from ethanol-hexane to give 10.8 g (65%) of the title compound; m.p.=160°–161° C.

IR (KBr) $ν_{max}$: 3400 cm$^{-1}$;

$^1$H NMR (CDCl$_3$) δ: 7.8–7.02 (m, 8H), 5.95 (s, 1H), 4.65 (q, 1H), 3.98 (s, 3H), 1.29 (d, 2H).

$^{13}$C NMR (CDCl$_3$) δ: 162.57, 162.37, 159.14, 156.71, 142.48, 140.54, 128.25, 128.13, 127.52, 127.42, 114.67, 114.41, 114.38, 78.56, 36.99, 33.43, 14.52.

Anal. Calcd. for C$_{17}$H$_{16}$F$_2$N$_4$O: C, 61.81; H, 4.88; N, 16.96. Found: C, 61.79; H, 4.90; N, 17.09.

C.
1,1-Bis(4-fluorophenyl)-2-(1-methyl-1H-tetrazol-5-yl)-1-propene

A slurry of 1,1-bis(4-fluorophenyl)-2-(1-methyl-1H-tetrazol-5-yl)propanol (8.25 g, 0.025 mole) [prepared in Step B] and 100 mg of p-toluene sulfonic acid monohydrate in xylene (60 mL) was heated to reflux with a Dean & Stark water collecting apparatus for a period of 12 hours. The reaction mixture was washed with 1N NaOH (10 mL) while it was warm and with water (100 mL). Concentration of the organic layer gave off-white crystals of product. This was purified by recrystallization from ethanol-hexane to give 7.1 g (91%) of the title compound as white crystals; m.p.=146°–147° C.

IR (KBr) $ν_{max}$: 1575; 1500 cm$^{-1}$.

$^1$H NMR (CDCl$_3$) δ: 7.42–6.85 (m, 8H), 3.53 (s, 3H), 2.14 (s, 3H);

$^{13}$C NMR (CDCl$_3$) δ: 163.37, 163.08, 160.13, 155.61, 144.60, 145.34, 136.47, 136.42, 136.24, 136.19, 131.65, 131.54, 131.11, 131.01, 119.53, 115.51, 115.27, 115.22, 33.50, 21.20.

Anal. Calcd. for C$_{17}$H$_{13}$F$_2$N$_4$: C, 65.37; H, 4.51; N, 17.94. Found: C, 65.64; H, 4.61; N, 18.09.

D.
3,3-Bis(4-fluorophenyl)-1-bromo-2-(1-methyl-1H-tetrazol-5-yl)-2-propene A slurry of 1,1-bis(4-fluorophenyl)-2-(1-methyl-1H-tetrazol-5-yl)-1-propene (61.46 g, 0.197 mole) [prepared in Step C], N-bromosuccinamide (35.06 g, 0.197 mole) and catalytic amount of azobis isobutyronitrile or benzoyl peroxide in carbon tetrachloride (1.2 liters) was heated to reflux in an inert atmosphere for a period of 2 hours. The reaction mixture was cooled to ambient temperature and the solid from the reaction was filtered. The filtrate was concentrated under reduced pressure and the solid obtained was recrystallized from toluene-hexane to give 72 g (93%) of the title compound as white crystals; m.p.=159°–160° C.

IR (KBr) $ν_{max}$: 1600 cm$^{-1}$.

$^1$H NMR (CDCl$_3$) δ: 7.5–7.1 (m, 8H), 4.44 (s, 2H), 3.53 (s, 3H).

$^{13}$C NMR (CDCl$_3$) δ: 163.94, 163.74, 160.60, 160.45, 143.42, 149.68, 135.20, 135.15, 134.69, 131.43, 131.31, 130.90, 130.80, 119.57, 115.94, 115.77, 115.65, 115.50.

Anal. Calcd. for C$_{17}$H$_{14}$F$_2$BrN$_4$: C, 52.19; H, 3.34; N, 14.32. Found: C, 52.58; H, 3.47; N, 14.49.

E.
3,3-Bis(4-fluorophenyl)-2-(1-methyl-1H-tetrazol-5-yl)-2-propenal

To a solution of sodium ethoxide (3.93 g of sodium metal, 0.17 mole) in 500 mL of absolute ethanol was added 2-nitropropane (16.66 g, 0.187 mole) slowly over 5 minutes. The bromo compound prepared in the above Step D (67.1 g, 0.17 mole) was added portionwise over a period of 10 minutes. The reaction mixture was stirred for 2 hours and the ethanol was removed in vacuo. The residue was dissolved in CH$_2$Cl$_2$ (500 mL), washed with water (250 mL) and dried over sodium sulfate. The organic layer was concentrated under reduced pressure to give an oil. The oil was dissolved in hot toluene (350 mL) and trituration with hexane (350 mL) gave 50.6 g (91%) of the title compound as white crystals; m.p.=135°–137° C.

EXAMPLE 81

[1,1-Bis(4-fluorophenyl)-2-(1-methyl-1H-tetrazol-5-yl)-1-propen-3-yl]triphenylphosphonium bromide A slurry of 3,3-bis(4-fluorophenyl)-1-bromo-2-(1-methyl-1H-tetrazol-5-yl)-2-propene (1.95 g, 0.005 mole) [prepared in Example 80, Step D] and triphenylphosphine (1.3 g, 0.005 mole) in cyclohexane (25 mL) was heated to reflux. The reaction mixture became a clear solution after 30 minutes and a white precipitate appeared after 1 hour. The mixture was heated for an additional 8 hours, cooled to ambient temperature and the solid was collected by filtration and washed with diethyl ether. This white powder was dried in vacuum at 50° C. to give 3.0 g (92%) of the title compound; m.p.=254°–255° C.

IR (KBr) $ν_{max}$: 3450, 1600, 1500, 1425 cm$^{-1}$.

$^1$H NMR (DMSO-d$_6$) δ: 7.92–6.80 (m, 23H), 4.94 (6d, 2H), 3.83 (s, 3H);

$^{13}$C NMR (DMSO-d$_6$) δ: 163.53, 163.36, 160.28, 160.87, 154.04, 153.89, 152.76, 135.11, 134.79, 134.16, 133.68, 133.54, 130.53, 130.45, 130.35, 130.21, 130.07, 118.02, 116.89, 116.18, 115.89, 115.62, 115.32, 111.43, 111.39, 34.22, 28.88, 28.22.

Anal. Calcd. for C$_{35}$H$_{28}$BrF$_2$N$_4$P: C, 64.31; H, 4.32; N, 8.57. Found: C, 64.02; H, 4.37; N, 8.89.

EXAMPLE 82

Methyl (±)-erythro-9,9-bis(4-fluorophenyl)-3,5-dihydroxy-8-(1-methyl-1H-tetrazol-5-yl)-6,8-nonadienoate To a slurry of the phosphonium bromide (0.326 g, 0.5 mmole) [prepared in Example 81] and methyl erythro-3,5-bis(diphenyl-t-butylsilyloxy)-6-oxo-hexanoate [prepared according to the general procedures described by P. Kapa, et al. in Tetrahedron Letters, 2435–2438 (1984) and in U.S. Pat. No. 4,571,428, issued Feb. 18, 1986 to P. K. Kapa] (0.26 g, 0.4 mmole) in dry dimethylformamide (1 mL) was added potassium t-butoxide (0.067 g, 0.6 mmole) at −20° C. (bath temperature) in an inert atmosphere. The slurry became a red solution and was stirred for 18 hours at −10° C. The reaction was worked up by adding ammonium chloride solution (10 mL) and extracting with methylene chloride (2×30 mL). The organic layer was dried over sodium sulfate and concentrate to give an oil. The oil was purified through a pad of silica gel and the major fraction was isolated as an oil (160 mg). The oil (160 mg) was stirred with 1M tetra-n-butyl ammonium fluoride solution in tetrahydrofuran (2 mL) and few drops of glacial acetic acid for a period of 18 hours. The reaction mixture was poured into water (10 mL) and extracted with ethyl acetate (3×20 mL). The organic layer was dried over sodium sulfate and concentrated to given an oil. The oil was purified by silica gel flash column chromatography eluting with ethyl acetate:hexane (2:1) to give 0.08 g (75%) of the title compound as an oil. MS (CI): m/e=471 for (M+H)+;

$^1$H NMR (CDCl$_3$) δ: 7.26–6.6 (m, 9H), 5.37 (dd, 1H), 4.44 (m, 1H), 4.24 (m, 1H), 3.71 (s, 3H), 3.56 (s, 3H), 2.47 (d, 2H), 1.58 (m, 2H).

A more polar fraction was also isolated (≃20 mg) and identified as the corresponding trans lactone.

EXAMPLE 83

4,4′-Difluoro-2,2′-dimethylbenzophenone

To a well stirred mixture of aluminum chloride (6.1 g, 46.0 mmoles) in carbon tetrachloride (14 mL) at 0° C., 3-fluorotoluene (1 g from a total of 10 g, 90.0 mmoles) was added and the mixture stirred for 10 minutes. The remainder of the 3-fluorotoluene in 9 mL of carbontetrachloride was added and the mixture stirred at 0° C. for 4 hours. The mixture was cooled to −20° C. and hydrolyzed by adding 25 mL 1N hydrochloric acid. The organic layer was separated and concentrated in vacuo. The residue was stirred for 16 hours with a mixture of benzene (20 mL), water (20 mL), and acetic acid (5 mL). The aqueous layer was separated and extracted with diethyl ether. The combined organic fractions were dried (MgSO$_4$) and concentrated in vacuo. Analytical TLC of the residue showed 3 spots; R$_f$=0.67, 0.59 and 0.56 [5% (v/v) ethyl acetate in hexane on silica gel]. Column chromatography on silica gel with 0.5% (v/v) ethyl acetate in hexane and collection of the appropriate fractions containing material having R$_f$=0.67 [5% (v/v) ethyl acetate in hexane] gave 1.3 g of the title compound; m.p.=50°–52° C. MS (CI): m/e=247 for (M+H)+;

$^1$H NMR (CDCl$_3$) δ: 7.26 (2H, dd), 6.96 (2H, dd), 6.87 (2H, dt), 2.42 (6H, s).

Anal. Calcd. for C$_{15}$H$_{12}$F$_2$O: C, 73.17; H, 4.92. Found: C, 73.34; H, 5.02.

EXAMPLE 84

2,4′-Difluoro-4,2′-dimethylbenzophenone

Concentration of the appropriate fractions from the silica gel column chromatography of Example 83 having material with R$_f$=0.59 gave 2.4 g of the title compound; m.p.=29°–31° C. MS (CI): m/e=347 for (M+H)+;

$^1$H NMR (CDCl$_3$) δ: 7.53 (1H, t), 7.39 (1H, dd), 7.19–6.85 (4H, m), 2.42 (3H, s), 2.39 (3H, s).

Anal. Calcd. for C$_{15}$H$_{12}$F$_2$O: C, 73.17; H, 4.92. Found: C, 73.34; H, 4.86.

EXAMPLE 85

2,2′-Difluoro-4,4′-dimethylbenzophenone

Concentration of the appropriate fractions from the silica gel column chromatography of Example 83 having material with R$_f$=0.56 and trituration of the residue with hexane gave 1.2 g of the title compound; m.p.=84°–85.5° C.

$^1$H NMR (CDCl$_3$) δ: 7.57 (2H, t, J$_{H-H}$=8 Hz, J$_{FH}$=8 Hz), 7.02 (2H, d, J$_{H-H}$=8 Hz), 6.89 (2H, d, J$_{FH}$=8 Hz), 2.39 (6H, s).

Anal. Calcd. for C$_{15}$H$_{12}$F$_2$O: C, 73.17; H, 4.92. Found: C, 73.19; H, 4.88.

EXAMPLE 86

1,1-Bis(4-fluoro-2-methylphenyl)-2-(1-methyl-1H-tetrazol-5-yl)ethanol

To a suspension of 1,5-dimethyltetrazole (3.8 g, 39.0 mmoles) in tetrahydrofuran (40 mL) at −40° C. was added butyl lithium (17.7 mL of a 2.2M solution, 39.0 mmoles). Aftering stirring for 10 minutes, 4,4′-difluoro-2,2′-dimethylbenzophenone (8 g, 32.5 mmoles) was added and the solution stirred for 3 hours. The reaction was quenched with 1N hydrochloric acid. The aqueous layer was separated and extracted with ethyl acetate. The combined organic phases were dried (MgSO$_4$) and concentrated in vacuo to give 7.5 g of the title compound; m.p.=186°–188° C.

anal. Calcd. for C$_{18}$H$_{18}$F$_2$N$_4$O: C: 62.99; H, 5.27; N, 16.27 Found: C, 63.01; H, 5.34; N, 16.18.

EXAMPLE 87

1,1-Bis(4-fluoro-2-methylphenyl)-2-(1-methyl-1H-tetrazol-5-yl)ethene

A mixture of 1,1-bis-(4-fluoro-2-methylphenyl)-2-(1-methyl-1H-tetrazol-5-yl)ethanol (0.5 g, 1.5 mmoles) and p-toluenesulfonic acid (0.2 g) was heated at reflux in toluene (30 mL) for 16 hours. The mixture was cooled, diluted with diethyl ether (50 mL) and extracted with saturated sodium bicarbonate solution and water. The organic layer was dried (MgSO$_4$) and concentrated in vacuo. The residue was triturated with diethyl ether to give 0.3 g of the title compound; m.p.=120°–125° C.

Anal. Calcd. for C$_{18}$H$_{16}$F$_2$N$_4$: C, 66.25; H, 4.95; N, 17.17. Found: C, 66.55; H, 4.92; N. 16.84.

EXAMPLE 88

3,3-Bis(4-fluoro-2-methylphenyl)-2-(1-methyl-1H-tetrazol-5-yl)-2-propenal

To a solution of 1,1-bis(4-fluoro-2-methylphenyl)-2-(1-methyl-1H-tetrazol-5-yl)ethene (1.6 g, 5.0 mmoles) in tetrahydrofuran at −70° C. was added butyl lithium (2.3 mL of 2.2M solution, 5.0 mmoles). After stirring for 0.25 hour, ethyl formate (0.44 g, 6.0 mmoles) was added and the mixture stirred for 2 hours. The reaction was quenched with 1N hydrochloric acid and the mixture was extracted with methylene chloride. The extracts were dried and concentrated in vacuo to give 1.0 g of the title compound; m.p.=135°–136° C.

Anal. Calcd. for C$_{19}$H$_{16}$F$_2$N$_4$O: C, 64.41; H, 4.56; N, 15.82. Found: C, 64.22; H, 4.59; N, 15.50.

EXAMPLE 89

5,5-Bis(4-fluoro-2-methylphenyl)-4-(1-methyl-1H-tetrazol-5-yl)-2,4-pentadienal A solution of 3,3-bis(4-fluoro-2-methylphenyl)-2-(1-methyl-1H-tetrazol-5-yl)-2-propenal (0.88 g, 2.5 mmoles) and triphenylphosphoranylidene acetaldehyde (0.75 g, 2.5 mmoles) in benzene (50 mL) was heated at reflux for 3 hours. The solvent was removed by evaporation and the crude residue purified by column chromatography on silica gel eluting with 1% (v/v) methanol in methylene chloride. The fractions containing material having $R_f=0.9$ [1:20 (v/v) methanol:methylene chloride] were combined and concentrated to give 0.8 g of the title compound; m.p.=75°–95° C. MS: M+ =380;

$^1$H NMR (CDCl$_3$) δ: 9.52 (1H, d), 7.30–6.67 (7H, m), 5.82 (1H, dd), 3.62 (3H, s), 2.23 (3H, s), 2.00 (3H, s).

Anal. Calcd. for $C_{21}H_{18}F_2N_4O$: C, 66.31; H, 4.78; N, 14.73. Found: C, 65.76; H, 4.85; N, 14.52.

EXAMPLE 90 tert-Butyl 9,9-bis(4-fluoro-2-methylphenyl)-5-hydroxy-8-(1-methyl-1H-tetrazol-5-yl)-3-oxo-6,8-nonadienoate To a solution of 5,5-bis(4-fluoro-2-methylphenyl)-4-(1-methyl-1H-tetrazol-5-yl)-2,4-pentadienal (1.0 g, 2.5 mmoles) in tetrahydrofuran at −50° C. was added the dianion of t-butyl acetoacetate (2.5 mL of a 1M solution, 2.5 mmoles) prepared by adding t-butyl acetoacetate (4.0 g, 25.0 mmoles) in tetrahydrofuran (4 mL) to a suspension of sodium hydride (1.0 g of 60% dispersion, 25.0 mmoles) in tetrahydrofuran at −5° C. followed by cooling to −30° C. and the addition of butyl lithium (11.4 mL of 2.2M solution, 25 mmoles). After stirring for 1.5 hours, analytical TLC indicated starting aldehyde and another 0.5 mL of dianion solution was added. The solution was stirred an additional 0.5 hour and quenched with 1N hydrochloric acid. The mixture was extracted with methylene chloride. The extracts were dried and concentrated in vacuo. The residue was purified by column chromatography on silica gel eluting with methanol in methylene chloride to produce 0.6 g of the title compound; m.p.=65°–72° C.

Anal. Calcd. for $C_{29}H_{32}F_2N_4O_4$: C, 64.48; H, 5.99; N, 10.41. Found: C, 64.50; H, 5.98; N. 10.16.

EXAMPLE 91 tert-Butyl (±)-erythro-9,9-bis(4-fluoro-2-methylphenyl)-3,5-dihydroxy-8-(1-methyl-1H-tetrazol-5-yl)-6,8-nonadienoate To a solution of t-butyl 9,9-bis(4-fluoro-2-methylphenyl)-5-hydroxy-8-(1-methyl-1H-tetrazol-5-yl)-3-oxo-6,8-nonadienoate (2.5 g, 4.6 mmoles) in tetra hydrofuran (30 mL) at −5° C. was added triethylborane (6.0 mL of a 1M solution, 6.0 mmoles) and the solution stirred for 1 hour. After cooling to −78° C., sodium borohydride (0.36 g, 9.0 mmoles) and methanol (2 mL) were added. The mixture was stirred at −78° C. for 2 hours and diluted with hexane (15 mL). The mixture was hydrolyzed with 1N hydrochloric acid. The aqueous layer was separated and extracted with methylene chloride. The combined organic solutions were dried and concentrated in vacuo. The residue was dissolved in methanol and the solution stirred for 18 hours. The solution was concentrated in vacuo and the residue purified by column chromatography on silica gel eluting with 1% (v/v) methanol in methylene chloride to produce 1.7 g of the title compound as a white powder; m.p.=75°–80° C.

$^1$H NMR (CDCl$_3$) δ: 7.15–6.60 (7H, m), 6.43 (1H, d), 5.26 (1H, dd), 4.42 (1H, m), 4.18 (1H, m), 3.92 (1H, s), 3.64 (3H, s), 2.39 (2H, d), 2.26 (3H, bs), 2.04 (3H, s), 1.57 (2H, m), 1.43 (9H, s);

Anal. Calcd. for $C_{29}H_{34}F_2N_4O_4$: C, 64.44; H, 6.34; N, 10.37. Found (corr. for 0.28% $H_2O$): C, 64.14; H, 6.41; N, 10.16.

EXAMPLE 92

Sodium (±)-erythro-9,9-bis(4-fluoro-2-methylphenyl)-3,5-dihydroxy-8-(1-methyl-1H-tetrazol-5-yl)-6,8-nonadienoate To a solution of t-butyl 9,9-bis(4-fluoro-2-methylphenyl)-3,5-dihydroxy-8-(1-methyl-1H-tetrazol-5-yl)-6,8-nonadienoate (1.65 g, 3.05 mmoles) in ethanol (50 mL) was added sodium hydroxide (3.05 mL of 1N solution, 3.05 mmoles) and the solution stirred at room temperature for 3 hours and at 50° C. for 1 hour. The solution was concentrated in vacuo to give 1.3 g of the title compound which appears to contain about one mole of water; m.p.=215°–225° C. (dec.).

Anal. Calcd. for $C_{25}H_{25}F_2N_4O_4Na\cdot H_2O$: C, 57.26; H, 5.19; N, 10.69. Found: C, 57.30; H, 5.20; N, 10.00.

EXAMPLE 93

1,1-Bis(2-fluoro-4-methylphenyl)-2-(1-methyl-1H-tetrazol-5-yl)ethanol

To a solution of 1,5-dimethyltetrazole (4.6 g, 4.7 mmoles) in tetrahydrofuran (40 mL) at −=° C. was added butyl lithium solution (21.4 mL of a 2.2M solution, 4.7 mmoles). After stirring for 10 minutes, a solution of 2,2'-difluoro-4,4'-dimethylbenzophenone in tetrahydrofuran (15 mL) was added. The solution was stirred for 2.5 hours during which time it was allowed to warm to −10° C. The reaction was quenched by adding 1N hydrochloric acid. The layers were separated and the aqueous layer was extracted with methylene chloride. The combined organic fractions were dried (MgSO$_4$) and evaporated. The residue was triturated with diethyl ether and crystallized from isopropyl acetate to give 8.0 g of the title compound; m.p.=150°–151° C. MS: M+ =344.

Anal. Calcd. for $C_{18}H_{18}F_2N_4O$: C, 62.79; H, 5.27; N, 16.27. Found: C, 62.84; H, 5.23; N, 16.28.

EXAMPLE 94

1,1-Bis(2-fluoro-4-methylphenyl)-2-(1-methyl-1H-tetrazol-5-yl)ethene

A suspension of 1,1-bis(2-fluoro-4-methylphenyl)-2-(1-methyl-1H-tetrazol-5-yl)ethanol (7.3 g, 21.0 mmoles) in toluene (200 mL) with p-toluene sulfonic acid (3 g) and the mixture heated at reflux for 14 hours. After cooling, the mixture was diluted with diethyl ether and extracted with saturated sodium bicarbonate solution and water. The organic layer was dried (MgSO$_4$) and evaporated. The residue was triturated with isopropyl ether to give the title compound; m.p.=58°–60° C.

Anal. Calcd. for $C_{18}H_{16}F_2N_4$: C, 66.25; H, 4.95; N, 17.17. Found: C, 66.27; H, 4.94; N. 16.93.

EXAMPLE 95

3,3-Bis(2-fluoro-4-methylphenyl)-2-(1-methyl-1H-tetrazol-5-yl)-2-propenal

To a solution of 1,1-bis(2-fluoro-4-methylphenyl)-2-(1-methyl-1H-tetrazol-5-yl)ethene (1.6 g, 5.0 mmoles) in tetrahydrofuran (20 mL) at −78° C. was added butyl lithium (2.3 mL of a 2.2M solution, 5 mmoles). After stirring for 15 minutes, ethyl formate (0.44 g, 6.0 mmoles) was added and the solution stirred with cooling for 2 hours. The reaction was quenched with 1N hydrochloric acid and the mixture extracted with diethyl ether. The extracts were dried (MgSO$_4$) and evaporated. The residue was crystallized from isopropyl acetate to give 0.66 g of the title compound; m.p.=154°–155° C.

Anal. Calcd. for $C_{19}H_{16}F_2N_4O$: C, 64.41; H, 4.56; N, 15.82; Found: C, 64.44; H, 4.63; N, 15.58.

EXAMPLE 96

5,5-Bis(2-fluoro-4-methylphenyl)-4-(1-methyl-1H-tetrazol-5-yl)-2,4-pentadienal A solution of 3,3-bis(2-fluoro-4-methylphenyl)-2-(1-methyl-1H-tetrazol-5-yl)-2-propenal (1.35 g, 3.8 mmoles) and triphenylphosphoranylidene acetaldehyde (1.16 g, 3.8 mmoles) in benzene was heated at reflux for 3 hours. The solvent was removed and the residue purified by column chromatography on silica gel eluting with 1% (v/v) methanol in methylene chloride. The fractions containing material having R$_f$=0.9 [methanol-methylene chloride; 1:20 (v/v)] were combined and concentrated to give 1.3 g of the title compound; m.p.=88°–108° C.

Anal. Calcd. for $C_{21}H_{18}F_2N_4O$: C, 66.31; H, 4.78; N, 14.73. Found: C, 66.34; H, 4.96; N, 14.37.

EXAMPLE 97 tert-Butyl 9,9-bis(2-fluoro-4-methylphenyl)-5-hydroxy-8-(1-methyl-1H-tetrazol-5-yl)-3-oxo-6,8-nonadienoate To a solution of 5,5-bis(2-fluoro-4-methylphenyl)-4-(1-methyl-1H-tetrazol-5-yl)-2,4-pentadienal (1.3 g, 3.4 mmoles) in tetrahydrofuran (15 mL) at −50° C. was added the dianion of t-butyl acetoacetate (3.4 mL of a 1M solution, 3.4 mmoles). After stirring for 2 hours, another 0.7 mL of dianion solution was added and the solution stirred for an additional hour. The reaction was quenched with 1N hydrochloric acid and the mixture extracted with methylene chloride. The extracts were dried (MgSO$_4$) and concentrated. The residue was purified by column chromatography on silica gel eluting with 1% (v/v) methanol in methylene chloride to give 1.3 g of the title compound; m.p.=55°–63° C.

$^1$H NMR (CDCl$_3$) δ: 7.05–6.53 (7H, m); 5.28 (1H, dd), 4.60 (1H, m), 3.75 (3H,s), 3.35 (2H, s), 3.05 (1H, bs), 2.69 (2H, d), 2.39 (3H, s), 2.33 (3H, s), 1.45 (9H, s).

Anal. Calcd. for $C_{29}H_{32}F_2N_4O_4$: C, 64.68; H, 5.99; N. 10.41. Found (corr. for 0.21% H$_2$O): C, 64.33, H, 6.07; N, 10.21.

EXAMPLE 98 t-Butyl (±)-erythro-9,9-bis(2-fluoro-4-methylphenyl)-3,5-dihydroxy-8-(1-methyl-1H-tetrazol-5-yl)-6,8-nonadienoate To a solution of t-butyl 9,9-bis(2-fluoro-4-methylphenyl)-5-hydroxy-8-(1-methyl-1H-tetrazol-5-yl)-3-oxo-6,8-nonadienoate (1.3 g, 2.4 mmoles) in tetra hydrofuran at −5° C. was added triethylborane (3.1 mL of 1M solution, 3.1 mmoles). After stirring at −5° C. for 1 hour, the solution was cooled to −75° C. and sodium borohydride (0.2 g, 4.8 mmoles) and methanol (1 mL) were added. After stirring at −75° C. for 2 hours, the mixture was diluted with 10 mL of hexane and hydrolyzed with excess 1N hydrochloric acid. The aqueous layer was separated and extracted with methylene chloride. The combined organic solutions were dried (MgSO$_4$) and concentrated in vacuo. The residue was dissolved in methanol and the solution stirred at room temperature for 19 hours. The solution was concentrated in vacuo to give 0.6 g of the title compound as a white powder; m.p.=73°–77° C.

Anal. Calcd. for $C_{29}H_{34}F_2N_4O_4$: C, 64.44; H, 6.34; N, 10.37. Found: C, 64.07; H, 6.45; N, 9.87.

EXAMPLE 99

Sodium (±)-erythro-9,9-bis(2-fluoro-4-methylphenyl)-3,5-dihydroxy-8-(1methyl-1H-tetrazol-5-yl)-6,8-nonadienoate To a solution of t-butyl 9,9-bis(2-fluoro-4-methylphenyl)-3,5-dihydroxy-8-(1-methyl-1H-tetrazol-5-yl)-6,8-nonadienoate (0.6 g, 1.1 mmoles) in ethanol (20 mL) was added sodium hydroxide (1.1 mL of 1N solution, 1.1 mmoles) and the solution stirred at room temperature for 3 hours and at 50° C. for 1 hour. The solution was concentrated in vacuo to produce 0.44 g of the title compound which appears to contain about one mole of water; m.p.=200°–205° C. (dec.).

Anal. Calcd. for $C_{25}H_{25}F_2N_4O_2$ Na H$_2$O: C, 57.26; H, 5.19; N, 10.69. Found: C, 57.00; H, 5.27; N, 10.05.

EXAMPLE 100

Sodium (3R,5S)-9,9-bis(4-fluorophenyl)-3,5-dihydroxy-8-(1-methyl-1H-tetrazol-5-yl)nona-6,8-dienoate

A. (1S)-2-Hydroxy-1,2,2-triphenylethyl (3S)-7,7-bis(4-fluorophenyl)-3-hydroxy-6-(1-methyl-1H-tetrazol-5-yl)hepta-4,6-dionate A solution of diisopropylamine (5.33 mL; 3.85 g; 38.1 mmole) in dry tetrahydrofuran (40 mL) was cooled to 0° C. and treated with buyllithium (15.2 mL of 2.5M solution in hexane; 38 mmole) and the mixture allowed to warm up to 23° C. over 15 minutes. This solution was cooled to −78° C. and added to a suspension of (S)-(−)-1,2,2-triphenyl-2-hydroxyethyl acetate (5.07 g; 19.2 mmole) [prepared according to the procedure described in Tetrahedron Letters, 5031–5034 (1984)] in dry tetrahydrofuran (40 mL) at −78° C. The mixture was allowed to warm up to 0° C. over 15 minutes. The resulting orange solution was cooled to −78° C. and treated with a solution of 5,5-bis(4-fluorophenyl)-4-(1-methyl-1Htetrazol-5-yl)-2,4-pentadienal (8 g; 22.73 mmole) in dry tetrahydrofuran (30 mL). After stirring at −78° C. for 20 minutes, the reaction was quenched with 2N HCl (80 mL) and the solvent removed by evaporation. The residue was extracted with ethyl acetate (3×50 mL) and the combined organic layers were dried (MgSO$_4$) and evaporated in vacuo. The residue was purified by silica gel column chromatography using 30% (v/v) ethyl acetate-hexane as eluent to afford 9.4 g (90% based on chiral acetate) of the title compound. [α]$_D$=−41.1° (c=1.16; CH$_2$Cl$_2$).

$^1$H NMR (DMSO-d$_6$) δ: 7.45–6.80 (m, 23H), 6.54 (s, 1H), 6.50 (d, J=16.0 Hz, 1H), 6.05 (s, 1H), 5.15 (dd, $J=15.6$ Hz, $J'=5.2$ Hz, 1H), 5.02 (d, $J=5.3$ Hz, 1H), 4.33 (m, 1H), 3.70 (s, 0.3H minor diastereoisomer), 3.65 (s, 2.7H major diastereoisomer), 2.29 (m, 2H).

$^{13}$C NMR (DMSO-d$_6$) δ: 194.01, 170.16, 169.32, 163.64, 163.16, 160.36, 159.90, 153.00, 147.77, 145.95, 145.09, 144.50, 138.00, 136.88, 136.42, 135.40, 133.04, 132.28, 131.76, 131.00, 128.54, 127.38, 127.05, 126.61, 126.44, 125.74, 121.40, 115.94, 115.60, 115.40, 115.06, 78.74, 78.36, 67.50 (minor diastereomer), 66.75 (major diastereomer), 59.67, 41.97, 33.47, 20.68, 14.01.

B. Methyl (3S)-7,7-bis(4-fluorophenyl)-3-hydroxy-6-(1-methyl-1H-tetrazol-5-yl)hepta-4,6-dienoate A solution of the triphenyl ester prepared in Step A (9.4 g; 13.74 mmole) in dry methanol (40 mL) was added to a solution of sodium metal (2.1 g, 91 mmole) in dry methanol (300 mL) and the resulting mixture stirred at 23° C. for 30 minutes. The reaction was quenched with 2N HCl (100 mL) and the solvent removed by evaporation. The residue was diluted with water (100 mL) and extracted with ethyl acetate (3×70 mL). The combined organic layers were dried (MgSO$_4$) and evaporated. The residue was purified by silica gel column chromatography using 40% (v/v) ethyl acetate-hexane as eluent to afford 4.08 g (70%) of the title compound. $[\alpha]_D = +28.94°$ (c=0.85; CH$_2$Cl$_2$).

IR (Film) $\nu_{max}$: 3400 (br), 1735, 1500, 1220 cm$^{-1}$.

$^1$H NMR (CDCl$_3$) δ: 7.30–6.60 (m, 8H), 6.725 (dd, $J=15.8$ Hz, $J'=1.4$ Hz, 1H), 6.34 (dd, $J=15.9$Hz, $J'=5.6$ Hz, 1H), 4.56 (br s, 1H), 3.69 (s, 3H), 3.60 (s, 3H), 3.14 (br s, 1H), 2.50 (m, 2H).

$^{13}$C NMR (CDCl$_3$) δ: 172.27, 164.61, 164.20, 161.29, 160.88, 153.43, 147.46, 136.04, 135.26, 132.38, 132.26, 131.48, 131.37, 128.01, 120.96, 115.91, 115.56, 68.17, 51.85, 40.84, 33.57.

C. tert-Butyl (5S)-9,9-bis(4-fluorophenyl)-5-hydroxy-8-(1-methyl-1H-tetrazol-5-yl)-3-oxo-nona-6,8-dienoate A solution of diisopropylamine (2.77 mL; 2 g; 19.8 mmole) in dry tetrahydrofuran (15 mL) was cooled to 0° C. and treated with butyllithium (8.1 mL of 2.5M solution in hexane; 20.25 mmole) and the resulting mixture allowed to warm up to 23° C. over 15 minutes. The solution was cooled to 0° C. and t-butylacetate (2.55 mL; 2.2 g; 18.9 mmole) was added and the solution stirred at 0° C. for 15 minutes, cooled to −78° C., then added to a solution of the methyl ester prepared in Step B (2 g; 4.69 mmole) in dry tetrahydrofuran (20 mL) at −78° C. The resulting solution was allowed to warm up to 23° C. over 30 minutes and quenched with 2N HCl (20 mL). The solvent was removed by evaporation under reduced pressure and the residue diluted with water (30 mL) and extracted with ethyl acetate (3×30 mL). The combined organic layers were dried (MgSO$_4$) and evaporated in vacuo and the residue purified by silica gel column chromatography using 35% (v/v) ethyl acetate-hexane as eluent to afford 1.858 g (78%) of the title compound. $[\alpha]_D^{25} = +19.44°$ (c=1.08; CH$_2$Cl$_2$).

IR (Film) $\nu_{max}$: 3400 (br), 1735, 1710, 1595, 1510, 1220, 1155 cm$^{-1}$.

$^1$H NMR (CDCl$_3$) δ: 7.30–6.80 (m, 8H), 6.72 (dd, $J=15.6$ Hz, $J'=0.9$ Hz, 1H), 5.30 (dd, $J=15.6$ Hz, $J'=5.5$ Hz, 1H), 4.61 (br, 1H), 3.56 (s, 3H), 3.35 (s, 2H), 2.70 (m, 2H), 1.45 (s, 9H).

$^{13}$C NMR (CDCl$_3$) δ: 202.88, 168.05, 164.61, 164.16, 161.29, 160.85, 153.50, 147.30, 136.01, 132.40, 132.29, 131.51, 131.39, 127.88, 121.00, 115.88, 115.83, 115.60, 115.54, 82.35, 67.85, 51.10, 49.10, 33.59, 27.99.

D. tert-Butyl (3R,5S)-9,9-bis(4-fluorophenyl)-3,5-dihydroxy-8-(1-methyl-1H-tetrazol-5-yl)nona-6,8-dienoate A solution of the β-ketoester prepared in Step C (1.85 g; 3.62 mmole) in dry tetrahydrofuran (30 mL) was treated with triethylborane (3.9 mL of 1M solution in THF; 3.9 mmole) and the mixture was stirred at 23° C. for 1 hour while dry air was bubbled through the solution. Methanol (600 l) was added and the mixture cooled to −78° C. and treated with sodium borohydride (320 mg; 8.42 mmole) and the mixture stirred at −78° C. for 20 minutes. The reaction was quenched with 2N HCl (20 mL) and the solvent removed by evaporation. The residue was diluted with water (30 mL) and extracted with ethyl acetate (3×20 mL). The combined organic extracts were dried (MgSO$_4$) and evaporated and the residue dissolved in methanol (30 mL) and stood at 23° C. for 3 hours. The solvent was removed by evaporation in vacuo and the residue purified by silica gel column chromatography using 40% (v/v) ethyl acetate-hexane as eluent to afford 962 mg (52%) of the title compound.

$^1$H NMR (CDCl$_3$) δ: 7.30–6.80 (8H, m), 6.71 (d, $J=15.6$ Hz, 1H), 5.34 (dd, $J=15.6$Hz, $J'=7$ Hz, 1H), 4.43 (br s, 1H), 4.15 (br s, 1H), 3.95 (m, 2H), 3.58 (s, 3H), 2.36 (d, $J=6.1$ Hz, 2H), 1.6 (m, 2H), 1.45 (s, 9H).

$^{13}$C NMR (CDCl$_3$) δ: 172.00, 164.52, 164.12, 153.57, 146.79, 137.98, 132.38, 132.26, 131.46, 131.35, 127.00, 121.25, 115.85, 115.80, 115.57, 115.51, 81.66, 71.88, 68.54, 42.34, 42.36, 33.59, 28.10.

E. Sodium (3R,5S)-9,9-bis(4-fluorophenyl)-3,5-dihydroxy 8-(1-methyl-1H-tetrazol-5-yl)nona-6,8-dienoate A solution of the dihydroxyester prepared in Step D (35 mg; 0.068 mmole) in ethanol (2 mL) was treated with 1N NaOH solution (68 l; 0.068 mmole) and the mixture stirred for 30 minutes at 23° C. The solvent was removed by evaporation in vacuo and the residue dissolved in water (2 mL) and lyophilized to afford 36 mg (100%) of the title compound; m.p.>110° C. decomp. $[\alpha]_D^{25} = -22.2°$ (c=0.32, H$_2$O). The $^1$H NMR and $^{13}$C NMR are identical to the (±)-erythro product prepared in Example 12.

EXAMPLE 101

Ethyl 1-Methyl-5-tetrazolylacetate

To a solution of 1,5-dimethyltetrazole (10 g) in 100 mL of dry tetrahydrofuran and 20 mL of hexamethylphosphoramide at −78° C. (dry ice-acetone) under an argon atmosphere was added dropwise 50 mL (1.2 equivalent) of n-butyllithium (2.5M in hexane). The deprotonation of 1,5-dimethyltetrazole was allowed to proceed at −78° C. for 40 minutes, then at −20° C. to 30 minutes. The anion solution was rechilled at −78° C. and transferred via a cannula over a period of 45 minutes into a cold (−78° C.) solution containing 12 mL of ethyl chloroformate in 50 mL of tetrahydrofuran. The reaction mixture was diluted with aqueous 2N HCl and saturated aqueous solution of sodium chloride and then extracted with ethyl acetate. The residue from the organic extract was purified by silica gel flash chromatography. The appropriate fractions were combined and evaporated to give 4 g of product. The product was further purified by crystallization from ethyl acetate-hexanes to yield 3.52 g (21%) of the title compound; m.p.=64°-66° C.

Anal. Calcd. for $C_6H_{10}N_4O_2$: C, 42.35; H, 5.92; N, 32.92. Found: C, 42.40; H, 5.98; N, 33.15.

EXAMPLE 102

Ethyl 3,3-bis(4-fluorophenyl)-2-(1-methyl-1H-tetrazol-5-yl)-2-propenoate

A mixture of titanium tetrachloride (2 mL) and carbon tetrachloride (2 mL) was added to 15 mL of tetrahydrofuran at −78° C. under an argon atmosphere. The suspension was stirred at −78° C. for 30 minutes before 0.2 g of 4,4'-difluorobenzophenone was added. After stirring for an additional 30 minutes, a solution of 0.15 g of ethyl 1-methyl-5-tetrazolylacetate in 1 mL of dry pyridine was added dropwise. The dark brownish suspension was stirred at −78° C. for 15 minutes, then was allowed to warm to 0° C. forming a thick paste. The mixture was allowed to stand for 24 hours at ambient temperature before it was poured into water. The aqueous mixture was extracted with ethyl acetate to yield crude product. Analytical TLC eluted five times with 20% (v/v) ethyl acetate in hexanes showed the desired product at $R_f$=0.3. Pruification by preparative chromatography on two 20×20 cm² 0.25 mm TLC plates eluted twice with 20% (v/v) ethyl acetate in hexanes to give the title compound which was identical to the compound of Example 3, Step A.

EXAMPLE 103

Erythro-9,9-bis(fluorophenyl)-3,5-dihydroxy-8-(1-methyl-1H-tetrazol-5-yl)-6,8-nonadienoic acid hydrate

A.
5,5-Bis(4-fluorophenyl)-4-(1-methyl-1H-tetrazol-5-yl)-2,4-pentadienal

A mixture of 448 g (1.37 mol) of 3,3-bis(4-fluorophenyl)-2-(1-methyl-1H-tetrazol-5-yl)-2-propenal and 445 g (1.46 mol) of triphenylphosphoranylidene acetaldehyde in 5.5 L of toluene was heated with stirring to 55° C. After turning off the heat source, the temperature rose to 62° C. After 20 minutes, heat was applied and 60° C. was maintained for 30 minutes. Analytical TLC indicated that the reaction was complete (50% ethyl acetate in hexane). Lithium bromide (128 g, 1.47 mol) was added and the mixture was stirred at 60° C. for 1 hour. The reaction mixture was filtered and the filtrate was concentrated under reduced pressure. The residue was dissolved in 900 mL of boiling absolute ethanol. To this solution was slowly added 900 mL of hexane. After 16 hours at ambient temperature and 2 hours at cold freezer temperature, the mixture was filtered to give 418 g (86.6%) of the title compound; m.p.=161°-165° C.

Anal. Calcd. for $C_{19}H_{14}N_4F_2O$: C, 64.77; H, 4.00; N, 15.90 Found: C, 64.94; H, 3.97; N, 15.82.

B. tert-Butyl 9,9-bis(4-fluorophenyl)-5-hydroxy-8-(1-methyl-1H-tetrazol-5-yl)-3-oxo-6,8-nonadienoate A solution of 144 g (0.91 mol) of t-butyl acetoacetate in 400 mL of tetrahydrofuran was added dropwise over 1.5 hours to a mixture of 44.0 g (1.10 mol) of sodium hydride (60% in mineral oil) in 100 mL of hexane and 500 mL of tetrahydrofuran under nitrogen at 0° C. After the addition, this mixture was stirred for 2.3 hours. A solution 2.5M n-butyllithium in hexane (360 mL, 0.91 mol) was added dropwise over 1 hour. After stirring at 0° C. for 1 hour, 200 g (0.57 mol) of the aldehyde prepared in Step A was added all at once and the temperature rose to 20° C. After stirring for 1 hour in an ice-water bath, 1200 mL of 10% aqueous hydrochloric acid was added over 1 hour. The organic layer was washed with 2×300 mL of water, 300 mL of saturated sodium chloride solution, dried with anhydrous magnesium sulfate and filtered. The filtrate was evaporated under reduced pressure to give the title compound which was used without further purification.

C. tert-Butyl erythro-9,9-bis(4-fluorophenyl)-3,5-dihydroxy-8-(1-methyl-1H-tetrazol-5-yl)-6,8-nonadienoate The product of Step B was dissolved in 1 L of tetrahydrofuran and 908 mL (0.908 mol) of 1.0M triethylborane in tetrahydrofuran was added over 45 minutes. Air was bubbled into the solution for 5 minutes creating a lighter colored solution. The resulting solution was stirred for 2 hours at room temperature. The mixture was cooled to −74° C. and 4.0 g of sodium borohydride was added. After 15 minutes, an additional 32.0 g (36.0 g total, 0.951 mol) of sodium borohydride was added. After stirring for 1 hour, 540 mL of methanol was carefully added over 1.5 hours. The reaction mixture was diluted with 540 mL of 10% aqueous hydrohloric acid and then stirred at room temperature for 16 hours. Water (200 mL) was added, and the organic solvent was removed under reduced pressure. The aqueous mixture was extracted with 2×500 mL of methylene chloride, combined and washed with 2×400 mL of water. The organic layer was evaporated under reduced pressure to give the title compound which was used without further purification.

D.
Erythro-9,9-bis(4-fluorophenyl)-3,5-dihydroxy-8-(1-methyl-1H-tetrazol-5-yl)-6,8-nonadienoic acid hydrate The product of Step C was dissolved in 1 L of 95% ethanol, treated with 1 L of 1N aqueous sodium hydroxide solution and stirred at room temperature for 60 hours. This was diluted with 2 L of water then washed with 2×800 mL of hexane and 5×800 mL of diethyl ether. To the stirred aqueous layer was added dropwise 1.04 L of 1N hydrochloric acid over a period of 4 hours. The mixture was filtered, washed with water and dried to give 245 g (91%) of the title compound as a monohydrate; m.p.=111°-120° C. (dec.).

Anal. Calcd. for $C_{23}H_{22}F_2N_4O_4 \cdot H_2O$ C, 58.22; H, 5.10; N, 11.81; $H_2O$, 3.80 Found: C, 59.28; H, 5.12; N, 11.53; $H_2O$, 3.02.

A sample was recrystallized from 50% aqueous methanol. The solution at 74° C. was cooled slowly and seeded. After stirring at ambient temperature for 16 hours, the solid was collected by filtration, washed with 50% aqueous methanol and air dried to give the title compound; m.p.=107°-115° C. This product was recrystallized from 90% aqueous ethyl acetate. The solution at reflux temperature was slowly cooled and seeded at 50° C. After stirring at ambient temperature for 16 hours, the solid was collected, washed with cold aqueous ethyl acetate and air dried to give the title compound; m.p.=122°-128° C. (dec.).

EXAMPLE 104

Potassium
(±)-erythro-9,9-bis(4-fluorophenyl)-3,5-dihydroxy-8-(1-methyl-1H-tetrazol-5-yl)-6,8-nonadienoate To a hot solution of erythro-9,9-bis(4-fluorophenyl)-3,5-dihydroxy-8-(1-methyl-1H-tetrazol-5-yl)-6,8-nonadienoic acid hydrate (20.0 g, 42 mmol) in 200 mL of 2-propanol was added 3.0 g of potassium hydroxide in 50 mL of 2-propanol. The mixture was evaporated under reduced pressure and the residue was dissolved in 100 mL of 2-propanol, cooled and the solvent decanted. The residue was then dissolved in 100 mL of 2-propanol, heated to reflux temperature and stirred as the solution gradually cooled to ambient temperature. After 3 hours, the solid was collected by filtration, washed with 2-propanol and dried in vacuo at 50° C. The product was pulverized and dried at 82° C. under high vacuum for 16 hours to give 10.5 g of the title compound; m.p.=131°–145° C. (softens at 127° C.).

Anal. Calcd. for $C_{23}H_{21}N_4O_4F_2K.0.3H_2O$: C, 55.26; H, 4.36; N, 11.21; $H_2O$, 1.08 Found: C, 55.44; H, 4.47; N, 11.05; $H_2O$, 1.38.

EXAMPLE 105

Trans-6-[4,4-bis(4-fluorophenyl)-3-(1-methyl-1H-tetrazol-5-yl)-1,3-butadienyl]-tetrahydro-4-hydroxy-2H-pyran-2-one Method A. A mixture of 308 g (0.649 mol) of acid prepared in Example 103 and 149 g (0.724 mol) of dicyclohexylcarbodiimide in 6.2 L of ethyl acetate was stirred at room temperature. After 6 hours, the mixture was filtered and the solvent removed under reduced pressure. This residue in 500 mL of toluene was combined with a similar residue in 500 mL of toluene prepared from a second experiment using 310 g of the acid prepared in Example 103 and 148 g of dicyclohexylcarbodiimide. The combined solution was diluted with 1 L of toluene and warmed to 60° C. After stirring the seeded mixture for 5.5 hours, the solid was collected by filtration, washed with 300 mL of toluene and air dried to give 446 g (78.2%) of the title compound; m.p.=146°–148° C.

Anal. Calcd. for $C_{23}H_{20}F_2N_4O_3$: C, 63.01; H, 4.60; N, 12.78 Found: C, 62.93; H, 4.81; N, 12.78.

Method B. A mixture of 4.3 g of acid prepared in Example 103 in 40 mL of toluene was heated to reflux and the water which was produced was removed using a Dean-Stark trap. After 5 hours, the product was collected by filtration, washed with toluene and air dried to give 3.5 g of the title compound; m.p.=151°–154° C.

Anal. Calcd. for $C_{23}H_{20}F_2N_4O_3$: C, 63.01; H, 4.60; N, 12.78 Found: C, 62.78; H, 4.64; N, 12.72.

EXAMPLE 106

Ethyl
3,3-bis(4-fluorophenyl)-2-[2-(triphenylmethyl)-2H-tetrazol-5-yl]-2-propenoate To a suspension of 0.64 g (16 mmol) 50% sodium hydride in 7.5 mL of dry dimethylformamide was added 5.7 g (16 mmol) of ethyl 3,3-bis(4-fluorophenyl)-2-(1H-tetrazol-5-yl)-2-propenoate and the resultant mixture stirred for 30 minutes. To the resultant solution, 5.7 g (18 mmol) bromotriphenylmethane was added and the mixture stirred for 24 hours. The mixture was diluted to 200 mL with water and the insoluble collected by filtration. The product was recrystallized from ethyl acetate to give 6.1 g of the title compound; m.p.=161°–162° C. (dec).

Anal. Calcd. for $C_{37}H_{28}F_2N_4O_2$: C, 74.24; H, 4.72; N, 9.36 Found: C, 74.31; H, 4.74; N, 9.63

EXAMPLE 107

3,3-Bis(4-fluorophenyl)-2-[2-(triphenylmethyl)-2H-tetrazol-5-yl]-2-propenol

To a stirred solution of 3 g (5 mmol) ethyl 3,3-bis(4-fluorophenyl)-2-[2-triphenylmethyl-2H-tetrazol-5-yl]-2-propenoate in 50 mL of methylene chloride at −70° C., 10 mL (15 mmol) diisobutylaluminium hydride solution (1.5M in methylene chloride) was added and the solution stirred for 3 hours. The reaction was quenched with water and the mixture extracted with methylene chloride. The combined organic fractions were dried with magnesium sulfate and concentrated in vacuo to give 2.1 g of the title compound; m.p.=176°–178° C.

Anal. Calcd. for $C_{35}H_{26}F_2N_4O$: C, 75.53; H, 4.71; N, 10.07 Found: C, 75.75; H, 4.57; N, 10.22

EXAMPLE 108

3,3-Bis(4-fluorophenyl)-2-[2-(triphenylmethyl)-2H-tetrazol-5-yl]-2-propenal

To a solution of 2.2 g (4.0 mmol) 3,3-bis(4-fluorophenyl)-2-[2-(triphenylmethyl)-2H-tetrazol-5-yl]-2-propenol in 100 mL methylene chloride was added 7 g of activated manganese dioxide. After stirring the resultant mixture for 20 hours, the insolubles were removed by filtration and the filtrate concentrated in vacuo to give a quantative yield of the title compound; m.p.=208° C. (dec).

Anal. Calcd. for $C_{35}H_{24}F_2N_4O$: C, 75.81; H, 4.37; N, 10.11 Found: C, 73.56; H, 4.44; N, 9.54.

EXAMPLE 109

5,5-Bis(4-fluorophenyl)-4-[2-(triphenylmethyl)-2H-tetrazol-5-yl]-2,4-pentadienal To a solution of 1.75 g (3.15 mmol) 3,3-bis(4-fluorophenyl)-2-[2-(triphenylmethyl)-2H-tetrazol-5-yl]-2-propenal in 50 mL of dry benzene was added 0.96 g (3.15 mmol) triphenylphosphoranylidene acetaldehyde and the solution heated at reflux for 96 hours. The solution was concentrated in vacuo and the residue purified by chromatography on alumina (Alcoa Chemicals, grade F-20) eluting with 10% ethyl acetate in hexane to give upon concentration of the appropriate fractions 0.95 g of the title compound; m.p.=122°–124° C.

Anal. Calcd. for $C_{37}H_{26}F_2N_4O$: C, 76.54; H, 4.52; N, 9.65 Found: C, 75.84; H, 4.86; N, 9.46

EXAMPLE 110 tert-Butyl
9,9-bis(4-fluorophenyl)-5-hydroxy-3-oxo-8-[2-(triphenylmethyl)-2H-tetrazol-5-yl]-6,8-nonadienoate A solution of the dianion of tert-butyl acetoacetate (1.2 mL of a 0.5M solution, 0.6 mmol) prepared as described in Example 90, was added to a solution of 5,5-bis(4-fluorophenyl)-4-[2-(triphenylmethyl-2H-tetrazol-5-yl]-2,4-pentadienal in tetrahydrofuran at −70° C. After stirring for 2.5 hours at −70° C., the reaction was quenched with a saturated solution of ammonium chloride. The mixture was extracted with diethyl ether, the ether solution dired (MgSO4) and concentrated in vacuo to give the title compound as an oil which was used without purification. MS: m/e=738 for (M+).

EXAMPLE 111

Disodium
(±)-erythro-9,9-bis(4-fluorophenyl)-3,5-dihydroxy-8-
(1H-tetrazol-5-yl)-6,8-nonadienoate

A. tert-Butyl
(±)-erythro-9,9-bis(4-fluorophenyl)-3,5-dihydroxy-8-
[2-(triphenylmethyl)-2H-tetrazol-5-yl]-6,8-nonadienoate.

To a solution of tert-butyl 9,9-bis(4-fluorophenyl)-5-hydroxy-3-oxo-8-[2-(triphenylmethyl)-2H-tetrazol-5-yl]-6,8-nonadienoate (2.8 g, 3.8 mmol) in tetrahydrofuran at 0° C. was added triethylborane (3.8 mL, 1M solution) in tetrahydrofuran. After stirring for 0.5 hours, the solution was cooled to −70° C. and sodium borohydride (0.4 g, 10 mmol) and methanol (2 mL) were added. After stirring for 3 hours at −70° C., the reaction was quenched with water and the mixture extracted with diethyl ether. The extracts were dried over MgSO$_4$ and concentrated in vacuo. The residual gum was dissolved in 100 mL of methanol and the solution stirred at room temperature overnight. The methanol solution was concentrated in vacuo to give 3.0 g of title compound as a gum which was used in the next step without further purification.

B. tert-Butyl
(±)-erythro-9,9-bis(4-fluorophenyl)-3,5-dihydroxy-8-
(1H-tetrazol-5-yl)-6,8-nonadienoate A solution of the compound prepared in Step A (0.8 g, 1.08 mmol) in 50 mL methanol was acidified with 3 mL 1N hydrochloric acid. After stirring at room temperature for 2 hours, the solution was concentrated in vacuo. The residue was washed several times with hexane and the residue dried in vacuo to give 0.5 g of the title compound as a gummy solid which was used in the next step without further purification.

C. Disodium
(±)-erythro-9,9-bis(4-fluorophenyl)-3,5-dihydroxy-8-
(1H-tetrazol-5-yl)-6,8-nonadienoate The product from Step B was dissolved in 50 mL of ethanol and 2 mL (2 mmol) 1N sodium hydroxide solution was added. After stirring at room temperature for 16 hours, the solution was concentrated in vacuo. The residue was dissolved in water and extracted with diethyl ether. The aqueous solution was concentrated in vacuo to give 0.45 g of the title compound as a dry powder; m.p.=100°–105° C.

EXAMPLE 112

Dimethyl
[3,3-bis(4-fluorophenyl)-2-(1-methyl-1H-tetrazol-5-yl)-2-propen-1-yl] phosphonate A slurry of 3,3-bis-(4-fluorophenyl)-1-bromo-2-(1-methyl-1H-tetrazol-5-yl)-2-propene (1.17 g, 3.0 mmol) and trimethyl phosphite (0.41 g, 3.3 mmol) was heated at 100° C. for 5 minutes. After cooling to ambient temperature, excess trimethylphosphite was removed in vacuo to give a light yellow solid. This solid was recrystallized from ethylacetate/hexane mixture to give the title compound as a pure white solid; m.p.=140°–141° C.

IR (KBr) $\nu_{max}$: 1604, 1511 cm$^{-1}$;

$^1$H NMR (CDCl$_3$) δ: 7.7–6.8 (8H, m), 3.6 (3H, s), 3.5 (3H, s), 3.42 (3H, s), 3.2 (2H, d);

Anal. Calcd. for C$_{19}$H$_{19}$F$_2$O$_3$N$_4$P: C, 54.29; H, 4.56; N, 13.33 Found: C, 53.83; H, 4.48; N, 13.50.

EXAMPLE 113

Methyl
(±)-erythro-9,9-bis(4-fluorophenyl)-3,5-dihydroxy-8-
(1-methyl-1H-tetrazol-5-yl)-6,8-nonadienoate To a solution of the phosphonate (0.84 g, 2.0 mmol) [prepared in Example 112] was added one equivalent of n-BuLi (2.0 mmol) at −78° C. (dry ice/acetone) and the resulting deep red-colored solution was stirred at −78° C. for 15 minutes. Methyl erythro-3,5-bis (diphenyl-t-butylsilyloxy)-6-oxo-hexanoate [prepared according to the general procedures described by P. Kapa, et al., in *Tetrahydron Letters*, 2435-2438 (1984) and in U.S. Pat. No. 4,571,428, issued Feb. 18, 1986 to P. Kapa] (1.30 g, 2.0 mmol) in THF (2 mL) was added and the mixture stirred for 24 hours. The reaction mixture was allowed to warm to room temperature during the course of this time. The reaction was quenched by adding 5 mL) of NH$_4$Cl and then extracted with ethyl acetate (2×20 mL). The organic layer was dried (Na$_2$SO$_4$) and evaporated under reduced pressure to a yellow oil. The oil was stirred with 1M-tetra-n-butyl ammonium fluoride solution in tetrahydrofuran (4 mL) containing a few drops of glacial acetic acid for a period of 24 hours. The reaction mixture was poured into water (20 mL) and extracted with methylene chloride (3×20 mL). The organic layer was dried (Na$_2$SO$_4$), concentrated, and the oil was purified by silica gel flash column chromatography eluting with ethyl acetate: hexane (2:1) to give 0.284 g (41%) of the title compound as an oil. MS (CI): m/e=471 for (M+H)$^+$;

$^1$H NMR (CDCl$_3$) δ: 7.26–6.6 (9H, m), 5.29 (1H, dd), 4.42 (1H, m), 4.28 (1H, m), 3.69 (3H, s), 3.54 (3H, s), 2.42 (2H, d), 1.5 (2H, m).

EXAMPLE 114

1-(4-Fluorophenyl)-2-(1-methyl-1H-tetrazol-5-yl)-1-phenylethanol

A solution of 1,5-dimethyltetrazole (29.25 g; 0.298 mole) in dry THF (400 mL) was cooled to −78° C. and treated with n-butyllithium (133 mL of a 2.5M solution in hexane; 0.3325 mole) over 30 minutes. The mixture was stirred at −78° C. for 30 minutes and treated with 4-fluorobenzophenone (50 g; 0.25 mole). The mixture was stirred at −78° C. for 30 minutes and allowed to warm up to 23° C. over 2 hours. The reaction was quenched with 2N HCl (100 mL) and the organic solvent was removed by evaporation. The residue was extracted with CHCl$_3$ (2×100 mL) and the combined organic layers were dried (Na$_2$SO$_4$) and evaporated to afford a brown oil. Purification by chromatography using 20% EtOAc-hexane as eluent afforded the title compound as a white solid (46.3 g; 62%). m.p.=113°–114° C. (crystallized from EtOAc-hexane). MS (CI): m/e=299 for (M+H)$^+$;

IR (KBr) $\nu_{max}$: 3300 (br), 1605, 1510 cm$^{-1}$;

$^1$H NMR δ: 7.34–7.15 (m, 7H), 6.93 (m, 2H), 4.93 (s, 1H), 3.73 (s, 2H), 3.67 (s, 3H) ppm;

$^{13}$C NMR δ: 163.57, 160.29, 152.28, 144.94, 141.12, 141.08, 128.43, 127.87, 127.75, 127.67, 125.76, 115.25, 114.96, 77.03, 35.82, 33.45 ppm;

Anal. Calcd. for C$_{16}$H$_{15}$FN$_4$O: C, 64.42; H, 5.07; N, 18.79 Found: C, 64.32; H, 5.05; N, 18.84

EXAMPLE 115

(E)-1-(4-Fluorophenyl)-2-(1-methyl-1H-tetrazol-5-yl)-1-phenylethene
and(Z)-1-(4-Fluorophenyl)-2-(1-methyl-1H-tetrazol-5-yl)-1-phenylethene A mixture of the tetrazolylethanol (3.2 g; 10.74 mmole) (prepared in Example 114) and potassium hydrogen sulfate (800 mg) was heated at 195° C. for 30 minutes. After cooling to 100° C., chloroform (30 mL) was added and the mixture triturated until most of the solid had dissolved. The insoluble inorganic material was removed by filtration and the solvent removed by evaporation to afford a mixture of the title compounds as a light brown solid (2.8 g; 93%). Crystallized from EtOAc-hexane. MS (CI); m/e=281 for (M+H)$^+$;

IR (KBr) $\nu_{max}$: 1640, 1600, 1510, 1445, 1220 cm$^{-1}$;

$^1$H NMR δ: 7.50–6.90 (m, 9H), 6.75 (s, 1H), 3.60 (s, 1.7H), 3.43 (s, 1.3H) ppm;

$^{13}$C NMR δ: 165.19, 164.58, 161.26, 153.14, 152.97, 152.22, 152.13, 140.53, 137.81, 136.71, 133.99, 133.94, 131.74, 131.62, 130.38, 129.67, 129.29, 128.85, 128.65, 128.38, 115.97, 115.74, 115.66, 115.45, 108.29, 108.15, 33.70 ppm;

Anal. Calcd. for $C_{16}H_{13}FN_4$: C, 68.56; H, 4.68; N, 19.99 Found: C, 68.63; H, 4.77; N, 20.37

EXAMPLE 116

(E)-3-(4-Fluorophenyl)-2-(1-methyl-1H-tetrazol-5-yl)-3-phenylpropenal and
(Z)-3-(4-fluorophenyl)-2-(1-methyl-1H-tetrazol-5-yl)-3-phenylpropenal A suspension of the olefin (20 g; 71.43 mmole) (prepared in Example 115) in dry THF (200 mL) was cooled to −78° C. and treated with n-butyllithium (31.5 mL of 2.5M solution in hexane; 78.75 mmole) and the resulting mixture stirred at −78° C. for 30 minutes. Ethyl formate (6.9 g; 93 mmole) was added and the mixture stirred at −78° C. for 2 hours and allowed to warm up to 23° C. over 1 hour. The reaction was quenched with 2N HCl (100 mL), the organic solvent was removed by evaporation and the residue extracted with EtOAc (3×75 mL). The combined organic layers were dried (MgSO$_4$), evaporated and the residue purified by chromatography using 35% EtOAc-hexane as eluent to afford the title compound as a mixture of aldehydes (7.75 g; 35%). MS (CI): m/e=309 for (M+H)$^+$;

$^1$H NMR δ: 9.67 (s, 0.66H), 9.64 (s, 0.33H), 7.70–6.90 (m, 9H), 3.74 (s, 1H), 3.68 (s, 2H) ppm;

EXAMPLE 117

(E),(E)-5-(4-Fluorophenyl)-4-(1-methyl-1H-tetrazol-5-yl)-5-phenyl-2,4-pentadienal A mixture of the mixed aldehydes (5.1 g; 16.56 mmole) (prepared in Example 116) and formylmethylenetriphenylphosphorane (5.05 g; 16.56 mmole) and benzene (200 mL) was heated together under reflux in a nitrogen atmosphere for 2 hours. The solvent was removed by evaporation and the residue purified by chromatography using 30% EtOAc-hexane as eluent to afford the product as an orange foam (4.56 g). Fractional crystallization from EtOAc-hexane afforded the title compound as orange crystals (0.93 g; 17%); m.p.=137°–138° C. (crystallized from EtOAc-hexane). MS (CI): m/e=335 for (M+H)$^+$;

$^1$H NMR δ: 9.54 (d, J=7.5 Hz, 1H), 7.47 (d, J=15.6 Hz, 1H), 7.35–6.80 (m, 9H), 5.84 (dd, J=7.4 Hz, J'=15.7 Hz, 1H), 3.50 (s, 3H) ppm;

$^{13}$C NMR δ: 192.54, 147.86, 132.09, 131.97, 130.64, 130.41, 128.96, 116.17, 115.87, 33.62 ppm.

EXAMPLE 118

Ethyl
(E),(E)-9-(4-fluorophenyl)-5-hydroxy-8-(1-methyl-1H-tetrazol-5-yl)-9-phenyl-3-oxonona-6,8-dienoate A suspension of sodium hydride (175 mg; 80% dispersion; 5.83 mmole) in dry THF (10 mL) was cooled to 0° C. and treated with ethyl acetoacetate (725 μL; 740 mg; 5.69 mmole) and stirred at 0° C. for 10 minutes. Butyllithium (2.3 mL of 2.5M solution; 5.75 mmole) was added and the mixture stirred at 0° C. for 15 minutes. A solution of aldehyde (860 mg; 2.57 mmole) prepared for Example 117) in dry THF (10 mL) was added and the mixture stirred at 0° C. for 15 minutes. The reaction was quenched by the addition of 2N HCl (30 mL) and the organic solvent removed by evaporation. The residue was extracted with EtOAc and the combined organic extracts were dried (MgSO$_4$) and evaporated. The residue was purified by chromatography using 40% EtOAc-hexane as eluent to afford the title compound as a yellow gum (954 mg; 80%). MS (CI): m/e=465 for (M+H)$^+$;

IR (film) $\nu_{max}$: 3400 (br), 1730, 1600, 1510 cm$^{-1}$;

$^1$H NMR δ : 7.20–6.60 (m, 9H), 6.54 (d, J=15.6 Hz, 1H), 5.16 (dd, 1H), 4.40 (br, 1H), 4.00 (q and br, 3H), 3.31 (s, 3H), 3.25 (s, 2H), 2.52 (m, 2H), 1.08 (t, 3H) ppm.

EXAMPLE 119

Ethyl
(±)-(E),(E)-erythro-9-(4-fluorophenyl)-3,5-dihydroxy-8-(1-methyl-1H-tetrazol-5-yl)-9-phenylnona-6,8-dienoate A solution of the β-ketoester (950 mg; 2.045 mmole) (prepared in Example 118) in dry THF (20 mL) was treated with a solution of triethylborane (2.25 mL of 1M soln. in THF: 2.25 mmole) and stirred at 23° C. for 1 hour. Methanol (400 μL) was added and the mixture cooled to −78° C. and treated with NaBH$_4$ (200 mg; 5.26 mmole). After 1 hour the reaction was quenched by the addition of 2N HCl and the organic solvent removed by evaporation. The residue was extracted with EtOAc and the combined organic extracts were dried (MgSO$_4$) and evaporated. The residue was purified by chromatography using 60% EtOAc-hexane as eluent to afford the title compound as a yellow gum (330 mg; 35%). MS (CI): m/e=467 for (M+H)$^+$;

IR (KBr) $\nu_{max}$: 3400 (br), 1725, 1600, 1500 cm$^{-1}$;

$^1$H NMR δ : 7.30–6.80 (m, 9H), 6.70 (dd, J=1.0 Hz, J'=15.6 Hz, 1H), 5.35 (dd, J=5.9 Hz, J'=15.7 Hz, 1H), 4.41 (m, 1H), 4.25 (br s, 1H), 4.15 (q, J=7.1 Hz, 2H), 3.83 (br m, 2H), 3.52 (s, 3H), 2.45 (d, J=6.1 Hz, 2H), 1.60 (m, 2H), 1.26 (t, J=6.1 Hz, 3H) ppm;

$^{13}$C NMR δ : 172.40, 164.47, 161.17, 153.66, 148.07, 139.94, 138.21, 137.75, 135.55, 132.40, 132.30, 130.36, 129.82, 129.46, 128.67, 128.47, 127.29, 121.05, 115.74, 115.45, 71.89, 69.35, 68.34, 60.83, 60.34, 42.34, 41.53, 41.22, 33.56, 14.13 ppm.

EXAMPLE 120

Sodium (±)-(E),(E)-erythro-9-(4-fluorophenyl)-3,5-dihydroxy-8-(1-methyl-1H-tetrazol-5-yl)-9-phenylnona-6,8-dienoate hydrate A solution of dihydroxyester (160 mg; 0.343 mmole) (prepared in Example 119) in EtOH (5 mL) was treated with 1N NaOH (343 μL; 0.343 mmole) and the resulting solution stirred at 23° C. for 1 hour. The solvent was removed by evaporation and the residue was dissolved in water (2 mL) and lyophilized to afford the title compound as a light brown solid (155 mg); m.p.=130°–137° C.

IR (KBr) $\nu_{max}$: 3400 (br), 1560, 1510 cm$^{-1}$;

$^1$H NMR (DMSO-d$_6$) δ : 7.50–6.80 (m, 9H), 6.51 (d, J=15.7 Hz, 1H), 5.15 (dd, J=5.4 Hz, J'=15.7 Hz, 1H), 4.15 (m, 1H), 3.70 (s, 3H), 3.65 (br, 1H), 3.35 (br, 2H), 1.95 (m, 2H), 1.40 (m, 2H) ppm;

$^{13}$C NMR (DMSO-d$_6$) δ : 176.42, 163.42, 153.17, 146.07, 140.03, 139.73, 135.70, 135.64, 132.20, 132.09, 128.72, 128.42, 128.07, 127.98, 124.83, 121.51, 115.51, 115.22, 66.22, 65.69, 44.46, 43.59, 33.42 ppm.

Anal. Calcd. for C$_{23}$H$_{22}$FN$_4$O$_4$Na.H$_2$O: C, 57.74; H, 5.06; N, 11.72, Found: C, 58.70; H, 5.10; N, 11.16.

EXAMPLE 121

2(1-Methyltetrazol-5-yl)-1,1-diphenylethanol

A solution of 1,5-dimethyltetrazole (20 g; 0.204 mole) in dry THF (200 mL) was cooled to −78° C. and treated with n-butyllithium (91 mL of 2.5 molar solution in hexane; 0.227 mole) and the mixture stirred at −78° C. for 30 minutes. Benzophenone (31.1 g; 0.171 mole) was added and the mixture stirred at −78° C. for 30 minutes and allowed to warm up to 23° C. and stirred for 15 hours. The mixture was quenched with 2N HCl (100 mL) and extracted with EtOAc (3×150 mL). The combined organic layers were dried (MgSO$_4$) and evaporated. The residue was crystallized from EtOAc-Hexane to afford the title compound as a white solid (10.5 g; 22%); m.p.=175°–176° C. (crystallized from EtOAc-hexane). MS (CI): m/e=281 for (M+H)$^+$;

IR (KBr) $\nu_{max}$: 3300 (br), 1530, 1500 cm$^{-1}$;

$^1$H NMR δ : 7.50–7.20 (m, 10H), 5.45 (s, 1H), 3.82 (s, 2H), 3.80 (s, 3H) ppm;

$^{13}$C NMR δ : 152.36, 145.63, 128.16, 127.28, 126.05, 125.94, 77.70, 35.90, 33.76 ppm;

Anal. Calcd. for C$_{16}$H$_{16}$N$_4$: C, 68.56; H, 5.76; N, 20.00, Found: C, 68.62; H, 5.81; N, 20.10.

EXAMPLE 122

2,2-Diphenyl-1-(1-methyl-1H-tetrazol-5-yl)ethene

A mixture of 2(1-methyltetrazol-5-yl)-1,1-diphenylethanol (2.15 g; 7.68 mmole) and KHSO$_4$ (300 mg) was heated at 200° C. for 20 minutes. The cooled mixture (50° C.) was triturated with CHCl$_3$ (50 mL) and the organic solvent was decanted from the inorganic residue. Evaporation afforded the title compound as a cream solid (1.7 g; 85%); m.p.=147°–148° C. (crystallized from EtOAc-hexane). MS (CI): m/e=263 for (M+H)$^+$;

IR (KBr) $\nu_{max}$: 1640, 1500, 1445 cm$^{-1}$;

$^1$H NMR δ : 7.50–7.00 (m, 10H), 6.78 (s, 1H), 3.43 (s, 3H) ppm;

$^{13}$C NMR δ : 153.94, 152.18, 140.40, 137.83, 129.54, 129.37, 128.94, 128.59, 128.38, 128.28, 108.22, 33.56 ppm.

Anal. Calcd. for C$_{16}$H$_{14}$N$_4$: C, 73.27; H, 5.38; N, 21.36 Found: C, 73.25; H, 5.43; N, 21.43.

EXAMPLE 123

3,3-Diphenyl-2-(1-methyl-1H-tetrazol-5-yl)propenal

A solution of 2,2-diphenyl-1-(1-methyl-1H-tetrazol-5-yl)-ethene (3.75 g; 14.29 mmole) in dry THF (40 mL) was cooled to −78° C. and treated with n-butyllithium (6.3 mL of a 2.5 M soln. in hexane; 15.75 mmole) and the resulting mixture stirred at −78° C. for 30 minutes. Ethyl formate (1.5 mL; 18.58 mmole) was added and the mixture stirred at −78° C. for 2 hours. The reaction was quenched with 2N HCl and the solvent removed by evaporation. The residue was extracted with EtOAc (3×30 mL) and the combined organic layers were dried (MgSO$_4$) and evaporated. The residue was purified by chromatography using 25–35% EtOAc-hexane as eluent to afford starting material (1.35 g; 36%) and the desired title compound (1.65 g; 39%); m.p.=185°–186° C. (crystallized EtOAc-hexane). MS (EI): m/e=290 for M$^+$;

IR (KBr) $\nu_{max}$: 1675, 1600, 1445 cm$^{-1}$;

$^1$H NMR δ : 9.66 (s, 1H), 7.70–6.90 (m, 10H), 3.66 (s, 3H) ppm;

$^{13}$C NMR δ : 189.45, 167.79, 151.44, 138.35, 136.65, 131.54, 131.34, 130.96, 129.63, 128.71, 123.55, 33.91 ppm.

Anal. Calcd. for C$_{17}$H$_{14}$N$_4$O: C, 70.34; H, 4.87; N, 19.30, Found: C, 70.63; H, 4.99; N, 19.33.

EXAMPLE 124

(E)-4-(1-Methyl-1H-tetrazol-5-yl)-5,5-bis(phenyl)-2,4-pentadienal

A solution of the aldehyde (1.33 g; 4.57 mmole) (prepared in Example 123) and triphenylphosphoranylidene acetaldehyde (1.5 g; 4.87 mmole) was heated under reflux in benzene (50 mL) for 24 hours. The solvent was evaporated and the residue was purified by chromatography using 30% EtOAc-hexane as eluent to afford the title compound as a yellow foam (1 g; 71%). MS (CI): m/e=317 (M+H)$^+$;

$^1$H NMR δ : 9.53 (d, J=7.5 Hz, 1H), 7.55–7.10 (m, 10H), 6.69 (d, J=16 Hz, 1H), 5.84 (dd, J=16 Hz, J'=7.5 Hz, 1H), 3.50 (s, 3H) ppm.

EXAMPLE 125

Methyl (E)-9,9-diphenyl-3,5-dihydroxy-8-(1-methyl-1H-tetrazol-5-yl)-nona-6,8-dienoate Methylacetoacetate (0.525 mL; 4.87 mmole) was added to a suspension of sodium hydride (0.160 g; 80% disp. in mineral oil) in THF at 0° C. and stirred for 10 minutes. N-Butyllithium (2.14 mL; 2.5M solution in hexanes) was added and reaction stirred for 15 minutes. This solution was added to a solution of the aldehyde (1.0 g; 3.2 mmole) (prepared in Example 124) in THF at 0° C. and stirred for 30 minutes. The reaction was treated with 2N HCl (30 mL) and extracted with EtOAc (3×15 mL). The organic layer was dried with MgSO$_4$ and evaporated. The crude residue was triturated with hexane (3×25 mL) then dissolved in THF/CH$_3$OH (4:1; 20 mL) and treated with triethylborane (3.2 mL; 1M solution in THF). Air was bubbled through the solution for 10 minutes and the reaction stirred for an additional 50 minutes. The solution was then cooled to −78° C. and treated with sodium borohydride (120 mg; 3.2 mmole) and stirred for 1 hour. The reaction was quenched with 2M HCl (100 mL) and extracted with EtOAc (3×20 mL). The organic layers were dried with MgSO$_4$ and evaporated. The residue was dissolved in CH$_3$OH (30 mL) and stirred for 15 hours. The solvent was evaporated and residue purified by chromatography using 50% EtOAc-hexane as eluent to afford the title compound as a yellow oil (470 mg; 33%). MS (CI): m/e=435 (M+H)$^+$;

$^1$H NMR δ : 7.80–6.80 (m, 10H), 6.71 (d, J=16 Hz, 1H), 5.34 (dd, J=16 Hz, J'=6 Hz, 1H), 4.60–4.10 (m, 2H), 3.70 (s, 3H), 3.52 (s, 3H), 2.45 (d, J=6 Hz, 2H), 1.70–1.50 (m, 2H) ppm.

EXAMPLE 126

Sodium (±)-(E)-erythro-9,9-diphenyl-3,5-dihydroxy-8-(1-methyl-1H-tetrazol-5-yl)-nona-6,8-dienoate hydrate The methyl ester (470 mg; 1.08 mmole) (prepared in Example 125) was dissolved in ethanol (10 mL) and treated with 1N NaOH (1.08 mL). The reaction was stirred for 1 hour. The solvent was evaporated and residue was freeze-dried to afford a light yellow powder (500 mg; 100%); m.p.=145°–150° C.

IR ν$_{max}$: 3400 (br), 1610, 1425, 1360 cm$^{-1}$;

$^1$H NMR (DMSO-d$_6$) δ : 7.60–6.60 (m, 10H), 6.52 (d, J=16 Hz, 1H), 5.12 (dd, J=16 Hz, J'=5.5 Hz, 1H), 4.20–4.05 (m, 1H), 3.80–3.55 (m, 1H), 3.70 (s, 3H), 3.10 (br s, 2H) 2.10–1.10 (m, 5H) ppm.

Anal. Calcd. for C$_{23}$H$_{23}$N$_4$O$_4$Na.H$_2$O: C, 59.99; H, 5.47; N, 12.17 Found: C, 59.18; H, 5.46; N, 10.96.

EXAMPLE 127

2,2-Bis(4-methoxyphenyl)-1-(1-methyl-1H-tetrazol-5-yl)ethene

A solution of 1,5-dimethyltetrazole (20 g; 0.204 mole) in dry THF (200 mL) was cooled to −78° C. and treated with n-butyllithium (91 mL of 2.5M solution in hexane; 0.227 mole) and the mixture stirred at −78° C. for 30 minutes. 4,4'-Dimethoxybenzophenone (41.3 g; 0.171 mole) was added and the mixture stirred at −78° C. for 30 minutes, and allowed to warm up to 23° C. over 2 hours. The mixture was acidified with 2N HCl (100 mL) and the organic solvent removed by evaporation. The residue was extracted with EtOAc (3×300 mL) and the combined organic layers were dried (MgSO$_4$) and evaporated. The residue was crystallized from EtOAc-hexane to afford a light brown solid (48 g) which was found to be a mixture of the desired product and the initial aldol adduct (1,1-bis(4-methoxyphenyl)-2-(1-methyl-1H-tetrazol-5-yl)ethanol). This mixture was dissolved in xylene (180 mL) and heated under reflux for 1 hour with p-toluenesulfonic acid in a Dean-Stark apparatus. The cooled mixture was diluted with ether (100 mL) and the resulting solid removed by filtration to afford the title compound as a cream solid (40 g); m.p.=146°–147° C. (crystallized from EtOAc-hexane). MS (CI): m/e=323 for (M+H)$^+$;

IR (KBr) ν$_{max}$: 1605, 1520, 1250 cm$^{-1}$;

$^1$H NMR δ : 7.31 (d, J=7.8 Hz, 1H), 6.98 (d, J=7.8 Hz, 1H), 6.90 (d, J=7.8 Hz, 1H), 6.81 (d, J=8.6 Hz, 1H), 6.62 (s, 1H), 3.84 (s, 3H), 3.79 (s, 3H), 3.42 (s, 3H) ppm;

$^{13}$C NMR δ : 160.79, 160.16, 153.29, 133.33, 131.25, 130.32, 129.95, 127.36, 114.14, 113.69, 105.57, 55.40, 55.28, 33.71 ppm.

Anal. Calcd. for C$_{18}$H$_{18}$N$_4$O$_2$: C, 67.07; H, 5.63; N, 17.38 Found: C, 66.93; H, 5.63; N, 17.05.

EXAMPLE 128

3,3-Bis(4-methoxyphenyl)-2-(1-methyl-1H-tetrazol-5-yl)propenal

A solution of the olefin (4.6 g; 14.29 mmole) (prepared in Example 127) in dry THF (50 mL) was cooled to −78° C. and treated with n-butyllithium (6.3 mL of a 2.5M solution in hexane; 15.75 mmole) and the resulting solution stirred at −78° C. for 30 minutes. Ethyl formate (1.5 mL) was added and the mixture stirred at −78° C. for 2 hours. The mixture was quenched with 2N HCl and the organic solvent removed by evaporation. The residue was extracted with EtOAc (3×33 mL) and the combined organic layers were dried (MgSO$_4$) and evaporated. The residue was purified by column chromatography using 25–35% EtOAc-hexane as eluent to afford starting material (0.84 g; 18%). Further elution afforded the desired title compound (1.78 g; 36%); m.p.=130°–131° C. (crystallized from EtOAc-hexane). MS (CI): m/e 351 for (M+H)$^+$;

IR (KBr) ν$_{max}$: 1675, 1605, 1515, 1260 cm$^{-1}$;

$^1$H NMR δ : 9.59 (s, 1H), 7.30 (d, J=8.6 Hz, 1H), 7.00 (d, J=8.7 Hz, 1H), 6.90 (d, J=8.9 Hz, 1H), 6.74 (d, J=8.7 Hz, 1H), 3.90 (s, 3H), 3.77 (s, 3H), 3.67 (s, 3H) ppm;

$^{13}$C NMR δ : 189.51, 167.47, 162.59, 161.98, 152.30, 133.91, 132.29, 130.79, 129.35, 121.05, 114.20, 114.15, 55.80, 55.40, 33.94 ppm.

Anal. Calcd. for C$_{19}$H$_{19}$N$_4$O$_3$: C, 65.14; H, 5.18; N, 15.99 Found: C, 64.96; H, 5.22; N, 15.75.

EXAMPLE 129

5,5-Bis-(4-methoxyphenyl)-4-(1-methyl-1H-tetrazol-5yl)-penta-2,4-dienal

A solution of 3,3-bis(4-methoxyphenyl)-2-(1-methyl-1H-tetrazol-5-yl)propenal (1.7 g; 4.86 mmole) in benzene (100 mL) was treated with triphenylphosphoranylidene acetaldehyde (1.55 g; 5.1 mmole) and heated under reflux for 3 hours. The solvent was removed by evaporation and the residue purified by chromatography using 30% EtOAc-hexane as eluent to afford the title compound as a yellow foam (1.35 g; 74%). MS (CI): m/e=377 for (M+H)$^+$;

IR (KBr) ν$_{max}$: 1675, 1590, 1510 cm$^{-1}$;

$^1$H NMR δ : 9.52 (d, J=7.6 Hz, 1H), 7.53 (d, J=14.2 Hz, 1H), 7.23 (d, J=8.5 Hz, 1H), 7.00 (d, J=9.3 Hz, 1H), 6.86 (d, J=9.2 Hz, 1H), 6.70 (d, J=8.9 Hz, 1H), 5.83 (dd, J=7.6 Hz, J'=15.7 Hz, 1H), 3.91 (s, 3H), 3.75 (s, 3H), 3.50 (s, 3H) ppm;

$^{13}$C NMR δ : 192.89, 161.40, 160.97, 157.91, 153.29, 149.41, 133.90, 132.77, 132.29, 132.00, 131.71, 131.65, 131.25, 130.81, 117.21, 114.18, 114.12, 55.49, 55.32, 33.61 ppm.

EXAMPLE 130

Ethyl (E)-9,9-bis(4-methoxyphenyl)-5-hydroxy-8-(1-methyl-1H-tetrazol-5-yl)-3-oxonona-6,8-dienoate Ethyl acetoacetate (825 μL; 842 mg; 6.48 mmole) was added to a suspension of NaH (206 mg; 80% dispersion; 6.86 mmole) in dry THF (20 mL) at 0° C. and the resulting mixture stirred at 0° C. for 10 minutes. A solution of n-butyllithium (2.7 mL of 2.5M solution in hexane; 6.75 mmole) was added and the mixture stirred at 0° C. for 10 minutes. A solution of the aldehyde (1.3 g; 3.46 mmole) (prepared in Example 129) in dry THF (20 mL) was added and the mixture stirred at 0° C. for 15 minutes. After 2N HCl was added to quench the reaction, the solvent was removed by evaporation. The residue was diluted with water (30 mL), extracted with EtOAc (2×20 mL) and the combined organic layers were dried (MgSO$_4$) and evaporated. The residue was purified by chromatography using 40% EtOAc-hexane as eluent to afford the title compound as a yellow foam (1.165 g; 66%).

IR (KBr) $\nu_{max}$: 3450 (br), 1750, 1710, 1610, 1510 cm$^{-1}$;

$^1$H NMR δ : 7.30–6.60 (m, 9H), 5.27 (dd, J=6.1 Hz, J'=15.9 Hz, 1H), 4.68 (brs, 1H), 4.14 (q, J=7.1 Hz, 2H), 3.83 (s, 3H), 3.69 (s, 3H), 3.47 (s, 3H) 3.43 (s, 2H), 3.17 (brs, 1H), 2.70 (d, J=6.0 Hz, 2H), 1.23 (t, J=6.0 Hz, 3H) ppm;

$^{13}$C NMR δ : 202.48, 160.09, 159.70, 154.16, 149.40, 134.16, 132.57, 132.14, 131.99, 131.22, 129.08, 118.34, 113.79, 68.17, 61.47, 55.34, 55.17, 49.94, 49.33, 33.56, 14.09 ppm.

EXAMPLE 131

Ethyl (±)-(E)-erythro-9,9-bis(4-methoxyphenyl)-3,5-dihydroxy-8(1-methyl-1H-tetrazol-5-yl)nona-6,8-dienoate A solution of the β-ketoester (1 g; 1.97 mmole) (prepared in Example 130) in dry THF (50 mL) and methanol (300 μL) was treated with a solution of triethylborane (2.15 mL of 1M in THF) and the mixture stirred at 23° C. for 1 hour. The solution was cooled to −78° C. and treated with NaBH$_4$ (110 mg; 2.92 mmole). After 1 hour at −78° C. the reaction was quenched with 2N HCl and the solvent was removed by evaporation. The residue was diluted with water and extracted with EtOAc (3×30 mL). The combined organic extracts were dried (MgSO$_4$) and evaporated. The residue was purified by chromatography to afford the title compound as a light oil (136 mg).

IR (KBr) $\nu_{max}$: 3450 (br), 1750, 1710, 1610, 1510 cm$^{-1}$.

$^1$H NMR δ : 7.70–6.50 (m, 9H), 5.80 (dd, 1H), 4.45 (br, 1H), 4.15 (q, 2H), 3.85 (s, 3H), 3.72 (s, 3H), 3.50 (s, 3H), 2.45 (m, 2H), 1.55 (m, 2H), 1.26 (t, 3H) ppm;

$^{13}$C NMR δ : 172.38, 160.18, 159.29, 154.32, 148.92, 138.54, 136.19, 132.81, 132.29, 132.20, 132.11, 131.90, 131.51, 131.22, 128.59, 128.41, 128.36, 118.97, 113.90, 113.34, 72.15, 66.31, 60.75, 55.35, 55.20, 42.74, 42.14, 41.73, 41.48, 33.50, 14.18.

EXAMPLE 132

Sodium (±)-(E)-erythro-9,9-bis(4-methoxyphenyl)-3,5-dihydroxy-8-(1-methyl-1H-tetrazol-5-yl)nona-6,8-dienoate dihydrate A solution of the ester (95 mg; 0.196 mmole) (prepared in Example 131) in ethanol (15 mL) was treated with 1N NaOH solution (196 μL) and the mixture stirred at 23° C. for 1 hour. The solvent was removed by evaporation and the residue was dissolved in water (2 mL) and freeze dried to afford the title compound as a brown powder (95 mg; 100%); m.p.=175°–180° C.

IR (KBr) $\nu_{max}$: 3400 (br), 1600, 1575, 1510 cm$^{-1}$;

$^1$H NMR (DMSO-d$_6$) δ : 7.70–6.65 (m, 9H), 6.55 (d, J=15.5 Hz, 1H), 5.08 (dd, J=5.6 Hz, J'=15.7 Hz, 1H), 4.14 (br, 1H), 3.75 (s, 3H), 3.67 (s, 3H), 3.66 (s, 3H), 2.10–1.80 (br, 2H), 1.50–1.20 (br, 2H) ppm;

$^{13}$C NMR (DMSO-d$_6$ δ : 159.25, 158.80, 153.78, 138.13, 132.75, 131.88, 131.60, 131.42, 131.30, 130.41, 128.68, 128.53, 125.72, 113.74, 113.48, 68.56, 65.89, 55.14, 54.99, 44.68, 43.68, 33.34.

Anal. Calcd. for C$_{25}$H$_{27}$NaN$_4$O$_6$·2H$_2$O: C, 55.76; H, 5.81; N, 10.41 Found: C, 54.43; H, 5.04; N, 8.15.

EXAMPLE 133

Cis-2,2-dimethyl-6-(2-phenylethenyl)-1,3-dioxane-4-acetic acid methyl ester

Methyl 3,5-dihydroxy-7-phenyl-6-enoate (98% diastereomeric purity) (2.37 g, 9.48 mmol) was stirred with 2,2-dimethoxypropane (20 mL) and a catalytic amount of p-toluenesulfonic acid for 16 hours. The solution was partitioned between diethyl ether and dilute aqueous sodium bicarbonate solution. The organic layer was dried (Na$_2$SO$_4$) and concentrated under reduced pressure to afford a yellow solid. After recrystallization from isopropyl ether, 1.70 g (62%) of the title compound was obtained as a white solid; m.p.=84°–86.5° C.

Alternatively, 0.2 g of solid sodium carbonate can be added to the 2,2-dimethoxypropane solution and the solution stirred vigorously. The solid is filtered through a fluted filter paper. The excess 2,2-dimethoxypropane is removed under reduced pressure to afford a yellow solid which is recrystallized from isopropyl ether.

$^1$H NMR (CDCl$_3$) δ : 7.37–7.19 (5H, m), 6.59 (1H, d, J=15.9 Hz), 6.14 (1H, dd, J=15.9, 6.4 Hz), 4.57–4.35 (1H, m), 4.42–4.35 (1H, m), 3.68 (3H, s), 2.58 (1H, d, J=15.6, 6.9 Hz), 2.14 (1H, dd, J=15.6, 6.3 Hz), 1.74–1.61 (1H, m), 1.52 (3H, s), 1.43 (3H, s), 1.45–1.35 (1H, m).

Anal. Calcd. for C$_{17}$H$_{22}$O$_4$: C, 70.32; H, 7.63 Found: C, 70.24; H, 7.69.

EXAMPLE 134

Cis-2,2-dimethyl-6-(2-phenylethenyl)-1,3-dioxane-4-acetic acid

A solution of 2,2-dimethyl-6-(2-phenylethenyl)-1,3-dioxane-4-acetic acid methyl ester (8.5 g, 29.3 mmol) in 1N NaOH (32 mL) and methanol (64 mL) was heated to reflux for 45 minutes. After evaporation under reduced pressure, the aqueous solution was washed once with diethyl ether and acidified with 1N HCl (33 mL). The precipitate was collected and recrystallized from ethyl acetate/isopropyl ether to afford 7.2 g (90%) of the title compound as a colorless solid; m.p.=153°–155° C.

$^1$H NMR (CDCl$_3$) δ : 7.37–7.20 (5H, m), 6.60 (1H, d, J=16.0 Hz), 6.14 (1H, dd, J=16.0, 6.4 Hz), 4.59–4.54 (1H, m), 4.43–4.35 (1H, m), 2.62 (1H, dd, J=16.0, 7.2 Hz), 2.51 (1H, dd, J=16.0, 5.3 Hz), 1.77–1.72 (1H, m), 1.54 (3H, s), 1.46 (3H, s), 1.50–1.36 (1H, m).

Anal. Calcd. for C$_{16}$H$_{20}$O$_4$: C, 69.54; H, 7.30 Found: C, 69.20; H, 7.33.

EXAMPLE 135

Resolution of cis-2,2-dimethyl-6-(2-phenylethenyl)-1,3-dioxane-4-acetic acid

The racemic cis-2,2-dimethyl-6-(2-phenylethenyl)-1,3-dioxane-4-acetic acid (0.31 g, 1.1 mmol) (prepared in Example 134) was dissolved in a boiling solution of hexane/ethanol containing (1S,2R)-ephedrine (0.2 g, 1.1 mmol). The resulting solution was very slowly brought to room temperature to give 0.21 g (41.4%) of colorless chiral salt (the usage of diastereomerically pure seed crystal is recommended during the resolution): m.p.=170°-171° C.

The chiral acid was freed through an acidic workup (vide infra) and its enantiomeric purity was determined to be 100% by $^1$H NMR using L-phenyltrifluoromethyl carbinol as a chiral solvent. $[\alpha]_D^{25} = +5.45°$ (c=1, CHCl$_3$).

EXAMPLE 136

Cis-(4R,6S)-2,2-dimethyl-6-formyl-1,3-dioxane-4-acetic acid

The resolved salt of cis-2,2-dimethyl-6-(2-phenylethenyl)-1,3-dioxane-4-acetic acid and (1S,2R)-ephedrine (6.6 g, 14.9 mmol) (prepared in Example 135) was partitioned between 0.5N HCl (30 mL) and diethyl ether. The ether layer was washed with brine, dried (MgSO$_4$/Na$_2$SO$_4$), and concentrated under reduced pressure to afford 4.1 g (99.6%) of the free acid. This acid was dissolved in dry methylene chloride (100 mL) and ozone was passed through this solution at −78° C. until there was deep blue coloration. Excess ozone was removed by purging with nitrogen and the ozonide formed was decomposed by adding CH$_3$SCH$_3$ (5 mL) and warming the solution to room temperature and allowed to stand for 16 hours. The solution was concentrated under reduced pressure and the residue was dissolved in isoamyl ether (ca 100 mL). The benzaldehyde which was formed during the ozonolysis was azeotroped together with isoamyl ether under reduced pressure to afford the title compound.

$^1$H NMR (CDCl$_3$) δ : 9.57 (1H, s), 4.40–4.30 (2H, m), 2.60 (1H, dd, J=16.0, 7.0 Hz), 2.49 (1H, dd, J=16.0, 6.0 Hz), 1.88–1.83 (1H, m) 1.49 (3H, s), 1.46 (3H, s), 1.42–1.31 (1H, m).

EXAMPLE 137

Cis-(4R,6S)-6-[4,4-bis(4-fluorophenyl)-3-(1-methyl-1H-tetrazol-5-yl]-1,3-butadienyl]-2,2-dimethyl-1,3-dioxane-4-acetic acid The crude chiral acid prepared in Example 136 was dissolved in dry THF (50 mL) and the resulting solution was transferred to a 250 mL three-neck flask purged with nitrogen and equipped with a mechanical stirrer. After the solution was stirred vigorously and cooled to −78° C., n-BuLi (2.5M in hexane, 5.96 mL) was added dropwise. Toward the end of addition, the solution turned into a suspension of white solid-like gel.

A separate flask containing dimethyl [3,3-bis(4-fluorophenyl)-2-(1-methyl-1H-tetrazol-5yl)-2-propen-1-yl]phosphonate (6.2 g, 14.7 mmol) (prepared in Example 112) in THF (50 mL) under a nitrogen atmosphere was cooled to −78° C. and n-BuLi (2.5M in hexane, 5.96 mL) was added slowly. The resulting red-brown solution was stirred for 15 minutes at −78° C. This solution of phosphonate anion was transferred through a double ended needle to the above vigorously stirred suspension at −78° C. containing the lithium salt of the chiral acid. After the addition, the resulting brown solution was stirred for 30 minutes at −78° C. and 16 hours at ambient temperature. The THF solution was partitioned between 0.5N HCl and ethyl acetate. The organic phase was washed with brine (2x), dried (Na$_2$SO$_4$), and concentrated under reduced pressure. The residue was chromatagraphed on silica gel (66:33:1/diethyl ether:hexane:acetic acid) to afford 3.80 g (51.6% overall yield from the initial ephedrine salt; toluene was employed to azeotrope the residual acetic acid) of the title compound as a yellow form. $[\alpha]_D^{25} = +106.1°$ (c=2.23, CHCl$_3$).

$^1$H NMR (CDCl$_3$) δ : 7.24–6.82 (8H, m), 6.62 (1H, d, J=15.0 Hz), 5.32 (1H, dd, J=15.0, 5.7 Hz), 4.42–4.37 (1H, m), 4.30–4.23 (1H, m), 3.51 (3H, s), 2.53 (1H, dd, J=15.9, 7.0 Hz), 2.42 (1H, dd, J=15.9, 5.6 Hz), 1.62–1.57 (1H, m), 1.46 (3H, s), 1.33 (3H, s), 1.30–1.20 (1H, m).

EXAMPLE 138

Trans-(4R,6S)-6-[4,4-bis(4-fluorophenyl)-3-(1-methyl-1H-tetrazol-5-yl)-1,3-butadienyl]-tetrahydro-4-hydroxy-2H-pyran-2-one Cis-(4R,6S)-6-[4,4-bis(4-fluorophenyl)-3-(1-methyl-1H-tetrazol-5-yl)-1,3-butadienyl]-2,2-dimethyl-1,3-dioxane-4-acetic acid (3.7 g, 7.45 mmol) was dissolved in a solution of THF (90 mL) and 0.2N HCl (60 mL) and allowed to stand for 16 hours. The solution was partitioned between ethyl acetate and water. The organic layer was washed with brine (2x), dried (Na$_2$SO$_4$), and concentrated under reduced pressure. The residue was dissolved in dry methylene chloride (60 mL) and stirred for 4 hours in the presence of 1-cyclohexyl-3-(2-morpholinomethyl) carbodiimide metho-p-toluenesulfonate (6.6 g, 15.6 mmol). The solution was concentrated under reduced pressure and the residue was partitioned between ethyl acetate and water. The organic layer was dried (Na$_2$SO$_4$) and concentrated under reduced pressure. The residue was purified by chromatography on silica gel (1:1/ethyl acetate:diethyl ether). After recrystallization from ethyl acetate-hexane, 1.33 g (40.1%) of the title compound was obtained as a white solid; m.p.=172°-173° C. $[\alpha]_D^{25} = +237.8°$ (c=2.17, CHCl$_3$).

EXAMPLE 139

Methyl 3-hydroxy-5-oxo-6,8-decadienoate

To a cold (−30° C.) solution of methyl acetoacetate (41.5 g, 357 mmol) in THF (500 mL) was added lithium diisopropylamide (476 mL, 1.5M solution in cyclohexane, 714 mmol). The resultant solution was stirred for 15 minutes at −30° C. After cooling to −78° C., 2,4-hexadienal (34.3 g, 357 mmol) was added and the solution stirred for 10 minutes at −78° C. and for 16 hours at ambient temperature. The solution was concentrated under reduced pressure and the residual syrup was partitioned between 1N HCl and ethyl acetate. The organic layer was washed with brine (2x), dried (Na$_2$SO$_4$), and concentrated. The residue was purified by chromatography on silica gel (diethyl ether:hexane/2:1) to afford 18.5 g (24.4%) of the title compound as an oil.

$^1$H NMR for (E) (E) isomer (200 MHz, CDCl$_3$) δ : 6.3 (1H, dd, J=14.7, 11.9 Hz), 6.02 (1H, dd, J=14.7, 11.9 Hz), 5.75 (1H, dq, J=14.7, 6.4 Hz), 5.5 (1H, dd, J=18.7, 6.4 Hz), 4.74–4.5 (1H, m), 3.73 (3H, s), 3.51 (2H, s), 2.6 (2H, d, J=5.8 Hz), 1.77 (3H, d, J=6.4 Hz).

EXAMPLE 140

Methyl 3,5-dihydroxy-6,8-decadienoate

To a cold (−15°C.) solution of methyl 3-hydroxy-5-oxo-6,8-decadienoate (18.5 g, 86.9 mmol) in THF (300 mL) was added triethylborane (1M in THF, 113 mL, 113 mmol) and the solution was stirred for 20 minutes. After the mixture was cooled to −78° C., NaBH$_4$ (6 g, 159 mmol) and methanol (37.5 mL) were added. The solution was vigorously stirred for 30 minutes at −78° C. and at ambient temperature for 3 hours. The solvent was removed under reduced pressure and the residue was partitioned between 1N HCl and ethyl acetate. The organic layer was dried ($Na_2SO_4$) and concentrated. The residue was purified by chromatography on silica gel (diethyl ether:hexane/3:1) to afford 7.95 g (42.7%) of the title compound as a yellow oil.

$^1$H NMR for (E) (E) isomer (360 MHz, $CDCl_3$) δ : 6.18 (1H, dd, J=15.1, 10.4 Hz), 6.00 (1H, dd, J=15.1, 10.4 Hz), 5.69 (1H, dq, J=15.1, 7.0 Hz), 5.52 (1H, dd, J=15.1, 6.7 Hz), 4.46–4.37 (1H, m), 4.29–4.22 (1H, m), 3.69 (3H, s), 2.60–2.42 (2H, m), 1.72 (3H, d, J=7.0 Hz), 1.74–1.57 (2H, m).

EXAMPLE 141

Methyl cis-4-(1,3-pentadienyl)-1,5-dioxaspiro[5.5]undecane-2-acetate

Methyl 3,5-dihydroxy-6,8-decadienoate (7.6 g, 35.5 mmol) and p-toluenesulfonic acid (0.1 g) was added to cyclohexanone (10 g, 100 mmol) and stirred for 16 hours at ambient temperature. The yellow solution was loaded directly onto a silica gel column and the product eluted with diethyl ether:hexane (1:4). The appropriate fractions were combined to give 3.52 g (33.6%) of the title compound as a colorless oil.

$^1$H NMR for (E) (E) isomer (360 MHz, $CDCl_3$) δ : 6.16 (1H, dd, J=15.1, 10.6 Hz), 6.00 (1H, dd, J=15.1, 10.6 Hz), 5.71–5.65 (1H, dd, J=15.1, 6.5 Hz), 5.47 (1H, dd, J=15.1, 6.4 Hz), 4.44–4.39 (1H, m), 4.35–4.30 (1H, m), 3.66 (3H, s), 2.52 (1H, dd, J=1.54, 7.9 Hz), 2.30 (1H, dd, J=15.4, 6.5 Hz), 2.1–1.18 (12H, m), 1.72 (3H, d, J=6.5 Hz).

Anal. Calcd. for $C_{17}H_{26}O_4$: C, 69.36; H, 8.90, Found: C, 69.59; H, 9.16.

EXAMPLE 142

Cis-4-(1,3-pentadienyl)-1,5-dioxaspiro[5.5]undecane-2-acetic acid

Methyl 4-(1,3-pentadienyl)-1,5-dioxaspiro[5.5]undecane-2-acetate (3.5 g, 12.4 mmol) was heated to reflux in a solution of 1N NaOH (13 mL) and methanol (26 mL). Methanol was removed under reduced pressure and the remaining aqueous solution was acidified with 1N HCl and extracted with diethyl ether. The organic layer was dried ($Na_2SO_4$) and concentrated. The residual solid was recrystallized from ethyl acetate/hexane to afford 2.0 g (55.9%) of the title compound as a colorless solid; m.p.=144°–146.5° C.

$^1$NMR (360 MHz, $CDCl_3$) δ : 6.18 (1H, dd, J=18.0, 12.5 Hz), 5.72 (1H, dq, J=18.0, 7.7 Hz), 5.99 (1H, dd, J=18.0, 12.5 Hz), 5.48 (1H, dd, J=18.0, 7.6 Hz), 4.45–4.37 (1H, m), 4.37–4.25 (1H, m), 2.56 (1H, dd, J=18.9, 8.8 Hz), 2.48 (1H, dd, J=18.9, 6.1 Hz), 2.60–1.30 (12H, m), 1.73 (3H, d, J=7.7 Hz).

Anal. Calcd. for $C_{16}H_{24}O_4$: C, 68.54; H, 8.62 , Found: C, 68.36; H, 8.55.

EXAMPLE 143

Cis-4-[4,4-bis(4-fluorophenyl)-3-(1-methyl-1H-tetrazol-5-yl)-1,3-butadienyl]-1,5-dioxaspiro[5.5]undecane-2-acetic acid A. 4-Formyl-1,5-dioxaspiro[5.5]undecane-2-acetic acid Ozone was passed through a solution of 4-1,3-pentadienyl)-1,5-dioxaspiro[5.5]undecane-2-acetic acid (570 mg, 2.0 mmol) in methylene chloride (25 mL) at −78° C. After the solution had attained a blue color, nitrogen was passed through the solution to remove the excess ozone. Dimethyl sulfide (0.5 mL) was added and the solution was concentrated under reduced pressure to afford the title compound as a viscous oil which was used without further purification in the subsequent step.

$^1$H NMR (60 MHz, $CDCl_3$) δ : 9.57 (1H, s), 4.52–4.14 (2H, m), 2.60–2.31 (2H, m), 2.10–1.10 (12H, m).

B.

Cis-4-[4,4-bis(4-fluorophenyl)-3-(1-methyl-1H-tetrazol-5-yl)-1,3-butadienyl]-1,5-dioxaspiro[5.5]-undecane-2-acid To a solution of dimethyl [3,3-bis(4-fluorophenyl)-2-(1-methyl-1H-tetrazol-5-yl)-2-propenyl]phosphonate (1.7 g, 4 mmol) in THF (20 mL) at −78° C. was added n-BuLi (1.6 mL, 4 mmol, 2.5M in hexane). The resultant brown-red solution was stirred for 30 minutes at −78° C. Using a double ended needle, this solution was transferred to a solution containing 4-formyl-1,5-dioxaspiro[5.5]undecane-2-acetic acid (prepared in Step A) in THF (10 mL) and maintained at −78° C. After the transfer had been completed, the combined reaction mixture was stirred at −78° C. for 1 hour and at ambient temperature for 4 hours. The solution was then partitioned between 0.5N HCl and ethyl acetate. The organic layer was washed with brine (2x), dried ($Na_2SO_4$), and concentrated under reduced pressure. The residue was purified by chromatography on silica gel (diethyl ether:hexane:acetic acid/50:20:1) to afford 342 mg (31.9% overall yield) of the title compound as a yellow foam.

$^1$H NMR (360 MHz, $CDCl_3$) δ : 7.25–6.84 (8H, m), 6.66 (1H, d, J=16.0 Hz), 5.32 (1H, dd, J=16.0, 5.1 Hz), 4.45–4.25 (2H, m), 3.52 (3H, s), 2.56 (1H, dd, J=16.0, 7.6 Hz), 2.44 (1H, dd, J=16.0, 5.1 Hz), 1.89–1.17 (12H, m).

EXAMPLE 144

Trans-6-[4,4-bis(4-fluorophenyl)-3-(1-methyl-1H-tetrazol-5-yl)-1,3-butadienyl]-tetrahydro-4-hydroxy-2H-pyran-2-one A mixture of 4-[4,4-bis(4-fluorophenyl)-3-(1-methyl-1H-tetrazol-5-yl)-1,3-butadienyl]-1,5-dioxaspiro[5.5]undecane-2-acetic acid (280 mg, 0.52 mmol) in 20 mL of THF/0.5N HCl (1:1) was allowed to stand at ambient temperature for 26 hours. The solution was partitioned between brine and ethyl acetate. The organic layer was washed with brine (2x), dried ($Na_2SO_4$) and concentrated. The resultant foam (126 mg) was dissolved in dry methylene chloride (10 mL) and treated with 1-cyclohexyl-3-(2-morpholinomethyl) carbodiimide metho-p-toluenesulfonate (0.24 g). After 16 hours at ambient temperature, the solution was evaporated under reduced pressure and the residue was purified by silica gel chromatography using ethyl acetate as eluent. The appropriate fractions afforded 38 mg (16.6%) of the title compound as a colorless oil which is a racemic mixture of the compound of Example 7.

EXAMPLE 145

Methyl 2,2-dimethyl-6-formyl-1,3-dioxane-4-acetate

Cis-2,2-dimethyl-6-(2-phenylethenyl)-1,3-dioxane-4-acetic acid methyl ester (prepared in Example 133) was dissolved in methanol (10 mL) and ozone was passed through the solution at −78° C. until the color of the solution turned blue. The reaction mixture was purged with nitrogen to remove excess ozone then dimethyl sulfide was added and the temperature was allowed to warm up to room temperature. The reaction was evaporated in vacuo and the residual oil was purified by chromatography on silica gel using diethyl ether-hexane (3:1) as the eluent to afford the title compound.

$^1$H NMR (360MHz, CDCl$_3$) δ : 9.53 (1H, s), 4.40–4.23 (2H, m), 3.69 (3H, s), 2.53 (1H, dd, J=15.8, 7.02 Hz), 2.37 (1H, dd, J=15.8, 5.98 Hz), 1.85–1.76 (1H, m), 1.44 (3H, s), 1.40 (3H, s), 1.35–1.23 (1H, m).

EXAMPLE 146

The general procedures of Example 80, Steps B, C and D, and Examples 112, 137 and 138 are sequentially repeated, except that the 4,4'-difluorobenzophenone utilized in Example 80, Step B is replaced by an equimolar amount of (a) 2,2',4,4'-tetramethoxybenzophenone
(b) 3,3',4,4'-tetramethoxybenzophenone
(c) 2,2',4,4'-tetramethylbenzophenone
(d) 3,3',4,4'-tetramethylbenzophenone
(e) 3,3',5,5'-tetramethylbenzophenone
(f) 4'-fluoro-2,4,6-trimethylbenzophenone
(g) 2,2',3,3',4,4'-hexamethoxybenzophenone
(h) 2,2',4,4',6,6'-hexamethylbenzophenone
(i) 4'-methoxy-2,5-dimethylbenzophenone
(j) 4'-methoxy-2,4,6-trimethylbenzophenone
(k) 2,2',4,4'-tetrachlorobenzophenone
(l) 2,2',5,5'-tetrachlorobenzophenone
(m) 2,2',6,6'-tetrachlorobenzophenone
(n) 3,3'-dichlorobenzophenone
(o) 4,4'-dichlorobenzophenone
(p) 2,2'-dichloro-4,4'-dimethoxybenzophenone
(q) 2,4-dichloro-4'-trifluoromethylbenzophenone
(r) 2,2'-difluorobenzophenone
(s) 3,3'-difluorobenzophenone
(t) 2,2'-dimethoxybenzophenone
(u) 2,2'-dimethoxy-3,3'-dimethylbenzophenone
(v) 2,2'-dimethoxy-5,5'-dimethylbenzophenone
(w) 2,4-dimethoxy-2'-trifluoromethylbenzophenone
(x) 2,4-dimethoxy-4'-trifluoromethylbenzophenone
(y) 2',4'-dimethoxy-2,4,6-trimethylbenzophenone
(z) 2,2'-dimethylbenzophenone
(aa) 3,3'-dimethylbenzophenone
(bb) 4,4'-dimethylbenzophenone
(cc) 4'-fluoro-2,4-dimethoxybenzophenone
(dd) 4,4'-bis(trifluoromethyl)benzophenone
(ee) 4'-chloro-2,4,6-trimethylbenzophenone
(ff) 4,4'-dibromobenzophenone
(gg) 2,2'-dibromo-4,4'-dimethoxybenzophenone
(hh) 2-chloro-4,4'-dimethoxybenzophenone and
(ii) 2,2'-dichlorobenzophenone, respectively
and there is thereby produced (a) Trans-(4R,6S)-6-[4,4-bis(2,4-dimethoxyphenyl)-3-(1-methyl-1H-tetrazol-5-yl)-1,3-butadienyl]-tetrahydro-4-hydroxy-2H-pyran-2-one,
(b) Trans-(4R,6S)-6-[4,4-bis(3,4-dimethoxyphenyl)-3-(1-methyl-1H-tetrazol-5-yl)-1,3-butadienyl]-tetrahydro-4-hydroxy-2H-pyran-2-one.
(c) Trans-(4R,6S)-6-[4,4-bis(2,4-dimethylphenyl)-3-(1-methyl-1H-tetrazol-5-yl)-1,3-butadienyl]-tetrahydro-4-hydroxy-2H-pyran-2-one,
(d) Trans-(4R,6S)-6-[4,4-bis(3,4-dimethylphenyl)-3-(1-methyl-1H-tetrazol-5-yl)-1,3-butadienyl]-tetrahydro-4-hydroxy-2H-pyran-2one,
(e) Trans-(4R,6S)-6-[4,4-bis(3,5-dimethylphenyl)-3-(1-methyl-1H, tetrazol-5-yl)-1,3-butadienyl]-tetrahydro-4-hydroxy-2H-pyran-2-one,
(f) Trans-(4R,6S)-6-[4-(4-fluorophenyl)-4-(2,4,6-trimethyl-phenyl)-3-(1-methyl-1H-tetrazol-5-yl)-1,3-butadienyl]-tetrahydro-4-hydroxy-2H-pyran-2-one,
(g) Trans-(4R,6S)-6-[4,4-bis(2,3,4-trimethoxyphenyl)-3-(1-methyl-1H-tetrazol-5-yl)-1,3-butadienyl]-tetrahydro-4-hydroxy-2H-pyran-2-one,
(h) Trans-(4R,6S)-6-[4,4-bis(2,4,6-trimethylphenyl)-3-(1-methyl-1H-tetrazol-5-yl)-1,3-butadienyl]-tetrahydro-4-hydroxy-2H-pyran-2-one,
(i) Trans-(4R,6S)-6-[4-(4-methoxyphenyl)-4-(2,5-dimethylphenyl)-3-(1-methyl-1H-tetrazol-5-yl)-1,3-butadienyl]-tetrahydro-4-hydroxy-2H-pyran-2-one,
(j) Trans-(4R,6S)-6-[4-(4-methoxyphenyl),4-(2,4,6-trimethylphenyl)-3-(1-methyl-1H-tetrazol-5-yl)-1,3-butadienyl]-tetrahydro-4-hydroxy-2H-pyran-2-one,
(k) Trans-(4R,6S)-6-[4,4-bis(2,5-dichlorophenyl)-3-(1-methyl-1H-tetrazol-5-yl)-1,3-butadienyl]-tetrahydro-4-hydroxy-2H-pyran-2-one,
(k) Trans-(4R,6S)-6-[4,4-bis(2,5-dichlorophenyl)-3-(1-methyl-1H-tetrazol-5-yl)-1,3-butadienyl]-tetrahydro-4-hydroxy-2H-pyran-2-one,
(l) Trans-(4R,6S)-6-[4,4-bis(2,6-dichlorophenyl)-3-(1-methyl-1H-tetrazol-5-yl)-1,3-butadienyl]-tetrahydro-4-hydroxy-2H-pyran-2one,
(m) Trans-(4R,6S)-6-[4,4-bis(3-chlorophenyl)-3-(1-methyl-1H-tetrazol-5-yl)-1,3-butadienyl]-tetrahydro-4-hydroxy-2H-pyran-2-one,
(n) Trans-(4R,6S)-6-[4,4-bis(4-chlorophenyl)-3-(1-methyl-1H-tetrazol-5-yl)-1,3-butadienyl]-tetrahydro-4-hydroxy-2H-pyran-2one,
(o) Trans-(4R,6S)-6-[4,4-bis(2-chloro-4-methoxyphenyl)-3-(1-methyl-1H-tetrazol-5yl)-1,3-butadienyl]-tetrahydro-4-hydroxy-2H-pyran-2-one,
(p) Trans-(4R,6S)-6-[4-(2,4-dichlorophenyl)-4-(4-trifluoromethylphenyl)-3-(1-methyl-1H-tetrazol-5-yl)1,3-butadienyl]-tetrahydro-4-hydroxy-2H-pyran-2-one,
(q) Trans-(4R,6S)-6-[4,4-bis(2-fluorophenyl)-3-(1-methyl-1H-tetrazol-5-yl)-1,3-butadienyl]-tetrahydro-4-hydroxy-2H-pyran-2one,
(r) Trans-(4R,6S)-6-[4,4-bis(3-fluorophenyl)-3-(1-methyl-1H-tetrazol-5-yl)-1,3-butadienyl]-tetrahydro-4-hydroxy-2H-pyran-2-one,
(s) Trans-(4R,6S)-6-[4,4-bis(2-methoxyphenyl)-3-(1-methyl-1H-tetrazol-5-yl)-1,3-butadienyl]-tetrahydro-4-hydroxy-2H-pyran-2-one,
(t) Trans-(4R,6S)-6-[4,4-bis(2-methoxy-3-methylphenyl)-3-(1-methyl-1H-tetrazol-5-yl)-1,3-butadienyl]-tetrahydro-4-hydroxy-2H-pyran-2-one,
(u) Trans-(4R,6S)-6-[4,4-bis(2-methoxy-5-methylphenyl)-3-(1-methyl-1H-tetrazol-5-yl)-1,3-butadienyl]-tetrahydro-4-hydroxy-2H-pyran-2one,
(v) Trans-(4R,6S)-6-[4-(2,4-dimethoxy-(2-trifluoromethyl-phenyl)-3-(1-methyl-1H-tetrazol-5-yl)-1,3-butadienyl]-tetrahydro-4-hydroxy-2H-pyran-2-one,
(w) Trans-(4R,6S)-6-[4-(2,4-dimethoxy-4-(4-trifluoromethyl-phenyl)-3-(1-methyl-1H-tetrazol-5yl)-1,3-butadienyl]-tetrahydro-4-hydroxy-2H-pyran-2-one,
(x) Trans-(4R,6S)-6-[4-(2,4-dimethoxy-4-(2,4,6-trimethylphenyl)-3-(1-methyl-1H-tetrazol-5-yl)-1,3-butadienyl]-tetrahydro-4-hydroxy-2H-pyran-2-one, (z) Trans-(4R,6S)-6-[4,4-bis(2-methylphenyl)-3-(1-methyl-1H-tetrazol-5-yl)-1,3-butadienyl]-tetrahydro-4-hydroxy-2H-pyran-2-one,
(aa) Trans-(4R,6S)-6-[4,4-bis(3-methylphenyl)-3-(1-methyl-1H-tetrazol-5-yl)-1,3-butadienyl]-tetrahydro-4-hydroxy-2H-pyran-2-one,
(bb) Trans-(4R,6S)-6-[4,4-bis(4-methylphenyl)-3-(1-methyl-1H-tetrazol-5-yl)-1,3-butadienyl]-tetrahydro-4-hydroxy-2H-pyran-2-one,
(cc) Trans-(4R,6S)-6-[4-(4-fluorophenyl)-4-(2,4-dimethoxy-phenyl)-3-(1-methyl-1H-tetrazol-5-yl)-1,3-butadienyl]-tetrahydro-4-hydroxy-2H-pyran-2-one,
(dd) Trans-(4R,6S)-6-[4,4-bis(4-trifluoromethylphenyl)-3-(1-methyl-1H-tetrazol-5-yl)-1,3-butadienyl]-tetrahydro-4-hydroxy-2H-pyran-2-one,
(ee) Trans-(4R,6S)-6-[4-(4-chlorophenyl)-4-(2,4,6-trimethylphenyl)-3-(1-methyl-1H-tetrazol-5-yl)-1,3-butadienyl]-tetrahydro-4-hydroxy-2H-pyran-2-one,
(ff) Trans-(4R,6S)-6-[4,4-bis(4-bromophenyl)-3-(1-methyl-1H-tetrazol-5-yl)-1,3-butadienyl]-tetrahydro-4-hydroxy-2H-pyran-2-one,
(gg) Trans-(4R,6S)-6-[4,4-bis(2-bromo-4-methoxyphenyl)-3-(1-methyl-1H-tetrazol-5-yl)-1,3-butadienyl]-tetrahydro-4-hydroxy-2H-pyran-2-one,
(hh) Trans-(4R,6S)-6-[4-(2-chloro-4-methoxyphenyl)-4-(4-methoxyphenyl)-3-(1-methyl-1H-tetrazol-5-yl)-1,3-butadienyl]-tetrahydro-4-hydroxy-2H-pyran-2-one, and
(ii) Trans-(4R,6S)-6-[4,4-bis(2-chlorophenyl)-3-(1-methyl-1H-tetrazol-5-yl)-1,3-butadienyl]-tetrahydro-4-hydroxy-2H-pyran-2-one.

EXAMPLE 147

Methyl N-[9,9-bis(4-fluorophenyl)-3(R),5(S)-dihydroxy-8-(1-methyl-1H-tetrazol-5-yl)-1oxo-6,8-nonadien-1-yl]-L-leucinate When a solution of trans-(4R,6S)-6-[4,4-bis(4-fluorophenyl)-3-(1-methyl-1H-tetrazol-5-yl)-1,3-butadienyl]-tetrahydro-4-hydroxy-2H-pyran-2-one in tetrahydrofuran is treated with at least one equivalent of L-leucine methyl ester (prepared in situ from the hydrochloride salt) and heated to reflux temperature, the title compound is thereby produced.

EXAMPLE 148

The general procedure of Example 147 or Example 1 in U.S. Pat. No. 4,678,806 is repeated, except that the L-leucine methyl ester utilized therein is replaced by an equimolar amount of
(a) L-serine methyl ester,
(b) L-phenylalanine methyl ester and
(c) L-tyrosine methyl ester, respectively there is thereby produced
(a) methyl N-9,9-bis(4-fluorophenyl)-3(R),5(S)-dihydroxy-8-(1-methyl-1H-tetrazol-5yl)-1-oxo-6,8-nonadien-1-yl]-L-serinate,
(b) methyl N-9,9-bis(4-fluorophenyl)-3(R),5(S)-dihydroxy-8-(1-methyl-1H-tetrazol-5-yl)-1-oxo-6,8-nonadien-1-yl]-L-phenylalaninate and
(c) methyl N-9,9-bis(4-fluorophenyl)-3(R),5(S)-dihydroxy-8-(1-methyl-1H-tetrazol-5-yl)-1-oxo-6,8-nonadien-1-yl]-L-tyrosinate.

EXAMPLE 149

N-[9,9-bis(4-fluorophenyl)-3(R),5(S)-dihydroxy-8-(1-methyl-1H-tetrazol-5yl)-1-oxo-6,8-nonadien-1-yl]-L-leucine When a solution of the compound from Example 147 in dioxane-water is treated at a temperature of about 0° C. with 1N NaOH and then acidified after workup, the title compound is thereby produced.

EXAMPLE 150

The general procedure of Example 149 or Example 2 in U.S. Pat. No. 4,678,806 is repeated, except that the compound from Example 147 utilized therein is replaced by the compounds from Example 148, there is thereby produced
(a) N-[9,9-bis(4-fluorophenyl)-3(R),5(S)-dihydroxy-8-(1-methyl-1H-tetrazol-5-yl)-1-oxo-6,8-nonadien-1-yl]-L-serine,
(b) N-[9,9-bis(4-fluorophenyl)-3(R),5(S)-dihydroxy-8-(1-methyl-1H-tetrazol-5-yl)-1-oxo-6,8-nonadien-1-yl]-L-phenylalanine and
(c) N-[9,9-bis(4-fluorophenyl)-3(R),5(S)-dihydroxy-8-(1-methyl-1H-tetrazol-5-yl)-1-oxo-6,8-nonadien-1-yl]-L-tyrosine.

What is claimed is:
1. A compound of the formula

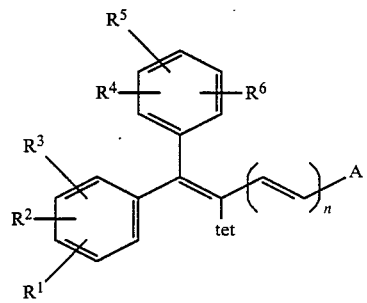

wherein
$R^1$ and $R^4$ each are independently hydrogen, halogen, $C_{1-4}$ alkyl, $C_{1-4}$ alkoxy, or trifluoromethyl;
$R^2, R^3, R^5$ and $R^6$ each are independently hydrogen, halogen $C_{1-4}$ alkyl or $C_{1-4}$ alkoxy;
tet is

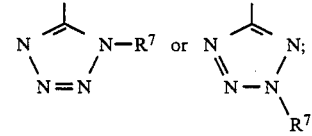

n is an integer of from 0 to 2, inclusive;
A is

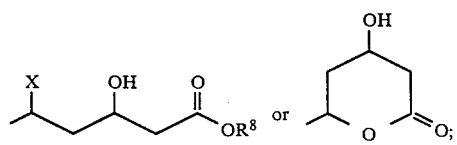

$R^7$ is hydrogen, $C_{1-4}$ alkyl, $C_{1-4}$ alkoxy(lower) alkyl or (2-methoxyethoxy)methyl;
X is —OH or =O; and $R^8$ is hydrogen, a hydrolyzable ester group or a cation to form a non-toxic pharmaceutically acceptable salt.

2. A compound of claim 1 having the formula

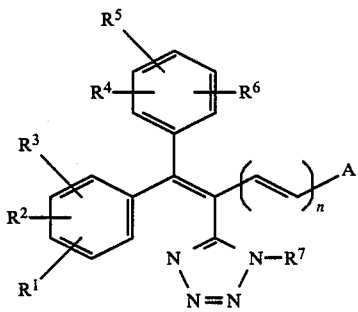

wherein $R^1$ and $R^4$ each are independently hydrogen, halogen, $C_{1-4}$ alkyl, $C_{1-4}$ alkoxy or trifluoromethyl;

$R^2, R^3, R^5$ and $R^6$ each are independently hydrogen, halogen, $C_{1-4}$ alkyl or $C_{1-4}$ alkoxy;

n is an integer of from 0 to 2 inclusive;

A is

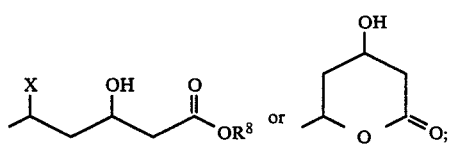

$R^7$ is hydrogen, $C_{1-4}$ alkyl, $C_{1-4}$ alkoxy(lower) alkyl or (2-methoxyethoxy)methyl;

X is —OH or =O; and $R^8$ is hydrogen, a hydrolyzable ester group or a cation to form a non-toxic pharmaceutically acceptable salt.

3. A compound of claim 2 wherein n=1.

4. A compound of claim 3 having the formula

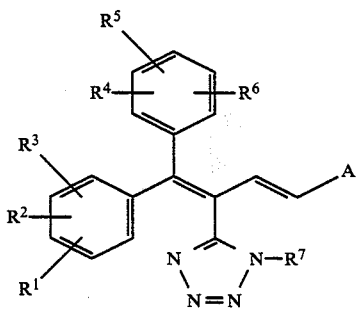

wherein $R^1, R^2, R^3, R^4, R^5$, and $R^6$ each are independently hydrogen, fluoro, chloro, methyl or methoxy;

A is

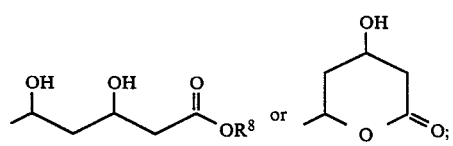

$R^7$ is hydrogen or $C_{1-4}$ alkyl; and $R^8$ is hydrogen, $C_{1-6}$ alkyl or a cation to form a non-toxic pharmaceutically acceptable salt.

5. The compound of claim 1 which is ethyl erythro-9,9-bis(4-fluorophenyl)-3,5-dihydroxy-8-(1-methyl-1H-tetrazol-5-yl)-6,8-nonadienoate.

6. The compound of claim 1 which is erythro-9,9-bis(4-fluorophenyl)-3,5-dihydroxy-8-(1-methyl-1H-tetrazol-5-yl)-6,8-nonadienoic acid or a non-toxic pharmaceutically acceptable salt or hydrate thereof.

7. The compound of claim 6 which is the (3R,5S) enantiomer of 9,9-bis(4-fluorophenyl)-3,5-dihydroxy-8-(1-methyl-1H-tetrazol-5-yl)-6,8-nonadienoic acid or a non-toxic pharmaceutically acceptable salt or hydrate thereof.

8. The compound of claim 6 which is erythro-9,9-bis(4-fluorophenyl)-3,5-dihydroxy-8-(1-methyl-1H-tetrazol-5-yl)-6,8-nonadienoic acid monohydrate.

9. The compound of claim 8 which is the (3R,5S) enantiomer of 9,9-bis(4-fluorophenyl)-3,5-dihydroxy-8-(1-methyl-1H-tetrazol-5-yl)-6,8-nonadienoic acid monohydrate.

10. The compound of claim 6 which is sodium erythro-9,9-bis(4-fluorophenyl)-3,5-dihydroxy-8-(1-methyl-1H-tetrazol-5-yl)-6,8-nonadienoate.

11. The compound of claim 10 which is the (3R,5S) enantiomer of sodium 9,9-bis(4-fluorophenyl)-3,5-dihydroxy-8-(1-methyl-1H-tetrazol-5-yl)-6,8-nonadienoate.

12. The compound of claim 6 which is potassium erythro-9,9-bis(4-fluorophenyl)-3,5-dihydroxy-8-(1-methyl-1H-tetrazol-5-yl)-6,8-nonadienoate.

13. The compound of claim 12 which is the (3R,5S) enantiomer of potassium 9,9-bis(4-fluorophenyl)-3,5-dihydroxy-8-(1-methyl-1H-tetrazol-5-yl)-6,8-nonadienoate.

14. The compound of claim 1 which is trans-6-[4,4-bis(4-fluorophenyl)-3-(1-methyl-1H-tetrazol-5-yl)-1,3-butadienyl]-tetrahydro-4-hydroxy-2H-2H-pyran-2-one.

15. The compound of claim 14 which is the (4R,6S) enantiomer of 6-[4,4-bis(4-fluorophenyl)-3-(1-methyl-1H-tetrazol-5-yl)-1,3-butadienyl]-tetrahydro-4-hydroxy-2H-pyran-2-one.

16. The compound of claim 1 which is erythro-11,11-bis(4-fluorophenyl)-3,5-dihydroxy-10-(1-methyl-1H-tetrazol-5-yl)-6,8,10-undecatrienoic acid or a non-toxic pharmaceutically acceptable salt.

17. The compound of claim 1 which is trans-6-[4,4-bis(4-fluorophenyl)-3-(2-methyl-2H-tetrazol-5-yl)-1,3-butadienyl]-tetrahydro-4-hydroxy-2H-pyran-2-one.

18. The compound of claim 1 which is erythro-9,9-bis(4-fluorophenyl)-3,5-dihydroxy-8-(2-methyl-2H-tetrazol-5-yl)-6,8-nonadienoic acid or a non-toxic pharmaceutically acceptable salt.

19. The compound of claim 1 which is 9,9-bis(4-fluorophenyl)-3-hydroxy-8-(1-methyl-1H-tetrazol-5-yl)-5-oxo-6,8-nonadienoic acid or a non-toxic pharmaceutically acceptable salt.

20. The compound of claim 1 which is erythro-9,9-bis(4-fluorophenyl)-3,5-dihydroxy-8-[1-(1-methylethyl)-1H-tetrazol-5-yl]-6,8-nonadienoic acid or a non-toxic pharmaceutically acceptable salt.

21. The compound of claim 1 which is ethyl erythro-9,9-bis(4-fluorophenyl)-3,5-dihydroxy-8-[1-(1-methylethyl)-1H-tetrazol-5-yl]-6,8-nonadienoate.

22. The compound of claim 1 which is erythro-9,9-bis(4-fluoro-3-methylphenyl)-3,5-dihydroxy-8-(1-methyl-1H-tetrazol-5-yl)-6,8-nonadienoic acid or a non-toxic pharmaceutically acceptable salt.

23. The compound of claim 1 which is trans-6-[4,4-bis(4-fluoro-3-methylphenyl)-3-(1-methyl-1H-tetrazol-5-yl)-1,3-butadienyl]-tetrahydro-4-hydroxy-2H-pyran-2-one.

24. The compound of claim 1 which is erythro-9,9-bis(4-fluorophenyl)-3,5-dihydroxy-8-(1-ethyl-1H-tetrazol-5-yl)-6,8-nonadienoic acid or a non-toxic pharmaceutically acceptable salt.

25. The compound of claim 1 which is erythro-9,9-bis(2,4-dimethylphenyl)-3,5-dihydroxy-8-(1-methyl-1H-tetrazol-5-yl)-6,8-nonadienoic acid or a non-toxic pharmaceutically acceptable salt.

26. The compound of claim 1 which is erythro-9,9-bis(4-fluorophenyl)-3,5-dihydroxy-8-[1-(2-methoxyethoxy)-methyl-1H-tetrazol-5-yl]-6,8-nonadienoic acid or a non-toxic pharmaceutically acceptable salt.

27. The compound of claim 1 which is erythro-9,9-bis(4-fluoro-2-methylphenyl)-3,5-dihydroxy-8-(1-methyl-1H-tetrazol-5-yl)-6,8-nonadienoic acid or a non-toxic pharmaceutically acceptable salt.

28. The compound of claim 27 which is the (3R,5S) enantiomer of 9,9-bis(4-fluoro-2-methylphenyl)-3,5-dihydroxy-8-(1-methyl-1H-tetrazol-5-yl)-6,8-nonadienoic acid or a non-toxic pharmaceutically acceptable salt.

29. The compound of claim 1 which is trans-6-[4,4-bis(4-fluoro-2-methylphenyl)-3-(1-methyl-1H-tetrazol-5-yl)-1,3-butadienyl]-tetrahydro-4-hydroxy-2H-pyran-2-one.

30. The compound of claim 29 which is the (4R,6S) enantiomer of 6-[4,4-bis(4-fluoro-2-methylphenyl)-3-(1-methyl-1H-tetrazol-5-yl)-1,3-butadienyl]-tetrahydro-4-hydroxy-2H-pyran-2-one.

31. The compound of claim 1 which is erythro-9,9-bis(2-fluoro-4-methylphenyl)-3,5-dihydroxy-8-(1-methyl-1H-tetrazol-5-yl)-6,8-nonadienoic acid or a non-toxic pharmaceutically acceptable salt.

32. The compound of claim 1 which is erythro-9-(4-fluorophenyl)-3,5-dihydroxy-8-(1-methyl-1H-tetrazol-5-yl)-9-phenylnona-6,8-dienoic acid or a non-toxic pharmaceutically acceptable salt.

33. The compound of claim 32 which is the (3R,5S) enantiomer of 9-(4-fluorophenyl)-3,5-dihydroxy-8-(1-methyl-1H-tetrazol-5-yl)-9-phenylnona-6,8-dienoic acid or a non-toxic pharmaceutically acceptable salt.

34. The compound of claim 1 which is trans-6-[4-(4-fluorophenyl)-4-phenyl-3-(1-methyl-1H-tetrazol-5-yl)-1,3-butadienyl]-tetrahydro-4-hydroxy-2H-pyran-2-one.

35. The compound of claim 34 which is the (4R,6S) enantiomer of 6-[4-(4-fluorophenyl)-4-phenyl-3-(1-methyl-1H-tetrazol-5-yl)-1,3-butadienyl]-tetrahydro-4-hydroxy-2H-pyran-2-one.

36. The compound of claim 1 which is erythro-9,9-diphenyl-3,5-dihydroxy-8-(1-methyl-1H-tetrazol-5-yl)-6,8-nonadienoic acid or a non-toxic pharmaceutically acceptable salt.

37. The compound of claim 1 which is erythro-9,9-bis(4-methoxyphenyl)-3,5-dihydroxy-8-(1-methyl-1H-tetrazol-5-yl)-6,8-nonadienoic acid or a non-toxic pharmaceutically acceptable salt.

38. A compound of the formula

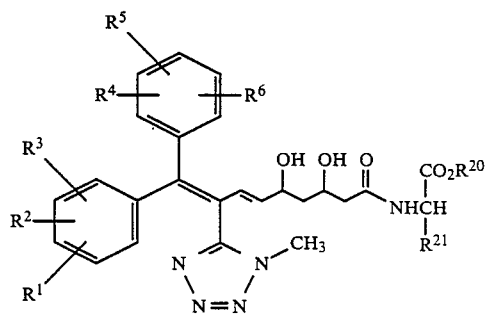

wherein
$R^1$ and $R^4$ each are independently hydrogen, halogen, $C_{1-4}$ alkyl, $C_{1-4}$ alkoxy, or trifluoromethyl;
$R^2$, $R^3$, $R^5$ and $R^6$ each are independently hydrogen, halogen, $C_{1-4}$ alkyl or $C_{1-4}$ alkoxy;
$R^{20}$ is hydrogen, $C_{1-6}$ alkyl or a metal cation and
$R^{21}$ is $C_{1-6}$ alkyl, hydroxy $C_{1-6}$ alkyl, phenyl $C_{1-6}$ alkyl, hydroxyphenyl $C_{1-6}$ alkyl, amido $C_{1-6}$ alkyl, $C_{1-6}$ alkoxycarbonyl $C_{1-6}$ alkyl, imidazol-4-yl-$C_{1-6}$ alkyl, $C_{1-6}$ alkylthio $C_{1-6}$ alkyl, or indol-3-yl $C_{1-6}$ alkyl in which the amido ester moiety is in the L-configuration.

39. A compound of claim 38 wherein $R^{20}$ is hydrogen, $C_{1-2}$ alkyl or a metal cation and $R^{21}$ is $C_{1-4}$ alkyl, hydroxy $C_{1-2}$ alkyl, phenyl $C_{1-2}$ alkyl, hydroxyphenyl $C_{1-2}$ alkyl, amido $C_{1-2}$ alkyl, $C_{1-2}$ alkoxycarbonyl $C_{1-2}$ alkyl, imidazol-4-yl $C_{1-2}$ alkyl, $C_{1-2}$ alkylthio $C_{1-2}$ alkyl or indol-3-yl $C_{1-2}$ alkyl in which the amido ester moiety is in the L-configuration.

40. A compound of claim 39 wherein $R^{21}$ is $C_{1-4}$ alkyl, hydroxymethyl, phenylmethyl or hydroxyphenylmethyl in which the amido ester moiety is in the L-configuration.

* * * * *

UNITED STATES PATENT AND TRADEMARK OFFICE
CERTIFICATE OF CORRECTION

PATENT NO. : 4,897,490

DATED : January 30, 1990

INVENTOR(S) : Sing-Yuen Sit and John J. Wright

It is certified that error appears in the above-identified patent and that said Letters Patent is hereby corrected as shown below:

Title page:

In Item [73], the Assignee "Bristol-Meyers Company" should read -- Bristol-Myers Company --.

In Claim 14, Line 38 thereof should read -- butadienyl]-tetrahydro-4-hydroxy-2H-pyran-2-one. --.

Signed and Sealed this

Twenty-fifth Day of June, 1991

Attest:

HARRY F. MANBECK, JR.

Attesting Officer

Commissioner of Patents and Trademarks